United States Patent
Stupple et al.

(10) Patent No.: US 9,856,252 B2
(45) Date of Patent: Jan. 2, 2018

(54) 2-(HETERO)ARYL-BENZIMIDAZOLE AND IMIDAZOPYRIDINE DERIVATIVES AS INHIBITORS OF ASPARAGIME EMETHYL TRANSFERASE

(71) Applicant: Cancer Therapeutics CRC Pty Ltd, Bundoora, Victoria (AU)

(72) Inventors: Paul Anthony Stupple, Bundoora (AU); Scott Raymond Walker, Parkville (AU); Jo-Anne Pinson, Parkville (AU); Helen Rachel Lagiakos, Parkville (AU); Gillian Elizabeth Lunniss, Parkville (AU); Ian Peter Holmes, Bundoora (AU); Alexandra Elizabeth Stupple, Parkville (AU); Ylva Elisabet Bergman, Parkville (AU); Richard Charles Foitzik, Parkville (AU); Wilhelmus Johannes Antonius Kersten, Bundoora (AU); Michelle Ang Camerino, Parkville (AU)

(73) Assignee: Cancer Therapeutics CRC Pty Ltd, Bundoora, Victoria (AU)

( * ) Notice: Subject to any disclaimer, the term of this patent is extended or adjusted under 35 U.S.C. 154(b) by 0 days.

(21) Appl. No.: 14/769,402

(22) PCT Filed: Feb. 20, 2014

(86) PCT No.: PCT/GB2014/050491
§ 371 (c)(1),
(2) Date: Aug. 20, 2015

(87) PCT Pub. No.: WO2014/128465
PCT Pub. Date: Aug. 28, 2014

(65) Prior Publication Data
US 2016/0222005 A1   Aug. 4, 2016

(30) Foreign Application Priority Data
Feb. 20, 2013 (GB) .................. 1302927.7

(51) Int. Cl.
| | | |
|---|---|---|
| C07D 413/00 | (2006.01) | |
| C07D 401/00 | (2006.01) | |
| C07D 513/02 | (2006.01) | |
| C07D 471/04 | (2006.01) | |
| C07D 235/18 | (2006.01) | |
| C07D 519/00 | (2006.01) | |

(52) U.S. Cl.
CPC ......... *C07D 471/04* (2013.01); *C07D 235/18* (2013.01); *C07D 519/00* (2013.01)

(58) Field of Classification Search
CPC .................................................. C07D 471/04
USPC ................................ 546/118; 544/362, 127
See application file for complete search history.

(56) References Cited

U.S. PATENT DOCUMENTS

| | | | | |
|---|---|---|---|---|
| 2005/0101647 A1* | 5/2005 | Oda | ...................... | A61K 31/423 514/367 |
| 2006/0235037 A1 | 10/2006 | Purandare | | |
| 2010/0069431 A1 | 3/2010 | Iwata et al. | | |

FOREIGN PATENT DOCUMENTS

| | | |
|---|---|---|
| CN | 102417483 A | 4/2012 |
| DE | 261153 A1 | 10/1988 |
| WO | WO03035065 A1 | 5/2003 |
| WO | WO03082186 A2 | 10/2003 |
| WO | WO2004016611 A1 | 2/2004 |
| WO | WO2004024897 A2 | 3/2004 |
| WO | WO2005030206 A1 | 4/2005 |
| WO | WO2005042495 A1 | 5/2005 |
| WO | WO2006080821 A1 | 8/2006 |
| WO | WO2008061303 A1 | 5/2008 |
| WO | WO2009005551 A2 | 1/2009 |
| WO | WO2009113085 A1 | 9/2009 |
| WO | WO2009139076 A1 | 11/2009 |
| WO | WO2010025295 A2 | 3/2010 |
| WO | WO2012108689 A2 | 8/2012 |

OTHER PUBLICATIONS

Secci, Daniela et al: "Conventional and microwave-assisted synthesis of benzimidazole derivatives and their in vitro inhibition of human cyclooxygenase", Journal of Heterocyclic Chemistry, 49(5), 1187-1195.

(Continued)

*Primary Examiner* — Shengjun Wang
(74) *Attorney, Agent, or Firm* — Stites & Harbison PLLC; Richard S. Myers, Jr.

(57) ABSTRACT

Substituted benzimidazole and 3H-imidazo[4,5-b]pyridines or formula I: where X and Y respectively are selected from: (i) N and N; and (ii) N and $CR^4$; $A^2$ is selected from: a $C_5$ heteroarylene group, containing 2 or 3 ring heteroatoms, where the bonds to L1 and the core are β to one another; $L^1$ is selected from: (i) $^{A1}$—O—$CH_2$—$^{A2}$; (ii) $^{A1}$—$CH_2$—O—$^{A2}$; (iii) $^{A1}$—C(=O)—NH—$^{A2}$; (iv) $^{A1}$—CH(OH)—$^{A2}$; (v) $^{A1}$—$CH_2$—NH—C(=O)—$^{A2}$; (vi) $^{A1}$—S—$CH_2$—$^{A2}$; (vii) $^{A1}$—$CH_2$—S—$^{A2}$; (viii) $^{A1}$—$CH_2$—$^{A2}$; and (ix) $^{A1}$—$CH(CH_3)$—O—$^{A2}$; A1 is phenyl, optionally substituted by F or $CF_3$; their use as pharmaceuticals, and in particular, in treating cancer and hemoglobinopathies.

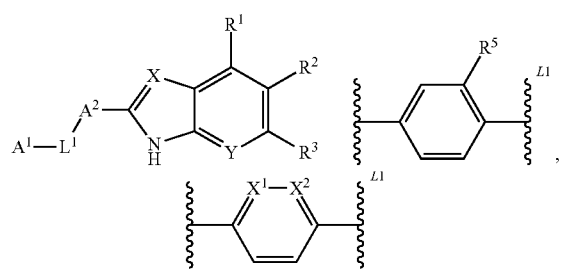

16 Claims, No Drawings

(56) References Cited

OTHER PUBLICATIONS

Rostamizadeh, Shahnaz et al: "Aqueous 1 M Glucose Solution as a Novel and Fully Green Reaction Medium and Catalyst for the Oxidant-Free Synthesis of 2-Arylbenzimidazoles", Synthetic Communications, 41(12), 1794-1884.
Chen, Yong-Fei et al: "Design and synthesis of new heterocyclic Bcr-Abl inhibitors", Heterocyclic Communications , 16(2-3), 123-135.
Goeker, Hakan et al: "Synthesis and potent antifungal activity against Candida species of some novel 1H-benzimidazoles", Journal of Heterocyclic Chemistry , 46(5), 936-948.
Kaynak, F. Betul et al: 11 Synthesis and crystal structure of 1-benzyl-2-(4-benzyloxyphenyl)-5,6-dichloro-1H-benzimidazole, Structural Chemistry , 19(3), 477-488.
Kus, Canan et al: 11 Antimicrobial activity studies on some morpholinobenzimidazole derivatives 11, Ankara Universitesi Eczacilik Fakultesidergisi , 35(4), 237-244.
K Vijayakumar et al: "Available on line www Synthesis, Anti-Tumor, Anti-Diabetic, and Anti-Asthmatic Activitives of Some Novel Benzimidazole Derivatives", Pharm. Res, vol. 2, No. 4 Jan. 1, 2010 (Jan. 1, 2010), 2010, pp. 215-224.
Richards M L et al: "Substituted 2-phenyl-benzimidazole derivatives: novel compounds that suppress key markers of allergy", European Journal of Medicinal Chemistry, Editions Scientifique Elsevier, Paris, FR, vol. 41, No. 8, Aug. 1, 2006 (Aug. 1, 2006), pp. 950-969.
Zhang, Zeyuan et al: Synthesis and antifungal activity of novel 2,5-disubstituted-1,3,4-oxadiazoles containing benzimidazole moiety, Journal of Pesticide Science (Tokyo, Japan) ' 37(4), 338-341.
Aggarwal, et al., Nuclear Cyclin D1/CDK4 Kinase Regulates CUL4 Expression and Triggers Neoplastic Growth via Activation of the PRMT5 Methyltransferase; Cancer Cell, 2010, 18, 329-340.
Berger, Shelley L., Out of the jaws of death: PRMT5 steers p53, nature cell biology vol. 10 | No. 12 | Dec. 2008, pp. 1389-1390.
Gu, et al., Protein arginine methyltransferase 5 is essential for growth of lung cancer cells, Biochemical Journal Immediate Publication. Published on Jun. 18, 2012 as manuscript BJ20120768, pp. 1-20.
Chen, et al., Epigenetic changes during disease progression in a murine model of human chronic lymphocytic leukemia, PNAS, Aug. 11, 2009, vol. 106, No. 32, pp. 13433-13438.
Cho, et al., Arginine methylation controls growth regulation by E2F-1, The EMBO Journal vol. 31 | No. 7 | 2012, pp. 1785-1797.
Durant, et al., p53 methylation, Cell Cycle 8:6, Mar. 15, 2009, pp. 801-802.
He, et al., Induction of human fetal hemoglobin expression by adenosine-2',3'-dialdehyde, Journal of Translational Medicine 2013, 11:14, pp. 1-7.
Jansson, et al., Arginine methylation regulates the p53 response, nature cell biology vol. 10 | No. 12 | Dec. 2008, pp. 1431-1439.
Kanduri, et al., Differential genome-wide array-based methylation profiles in prognostic subsets of chronic lymphocytic leukemia, Blood, Jan. 14, 2010 vol. 115, No. 2, pp 296-305.
Karkhanis, et al., Versatility of PRMT5-induced methylation in growth control and development, Cell Press, 2011, pp. 1-9.
Kim, et al., Identification of Gastric Cancer-Related Genes Using a cDNA Microarray Containing Novel Expressed Sequence Tags Expressed in Gastric Cancer Cells, Clinical Cancer Research, Jan. 15, 2005, vol. 11, 473-482.
Krause, et al., Protein arginine methyltransferases: Evolution and assessment of their pharmacological and therapeutic potential, Pharmacology & Therapeutics 113 (2007) 50-87.
Le Guezennec, et al., MBD2/NuRD and MBD3/NuRD, Two Distinct Complexes with Different Biochemical and Functional Properties, Molecular and Cellular Biology, Feb. 2006, p. 843-851.
Micholas, et al., Abstract LB-254: PRMT5 is upregulated in malignant and metastatic melanoma, and regulates expression of the MITF transcription factor, Cancer Res Apr. 15, 2012 72; LB-254.
Pal, et al., mSin3A/Histone Deacetylase 2- and PRMT5-Containing Brg1 Complex Is Involved in Transcriptional Repression of the Myc Target Gene cad, Molecular and Cellular Biology, Nov. 2003, p. 7475-7487.
Pollack, et al., The Human Homologue of the Yeast Proteins Skb1 and Hsl7p Interacts with Jak Kinases and Contains Protein Methyltransferase Activity, J. Biol. Chem. 1999, 274:31531-31542.
Powers, et al., Protein Arginine Methyltransferase 5 Accelerates Tumor Growth by Arginine Methylation of the Tumor Suppressor Programmed Cell Death 4, Cancer Res Published OnlineFirst Jun. 23, 2011, pp. OF1-OF9.
Rank, et al., Identification of a PRMT5-dependent repressor complex linked to silencing of human fetal globin gene expression, Blood, Sep. 2, 2010 vol. 116, No. 9, pp. 1585-1592.
Scoumanne, et al., PRMT5 is required for cell-cycle progression and p53 tumor suppressor function, Nucleic Acids Research, 2009, vol. 37, No. 15 4965-4976.
Pal, et al., Low levels of miR-92b/96 induce PRMT5 translation and H3R8/H4R3 methylation in mantle cell lymphoma, The EMBO Journal (2007) 26, 3558-3569.
Wang, et al., Protein Arginine Methyltransferase 5 Suppresses the Transcription of the RB Family of Tumor Suppressors in Leukemia and Lymphoma Cells, Molecular and Cellular Biology, Oct. 2008, p. 6262-6277.
Gu, et al., Protein Arginine Methyltransferase 5 Functions in Opposite Ways in the Cytoplasm and Nucleus of Prostate cancer Cells, PLOS One, Aug. 2012 | vol. 7 | Issue 8, pp. e44033, pp. 1-13.

* cited by examiner

2-(HETERO)ARYL-BENZIMIDAZOLE AND IMIDAZOPYRIDINE DERIVATIVES AS INHIBITORS OF ASPARAGIME EMETHYL TRANSFERASE

The present invention relates to substituted benzimidazole and 3H-imidazo[4,5-b]pyridines, their use as pharmaceuticals, and in particular, in treating cancer and hemoglobinopathies.

BACKGROUND TO THE INVENTION

Posttranslational modification of proteins is a hallmark of signal transduction where cells are able to react quickly to changes or events in the cellular environment. Posttranslational modification of proteins expands the structural and functional diversity of the proteome. The role of acetylation and phosphorylation of proteins has been extensively studied as highly reversible reactions for fine-tuning responses to external stimuli or changes in the environmental conditions. Recently, the importance of other types of protein modifications, including ubiquitination and methylation has begun to be recognized.

The methylation of proteins and the enzymes that carry out these reactions has increased the dimensions of gene regulation by marking genes that are transcriptionally active or silenced. Protein methylation can occur on amino acids such as lysine, arginine, histidine, or proline, and on carboxy groups.

Arginine methylation of mainly nuclear proteins is an important posttranslational modification process involved in structural remodelling of chromatin, signal transduction, cellular proliferation, nucleocytoplasmic shuttling, translation, gene transcription, DNA repair, RNA processing, or mRNA splicing.

Methylation of proteins at arginine residues is catalysed by Protein Arginine Methyltransferase enzymes. The Protein Arginine Methyl Transferase (PRMT) family of enzymes are evolutionarily conserved between organisms but differ in the number of members in different organisms.

There are eleven members of the human PRMT family, eight of which have known enzymatic activity and target substrates. With the exception of PRMT2 and two recently identified putative PRMT genes (PRMT10 and PRMT11), all remaining proteins of the family possess enzymatic arginine methylation activity.

PRMTs are subdivided into two types based on the methylation that they catalyse at the guanidinium group of arginine residues of substrate proteins. There are three nitrogens in the guanidinium group, potentially all of which could be methylated; the two ψ-guanidino nitrogen atoms and the internal δ-guanidino nitrogen atom. Mono-methylation and dimethylation of arginine (MMA and DMA) is found in mammalian cells at one or both of the two ψ-guanidino nitrogen atoms; dimethylation may be either symmetric or asymmetric. The third methylated arginine is generated by monomethylation of the internal δ-guanidino nitrogen atom of arginine and has so far been documented only in yeast proteins. Type I PRMT enzymes catalyse the formation of MMA and asymmetric dimethylarginine by di-methylating the same nitrogen atom of the guanidinium group, whereas Type II PRMT enzymes catalyse the formation of MMA and symmetric di-methylarginine by mono-methylating each of the terminal nitrogen atoms. Type III enzymes methylate the internal δ-guanidino nitrogen atom.

Of the eight well characterised human PRMTs, PRMT1, 3, 4, 6 and 8 are Type I enzymes, and PRMT5, 7 and 9 are Type II enzymes.

PRMTs catalyse the methylation of the guanidino nitrogen atoms of arginine residues through the transfer of a methyl group from S-adenosyl methionine (SAM). A by-product of the enzymatic methylation step is S-adenosyl-L-homocysteine (AdoHcy), which is hydrolyzed to adenosine and homocysteine by AdoHcy hydrolase (Krause et al., 2007).

PRMT5

PRMT5 (aka JBP1, SKB1, IBP72, SKB1his and HRM-TIL5) is a Type II arginine methyltransferase, and was first identified in a two-hybrid search for proteins interacting with the Janus tyrosine kinase (Jak2) (Pollack et al., 1999).

PRMT5 plays a significant role in control and modulation of gene transcription. Inter alia, PRMT5 is known to methylate histone H3 at Arg-8 (a site distinct from that methylated by PRMT4) and histone H4 at Arg-3 (the same site methylated by PRMT1) as part of a complex with human SWI/SNF chromatin remodelling components BRG1 and BRM.

In addition to direct repressive histone marks induced by PRMT5, the enzyme's role in gene silencing is also mediated through the formation of multiprotein repressor complexes that include NuRD components, HDACs, MDB proteins and DNA methyltransferases, (Rank et al., 2010; Le Guezennec et al., 2006; Pal et al., 2003).

PRMT5 is involved in the methylation and functional modulation of the tumour suppressor protein p53. See (Berger, 2008; Durant et al., 2009; Jansson et al., 2008; Scoumanne et al., 2009). Most of the physiological functions of p53 are attributable to its role as a transcriptional activator, responding to agents that damage DNA. p53 status is wild type in approximately half of human cancer cases. These include 94% in cervix, 87% in blood malignancies, 85% in bones and endocrine glands, and 75% of primary breast cancer. Restoration of p53 in cancer cells harbouring wild type p53, by way of inhibiting mechanisms that suppress its function leads to growth arrest and apoptosis, and is regarded as a potentially effective means of tumour suppression.

p53 target genes have two alternative downstream effects: either they pause the cell cycle, allowing the DNA to be repaired, or, if repair is not possible, they activate processes leading to apoptosis (programmed cell death). How p53 'chooses' between these distinct outcomes is a central question in the field of tumour biology.

p53 is replete with posttranslational modifications. Phosphorylation was one of the first posttranslational modifications to be clearly defined on p53. In the last decade it has become additionally clear that p53 is modified not only by phosphorylation, but that it is extensively modified by lysine acetylation and methylation, among other modifications. Indeed, besides histone proteins p53 is the most common protein substrate known for these posttranslational modifications. However, despite the plethora of posttranslational modifications, p53 has not been identified, until recently, as a substrate for arginine methylation.

Jansson et al (Jansson et al., 2008) discovered that PRMT5 is physically associated with a p53 cofactor called Strap. A co-factor complex that contains Strap et al binds to p53 in response to DNA damage. Jansson et al demonstrated that PRMT5 methylates p53 in vitro, and mapped the sites of methylation (R333, R335 and R337). They developed an antibody that specifically detects p53 methylated on these sites and confirmed that p53 is methylated in vivo. Jansson et al went on to show that p53 methylation requires PRMT5 and is increased in response to etoposide, a DNA damaging agent.

The role of PRMT5 and p53 arginine methylation on cell cycle regulation and DNA damage response have been explored by both Jansson et al and Scoumanne et al (Jansson et al., 2008; Scoumanne et al., 2009). Although some differences are evident between the results from the two groups in respect of cell cycle regulation in unperturbed cells (which may be ascribed to cell type specific effects and/or the actual nature of the experimental arrangements), both groups report similar results with respect to the DNA damage response.

In response to DNA damage, caused by a variety of agents, including doxorubicin, camptothecin and UV light, and also in response to treatment with Nutlin-3, knockdown of PRMT5 results in an increase in sub-G1 population and concomitant reduction in G1 cells and, in the presence of p53, a significant increase in apoptosis. Knockdown of PRMT5 also resulted in a reduced level of p21, a key p53 target gene that regulates cell cycle arrest during the p53 response and MDM2, a p53 E3 ubiquitin ligase, but not PUMA, NOXA, AIP1 & APAF1, p53 target genes linked to apoptosis.

Knockdown of PRMT5 (but not PRMT1 or CARM1/PRMT4) results in decreased p53 stabilisation, decreased basal p53 levels, and decreased p53 oligomerisation, and also decreased expression of elF4E a major component of translational machinery involved in ribosome binding to mRNA. Indeed, elF4E is a potent oncogene, which has been shown to promote malignant transformation in vitro and human cancer formation.

Knockdown of PRMT5 would be expected to lead to a reduction in the level of arginine methylated p53. Consistent with arginine methylation status of p53 influencing the p53 response (reduced arginine methylation biasing the response to proapoptotic), Jannson et al showed that a p53 mutant in which each of the three critical arginine residues were substituted with lysine (p53KKK) retained the ability to induce apoptosis but its cell cycle arrest activity was significantly compromised.

Moreover, p53KKK also has a significantly reduced ability to induce transcription of p21, by contrast with APAF1. The promoter binding specificity of wild-type p53 to key target genes is also significantly affected by arginine methylating status: Knockdown of PRMT5 results in decreased p53 binding to the promoter regions of the p21 and (intriguingly) PUMA genes, but does not affect p53 binding to the promoter regions of NOXA or APAF1.

Taken together, it would seem that PRMT5 is a prosurvival factor, which regulates cell proliferation in unstressed conditions and modulates the p53 response during DNA damage. In particular, knockdown of PRMT5, leading to a reduction in the levels of arginine methylated p53, appears to bias the p53 DNA damage response to proapoptotic as opposed to cell cycle arrest.

PRMT5 is further linked to cancers in that it is aberrantly expressed in around half of human cancer cases. PRMT5 overexpression has been observed in patient tissue samples and cell lines of Prostate cancer (Gu et al., 2012), Lung cancer (Zhongping et al., 2012), Melanoma cancer (Nicholas et al., 2012), Breast cancer (Powers et al., 2011), Colorectal cancer (Cho et al., 2012), Gastric cancer (Kim et al., 2005), Esophagus and Lung carcinoma (Aggarwal et al., 2010) and B-Cell lymphomas and leukemia (Wang, 2008). Moreover, elevated expression of PRMT5 in Melanoma, Breast and Colorectal cancers has been demonstrated to correlate with a poor prognosis.

Lymphoid malignancies including CLL are associated with over-expression of PRMT5. PRMT5 is over-expressed (at the protein level) in the nucleus and cytosol in a number of patient derived Burkitt's lymphoma; mantle cell lymphoma (MCL); in vitro EBV-transformed lymphoma; leukaemia cell lines; and B-CLL cell lines, relative to normal CD19+B lymphocytes (Pal et al., 2007; Wang et al., 2008). Intriguingly, despite elevated levels of PRMT5 protein in these tumour cells, the levels of PRMT5 mRNA are reduced (by a factor of 2-5). Translation of PRMT5 mRNA is however, enhanced in lymphoma cells, resulting in increased levels of PRMT5 (Pal et al., 2007; Wang et al., 2008).

In addition to genomic changes, CLL, like almost all cancers, has aberrant epigenetic abnormalities characterised by global hypomethylation and hot-spots of repressive hypermethylation of promoters including tumour suppressor genes. While the role of epigenetics in the origin and progression of CLL remains unclear, epigenetic changes appear to occur early in the disease and specific patterns of DNA methylation are associated with worse prognosis (Chen et al., 2009; Kanduri et al., 2010). Global symmetric methylation of histones H3R8 and H4R3 is increased in transformed lymphoid cell lines and MCL clinical samples (Pal et al., 2007), correlating with the overexpression of PRMT5 observed in a wide variety of lymphoid cancer cell lines and MCL clinical samples.

PRMT5 is therefore a target for the identification of novel cancer therapeutics.

PRMT5 Function and Hemoglobinopathies

Hemoglobin is a major protein in red blood cells and is essential for the transport of oxygen from the lungs to the tissues. In adult humans, the most common haemoglobin type is a tetramer called hemoglobin A, consisting of two $\alpha$ and two $\beta$ subunits. In human infants, the hemoglobin molecule is made up of two $\alpha$ and two $\gamma$ chains. The gamma chains are gradually replaced by subunits as the infant grows. The developmental switch in human $\beta$-like globin gene subtype from foetal ($\gamma$) to adult ($\beta$) that begins at birth heralds the onset of the hemoglobinopathies $\beta$-thalassemia and sickle cell disease (SCD). In $\beta$-thalassemia the adult chains are not produced. In SCD a point mutation in the coding sequence in the $\beta$ globin gene leads to the production of a protein with altered polymerisation properties. The observation that increased adult $\gamma$-globin gene expression (in the setting of hereditary persistence of foetal haemoglobin (HPFH) mutations) significantly ameliorates the clinical severity of $\beta$-thalassemia and SCD has prompted the search for therapeutic strategies to reverse $\gamma$-globin gene silencing. To date, this has been achieved through pharmacological induction, using compounds that broadly influence epigenetic modifications, including DNA methylation and histone deacetylation. The development of more targeted therapies is dependent on the identification of the molecular mechanisms underpinning foetal globin gene silencing. These mechanisms have remained elusive, despite exhaustive study of the HPFH mutations, and considerable progress in many other aspects of globin gene regulation.

PRMT5 plays a critical role in triggering coordinated repressive epigenetic events that initiate with dimethylation of histone H4 Arginine 3 (H4R3me2s), and culminate in DNA methylation and transcriptional silencing of the $\gamma$-genes (Rank et al., 2010). Integral to the synchronous establishment of the repressive markers is the assembly of a PRMT5-dependent complex containing the DNA methyltransferase DNMT3A, and other repressor proteins (Rank et al., 2010). DNMT3A is directly recruited to bind to the PRMT5-induced H4R3me2s mark, and loss of this mark through shRNA-mediated knock-down of PRMT5, or enforced expression of a mutant form of PRMT5 lacking methyltransferase activity leads to marked upregulation of γ-gene expression, and complete abrogation of DNA methylation at the γ-promoter. Treatment of human erythroid progenitors with non-specific methyltransferase inhibitors (Adox and MTA) also resulted in upregulation of γ-gene expression (He Y, 2013). Inhibitors of PRMT5 thus have potential as therapeutics for hemoglobinopathies such as β-thalassemia and Sickle Cell Disease (SCD).

The present inventors have developed particular substituted benzimidazole and 3H-imidazo[4,5-b]pyridines which inhibit the activity of PRMT5 and therefore may be of use in treating conditions ameliorated by the inhibition of the activity of PRMT5.

SUMMARY OF THE INVENTION

Therefore, a first aspect of the present invention provides a compound of formula I:

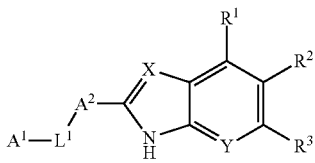

where
X and Y respectively are selected from:
(i) N and N; and
(ii) N and $CR^4$;
$A^2$ is selected from:

(i)

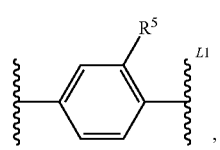

where $R^5$ is selected from H, Br, F, Me, OMe, carboxy, $C_{1-4}$ alkyl ester, carboxamide, $C_{5-7}$ N-containing heteroaryl group, which is optionally substituted by a $C_{1-4}$ alkyl group;

(ii)

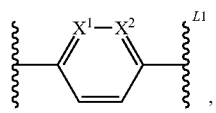

where one of $X^1$ and $X^2$ is N, and the other is CH;
(iii) a $C_5$ heteroarylene group, containing 2 or 3 ring heteroatoms, where the bonds to $L^1$ and the core are β to one another;
$L^1$ is selected from:
(i) $^{A1}$—O—$CH_2$—$^{A2}$;
(ii) $^{A1}$—$CH_2$—O—$^{A2}$;
(iii) $^{A1}$—C(=O)—NH—$^{A2}$;
(iv) $^{A1}$—CH(OH)—$^{A2}$;
(v) $^{A1}$—$CH_2$—NH—C(=O)—$^{A2}$;
(vi) $^{A1}$—S—$CH_2$—$^{A2}$;
(vii) $^{A1}$—$CH_2$—S—$^{A2}$
(viii) $^{A1}$—$CH_2$—$^{A2}$; and
(ix) $^{A1}$—CH($CH_3$)—O—$^{A2}$;
$A^1$ is phenyl, optionally substituted by F or $CF_3$;
(a) one of $R^1$, $R^2$, $R^3$ and $R^4$ (if present) is selected from:
(i) H;
(ii) Halo;
(iii) $NH_2$;
(iv) $NMe_2$;
(iv) $C_{1-4}$ alkyl;
(v) OMe;
(vi) $OCF_3$;
(vii) $CF_3$;
(viii) CN;
(ix) —$CH_2$-carboxy;
(x) —$CH_2$—$C_{1-4}$ alkylester;
(xi) —$CH_2$-carboxamide;
(xii) —NH—$C_2H_4$—NH—C(=O)—$C_{1-4}$ alkyl;
(xiii) $L^2$-$A^3$, where $L^2$ is selected from the group consisting of: a single bond, $CH_2$, O, NH, NMe, NH—$CH_2$, and NMe-$CH_2$; and $A^3$ is selected from:
(xiii-i) a $C_{5-10}$ N-containing heterocyclic group, which is optionally substituted by one or two groups selected from OH, $NH_2$, $CH_2N(R^6)_2$, $C_{1-4}$ alkyl, $C_{1-4}$ alkylacyl, $C_{1-4}$ alkyl ester, oxo and $C_{1-4}$ alkyl sulfonyl, where each $R^6$ is independently selected from H, $C_{1-4}$ alkyl, $C_{1-4}$ alkylacyl and $C_{1-4}$ alkyl ester;
(xiii-ii) a $C_{5-7}$ N-containing heteroaryl group, which is optionally substituted by a $C_{1-4}$ alkyl group;
(xiii-iii) a $C_{5-7}$ non-N-containing heterocyclic group;
(b) another of $R^1$, $R^2$, $R^3$ and $R^4$ (if present) is selected from:
(i) H;
(ii) Halo;
(iii) $NH_2$;
(iv) $NMe_2$;
(iv) Me;
(v) OMe;
(vi) $OCF_3$;
(vii) $CF_3$;
(viii) CN;
(c) the other one or two of $R^1$, $R^2$, $R^3$ and $R^4$ (if present) are H.

In some embodiments, the first aspect may not include the compound:

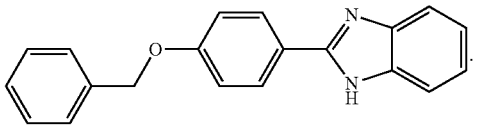 [SMILES: c1ccc(COc2ccc(-c3nc4ccccc4[nH]3)cc2)cc1]

A second aspect of the present invention provides a compound of the first aspect of the invention for use in a method of therapy. The second aspect also provides a pharmaceutical composition comprising a compound of the first aspect, and a pharmaceutically acceptable excipient.

A third aspect of the present invention provides a method of treatment of cancer, comprising administering to a patient in need of treatment, a compound of the first aspect of the invention or a pharmaceutical composition of the second aspect of the invention. The third aspect of the present invention also provides the use of a compound of the first aspect of the invention in the manufacture of a medicament for treating cancer, and a compound of the first aspect of the invention or pharmaceutical composition of the second aspect of the invention for use in the treatment of cancer.

As described below, the compound of the first aspect may be administered simultaneously or sequentially with radiotherapy and/or chemotherapy in the treatment of cancer.

A fourth aspect of the present invention provides a method of treatment of hemoglobinopathies, comprising administering to a patient in need of treatment, a compound of the first aspect of the invention or a pharmaceutical composition of the second aspect of the invention. The fourth aspect of the present invention also provides the use of a compound of the first aspect of the invention in the manufacture of a medicament for treating hemoglobinopathies, and a compound of the first aspect of the invention or pharmaceutical composition of the second aspect of the invention for use in the treatment of hemoglobinopathies.

Definitions $C_5$ heteroarylene group, containing 2 or 3 ring heteroatoms, where the bonds to L1 and the core are β to one another: This term as used herein, pertains to a divalent moiety obtained by removing a hydrogen atom from two ring atoms of a monocyclic heteroaryl compound, which moiety has 5 ring atoms, of which 2 or 3 are ring heteroatoms. Examples of such monocyclic heteroarylene groups include, but are not limited to, those derived from:
$N_1O_1$: oxazole, isoxazole;
$N_2O_1$: oxadiazole (furazan);
$N_1S_1$: thiazole, isothiazole;
$N_2$: imidazole (1,3-diazole), pyrazole (1,2-diazole); and
$N_3$: triazole.

Examples of such groups are:

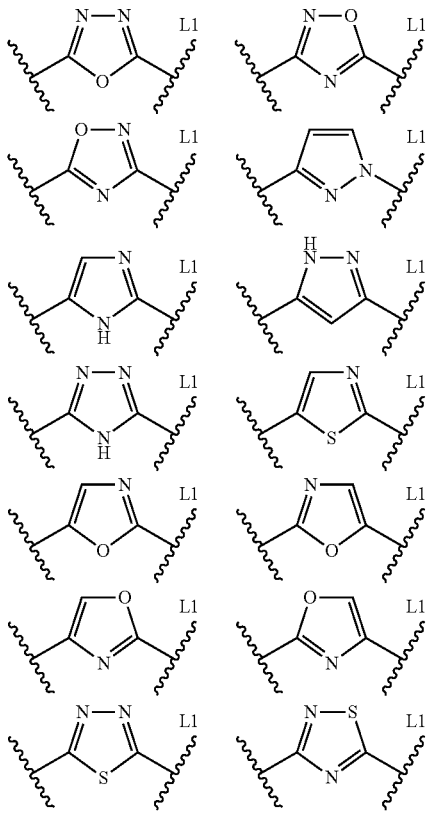

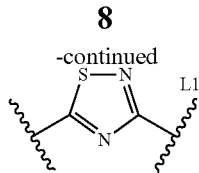

$C_{5-7}$ N-containing heterocyclic group: The term "$C_{5-7}$ N-containing heterocyclic group" as used herein, pertains to a monovalent moiety obtained by removing a hydrogen atom from a ring atom of a monocyclic heterocyclic compound, which moiety has from 5 to 7 ring atoms, of which from 1 to 4 are ring heteroatoms, at least one of which is nitrogen.

In this context, the prefixes (e.g. $C_{5-7}$, $C_{5-6}$, etc.) denote the number of ring atoms, or range of number of ring atoms, whether carbon atoms or heteroatoms. For example, the term "$C_{5-6}$ heterocyclyl", as used herein, pertains to a heterocyclyl group having 5 or 6 ring atoms.

Examples of $C_{5-7}$ N-containing heterocyclic groups include, but are not limited to, those derived from:
$N_1$: pyrrolidine (tetrahydropyrrole) ($C_5$), pyrroline (e.g., 3-pyrroline, 2,5-dihydropyrrole) ($C_5$), 2H-pyrrole or 3H-pyrrole (isopyrrole, isoazole) ($C_5$), piperidine ($C_6$), dihydropyridine ($C_6$), tetrahydropyridine ($C_6$), azepine ($C_7$);
$N_2$: imidazolidine ($C_5$), pyrazolidine (diazolidine) ($C_5$), imidazoline ($C_5$), pyrazoline (dihydropyrazole) ($C_5$), piperazine ($C_6$);
$N_1O_1$: tetrahydrooxazole ($C_5$), dihydrooxazole ($C_5$), tetrahydroisoxazole ($C_5$), dihydroisoxazole ($C_5$), morpholine ($C_6$), tetrahydrooxazine ($C_6$), dihydrooxazine ($C_6$), oxazine ($C_6$);
$N_1S_1$: thiazoline ($C_5$), thiazolidine ($C_5$), thiomorpholine ($C_6$);
$N_2O_1$: oxadiazine ($C_6$); and,
$N_1O_1S_1$: oxathiazine ($C_6$).

Where the ring contains a S heteroatom, it may be oxidised. For example, where the $C_{5-7}$ N-containing heterocyclic group is thiomorpholine, the S may be singly or doubly oxidised, i.e.:

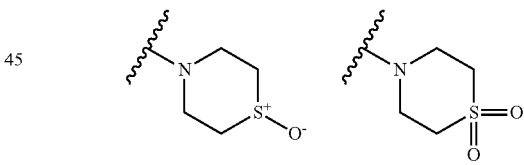

$C_{5-10}$ N-containing heterocyclic group: The term "$C_{5-10}$ N-containing heterocyclic group" as used herein, pertains to a monovalent moiety obtained by removing a hydrogen atom from a ring atom of a monocyclic or bicyclic heterocyclic compound, each ring of which moiety has from 5 to 7 ring atoms, of which from 1 to 4 are ring heteroatoms, and at least one of the ring heteroatoms is nitrogen. Thus the term encompasses the term "$C_{5-7}$ N-containing heterocyclic group" defined above.

Examples of $C_{5-10}$ N-containing heterocyclic groups include, but are not limited to, those listed above for "$C_{5-7}$ N-containing heterocyclic group" and those derived from:
$N_1$: indoline ($C_9$); isoindoline ($C_9$).

$C_{5-7}$ non-N-containing heterocyclic group: The term "$C_{5-7}$ non-N-containing heterocyclic group" as used herein, pertains to a monovalent moiety obtained by removing a hydrogen atom from a ring atom of a monocyclic heterocyclic compound, which moiety has from 5 to 7 ring atoms, of which from 1 to 4 are ring heteroatoms, none of which is nitrogen.

In this context, the prefixes (e.g. $C_{5-7}$, $C_{5-6}$, etc.) denote the number of ring atoms, or range of number of ring atoms, whether carbon atoms or heteroatoms. For example, the term "$C_{5-6}$ heterocyclyl", as used herein, pertains to a heterocyclyl group having 5 or 6 ring atoms.

Examples of $C_{5-7}$ non-N-containing heterocyclic groups include, but are not limited to, those derived from:

$O_1$: oxolane (tetrahydrofuran) ($C_5$), oxole (dihydrofuran) ($C_5$), oxane (tetrahydropyran) ($C_6$), dihydropyran ($C_6$), pyran ($C_6$), oxepin ($C_7$);

$S_1$: thiolane (tetrahydrothiophene) ($C_5$), thiane (tetrahydrothiopyran) ($C_6$), thiepane ($C_7$);

$O_2$: dioxolane ($C_5$), dioxane ($C_6$), and dioxepane ($C_7$);

$O_3$: trioxane ($C_6$); and $O_1S_1$: oxathiole ($C_5$) and oxathiane (thioxane) ($C_6$).

$C_{5-7}$ N-containing heteroaryl group: The term "$C_{5-7}$ N-containing heteroaryl group", as used herein, pertains to a monovalent moiety obtained by removing a hydrogen atom from an aromatic ring atom of a monocyclic aromatic compound, which moiety has from 5 to 7 ring atoms, of which from 1 to 4 are ring heteroatoms, at least one of which is nitrogen.

In this context, the prefixes (e.g. $C_{5-7}$, $C_{5-6}$, etc.) denote the number of ring atoms, or range of number of ring atoms, whether carbon atoms or heteroatoms. For example, the term "$C_{5-6}$ heteroaryl" as used herein, pertains to a heteroaryl group having 5 or 6 ring atoms.

Examples of $C_{5-7}$ N-containing heteroaryl groups include, but are not limited to, those derived from:

$N_1$: pyrrole (azole) ($C_5$), pyridine (azine) ($C_6$);

$N_1O_1$: oxazole ($C_5$), isoxazole ($C_5$), isoxazine ($C_6$);

$N_2O_1$: oxadiazole (furazan) ($C_5$);

$N_3O_1$: oxatriazole ($C_5$);

$N_1S_1$: thiazole ($C_5$), isothiazole ($C_5$);

$N_2$: imidazole (1,3-diazole) ($C_5$), pyrazole (1,2-diazole) ($C_5$), pyridazine (1,2-diazine) ($C_6$), pyrimidine (1,3-diazine) ($C_6$) (e.g., cytosine, thymine, uracil), pyrazine (1,4-diazine) ($C_6$);

$N_3$: triazole ($C_5$), triazine ($C_6$); and, $N_4$: tetrazole ($C_5$).

Halo: F, Cl, Br, I.

Optional Substituents $C_{1-4}$ alkyl: The term "$C_{1-4}$ alkyl" as used herein, pertains to a monovalent moiety obtained by removing a hydrogen atom from a carbon atom of a saturated hydrocarbon compound having from 1 to 4 carbon atoms and that maybe cyclised having 3-4 carbon atoms.

Examples of saturated alkyl groups include, but are not limited to, methyl ($C_1$), ethyl ($C_2$), propyl ($C_3$), and butyl ($C_4$).

Examples of saturated linear alkyl groups include, but are not limited to, methyl ($C_1$), ethyl ($C_2$), n-propyl ($C_3$), and n-butyl ($C_4$).

Examples of saturated branched alkyl groups include iso-propyl ($C_3$), iso-butyl ($C_4$), sec-butyl ($C_4$) and tert-butyl ($C_4$).

Examples of cyclised alkyl groups include cyclopropyl ($C_3$) and cyclobutyl ($C_4$)

$C_{1-4}$ alkyl groups may be themselves be substituted by an amino or protected amino group, i.e. $NH_2$ or NHProt, where Prot is an amino protecting group (e.g. Boc).

$C_{1-4}$ alkylacyl: —C(=O)R, wherein R is a $C_{1-4}$ alkyl group as defined above. Examples of $C_{1-4}$ alkylacyl groups include, but are not limited to, —C(=O)$CH_3$ (acetyl), —C(=O)$CH_2CH_3$ (propionyl), —C(=O)C($CH_3$)$_3$ (t-butyryl), —C(=O)CH($CH_3$)$NR^{C1}R^{C2}$ where $R^{C1}$ and $R^{C2}$ are independently selected from H and a $C_{1-4}$ alkyl group as defined above.

Carboxy: —C(=O)OH.

Carboxamide: —C(=O)$NR^{C1}R^{D2}$, where $R^{C1}$ and $R^{C2}$ are independently selected from H and a $C_{1-4}$ alkyl group as defined above. Examples of carboxamide groups include, but are not limited to, —C(=O)$NHCH_3$, —C(=O)$NHCH_2CH_3$, —C(=O)N($CH_3$)$_2$ and —C(=O)N($C_2H_5$)$_2$.

$C_{1-4}$ alkyl ester: —C(=O)OR, wherein R is a $C_{1-4}$ alkyl group. Examples of $C_{1-4}$ alkyl ester groups include, but are not limited to, —C(=O)$OCH_3$, —C(=O)$OCH_2CH_3$, and —C(=O)OC($CH_3$)$_3$.

Oxo (keto, -one): =O.

$C_{1-4}$ alkyl sulfonyl: —S(=O)$_2$R, wherein R is a $C_{1-4}$ alkyl group. Examples of $C_{1-4}$ alkyl sulfonyl groups include, but are not limited to, —S(=O)$_2CH_3$ (methanesulfonyl, mesyl) and —S(=O)$_2CH_2CH_3$ (esyl).

Includes Other Forms

Unless otherwise specified, included in the above are the well known ionic, salt, solvate, and protected forms of these substituents. For example, a reference to carboxylic acid (—COOH) also includes the anionic (carboxylate) form (—COO$^-$), a salt or solvate thereof, as well as conventional protected forms. Similarly, a reference to an amino group includes the protonated form (—$N^+HR^1R^2$), a salt or solvate of the amino group, for example, a hydrochloride salt, as well as conventional protected forms of an amino group. Similarly, a reference to a hydroxyl group also includes the anionic form (—O$^-$), a salt or solvate thereof, as well as conventional protected forms.

Salts

It may be convenient or desirable to prepare, purify, and/or handle a corresponding salt of the active compound, for example, a pharmaceutically-acceptable salt. Examples of pharmaceutically acceptable salts are discussed in Berge, et al., *J. Pharm. Sci.*, 66, 1-19 (1977).

For example, if the compound is anionic, or has a functional group which may be anionic (e.g. —COOH may be —COO$^-$), then a salt may be formed with a suitable cation. Examples of suitable inorganic cations include, but are not limited to, alkali metal ions such as Na$^+$ and K+, alkaline earth cations such as Ca$^{2+}$ and Mg$^{2+}$, and other cations such as Al$^{+3}$. Examples of suitable organic cations include, but are not limited to, ammonium ion (i.e. $NH_4^+$) and substituted ammonium ions (e.g. $NH_3R^+$, $NH_2R_2^+$, $NHR_3^+$, $NR_4^+$). Examples of some suitable substituted ammonium ions are those derived from: ethylamine, diethylamine, dicyclohexylamine, triethylamine, butylamine, ethylenediamine, ethanolamine, diethanolamine, piperazine, benzylamine, phenylbenzylamine, choline, meglumine, and tromethamine, as well as amino acids, such as lysine and arginine. An example of a common quaternary ammonium ion is N($CH_3$)$_4^+$.

If the compound is cationic, or has a functional group which may be cationic (e.g. —$NH_2$ may be —$NH_3^+$), then a salt may be formed with a suitable anion. Examples of suitable inorganic anions include, but are not limited to, those derived from the following inorganic acids: hydrochloric, hydrobromic, hydroiodic, sulfuric, sulfurous, nitric, nitrous, phosphoric, and phosphorous.

Examples of suitable organic anions include, but are not limited to, those derived from the following organic acids: 2-acetyoxybenzoic, acetic, ascorbic, aspartic, benzoic, camphorsulfonic, cinnamic, citric, edetic, ethanedisulfonic, ethanesulfonic, fumaric, glucheptonic, gluconic, glutamic, glycolic, hydroxymaleic, hydroxynaphthalene carboxylic, isethionic, lactic, lactobionic, lauric, maleic, malic, methanesulfonic, mucic, oleic, oxalic, palmitic, pamoic, pantothenic, phenylacetic, phenylsulfonic, propionic, pyruvic, salicylic, stearic, succinic, sulfanilic, tartaric, toluenesulfonic, trifluoroacetic acid and valeric. Examples of suitable polymeric organic anions include, but are not limited to, those derived from the following polymeric acids: tannic acid, carboxymethyl cellulose.

Solvates

It may be convenient or desirable to prepare, purify, and/or handle a corresponding solvate of the active compound. The term "solvate" is used herein in the conventional sense to refer to a complex of solute (e.g. active compound, salt of active compound) and solvent. If the solvent is water, the solvate may be conveniently referred to as a hydrate, for example, a mono-hydrate, a di-hydrate, a tri-hydrate, etc.

Isomers

Certain compounds of the invention may exist in one or more particular geometric, optical, enantiomeric, diastereomeric, epimeric, atropic, stereoisomeric, tautomeric, conformational, or anomeric forms, including but not limited to, cis- and trans-forms; E- and Z-forms; c-, t-, and r-forms; endo- and exo-forms; R-, S-, and meso-forms; D- and L-forms; d- and l-forms; (+) and (−) forms; keto-, enol-, and enolate-forms; syn- and anti-forms; synclinal- and anticlinal-forms; α- and β-forms; axial and equatorial forms; boat-, chair-, twist-, envelope-, and halfchair-forms; and combinations thereof, hereinafter collectively referred to as "isomers" (or "isomeric forms").

The term "chiral" refers to molecules which have the property of non-superimposability of the mirror image partner, while the term "achiral" refers to molecules which are superimposable on their mirror image partner.

The term "stereoisomers" refers to compounds which have identical chemical constitution, but differ with regard to the arrangement of the atoms or groups in space.

"Diastereomer" refers to a stereoisomer with two or more centers of chirality and whose molecules are not mirror images of one another. Diastereomers have different physical properties, e.g. melting points, boiling points, spectral properties, and reactivities. Mixtures of diastereomers may separate under high resolution analytical procedures such as electrophoresis and chromatography.

"Enantiomers" refer to two stereoisomers of a compound which are non-superimposable mirror images of one another.

Stereochemical definitions and conventions used herein generally follow S. P. Parker, Ed., *McGraw-Hill Dictionary of Chemical Terms* (1984) McGraw-Hill Book Company, New York; and Eliel, E. and Wilen, S., "Stereochemistry of Organic Compounds", John Wiley & Sons, Inc., New York, 1994. The compounds of the invention may contain asymmetric or chiral centers, and therefore exist in different stereoisomeric forms. It is intended that all stereoisomeric forms of the compounds of the invention, including but not limited to, diastereomers, enantiomers and atropisomers, as well as mixtures thereof such as racemic mixtures, form part of the present invention. Many organic compounds exist in optically active forms, i.e., they have the ability to rotate the plane of plane-polarized light. In describing an optically active compound, the prefixes D and L, or R and S, are used to denote the absolute configuration of the molecule about its chiral center(s). The prefixes d and l or (+) and (−) are employed to designate the sign of rotation of plane-polarized light by the compound, with (−) or l meaning that the compound is levorotatory. A compound prefixed with (+) or d is dextrorotatory. For a given chemical structure, these stereoisomers are identical except that they are mirror images of one another. A specific stereoisomer may also be referred to as an enantiomer, and a mixture of such isomers is often called an enantiomeric mixture. A 50:50 mixture of enantiomers is referred to as a racemic mixture or a racemate, which may occur where there has been no stereoselection or stereospecificity in a chemical reaction or process. The terms "racemic mixture" and "racemate" refer to an equimolar mixture of two enantiomeric species, devoid of optical activity.

Note that, except as discussed below for tautomeric forms, specifically excluded from the term "isomers", as used herein, are structural (or constitutional) isomers (i.e. isomers which differ in the connections between atoms rather than merely by the position of atoms in space). For example, a reference to a methoxy group, —OCH$_3$, is not to be construed as a reference to its structural isomer, a hydroxymethyl group, —CH$_2$OH. Similarly, a reference to ortho-chlorophenyl is not to be construed as a reference to its structural isomer, meta-chlorophenyl. However, a reference to a class of structures may well include structurally isomeric forms falling within that class (e.g. C$_{1-7}$ alkyl includes n-propyl and iso-propyl; butyl includes n-, iso-, sec-, and tert-butyl; methoxyphenyl includes ortho-, meta-, and para-methoxyphenyl).

The above exclusion does not pertain to tautomeric forms, for example, keto-, enol-, and enolate-forms, as in, for example, the following tautomeric pairs: keto/enol (illustrated below), imine/enamine, amide/imino alcohol, amidine/amidine, nitroso/oxime, thioketone/enethiol, N-nitroso/hyroxyazo, and nitro/aci-nitro.

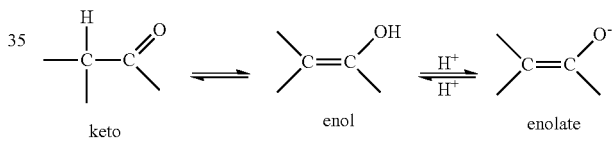

The term "tautomer" or "tautomeric form" refers to structural isomers of different energies which are interconvertible via a low energy barrier. For example, proton tautomers (also known as prototropic tautomers) include interconversions via migration of a proton, such as keto-enol and imine-enamine isomerizations. Valence tautomers include interconversions by reorganization of some of the bonding electrons.

Note that specifically included in the term "isomer" are compounds with one or more isotopic substitutions. For example, H may be in any isotopic form, including $^1$H, $^2$H (D), and $^3$H (T); C may be in any isotopic form, including $^{12}$C, $^{13}$C, and $^{14}$C; O may be in any isotopic form, including $^{16}$O and $^{18}$O; and the like.

Examples of isotopes that can be incorporated into compounds of the invention include isotopes of hydrogen, carbon, nitrogen, oxygen, phosphorous, fluorine, and chlorine, such as, but not limited to $^2$H (deuterium, D), $^3$H (tritium), $^{11}$C, $^{13}$C, $^{14}$C $^{15}$N, $^{18}$F, $^{31}$P, $^{32}$, $^{35}$S, $^{36}$Cl, and $^{125}$I. Various isotopically labeled compounds of the present invention, for example those into which radioactive isotopes such as 3H, 13C, and 14C are incorporated. Such isotopically labelled compounds may be useful in metabolic studies, reaction kinetic studies, detection or imaging techniques, such as positron emission tomography (PET) or single-photon emission computed tomography (SPECT) including drug or substrate tissue distribution assays, or in radioactive treatment of patients. Deuterium labelled or substituted therapeutic compounds of the invention may have improved DMPK (drug metabolism and pharmacokinetics) properties, relating to distribution, metabolism, and excretion (ADME). Substitution with heavier isotopes such as deuterium may afford certain therapeutic advantages resulting from greater metabolic stability, for example increased in vivo half-life or reduced dosage requirements. An 18F labeled compound may be useful for PET or SPECT studies. Isotopically labeled compounds of this invention and prodrugs thereof can generally be prepared by carrying out the procedures disclosed in the schemes or in the examples and preparations described below by substituting a readily available isotopically labeled reagent for a non-isotopically labeled reagent. Further, substitution with heavier isotopes, particularly deuterium (i.e., 2H or D) may afford certain therapeutic advantages resulting from greater metabolic stability, for example increased in vivo half-life or reduced dosage requirements or an improvement in therapeutic index. It is understood that deuterium in this context is regarded as a substituent. The concentration of such a heavier isotope, specifically deuterium, may be defined by an isotopic enrichment factor. In the compounds of this invention any atom not specifically designated as a particular isotope is meant to represent any stable isotope of that atom.

Unless otherwise specified, a reference to a particular compound includes all such isomeric forms, including (wholly or partially) racemic and other mixtures thereof. Methods for the preparation (e.g. asymmetric synthesis) and separation (e.g. fractional crystallisation and chromatographic means) of such isomeric forms are either known in the art or are readily obtained by adapting the methods taught herein, or known methods, in a known manner.

Therapeutic Indications

Compounds disclosed herein may provide a therapeutic benefit in a number of disorders, in particular, in the treatment or prevention of cancers and hemoglobinopathies.

Cancer

Modulators of PRMT5 mediated post-translational arginine methylation of p53 may regulate a pro-apoptotic p53 response, and may therefore be useful as therapeutic agents, for example in the treatment of cancer. Such agents may also be useful as therapeutic agents for the treatment of cancers which exhibit overexpression of PRMT5.

A "cancer" may be any form of cancer. In particular, a cancer can comprise any one or more of the following: leukemia, acute lymphocytic leukemia (ALL), acute myeloid leukemia (AML), chronic lymphocytic leukemia (CLL), chronic myeloid leukemia (CML), non-Hodgkin's lymphoma, Hodgkin's disease, prostate cancer, lung cancer, melanoma, breast cancer, colon and rectal cancer, colon cancer, squamous cell carcinoma and gastric cancer.

Alternatively, the cancer may comprise adrenocortical cancer, anal cancer, bladder cancer, blood cancer, bone cancer, brain tumor, cancer of the female genital system, cancer of the male genital system, central nervous system lymphoma, cervical cancer, childhood rhabdomyosarcoma, childhood sarcoma, endometrial cancer, endometrial sarcoma, esophageal cancer, eye cancer, gallbladder cancer, gastrointestinal tract cancer, hairy cell leukemia, head and neck cancer, hepatocellular cancer, hypopharyngeal cancer, Kaposi's sarcoma, kidney cancer, laryngeal cancer, liver cancer, malignant fibrous histiocytoma, malignant thymoma, mesothelioma, multiple myeloma, myeloma, nasal cavity and paranasal sinus cancer, nasopharyngeal cancer, nervous system cancer, neuroblastoma, oral cavity cancer, oropharyngeal cancer, osteosarcoma, ovarian cancer, pancreatic cancer, parathyroid cancer, penile cancer, pharyngeal cancer, pituitary tumor, plasma cell neoplasm, primary CNS lymphoma, rectal cancer, respiratory system, retinoblastoma, salivary gland cancer, skin cancer, small intestine cancer, soft tissue sarcoma, stomach cancer, stomach cancer, testicular cancer, thyroid cancer, urinary system cancer, uterine sarcoma, vaginal cancer, vascular system, Waldenstrom's macroglobulinemia and/or Wilms' tumor. Cancers may be of a particular type. Examples of types of cancer include lymphoma, melanoma, carcinoma (e.g. adenocarcinoma, hepatocellular carcinoma, medullary carcinoma, papillary carcinoma, squamous cell carcinoma), astrocytoma, glioma, medulloblastoma, myeloma, meningioma, neuroblastoma, sarcoma (e.g. angiosarcoma, chrondrosarcoma, osteosarcoma).

The cancer may be a PRMT5 overexpressing cancer. The cancer may over express PRMT5 protein relative to non-cancerous tissue. In some cases, the cancer overproduces PRMT5 mRNA relative to non-cancerous tissue.

Alternatively or additionally, the cancer may be a p53 overexpressing cancer. The cell may overexpress p53 protein relative to non-cancerous tissue. It may overproduce p53 mRNA as compared to non-cancerous tissue. In some cases, the level of p53 protein and/or mRNA in the cell is at a level approximately equivalent to that of a non-cancerous cell.

The agents described herein may be useful in combination with other anti-cancer therapies. They may act synergistically with chemo- or radiotherapy, and/or with p53 targeted drugs.

An inhibitor of PRMT5 would in all likelihood augment the effects of drugs (such as the nutlins) that restore p53. Inhibition of PRMT5, resulting in decreased arginine-methylated p53, may sensitize tumour cells to chemo- and radiotherapy by switching, or at least biasing, the cellular outcome to apoptosis.

Combination Therapies p53 is activated by DNA damage. PRMT5 is part of the complex of proteins that activate and modulate p53 activity in response to DNA damage. It is likely that inhibition of PRMT5, resulting in decreased arginine-methylated p53, would sensitize tumour cells to chemo- and radiotherapy by switching or at least biasing the cellular outcome to apoptosis. PRMT5 inhibition is likely to synergize well with low dose chemo- or radiotherapy, by stabilizing p53, and biasing the cellular outcome to apoptosis.

Biasing the p53 response towards apoptosis would in all likelihood be of benefit, and an agent that so biases the response would be expected to augment the effect of a p53 resurrecting drug. Thus, in some cases, a PRMT5 modulator disclosed herein may be administered in conjunction with a radiotherapeutic or chemotherapeutic regime. It may be administered in conjunction with a drug that resurrects cellular p53 activity, for example, a p53 agonist. The PRMT5 modulator may be administered simultaneously or sequentially with radio and/or chemotherapy. Suitable chemotherapeutic agents and radiotherapy protocols will be readily appreciable to the skilled person. In particular, the compound described herein may be combined with low dose chemo or radio therapy. Appropriate dosages for "low dose" chemo or radio therapy will be readily appreciable to the skilled practitioner.

Hemoglobinopathies

The compounds disclosed herein may be useful in the treatment or prevention of conditions that may benefit from the increased expression of γ-globin genes, for example, due to the release of repressive methylation of these genes. The compounds disclosed herein may be useful in the treatment or prevention of hemoglobinopathies. A hemaglobinopathy is a condition associated with the presence of abnormal haemoglobin in the blood of a subject. Such conditions include β-thalassemia and Sickle Cell Disease, α-thalassemia and α-thalassemia.

Hemoglobinopathies treatable by the compounds disclosed herein may be ameliorated by the re-activation of the subjects γ-globin genes (γ genes). In such cases, the subject is not a fetal mammal.

Methods of Treatment

The compounds of the present invention may be used in a method of therapy. Also provided is a method of treatment, comprising administering to a subject in need of treatment a therapeutically-effective amount of a compound of the invention. The term "therapeutically effective amount" is an amount sufficient to show benefit to a patient. Such benefit may be at least amelioration of at least one symptom. The actual amount administered, and rate and time-course of administration, will depend on the nature and severity of what is being treated. Prescription of treatment, e.g. decisions on dosage, is within the responsibility of general practitioners and other medical doctors.

As described above, the anti cancer treatment defined herein may be applied as a sole therapy or may involve, in addition to the compound of the invention, conventional surgery or radiotherapy or chemotherapy. Such chemotherapy may include one or more of the following categories of anti-tumour agents:—

(i) other antiproliferative/antineoplastic drugs and combinations thereof, as used in medical oncology, such as alkylating agents (for example cisplatin, oxaliplatin, carboplatin, cyclophosphamide, nitrogen mustard, melphalan, chlorambucil, busulphan, temozolamide and nitrosoureas); antimetabolites (for example gemcitabine and antifolates such as fluoropyrimidines like 5 fluorouracil and tegafur, raltitrexed, methotrexate, cytosine arabinoside, and hydroxyurea); antitumour antibiotics (for example anthracyclines like adriamycin, bleomycin, doxorubicin, daunomycin, epirubicin, idarubicin, mitomycin-C, dactinomycin and mithramycin); antimitotic agents (for example *vinca* alkaloids like vincristine, vinblastine, vindesine and vinorelbine and taxoids like taxol and docetaxel (Taxotere) and polokinase inhibitors); and topoisomerase inhibitors (for example epipodophyllotoxins like etoposide and teniposide, amsacrine, topotecan and camptothecin);

(ii) cytostatic agents such as antioestrogens (for example tamoxifen, fulvestrant, toremifene, raloxifene, droloxifene and iodoxyfene), antiandrogens (for example bicalutamide, flutamide, nilutamide and cyproterone acetate), LHRH antagonists or LHRH agonists (for example goserelin, leuprorelin and buserelin), progestogens (for example megestrol acetate), aromatase inhibitors (for example as anastrozole, letrozole, vorazole and exemestane) and inhibitors of 5*-reductase such as finasteride;

(iii) anti-invasion agents (for example c-Src kinase family inhibitors like 4-(6-chloro-2,3-methylenedioxyanilino)-7-[2-(4-methylpiperazin-1-yl)ethoxy]-5-tetrahydropyran-4-yloxyquinazoline (AZD0530; International Patent Application WO 01/94341), N-(2-chloro-6-methylphenyl)-2-{6-[4-(2-hydroxyethyl)piperazin-1-yl]-2-methylpyrimidin-4-ylamino}thiazole-5-carboxamide (dasatinib, BMS-354825; J. Med. Chem., 2004, 47, 6658-6661 and and 4-((2,4-dichloro-5-methoxyphenyl)amino)-6-methoxy-7-(3-(4-methylpiperazin-1-yl)propoxy)quinoline-3-carbonitrile (bosutinib, SKI-606; Cancer research (2003), 63(2), 375-81), and metalloproteinase inhibitors like marimastat, inhibitors of urokinase plasminogen activator receptor function or antibodies to Heparanase);

(iv) inhibitors of growth factor function: for example such inhibitors include growth factor antibodies and growth factor receptor antibodies (for example the anti erbB2 antibody trastuzumab [HerceptinT], the anti-EGFR antibody panitumumab, the anti erbB1 antibody cetuximab [Erbitux, C225] and any growth factor or growth factor receptor antibodies disclosed by Stern et al. Critical reviews in oncology/haematology, 2005, Vol. 54, pp 11-29); such inhibitors also include tyrosine kinase inhibitors, for example inhibitors of the epidermal growth factor family (for example EGFR family tyrosine kinase inhibitors such as N-(3-chloro-4-fluorophenyl)-7-methoxy-6-(3-morpholinopropoxy)quinazolin-4-amine (gefitinib, ZD1839), N-(3-ethynylphenyl)-6,7-bis(2-methoxyethoxy)quinazolin-4-amine (erlotinib, OSI 774) and 6-acrylamido-N-(3-chloro-4-fluorophenyl)-7-(3-morpholinopropoxy)-quinazolin-4-amine (CI 1033), erbB2 tyrosine kinase inhibitors such as lapatinib, inhibitors of the hepatocyte growth factor family, inhibitors of the platelet-derived growth factor family such as imatinib, inhibitors of serine/threonine kinases (for example Ras/Raf signalling inhibitors such as farnesyl transferase inhibitors, for example sorafenib (BAY 43-9006)), inhibitors of cell signalling through MEK and/or AKT kinases, inhibitors of the hepatocyte growth factor family, c-kit inhibitors, abl kinase inhibitors, IGF receptor (insulin-like growth factor) kinase inhibitors; aurora kinase inhibitors (for example AZD1152, PH739358, VX-680, MLN8054, R763, MP235, MP529, VX-528 AND AX39459) and cyclin dependent kinase inhibitors such as CDK2 and/or CDK4 inhibitors;

(v) antiangiogenic and antilymphangiogenic agents such as those which inhibit the effects of vascular endothelial growth factor, [for example the anti vascular endothelial cell growth factor A (VEGFA) antibody bevacizumab (AvastinT), the anti vascular endothelial cell growth factor A (VEGFA) antibody ranibizumab, the anti-VEGF aptamer pegaptanib, the anti vascular endothelial growth factor receptor 3 (VEGFR3) antibody IMC-3C$_5$, the anti vascular endothelial cell growth factor C (VEGFC) antibody VGX-100, the anti vascular endothelial cell growth factor D (VEGFD) antibody VGX-200, the soluble form of the vascular endothelial growth factor receptor 3 (VEGFR3) VGX-300 and VEGF receptor tyrosine kinase inhibitors such as 4-(4-bromo-2-fluoroanilino)-6-methoxy-7-(1-methylpiperidin-4-ylmethoxy)quinazoline (vandetanib; ZD6474; Example 2 within WO 01/32651), 4-(4-fluoro-2-methylindol-5-yloxy)-6-methoxy-7-(3-pyrrolidin-1-ylpropoxy)quinazoline (cediranib; AZD2171; Example 240 within WO 00/47212), vatalanib (PTK787; WO 98/35985), pazopanib (GW786034), axitinib (AG013736), sorafenib and sunitinib (SU11248; WO 01/60814), compounds such as those disclosed in International Patent Applications WO97/22596, WO 97/30035, WO 97/32856 and WO 98/13354 and compounds that work by other mechanisms (for example linomide, inhibitors of integrin avb3 function and angiostatin)];

(vi) vascular damaging agents such as Combretastatin A4 and compounds disclosed in International Patent Applications WO 99/02166, WO 00/40529, WO 00/41669, WO 01/92224, WO 02/04434 and WO 02/08213;

(vii) antisense therapies, for example those which are directed to the targets listed above, such as ISIS 2503, an anti-ras antisense;

(viii) gene therapy approaches, including for example approaches to replace aberrant genes such as aberrant p53 or aberrant BRCA1 or BRCA2, GDEPT (gene directed enzyme pro drug therapy) approaches such as those using cytosine deaminase, thymidine kinase or a bacterial nitroreductase enzyme and approaches to increase patient tolerance to chemotherapy or radiotherapy such as multi drug resistance gene therapy; and (ix) immunotherapy approaches, including for example ex vivo and in vivo approaches to increase the immunogenicity of patient tumour cells, such as transfection with cytokines such as interleukin 2, interleukin 4 or granulocyte macrophage colony stimulating factor, approaches to decrease T cell energy, approaches using transfected immune cells such as cytokine transfected dendritic cells, approaches using cytokine transfected tumour cell lines and approaches using anti idiotypic antibodies Administration The active compound or pharmaceutical composition comprising the active compound may be administered to a subject by any convenient route of administration, whether systemically/peripherally or at the site of desired action, including but not limited to, oral (e.g. by ingestion); topical (including e.g. transdermal, intranasal, ocular, buccal, and sublingual); pulmonary (e.g. by inhalation or insufflation therapy using, e.g. an aerosol, e.g. through mouth or nose); rectal; vaginal; parenteral, for example, by injection, including subcutaneous, intradermal, intramuscular, intravenous, intraarterial, intracardiac, intrathecal, intraspinal, intracapsular, subcapsular, intraorbital, intraperitoneal, intratracheal, subcuticular, intraarticular, subarachnoid, intravitreal and intrasternal; by implant of a depot, for example, subcutaneously, intravitreal or intramuscularly. The subject may be a eukaryote, an animal, a vertebrate animal, a mammal, a rodent (e.g. a guinea pig, a hamster, a rat, a mouse), murine (e.g. a mouse), canine (e.g. a dog), feline (e.g. a cat), equine (e.g. a horse), a primate, simian (e.g. a monkey or ape), a monkey (e.g. marmoset, baboon), an ape (e.g. gorilla, chimpanzee, orangutan, gibbon), or a human.

Formulations

While it is possible for the active compound to be administered alone, it is preferable to present it as a pharmaceutical composition (e.g. formulation) comprising at least one active compound, as defined above, together with one or more pharmaceutically acceptable carriers, adjuvants, excipients, diluents, fillers, buffers, stabilisers, preservatives, lubricants, or other materials well known to those skilled in the art and optionally other therapeutic or prophylactic agents.

Thus, the present invention further provides pharmaceutical compositions, as defined above, and methods of making a pharmaceutical composition comprising admixing at least one active compound, as defined above, together with one or more pharmaceutically acceptable carriers, excipients, buffers, adjuvants, stabilisers, or other materials, as described herein.

The term "pharmaceutically acceptable" as used herein pertains to compounds, materials, compositions, and/or dosage forms which are, within the scope of sound medical judgement, suitable for use in contact with the tissues of a subject (e.g. human) without excessive toxicity, irritation, allergic response, or other problem or complication, commensurate with a reasonable benefit/risk ratio. Each carrier, excipient, etc. must also be "acceptable" in the sense of being compatible with the other ingredients of the formulation.

Suitable carriers, excipients, etc. can be found in standard pharmaceutical texts, for example, *Remington's Pharmaceutical Sciences*, 18th edition, Mack Publishing Company, Easton, Pa., 1990.

The formulations may conveniently be presented in unit dosage form and may be prepared by any methods well known in the art of pharmacy. Such methods include the step of bringing into association the active compound with the carrier which constitutes one or more accessory ingredients. In general, the formulations are prepared by uniformly and intimately bringing into association the active compound with liquid carriers or finely divided solid carriers or both, and then if necessary shaping the product.

Formulations may be in the form of liquids, solutions, suspensions, emulsions, elixirs, syrups, tablets, losenges, granules, powders, capsules, cachets, pills, ampoules, suppositories, pessaries, ointments, gels, pastes, creams, sprays, mists, foams, lotions, oils, boluses, electuaries, or aerosols.

Formulations suitable for oral administration (e.g. by ingestion) may be presented as discrete units such as capsules, cachets or tablets, each containing a predetermined amount of the active compound; as a powder or granules; as a solution or suspension in an aqueous or non-aqueous liquid; or as an oil-in-water liquid emulsion or a water-in-oil liquid emulsion; as a bolus; as an electuary; or as a paste.

A tablet may be made by conventional means, e.g., compression or moulding, optionally with one or more accessory ingredients. Compressed tablets may be prepared by compressing in a suitable machine the active compound in a free-flowing form such as a powder or granules, optionally mixed with one or more binders (e.g. povidone, gelatin, acacia, sorbitol, tragacanth, hydroxypropylmethyl cellulose); fillers or diluents (e.g. lactose, microcrystalline cellulose, calcium hydrogen phosphate); lubricants (e.g. magnesium stearate, talc, silica); disintegrants (e.g. sodium starch glycolate, cross-linked povidone, cross-linked sodium carboxymethyl cellulose); surface-active or dispersing or wetting agents (e.g. sodium lauryl sulfate); and preservatives (e.g. methyl p-hydroxybenzoate, propyl p-hydroxybenzoate, sorbic acid). Moulded tablets may be made by moulding in a suitable machine a mixture of the powdered compound moistened with an inert liquid diluent. The tablets may optionally be coated or scored and may be formulated so as to provide slow or controlled release of the active compound therein using, for example, hydroxypropylmethyl cellulose in varying proportions to provide the desired release profile. Tablets may optionally be provided with an enteric coating, to provide release in parts of the gut other than the stomach.

Formulations suitable for topical administration (e.g. transdermal, intranasal, ocular, buccal, and sublingual) may be formulated as an ointment, cream, suspension, lotion, powder, solution, past, gel, spray, aerosol, or oil. Alternatively, a formulation may comprise a patch or a dressing such as a bandage or adhesive plaster impregnated with active compounds and optionally one or more excipients or diluents.

Formulations suitable for topical administration in the mouth include losenges comprising the active compound in a flavoured basis, usually sucrose and acacia or tragacanth; pastilles comprising the active compound in an inert basis such as gelatin and glycerin, or sucrose and acacia; and mouthwashes comprising the active compound in a suitable liquid carrier.

Formulations suitable for topical administration to the eye also include eye drops wherein the active compound is dissolved or suspended in a suitable carrier, especially an aqueous solvent for the active compound.

Formulations suitable for nasal administration, wherein the carrier is a solid, include a coarse powder having a particle size, for example, in the range of about 20 to about 500 microns which is administered in the manner in which snuff is taken, i.e. by rapid inhalation through the nasal passage from a container of the powder held close up to the nose. Suitable formulations wherein the carrier is a liquid for administration as, for example, nasal spray, nasal drops, or by aerosol administration by nebuliser, include aqueous or oily solutions of the active compound.

Formulations suitable for administration by inhalation include those presented as an aerosol spray from a pressurised pack, with the use of a suitable propellant, such as dichlorodifluoromethane, trichlorofluoromethane, dichorotetrafluoroethane, carbon dioxide, or other suitable gases.

Formulations suitable for topical administration via the skin include ointments, creams, and emulsions. When formulated in an ointment, the active compound may optionally be employed with either a paraffinic or a water-miscible ointment base. Alternatively, the active compounds may be formulated in a cream with an oil-in-water cream base. If desired, the aqueous phase of the cream base may include, for example, at least about 30% w/w of a polyhydric alcohol, i.e., an alcohol having two or more hydroxyl groups such as propylene glycol, butane-1,3-diol, mannitol, sorbitol, glycerol and polyethylene glycol and mixtures thereof. The topical formulations may desirably include a compound which enhances absorption or penetration of the active compound through the skin or other affected areas. Examples of such dermal penetration enhancers include dimethylsulfoxide and related analogues.

When formulated as a topical emulsion, the oily phase may optionally comprise merely an emulsifier (otherwise known as an emulgent), or it may comprises a mixture of at least one emulsifier with a fat or an oil or with both a fat and an oil. Preferably, a hydrophilic emulsifier is included together with a lipophilic emulsifier which acts as a stabiliser. It is also preferred to include both an oil and a fat. Together, the emulsifier(s) with or without stabiliser(s) make up the so-called emulsifying wax, and the wax together with the oil and/or fat make up the so-called emulsifying ointment base which forms the oily dispersed phase of the cream formulations.

Suitable emulgents and emulsion stabilisers include Tween 60, Span 80, cetostearyl alcohol, myristyl alcohol, glyceryl monostearate and sodium lauryl sulphate. The choice of suitable oils or fats for the formulation is based on achieving the desired cosmetic properties, since the solubility of the active compound in most oils likely to be used in pharmaceutical emulsion formulations may be very low. Thus the cream should preferably be a non-greasy, non-staining and washable product with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters known as Crodamol CAP may be used, the last three being preferred esters. These may be used alone or in combination depending on the properties required.

Alternatively, high melting point lipids such as white soft paraffin and/or liquid paraffin or other mineral oils can be used.

Formulations suitable for rectal administration may be presented as a suppository with a suitable base comprising, for example, cocoa butter or a salicylate.

Formulations suitable for vaginal administration may be presented as pessaries, tampons, creams, gels, pastes, foams or spray formulations containing in addition to the active compound, such carriers as are known in the art to be appropriate.

Formulations suitable for parenteral administration (e.g. by injection, including cutaneous, subcutaneous, intramuscular, intravenous and intradermal), include aqueous and non-aqueous isotonic, pyrogen-free, sterile injection solutions which may contain anti-oxidants, buffers, preservatives, stabilisers, bacteriostats, and solutes which render the formulation isotonic with the blood of the intended recipient; and aqueous and non-aqueous sterile suspensions which may include suspending agents and thickening agents, and liposomes or other microparticulate systems which are designed to target the compound to blood components or one or more organs. Examples of suitable isotonic vehicles for use in such formulations include Sodium Chloride Injection, Ringer's Solution, or Lactated Ringer's Injection. Typically, the concentration of the active compound in the solution is from about 1 ng/mL to about 10 µg/mL, for example from about 10 ng/ml to about 1 µg/mL. The formulations may be presented in unit-dose or multi-dose sealed containers, for example, ampoules and vials, and may be stored in a freeze-dried (lyophilised) condition requiring only the addition of the sterile liquid carrier, for example water for injections, immediately prior to use. Extemporaneous injection solutions and suspensions may be prepared from sterile powders, granules, and tablets. Formulations may be in the form of liposomes or other microparticulate systems which are designed to target the active compound to blood components or one or more organs.

Dosage

It will be appreciated by one of skill in the art that appropriate dosages of the compound, and compositions comprising the compound, can vary from patient to patient. Determining the optimal dosage will generally involve the balancing of the level of therapeutic benefit against any risk or deleterious side effects. The selected dosage level will depend on a variety of factors including, but not limited to, the activity of the particular compound, the route of administration, the time of administration, the rate of excretion of the compound, the duration of the treatment, other drugs, compounds, and/or materials used in combination, the severity of the condition, and the species, sex, age, weight, condition, general health, and prior medical history of the patient. The amount of compound and route of administration will ultimately be at the discretion of the physician, veterinarian, or clinician, although generally the dosage will be selected to achieve local concentrations at the site of action which achieve the desired effect without causing substantial harmful or deleterious side-effects.

Administration can be effected in one dose, continuously or intermittently (e.g., in divided doses at appropriate intervals) throughout the course of treatment. Methods of determining the most effective means and dosage of administration are well known to those of skill in the art and will vary with the formulation used for therapy, the purpose of the therapy, the target cell(s) being treated, and the subject being treated. Single or multiple administrations can be carried out with the dose level and pattern being selected by the treating physician, veterinarian, or clinician.

In general, a suitable dose of the active compound is in the range of about 100 ng to about 25 mg (more typically about 1 µg to about 10 mg) per kilogram body weight of the subject per day. Where the active compound is a salt, an ester, an amide, a prodrug, or the like, the amount administered is calculated on the basis of the parent compound and so the actual weight to be used is increased proportionately.

In one embodiment, the active compound is administered to a human patient according to the following dosage regime: about 100 mg, 3 times daily.

In one embodiment, the active compound is administered to a human patient according to the following dosage regime: about 150 mg, 2 times daily.

In one embodiment, the active compound is administered to a human patient according to the following dosage regime: about 200 mg, 2 times daily.

However in one embodiment, the active compound is administered to a human patient according to the following dosage regime: about 50 or about 75 mg, 3 or 4 times daily.

In one embodiment, the active compound is administered to a human patient according to the following dosage regime: about 100 or about 125 mg, 2 times daily.

Treatment

The term "treatment," as used herein in the context of treating a condition, pertains generally to treatment and therapy, whether of a human or an animal (e.g., in veterinary applications), in which some desired therapeutic effect is achieved, for example, the inhibition of the progress of the condition, and includes a reduction in the rate of progress, a halt in the rate of progress, regression of the condition, amelioration of the condition, and cure of the condition. Treatment as a prophylactic measure (i.e., prophylaxis, prevention) is also included.

The term "therapeutically-effective amount," as used herein, pertains to that amount of an active compound, or a material, composition or dosage from comprising an active compound, which is effective for producing some desired therapeutic effect, commensurate with a reasonable benefit/risk ratio, when administered in accordance with a desired treatment regimen.

Similarly, the term "prophylactically-effective amount," as used herein, pertains to that amount of an active compound, or a material, composition or dosage from comprising an active compound, which is effective for producing some desired prophylactic effect, commensurate with a reasonable benefit/risk ratio, when administered in accordance with a desired treatment regimen.

The Subject/Patient

The subject/patient may be an animal, mammal, a placental mammal, a marsupial (e.g., kangaroo, wombat), a monotreme (e.g., duckbilled platypus), a rodent (e.g., a guinea pig, a hamster, a rat, a mouse), murine (e.g., a mouse), a lagomorph (e.g., a rabbit), avian (e.g., a bird), canine (e.g., a dog), feline (e.g., a cat), equine (e.g., a horse), porcine (e.g., a pig), ovine (e.g., a sheep), bovine (e.g., a cow), a primate, simian (e.g., a monkey or ape), a monkey (e.g., marmoset, baboon), an ape (e.g., gorilla, chimpanzee, orangutan, gibbon), or a human.

Furthermore, the subject/patient may be any of its forms of development, for example, a foetus. In one preferred embodiment, the subject/patient is a human.

General Synthesis Methods

The compounds of the invention can be prepared employing the following general methods and using procedures described in detail in the examples. The reaction conditions referred to are illustrative and non-limiting.

Compounds of formula I, as described above, can be prepared by synthetic strategies outlined below, wherein the definitions above apply.

In the following discussion, the terms A-, B- and C-ring are used, and are defined as:

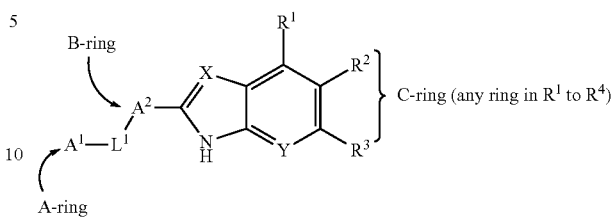

Scheme A

This scheme illustrates how to form the imidazole ring at the centre of compounds of the present invention. The ring may be prepared by coupling a commercial or synthetic (hetero)aryl diamine (as prepared in Scheme F) with a commercial or synthetic (hetero)aryl carboxylic acid to prepare an amide with either amine group in the (hetero)aryl diamine, or a mixture of amides formed with either amine group in the (hetero)aryl diamine. Methods to form such amides will be apparent to those skilled in the art, but include for example the use of reagents such as polyphosphoric acid, coupling agents such as HATU and EDCI, and the use of activated forms of the (hetero)aryl carboxylic acid such as the corresponding acyl halide or N-hydroxysuccinimide ester.

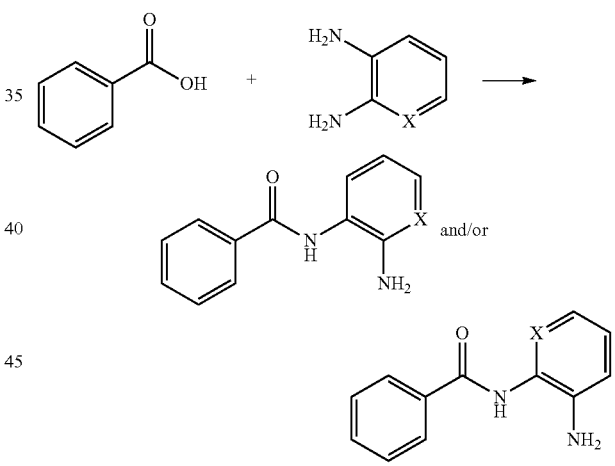

The amide or mixture of amides may be further treated to form the imidazole ring. Formation of the imidazole ring may be achieved with the same conditions used for the production of the amide, or by the use of additional reagents to promote ring formation. Reagents suitable for forming an imidazole ring will be apparent to those skilled in the art, but include for example the use of acids such as acetic acid and polyphosphoric acid.

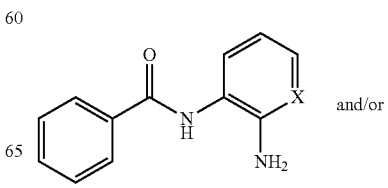

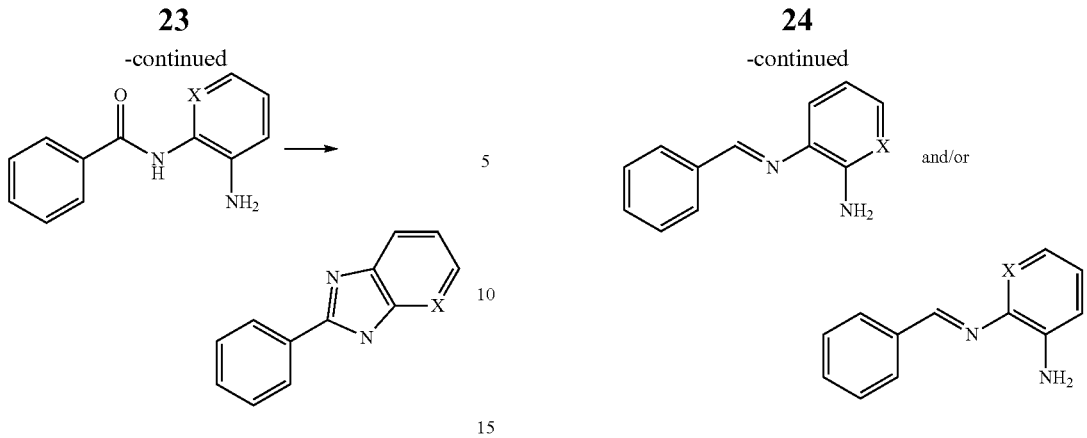

An example of a commercially available (hetero)aryl carboxylic acid which is useful for preparing compounds of the invention is

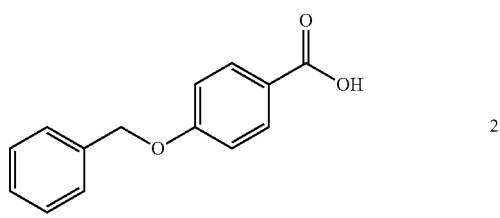

An example of a commercially available (hetero)aryl diamine which is useful for preparing compounds such as of the invention is

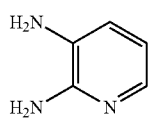

Compounds with additional functional groups sensitive to the reagents or conditions required for Scheme A may be prepared with Scheme B or C.

Scheme B

This scheme illustrates an alternative route to forming the imidazole ring at the centre of compounds of the present invention. The ring may be prepared by reacting a commercial or synthetic (hetero)aryl diamine (as prepared in Scheme F) with a commercial or synthetic (hetero)aryl aldehyde to form an intermediate imine with either amine group of the (hetero)aryl diamine or a mixture of such imines. Conditions to form an imine will be apparent to those skilled in the art, but may include the use of additional reagents to promote the reaction. The reagents may be acidic, such as for example acetic acid, or may be basic, such as for example sodium acetate. These conditions may include the removal of water from the reaction, by for example distillation or trapping of the water with chemical reagents such as for example molecular sieves.

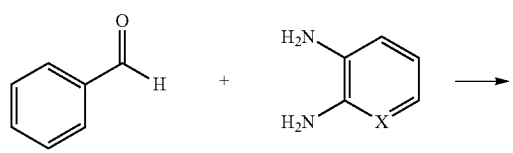

The formed imine may be present as an alternative functional group in equilibrium with the imine, such as for example an imidazoline. The imine may be wholly or partly present as for example an imidazoline depending on reaction conditions and the substituents of the (hetero)aryl aldehyde and (hetero)aryl diamine.

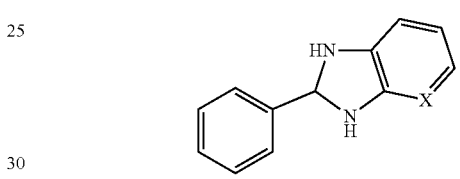

The imine, mixture of imines or imine equivalent may be further treated with an oxidant to produce the imidazole ring. Oxidation may occur in a separate operation to formation of the imine, mixture of imines or imine equivalent, or it may occur in the same operation. Suitable oxidants include for example transition metal compounds such as for example iron(III) chloride, organic oxidants such as for example (diacetoxyiodo)benzene or elemental oxidants such as for example oxygen. Suitable oxidants may include atmospheric oxygen present in air.

An example of a commercially available (hetero)aryl aldehyde which is useful for preparing compounds of the present invention is

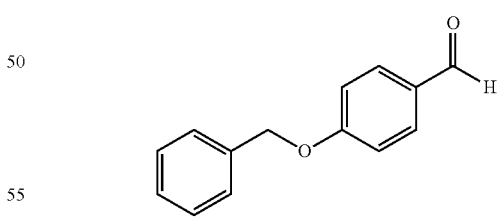

Scheme C

This scheme illustrates a further alternative route to forming the imidazole ring at the centre of compounds of the present invention. The ring may be prepared by reacting a commercial or synthetic (hetero)aryl nitro amino compound (as prepared in Schemes D and E) with a commercial or synthetic (hetero)aryl aldehyde in the presence of a reducing agent. Suitable reducing agents include for example sodium dithionite.

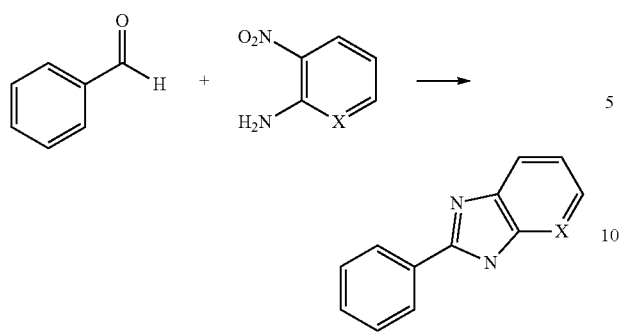

Scheme D (Hetero)aryl nitro amino compounds of use in for example Scheme C may be prepared for example by reaction of commercial or synthetic (hetero)aryl halide compounds with commercial or synthetic nucleophiles. Suitable compounds may include (hetero)aryl fluorides, (hetero)aryl chlorides, (hetero)aryl bromides and (hetero)aryl iodides. Suitable nucleophiles include for example compounds containing suitable carbon, oxygen, sulphur or nitrogen atoms. The substitution may require the use of additional reagents in some cases. Suitable additional reagents will be known to those skilled in the art, and include for example compounds of copper or palladium.

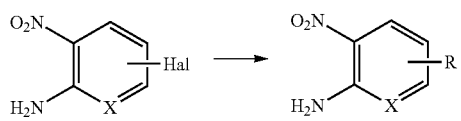

Scheme E (Hetero)aryl nitro amino compounds of use in for example Scheme C may also be prepared for example by reaction of commercial or synthetic (hetero)aryl halide compounds with compounds of tin, zinc or boron in the presence of suitable reagents. Suitable compounds of tin, zinc or boron may contain (hetero)aryl, (hetero)alkenyl or (hetero)alkyl groups. Suitable halide compounds may include (hetero)aryl chlorides, (hetero)aryl bromides and (hetero)aryl iodides. Suitable reagents may include transition metal catalysts, and include for example compounds of palladium.

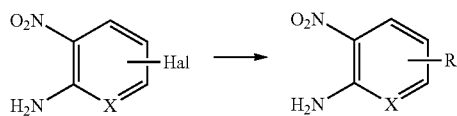

R represents any one or more of $R^1$ to $R^4$

Scheme F (Hetero)aryl diamine compounds of use in for example Scheme A and Scheme B may be prepared by reduction of (hetero)aryl nitro amino compounds prepared in Schemes D and E. Reduction is not limited to reduction of the (hetero)aryl nitro group to a (hetero)aryl amine group, and may include other groups within the (hetero)aryl nitro amino compound as desired. Methods for reduction will be apparent to those skilled in the art. Reduction may be achieved with catalytic hydrogenation utilising for example palladium on carbon, platinum or compounds of platinum. Reduction may be achieved with non-catalytic reagents, such as for example transition metals in the presence of a source of hydrogen atoms. Suitable metals include for example zinc, iron and indium, in the presence of for example ammonium chloride.

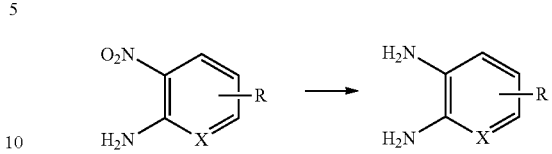

R represents $R^1$ to $R^4$

Compounds of Formula I may also be prepared by functionalization of an imidazopyridine, as described in Schemes G, H and I.

Scheme G

Compounds varying at for example the C-ring may be prepared by reaction of a suitably substituted B-ring with an electrophile. Suitable B-ring substitutions will be apparent to those skilled in the art, and include for example phenol and amine groups. Suitable electrophiles will be apparent to one skilled in the art, and include for example alkyl chlorides, bromides, iodides and sulfonates. Alternatively, alkylation may be achieved by alcohols activated by treatment with for example an azocarboxylate and a phosphine. Alkylation may be controlled where necessary by the use of protecting groups. Suitable protecting groups will be known to those skilled in the art (for example *Greene's Protective Groups in Organic Synthesis, 4th Edition*) and include for example SEM (2-(trimethylsilyl)ethoxymethyl) and Boc (tert-butyl carbamate) groups.

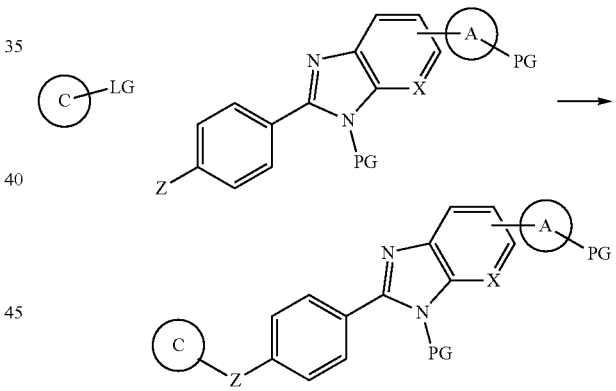

Scheme H

Compounds varying at for example the A-ring may be prepared by reaction of a suitably halogenated imidazopyridine with a coupling partner containing the A-ring. Suitable halogenated imidazopyridines include fluoride, chloride, bromide and iodide substituted imidazopyridines. A variety of reactions may be used to introduce the A-ring, such as for example transition metal catalysed coupling reactions of for example boron, tin and zinc compounds. Substitution of the halogen by suitable nucleophiles in the presence or absence of other reagents such as for example transition metal compounds is also suitable. Reaction may be controlled where necessary by the use of protecting groups. Suitable protecting groups will be known to those skilled in the art (for example *Greene's Protective Groups in Organic Synthesis, 4th Edition*), and include for example SEM (2-(trimethylsilyl)ethoxymethyl) and Boc (tert-butyl carbamate) groups.

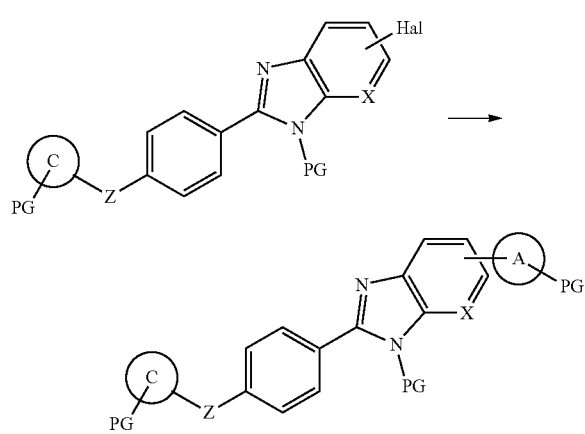

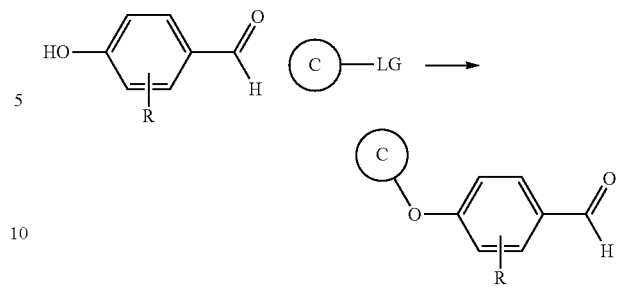

Scheme K

Additional carboxylic acids or aldehydes to those represented in Schemes A, B, C and J may also be used in these cyclisation steps. As indicated below these may be commercially available or synthesised using a range of synthetic techniques known to one skilled in the art (for example March's Advanced Organic Chemistry: Reactions, Mechanisms, and Structure, 7th Edition).

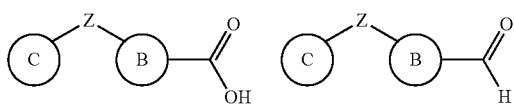

Examples of commercially available aldehydes are shown below but not limited to

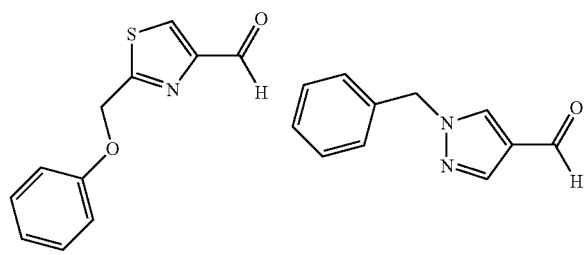

Scheme I

Compounds may be prepared by modification of the A, B or C ring by reaction of a suitable substituent with a suitable reaction partner. Suitable substituents will be known to those skilled in the art, but include for example amine, alcohol, thiol, thioether, ester, amide, carbamate, halogen and sulfonate groups. Suitable reactions vary depending on the substituent, but include for example alkylation, amide formation, ester formation, carbamate formation, urea formation, transition metal catalysed coupling reactions, oxidation, reduction, ester hydrolysis, amide hydrolysis, and carbamate cleavage. Reaction may be controlled where necessary by the use of protecting groups. Suitable protecting groups will be known to those skilled in the art (for example *Greene's Protective Groups in Organic Synthesis, 4th Edition*) and include for example SEM (2-(trimethylsilyl)ethoxymethyl) and Boc (tert-butyl carbamate) groups.

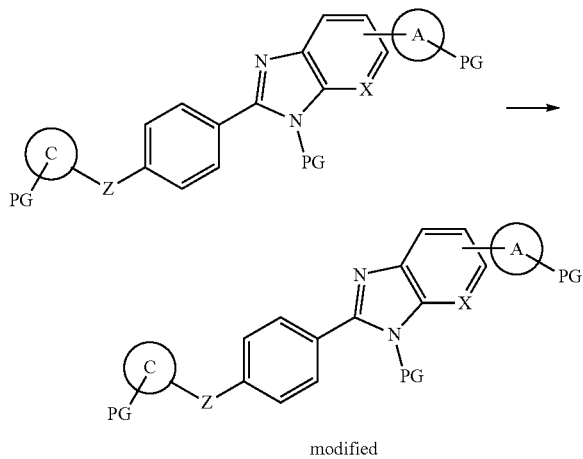

modified

Scheme J (Hetero)aryl aldehydes of use in for example Scheme C may be prepared by reaction of commercially available or synthesised phenols with an electrophile and a suitable base in a suitable solvent. Suitable electrophiles will be apparent to one skilled in the art, and may include but not limited to alkyl chlorides, bromides, iodides and sulfonates as examples.

Scheme L

A compound with a suitably functionalised B-ring, e.g. halogen or triflate may be derivatised using a range of organometallic reagents, e.g. derived from tin, zinc, aluminium, magnesium, or boron which may contain (hetero)aryl, (hetero)alkenyl or (hetero)alkyl groups in the presence of a suitable transition metal catalyst, e.g. derived from palladium, copper or iron. Suitable halogen-containing compounds may include (hetero)aryl chlorides, (hetero)aryl bromides and (hetero)aryl iodides. Other methods for the coupling to the B-ring may be used by one skilled in the art (for example *March's Advanced Organic Chemistry: Reactions, Mechanisms, and Structure, 7th Edition*).

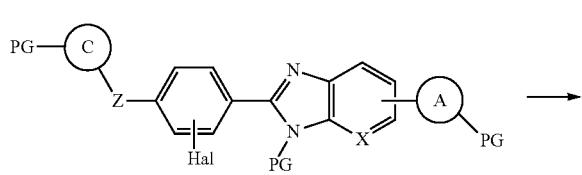

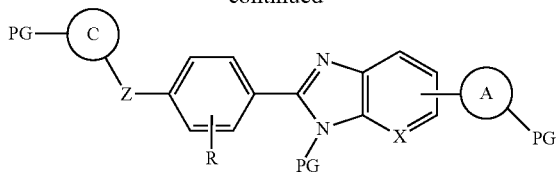

Further Embodiments

X and Y

In some embodiments, X and Y are N and N respectively.

In some embodiments, X and Y are N and $CR^4$ respectively.

$L^1$

In some embodiments, $L^1$ is $^{A1}$—O—$CH_2$—$^{A2}$.
In some embodiments, $L^1$ is $^{A1}$—$CH_2$—O—$^{A2}$.
In some embodiments, $L^1$ is $^{A1}$—C(=O)—NH—$^{A2}$.
In some embodiments, $L^1$ is $^{A1}$—CH(OH)—$^{A2}$.
In some embodiments, $L^1$ is $^{A1}$—$CH_2$—NH—C(=O)—$^{A2}$.
In some embodiments, $L^1$ is $^{A1}$—S—$CH_2$—$^{A2}$.
In some embodiments, $L^1$ is $^{A1}$—$CH_2$—S—$^{A2}$.
In some embodiments, $L^1$ is $^{A1}$—$CH_2$—$^{A2}$.
In some embodiments, $L^1$ is $^{A1}$—$CH(CH_3)$—O—$^{A2}$.

It may be preferred that $L^1$ is selected from:
(i) $^{A1}$—O—$CH_2$—$^{A2}$;
(ii) $^{A1}$—$CH_2$—O—$^{A2}$;
(iii) $^{A1}$—C(=O)—NH—$^{A2}$; and
(iv) $^{A1}$—CH(OH)—$^{A2}$.

$A^1$

In some embodiments, $A^1$ is unsubstituted phenyl.

In some embodiments, $A^1$ is phenyl substituted by $CF_3$. In some of these embodiments, the $CF_3$ is in the para position, i.e. $A^1$ is:

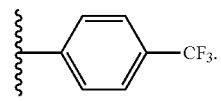

In some of these embodiments, the $CF_3$ is in the ortho position, i.e. $A^1$ is:

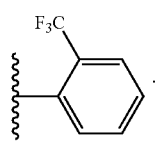

In some embodiments, $A^1$ is phenyl substituted by F. In some of these embodiments, the F is in the ortho position, i.e. $A^1$ is:

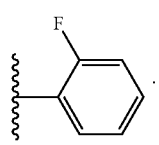 [SMILES: *c1ccccc1F]

In some of these embodiments, the F is in the meta position, i.e. $A^1$ is:

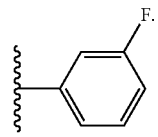 [SMILES: *c1cccc(F)c1]

In some of these embodiments, the F is in the para position, i.e. $A^1$ is:

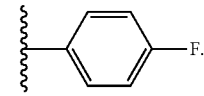

$A^2$

In some embodiments, $A^2$ is:

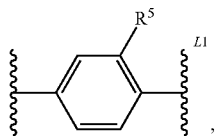

where $R^5$ is selected from H, Br, F, methyl, OMe, carboxy, $C_{1-4}$ alkyl ester, carboxamide, $C_{5-7}$ N-containing heteroaryl group, which is optionally substituted by a $C_{1-4}$ alkyl group.

In some of these embodiments, $R^5$ is H, so $A^2$ is:

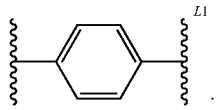

When $R^5$ is not H, it is selected from the group consisting of: Br, F, methyl, OMe, carboxy, $C_{1-4}$ alkyl ester, carboxamide, $C_{5-7}$ N-containing heteroaryl group, which is optionally substituted by a $C_{1-4}$ alkyl group.

When $R^5$ is $C_{1-4}$ alkyl ester, in some embodiments it may be methyl ester.

When $R^5$ is carboxamide, in some embodiments it may be —C(=O)NHMe.

When $R^5$ is a $C_{5-7}$ N-containing heteroaryl group, which is optionally substituted by a $C_{1-4}$ alkyl group, in some embodiments it may be N-methyl pyrazolyl, pyrazolyl or pyridyl.

In some embodiments, $A^2$ is:

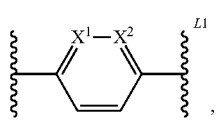

where one of $X^1$ and $X^2$ is N, and the other is CH.

In some of these embodiments, $A^2$ is:

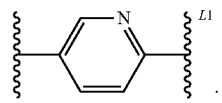

In others of these embodiments, $A^2$ is:

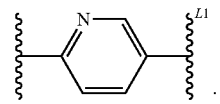

In some embodiments, $A^2$ is a $C_5$ heteroarylene group, containing 2 or 3 ring heteroatoms, where the bonds to L1 and the core are 3 to one another.

In some of these embodiments the $C_5$ heteroarylene group contains 2 ring heteroatoms. These ring heteroatoms may be selected from N and S in some of the embodiments. In some of the embodiments, $A^2$ may be:

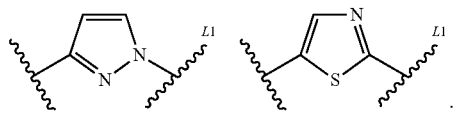

$R^1, R^2, R^3, R^4$

In some embodiments, one of $R^1$, $R^2$, $R^3$ and $R^4$ (if present) is $L^2$-$A^3$.

In some of these embodiments, $L^2$ is a single bond.
In some of these embodiments, $L^2$ is $CH_2$.
In some of these embodiments, $L^2$ is O.
In some of these embodiments, $L^2$ is NH.
In some of these embodiments, $L^2$ is NMe.
In some of these embodiments, $L^2$ is NH—$CH_2$.
In some of these embodiments, $L^2$ is NMe-$CH_2$.

It may be preferred that $L^2$ is selected from the group consisting of: a single bond, O, NH, NH—$CH_2$, and NMe-$CH_2$. It may be further preferred that $L^2$ is selected from the group consisting of: a single bond, O and NH. It may be most preferred that $L^2$ is a single bond. It may also be preferred that $L^2$ is $CH_2$.

In some embodiments, $A^3$ is a $C_{5-10}$ N-containing heterocyclic group, which is optionally substituted by one or two groups selected from OH, $NH_2$, $CH_2NH_2$, $C_{1-4}$ alkyl, $C_{1-4}$ alkylacyl, $C_{1-4}$ alkyl ester, oxo and $C_{1-4}$ alkyl sulfonyl.

In some embodiments, the $C_{5-10}$ N-containing heterocyclic group is 3-methyl-5,6,7,8-tetrahydro-[1,2,4]triazolo[4,3-a]pyrazinyl:

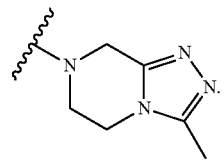 [SMILES: *N1CCn2c(C)nnc2C1]

In some embodiments, the $C_{5-10}$ N-containing heterocyclic group is a $C_{5-7}$ N-containing heterocyclic group.

In some embodiments, the $C_{5-7}$ N-containing heterocyclic group is selected from piperidinyl, tertahydropyridinyl, morpholino, thiomorpholino (including oxidised forms thereof) and piperazinyl. The heteroatoms may be in any location in the ring, which may be joined to the remainder of the molecule via a ring carbon or ring heteroatom.

In some embodiments when the $C_{5-7}$ N-containing heterocyclic group is piperidinyl, the optional substituents may be selected from $C_{1-4}$ alkyl groups (e.g. methyl, $CH_2NHBoc$), $C_{1-4}$ alkylacyl (e.g. —C(=O)$CH_3$ (acetyl), —C(=O)CH($CH_3$)$NH_2$) and $C_{1-4}$ alkyl ester (e.g. —C(=O)OC($CH_3$)$_3$). An optional substituent may also be hydroxy, $NH_2$, $CH_2NH_2$.

In some embodiments when the $C_{5-7}$ N-containing heterocyclic group is tetrahydropyridinyl, the group may be unsubstituted.

In some embodiments when the $C_{5-7}$ N-containing heterocyclic group is morpholino, the group may be unsubstituted.

In some embodiments when the $C_{5-7}$ N-containing heterocyclic group is thiomorpholino (including oxidised forms thereof), the group may be unsubstituted.

In some embodiments when the $C_{5-7}$ N-containing heterocyclic group is piperazinyl the optional substituents may be selected from $C_{1-4}$ alkyl groups (e.g. methyl), $C_{1-4}$ alkyl sulfonyl (e.g. —S(=O)$_2$$CH_2CH_3$ (esyl)) and oxo. Such piperazinyl groups substituted by oxo include, but are not limited to:

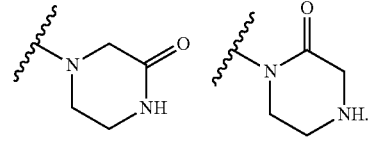

In some embodiments, $A^3$ is a $C_{5-7}$ N-containing heteroaryl group, which is optionally substituted by a $C_{1-4}$ alkyl group.

In some embodiments, the $C_{5-7}$ N-containing heteroaryl group is selected from pyridinyl and pyrazolyl.

In some embodiments when the $C_{5-7}$ N-containing heteroaryl group is pyridinyl, the group may be unsubstituted.

In some embodiments when the $C_{5-7}$ N-containing heteroaryl group is pyrazolyl, the optional substituents may be selected from $C_{1-4}$ alkyl groups (e.g. methyl).

In some embodiments, all of $R^1$, $R^2$, $R^3$ and $R^4$ (if present) are H.

In some embodiments, when any of $R^1$, $R^2$, $R^3$ and $R^4$ (if present) are halo, they may be Cl.

$R^1$

In some embodiments, $R^1$ is selected from H, Cl, Me, OMe and a $C_{5-7}$ N-containing heterocyclic group (e.g. piperidinyl, which may be unsubstituted). In further embodiments, $R^1$ may also be selected from —$CH_2$—$C_{1-4}$ alkylester (e.g. —$CH_2$-ethylester), —$CH_2$-carboxy, —$CH_2$-carboxamide (e.g. —$CH_2$—C(=O)NHMe, —$CH_2$—C(=O)NMe$_2$).

$R^2$

In some embodiments, $R^2$ is selected from H and a $C_{5-7}$ N-containing heterocyclic group (e.g. piperidinyl or piperazinyl, which may be unsubstituted, or substituted by a $C_{1-4}$ alkylacyl group (such as acetyl) or a $C_{1-4}$ alkyl ester (such as —C(=O)OC($CH_3$)$_3$). The $C_{5-7}$ N-containing heterocyclic group (e.g. piperidinyl) may also be substituted by $C_{1-4}$ alkyl (such as methyl) or a $C_{1-4}$ alkyl sulfonyl (such as —S(=O)$_2$CH$_3$).

$R^3$

In some embodiments, $R^3$ is selected from H, Cl, NH$_2$, NHMe, a $C_{5-7}$ N-containing heterocyclic group, which is optionally substituted and a $C_{5-7}$ N-containing heteroaryl group, which is optionally substituted. The $C_{5-7}$ N-containing heterocyclic group and a $C_{5-7}$ N-containing heteroaryl group are as described above. The $C_{5-7}$ N-containing heterocyclic group may be piperidinyl, tetrahydropyridinyl, piperazinyl, morpholino, thiomorpholino, 1,4-thiazinanyl 1,1-dioxide, 1,4-thiazinanyl 1-oxide, which may be unsubstituted, or substituted by oxo, OH, NH$_2$, CH$_2$NH$_2$, a $C_{1-4}$ alkylacyl group (such as acetyl) or a $C_{1-4}$ alkyl ester (such as —C(=O)OC(CH$_3$)$_3$), $C_{1-4}$ alkyl (such as methyl), $C_{1-4}$ alkyl sulfonyl (such as —S(=O)$_2$CH$_3$, —S(=O)$_2$C$_2$H$_5$, —S(=O)$_2$-cylcopropyl).

The $C_{5-7}$ N-containing heteroaryl group may be pyridyl or pyrazolyl, which may be optionally substituted by methyl.

$R^3$ may also be a $C_{1-4}$ alkyl group, such as methyl, ethyl and cyclopropyl; —NMe$_2$; —NH—C$_2$H$_4$—NH—C(=O)—C$_{1-4}$ alkyl (such as —NH—C$_2$H$_4$—NH—C(=O)—CH$_3$); —CH$_2$—C$_{1-4}$ alkylester (such as —CH$_2$—C(=O)—O—C$_2$H$_5$); —CH$_2$-carboxy.

In some embodiments, $R^3$ is $L^2$-$A^3$, where $A^3$ is a $C_{5-7}$ N-containing heterocyclic group, such as piperidinyl (optionally substituted by a $C_{1-4}$ alkyl ester) or piperazinyl. In these embodiments, $L^2$ may be selected from a single bond, —O—, —NH—, —NMe-, —CH$_2$— and —NH—CH$_2$—.

$R^4$

In some embodiments, $R^4$ is H.
In some embodiments, $R^4$ is Me.

$R^1, R^2, R^3, R^4$

In some embodiments, $R^1$ is H, one of $R^2$ or $R^3$ is H and the other is a $C_{5-7}$ N-containing heterocyclic group.

In some of these embodiments, the $C_{5-7}$ N-containing heterocyclic group may be selected from 4-piperidinyl, N-methyl-4-piperidinyl, or N-ethyl-4-piperidinyl.

In others of these embodiments, the $C_{5-7}$ N-containing heterocyclic group may be selected from piperazinyl, or N-methyl-piperazinyl.

In all of these embodiments, $R^4$ (if present) may be H.
In some embodiments, the compounds are of formula IA:

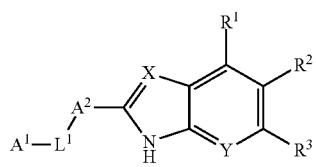

(IA)

wherein:
X and Y respectively are selected from:
(i) N and N; and
(ii) N and CR$^4$;
$A^2$ is:

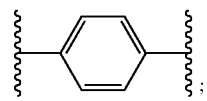

$L^1$ is selected from:
(i) $^{A1}$—O—CH$_2$—$^{A2}$;
(ii) $^{A1}$—CH$_2$—O—$^{A2}$;
(iii) $^{A1}$—C(=O)—NH—$^{A2}$;
(iv) $^{A1}$—CH(OH)—$^{A2}$; and
(v) $^{A1}$—CH$_2$—NH—C(=O)—$^{A2}$;
$A^1$ is phenyl, optionally substituted by CF$_3$;
(a) one of $R^1$, $R^2$, $R^3$ and $R^4$ (if present) is selected from:
(i) H;
(ii) Cl;
(iii) NH$_2$;
(iv) NMe$_2$;
(iv) Me;
(v) OMe;
(vi) —NH—C$_2$H$_4$—NH—C(=O)—C$_{1-4}$ alkyl;
(vii) $L^2$-$A^3$, where $L^2$ is selected from the group consisting of: a single bond, O, NH, NMe, NH—CH$_2$, and NMe-CH$_2$; and $A^3$ is selected from:
(vii-i) a $C_{5-7}$ N-containing heterocyclic group, which is optionally substituted by a group selected from $C_{1-4}$ alkyl, $C_{1-4}$ alkylacyl, $C_{1-4}$ alkyl ester, oxo and $C_{1-4}$ alkyl sulfonyl;
(vii-ii) a $C_{5-7}$ N-containing heteroaryl group, which is optionally substituted by a $C_{1-4}$ alkyl group;
(b) another of $R^1$, $R^2$, $R^3$ and $R^4$ (if present) is selected from:
(i) H;
(ii) Cl;
(iii) NH$_2$;
(iv) NMe$_2$;
(iv) Me;
(v) OMe;
(c) the other one or two of $R^1$, $R^2$, $R^3$ and $R^4$ (if present) are H.

EXAMPLES

The following are examples are provided solely to illustrate the present invention and are not intended to limit the scope of the invention, as described herein.

ACRONYMS

For convenience, many chemical moieties are represented using well known abbreviations, including but not limited to, methyl (Me), ethyl (Et), n-propyl (nPr), isopropyl (iPr), n-butyl (nBu), tert-butyl (tBu), n-hexyl (nHex), cyclohexyl (cHex), phenyl (Ph), biphenyl (biPh), benzyl (Bn), naphthyl (naph), methoxy (MeO), ethoxy (EtO), benzoyl (Bz), and acetyl (Ac).

For convenience, many chemical compounds are represented using well known abbreviations, including but not limited to, methanol (MeOH), ethanol (EtOH), isopropanol (i-PrOH), ether or diethyl ether (Et$_2$O), acetic acid (AcOH), acetonitrile (MeCN), dichloromethane (methylene chloride, DCM), trifluoroacetic acid (TFA), dimethylformamide (DMF), tetrahydrofuran (THF), dimethylsulfoxide (DMSO), meta-chloroperoxybenzoic acid (mCPBA), 1,1'-bis(diphenylphosphino)ferrocene (dppf), 2-dicyclohexylphosphino-2',6'-diisopropoxybiphenyl (Ruphos), tert-butyloxycarbonyl (Boc), 2-(trimethylsilyl)ethoxymethyl (SEM), 2-(1H-7-azabenzotriazol-1-yl)-1,1,3,3-tetramethyluronium hexafluorophosphate (HATU), 1-ethyl-3-(3-dimethylaminopropyl) carbodiimide (EDCI), 4-dimethylaminopyridine (DMAP), N,N-diisopropylethylamine (DIPEA), lithium bis(trimethylsilyl)amide (LiHMDS) and 1-hydroxybenzotriazole (HOBt), Tetrabutylammonium bromide (TBAB), Chloro-(2-dicyclohexylphosphino-2',6'-diisopropoxy-1,1'-biphenyl)[2-

(2-aminoethyl)phenyl]palladium(II)-methyl-t-butyl ether adduct (RuPhos palladacycle precatalyst), Lithium bis(trimethylsilyl)amide (LiHMDS), Bis(trimethylaluminum)-1,4-diazabicyclo[2.2.2]octane adduct (DABAL-AlMe$_3$), 2-Dicyclohexylphosphino-2',4',6'-triisopropylbiphenyl (XPhos), dimethoxyethane (DME).

General Experimental Details

Unless otherwise stated the following generalizations apply. $^1$NMR spectra were recorded on either a Bruker Avance DRX300 (300 MHz) or a Bruker Ultrashield plus (400 MHz). The multiplicity of a signal is designated by the following abbreviations: s, singlet; d, doublet; t, triplet; q, quartet; dd, doublet of doublets; dt, doublet of triplets; tt, triplet of triplets; br, broad; m, multiplet. All observed coupling constants, J, are reported in Hertz.

Analytical LC/MS data was generated using an Agilent 1200 Series LC coupled to an Agilent 6100 Series Single Quad MS (LCMS-A) or an Agilent 1260 Infinity LC coupled to a 6100 series Single Quad MS (LCMS-B). Preparative mass-directed HPLC was carried out using a Waters ZQ 3100.

LCMS Method A (LCMS-A)
Instrument: Agilent 6100 Series Single Quad LC/MS
Agilent 1200 Series HPLC
Pump: 1200 Series G1311A Quaternary pump
Autosampler: 1200 Series G1329A Thermostatted Autosampler
Detector: 1200 Series G1314B Variable Wavelength Detector
LC Conditions:
Reverse Phase HPLC analysis
Column: Luna C$_8$(2) 5 u 50×4.6 mm 100 A
Column temperature: 30° C.
Injection Volume: 5 µL
Solvent A: Water 0.1% Formic Acid
Solvent B: Acetonitrile 0.1% Formic Acid
Gradient: 5-100% B over 10 min
Detection: 254 nm or 214 nm
MS Conditions:
Ion Source: Quadrupole
Ion Mode: Multimode-ES
Drying gas temp: 300° C.
Vaporizer temperature: 200° C.
Capillary voltage (V): 2000 (positive)
Capillary voltage (V): 4000 (negative)
Scan Range: 100-1000
Step size: 0.1 sec
Acquisition time: 10 min LCMS Method B (LCMS-B)
Instrument:
Pump: 1260 Infinity G1312B Binary pump
Autosampler: 1260 Infinity G1367E 1260 HiP ALS
Detector: 1290 Infinity G4212A 1290 DAD
LC Conditions:
Reverse Phase HPLC analysis
Column: Poroshell 120 EC-C18
Column temperature: 35° C.
Injection Volume: 1 µL
Solvent A: Water 0.1% Formic Acid
Solvent B: Acetonitrile 0.1% Formic Acid
Gradient: 5-100% B over 3.8 mins
Detection: monitored at 254 nm and 214 nm
MS Conditions:
Ion Source: Quadrupole
Ion Mode: API-ES
Drying gas temp: 350° C.
Capillary voltage (V): 3000 (positive)
Capillary voltage (V): 3000 (negative)
Scan Range: 100-1000
Step size: 0.1 sec
Acquisition time: 5 min LCMS Method C (LCMS-C)
Instrument: Waters ZQ 3100 Mass Detector
Waters 2545-Pump
Waters SFO System Fluidics Organizer
Waters 2996 Diode Array Detector
Waters 2767 Sample Manager
LC Conditions:
Reverse Phase HPLC analysis
Column: XBridge™ C18 5 µm 4.6×100 mm
Injection Volume: 10 µL
Solvent A: Water 0.1% Formic Acid
Solvent B: Acetonitrile 0.1% Formic Acid
Gradient: 10-100% B over 10 minutes
Flow rate: 1.5 ml/min
Detection: 100-600 nm
MS Conditions:
Ion Source: Single-quadrupole
Ion Mode: ES positive
Source Temp: 150° C.
Desolvation Temp: 350° C.
Detection: Ion counting
Capillary (KV): 3.00
Cone (V): 30
Extractor (V): 3
RF Lens (V): 0.1
Scan Range: 100-1000 Amu
Scan Time: 0.5 sec
Acquisition time: 10 minutes
Gas Flow: 100 L/hr
Desolvation: 650 L/hr Preparative Mass-Directed HPLC
Instrument:
Waters ZQ 3100-Mass Detector
Waters 2545-Pump
Waters SFO System Fluidics Organizer
Waters 2996 Diode Array Detector
Waters 2767 Sample Manager
LC Conditions:
Reverse Phase HPLC analysis
Column: XBridge™ C18 5 µm 19×50 mm
Injection Volume 500 µL
Solvent A: Water 0.1% Formic Acid
Solvent B: Acetonitrile 0.1% Formic Acid
Gradient: 25-100% B over 10 min
Flow rate: 19 mL/min
Detection: 100-600 nm
MS Conditions:
Ion Source: Single-quadrupole
Ion Mode: ES positive
Source Temp: 150° C.
Desolvation Temp: 350° C.
Detection: Ion counting
Capillary (KV)-3.00
Cone (V): 30
Extractor (V): 3
RF Lens (V): 0.1
Scan Range: 100-1000 Amu
Scan Time: 0.5 sec
Acquisition time: 10 min
Gas Flow
Desolvation L/hour-650
Cone L/hour-100

Analytical thin-layer chromatography was performed on Merck silica gel 60 F254 aluminium-backed plates which were visualised using fluorescence quenching under UV light or acidic anisaldehyde or a basic KMnO$_4$ dip. Flash chromatography was performed on a Biotage Isolera purification system using either Grace or Biotage silica cartridges. Microwave irradiation was achieved using a CEM Explorer SP Microwave Reactor. Anhydrous solvents were purchased from Sigma-Aldrich and used where necessary. Other solvents were used as supplied from Merck KGaA. Molecular sieves were activated by heating under vacuum. Biotage Isolute phase separation cartridges were used for cartridge based phase separations. Extractions on SCX cartridges were performed with Varian Bond Elut SCX solid phase extraction cartridges.

Example 1: Synthesis of 2-(4-(phenoxymethyl)phenyl)-3H-imidazo[4,5-b]pyridine (1)

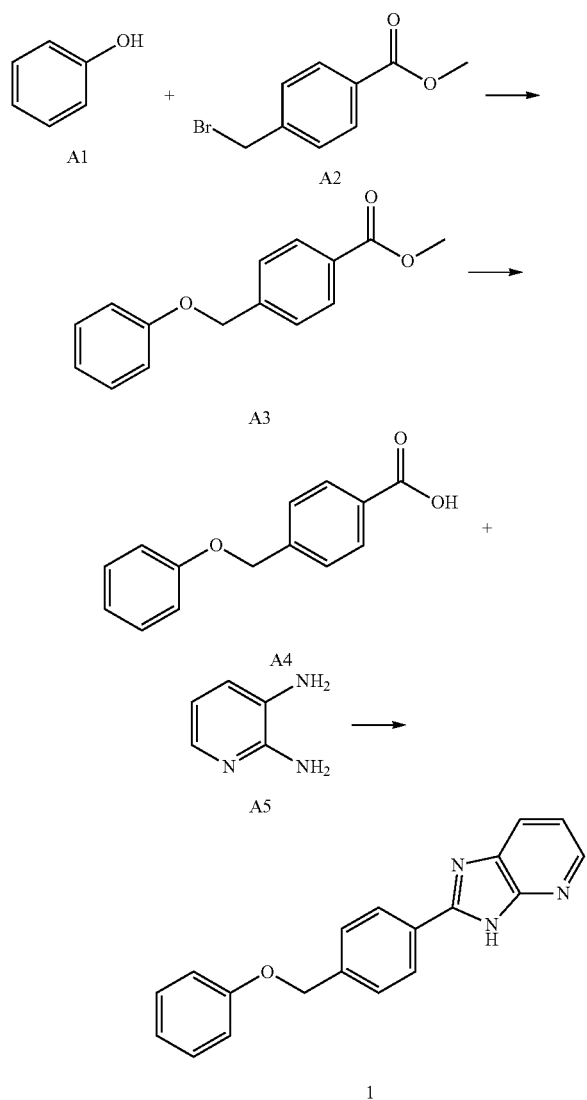

a) Methyl 4-(phenoxymethyl)benzoate (A3)

Methyl 4-(bromomethyl)benzoate A2 (0.400 g, 1.75 mmol), DMF (10 mL), phenol A1 (0.181 g, 1.92 mmol) and Cs$_2$CO$_3$ (0.853 g, 2.62 mmol) were stirred at room temperature for 18 hours. The mixture was poured into water (200 mL), stood for 20 minutes and filtered. The collected precipitate was air-dried followed by drying under high vacuum to give the title compound A3 as a white solid (0.386 g, 91%). $^1$H NMR (400 MHz, d$_6$-DMSO) δ 7.98 (d, J=8.3 Hz, 2H), 7.59 (d, J=8.4 Hz, 2H), 7.34-7.26 (m, 2H), 7.05-6.99 (m, 2H), 6.98-6.92 (m, 1H), 5.20 (s, 2H), 3.85 (s, 3H). LCMS-A rt 6.25 min, m/z (positive ion) 243.1 [M+H]$^+$.

b) 4-(Phenoxymethyl)benzoic acid (A4)

Methyl 4-(phenoxymethyl)benzoate A3 (0.382 g, 1.58 mmol) was dissolved in THF (12 mL); water (2 mL), MeOH (1 mL) and lithium hydroxide monohydrate (0.264 g, 6.31 mmol) were added. The reaction was stirred at room temperature for 20 hours then poured into 2 M aqueous HCl (200 mL). The solid was stood for 15 minutes and the solid collected by filtration. The collected solid was washed with 1 M aqueous HCl and water, then air-dried followed by drying under high vacuum to give the title compound A4 as a white solid (0.285 g, 79%). $^1$H NMR (400 MHz, d$_6$-DMSO) δ 7.96 (d, J=8.3 Hz, 2H), 7.56 (d, J=8.3 Hz, 2H), 7.34-7.25 (m, 2H), 7.02 (d, J=7.8 Hz, 2H), 6.95 (t, J=7.3 Hz, 1H), 5.19 (s, 2H). OH proton not observed. LCMS-A rt 5.71 min.

c) 2-(4-(Phenoxymethyl)phenyl)-3H-imidazo[4,5-b]pyridine (1)

4-(Phenoxymethyl)benzoic acid A4 (50 mg, 0.22 mmol), HOBt (36 mg, 0.26 mmol), EDCI (50 mg, 0.26 mmol), pyridine-2,3-diamine A5 (25 mg, 0.23 mmol), DMF (1 mL) and DIPEA (0.092 mL, 0.53 mmol) were stirred together at room temperature for 19 hours. The solution was added to water (20 mL), stood for twenty minutes and filtered. The collected solid (52 mg) was dissolved in glacial acetic acid (1 mL) and heated in the microwave (140° C./1 hour). The cooled mixture was concentrated in vacuo, the residue partitioned between EtOAc (25 mL) and 1 M pH 7 potassium phosphate buffer (25 mL). The aqueous phase was extracted with EtOAc (2×25 mL), and the combined EtOAc extracts dried over Na$_2$SO$_4$ and concentrated in vacuo. Column chromatography (4 g silica cartridge, 0-10% MeOH/DCM) gave the title compound as a white solid (32 mg, 48%). $^1$H NMR (400 MHz, d$_6$-DMSO) δ 13.69-13.04 (m, 1H), 8.34 (s, 1H), 8.25 (d, J=8.2 Hz, 2H), 8.03 (s, 1H), 7.64 (d, J=8.1 Hz, 2H), 7.34-7.28 (m, 2H), 7.25 (dd, J=8.0, 4.8 Hz, 1H), 7.05 (d, J=8.0 Hz, 2H), 6.96 (t, J=7.3 Hz, 1H), 5.20 (s, 2H). LCMS-A rt: 5.25 min; m/z (positive ion): 302.2 [M+H]$^+$; m/z (negative ion) 301.1 [M−H]$^−$.

Example 2: Synthesis of 2-(4-(benzyloxy)phenyl)-1H-imidazo[4,5-b]pyridine (2)

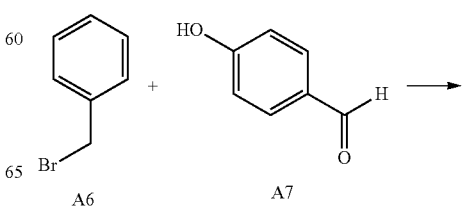

39

-continued

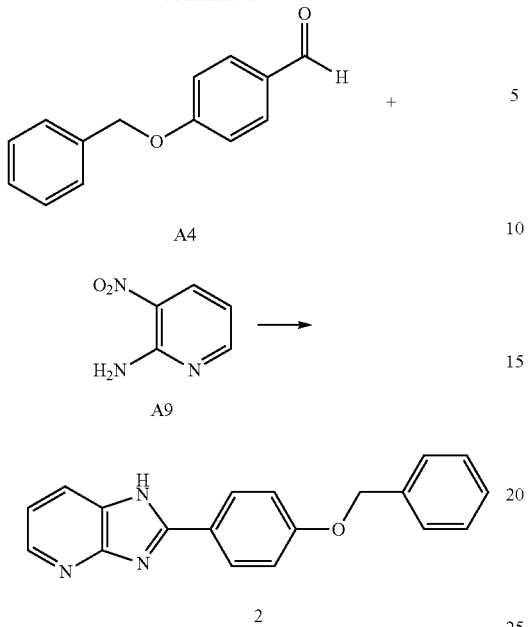

a) 4-(Benzyloxy)benzaldehyde (A8)

Benzyl bromide A6 (9.9 mL, 83 mmol) was added to a suspension of 4-hydroxybenzaldehyde A7 (10.0 g, 81.9 mmol) and $K_2CO_3$ (17.0 g, 122 mmol) in acetonitrile (100 mL). The resulting mixture was stirred vigorously at room temperature for 5 hours. The suspension was filtered and the collected solids were washed with acetonitrile (2×20 mL). The combined filtrates were concentrated in vacuo to give a solid residue which was suspended in petroleum benzine 40-60° C. (100 mL). The solid was collected via filtration, washed with petroleum benzine 40-60° C. (200 mL) and air dried to give the title compound (16 g, 92%) as a white solid. $^1$H NMR (400 MHz, $CDCl_3$) δ 9.89 (s, 1H), 7.87-7.82 (m, 2H), 7.48-7.34 (m, 5H), 7.12-7.06 (m, 2H), 5.16 (s, 2H).

b) 2-(4-(Benzyloxy)phenyl)-1H-imidazo[4,5-b]pyridine (2)

A solution of 2-amino-3-nitropyridine A9 (0.066 g, 0.47 mmol) and 4-(benzyloxy)benzaldehyde A8 (0.10 g, 0.47 mmol) in DMSO (5 mL) was treated with 1 M aqueous $Na_2S_2O_4$ (1.4 mL, 1.4 mmol). The reaction mixture was heated to 70° C. for 25 hours then cooled to room temperature and treated dropwise with 5 M aqueous $NH_4OH$ (1 mL). A light yellow precipitate was immediately formed, which was then collected by filtration, washed with water (2×10 mL) and dried under reduced pressure to give a light yellow solid. This was purified by silica gel chromatography (25 g silica cartridge, 0-10% MeOH in DCM) followed by preparative mass-directed HPLC to give the title compound (0.022 g, 15%) as a white solid. $^1$H NMR (400 MHz, $d_6$-DMSO) δ 13.30 (s, 1H), 8.42-7.83 (m, 4H), 7.73-6.94 (m, 8H), 5.21 (s, 2H). LCMS-A rt 4.72, m/z (positive ion) 302.2 [M+H]$^+$, m/z (negative ion) 300.0 [M−H]$^−$.

40

Example 3: Synthesis of N-(4-(3H-imidazo[4,5-b]pyridin-2-yl)phenyl)benzamide (3)

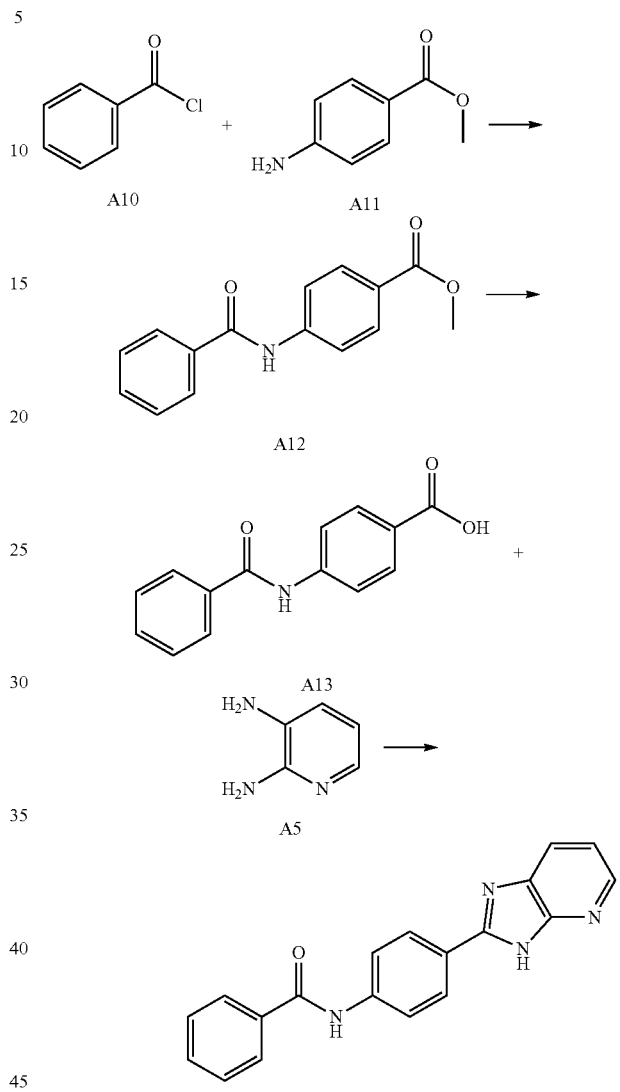

a) Methyl 4-benzamidobenzoate (A12)

To a suspension of methyl 4-aminobenzoate A11 (0.600 g, 3.97 mmol) in anhydrous DCM (10 mL) at 0° C. under $N_2$ was added DIPEA (0.761 mL, 0.564 mmol) followed by benzoyl chloride A10 (0.507 mL, 4.37 mmol). The cooling bath was removed and the reaction was stirred overnight, then diluted with DCM (50 mL) and washed with aqueous HCl (2 M, 2×50 mL). The organic phase was dried ($MgSO_4$) and concentrated in vacuo to give the title compound (1.00 g, 99%) as a white solid. $^1$H NMR (400 MHz, $CDCl_3$) δ 8.07-8.04 (m, 2H), 8.03 (br s, 1H), 7.90-7.84 (m, 2H), 7.77-7.72 (m, 2H), 7.61-7.54 (m, 1H), 7.53-7.47 (m, 2H), 3.91 (s, 3H). LCMS-A rt 5.31 min, m/z (positive ion) 256.2 [M+H]$^+$, m/z (negative ion) 254.1 [M−H]$^−$.

b) 4-Benzamidobenzoic acid (A13)

To a solution of methyl 4-benzamidobenzoate A12 (1.00 g, 3.92 mmol) in 4:1:1 v/v THF/MeOH/water (30 mL) was added LiOH—H₂O (0.505 g, 11.8 mmol). The solution was stirred at room temperature for 17 hours and then acidified with 1 M aqueous HCl. The precipitate was collected by filtration to give the title compound (0.886 g, 94%) as a white solid. ¹H NMR (400 MHz, d₆-DMSO) δ 10.54 (br s, 1H), 8.00-7.88 (m, 6H), 7.65-7.59 (m, 1H), 7.59-7.51 (m, 2H). LCMS-A rt 4.84 min, m/z (positive ion) 242.1 [M+H]⁺, m/z (negative ion) 240.1 [M−H]⁻.

c) N-(4-(3H-Imidazo[4,5-b]pyridin-2-yl)phenyl) benzamide (3)

4-Benzamidobenzoic acid A13 (0.10 g, 0.42 mmol), HOBt (0.067 g, 0.50 mmol), EDCI (0.095 g, 0.50 mmol), pyridine-2,3-diamine A5 (0.047 g, 0.46 mmol), DMF (2 mL) and DIPEA (0.17 mL, 1.0 mmol) were stirred together at room temperature for 19 hours. The solution was added to water (15 mL), stood for twenty minutes and filtered. The collected solid was dissolved in glacial acetic acid (3.0 mL) and heated in the microwave twice (140° C. for 1 hour, then 140° C. for 30 minutes). The cooled mixture was concentrated in vacuo, the residue partitioned between EtOAc (50 mL) and 1 M pH 7 potassium phosphate buffer (50 mL). The aqueous phase was extracted with EtOAc (2×25 mL), and the combined EtOAc extracts dried (MgSO₄) and concentrated in vacuo. The product was purified twice by silica gel chromatography (12 g silica cartridge, 50-100% EtOAc in petroleum benzine 40-60° C., then 12 g silica cartridge, 60-70% EtOAc in petroleum benzine 40-60° C.) to give the title compound (0.025 g, 19%) as a white solid. ¹H NMR (400 MHz, d₆-DMSO) δ 13.35 (brs, 1H) 10.51 (s, 1H), 8.31 (d, J=3.9 Hz, 1H), 8.22 (d, J=8.8 Hz, 2H), 8.04-7.93 (m, 4H), 7.65-7.60 (m, 1H), 7.60-7.53 (m, 2H), 7.22 (dd, J=7.9, 4.8 Hz, 1H). One NH proton not observed. LCMS-A rt 4.40 min, m/z (positive ion) 315.2 [M+H]⁺, m/z (negative ion) 313.1 [M−H]⁻.

Example 4: Synthesis of 2-(4-(benzyloxy)phenyl)-7-chloro-3H-imidazo[4,5-b]pyridine (4)

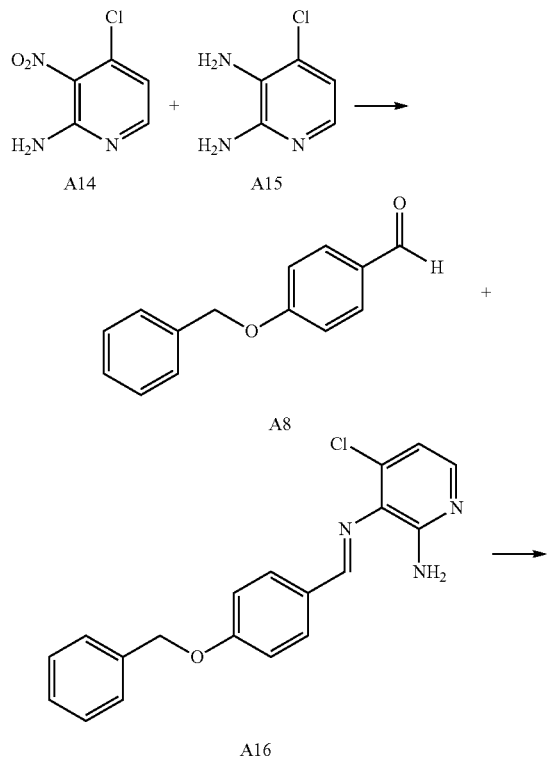

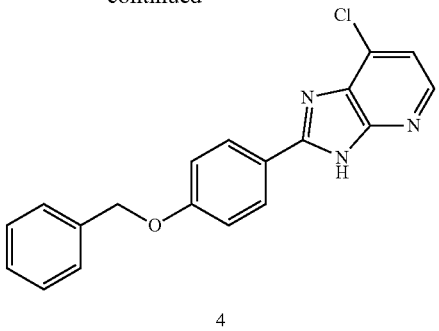

a) 4-Chloropyridine-2,3-diamine (A15)

Iron powder (1.126 g, 20.17 mmol) followed by NH₄Cl (1.079 g, 20.17 mmol) were added to a stirred suspension of 2-amino-4-chloro-3-nitropyridine A14 (0.700 g, 4.03 mmol) in i-PrOH (30 mL) and water (15 mL) at room temperature. The reaction was heated to 70° C. and stirred at this temperature for 2 hours. The reaction was cooled and filtered through a plug of celite which was washed with EtOAc (150 mL). The filtrate was washed with saturated aqueous NaHCO₃ (100 mL), brine (100 mL), dried (Na₂SO₄), filtered and concentrated in vacuo to give the title compound (0.555 g, 96%) as a brown solid. LCMS-A rt 1.34 min, m/z (positive ion) 144.1, 146.2 [M+H]⁺.

b) (E)-N³-(4-(Benzyloxy)benzylidene)-4-chloropyridine-2,3-diamine (A16)

4-Chloropyridine-2,3-diamine A15 (0.555 g, 3.87 mmol) and 4-(benzyloxy)benzaldehyde A8 (0.861 g, 4.06 mmol) were suspended in water (40 mL) and the reaction mixture was then heated at reflux for 22 hours. The reaction mixture was cooled and the water was evaporated in vacuo to give a brown solid. The crude material was purified by silica gel chromatography (40 g silica cartridge, 0-75% EtOAc in petroleum benzine 40-60° C.) to give the title compound (0.305 g, 23%) as a yellow solid. ¹H NMR (400 MHz, d₆-DMSO) δ 9.17 (s, 1H), 8.13-8.05 (m, 2H), 7.62 (d, J=5.1 Hz, 1H), 7.52-7.45 (m, 2H), 7.45-7.38 (m, 2H), 7.39-7.30 (m, 1H), 7.20 (d, J=5.1 Hz, 1H), 7.16 (d, J=8.8 Hz, 2H), 5.61 (s, 2H), 5.22 (s, 2H). LCMS-A m/z (positive ion) 338.1, 340.1 [M+H]⁺ No UV trace for product.

c) 2-(4-(Benzyloxy)phenyl)-7-chloro-3H-imidazo[4,5-b]pyridine (4)

(Diacetoxyiodo)benzene (0.436 g, 1.35 mmol) was added to a solution of (E)-N³-(4-(benzyloxy)benzylidene)-4-chloropyridine-2,3-diamine A16 (0.305 g, 0.903 mmol) in dry THF (12 mL) under an atmosphere of nitrogen. The reaction was stirred for 3 hours at room temperature, then concentrated in vacuo and diluted with EtOAc (150 mL) and saturated aqueous NaHCO₃ (100 mL). The layers were separated and the aqueous layer was extracted with EtOAc (100 mL). The combined organics were washed with brine (100 mL), dried (Na₂SO₄), filtered and concentrated in vacuo to give the crude product. The material was purified by silica gel chromatography (40 g silica cartridge, 0-100% EtOAc in cyclohexane, then 0-10% MeOH in DCM) to give the title compound (0.131 g, 43%) as a brown solid. ¹H NMR (400 MHz, d₆-DMSO) δ 13.72 (s, 1H), 8.33-8.17 (m, 3H), 7.54-7.45 (m, 2H), 7.46-7.39 (m, 2H), 7.38-7.31 (m, 2H), 7.22 (d, J=8.8 Hz, 2H), 5.22 (s, 2H). LC-MS-A rt 6.29 min, m/z (positive ion) 336.1, 338.1 [M+H]⁺.

Example 5: Synthesis of 2-(4-(benzyloxy)phenyl)-7-methyl-3H-imidazo[4,5-b]pyridine (5)

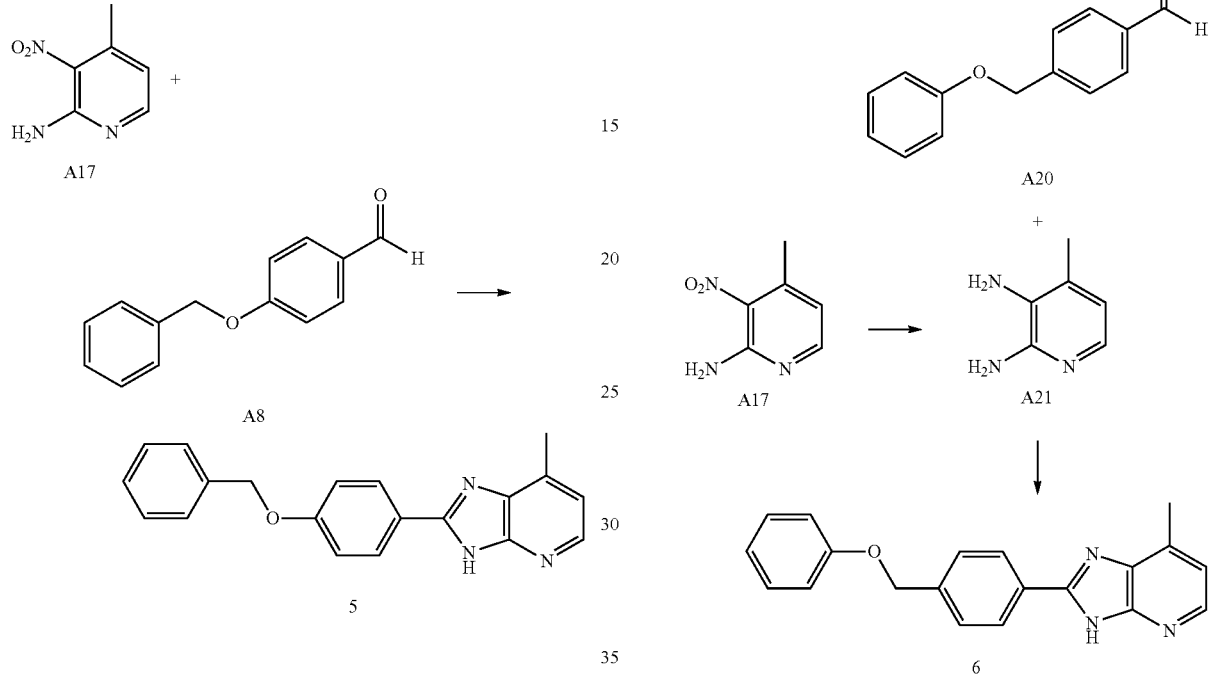

To a suspension of 4-(benzyloxy)benzaldehyde A8 (0.076 g, 0.36 mmol) and 4-methyl-3-nitropyridin-2-amine A17 (0.050 g, 0.33 mmol) in EtOH (2.0 mL) was added 1 M Na$_2$S$_2$O$_4$ solution (0.980 mL, 0.980 mmol). The resulting yellow suspension was irradiated in a microwave reactor at 110° C. for 15 minutes. The reaction was cooled to room temperature, then 28% w/w aqueous NH$_3$ (1 mL) was added and the reaction mixture was stirred for 5 minutes. The solution was filtered to give a yellow solid which was purified by silica gel chromatography (12 g silica cartridge, 0-100% EtOAc in petroleum benzine 40-60° C.) to give the title compound (0.014 g, 14%) as a white solid. ¹H NMR (400 MHz, d$_6$-DMSO): δ 13.16 (br s, 1H), 8.18 (d, J=8.8 Hz, 2H), 8.14 (d, J=4.9 Hz, 1H), 7.52-7.47 (m, 2H), 7.46-7.38 (m, 2H), 7.39-7.31 (m, 1H), 7.20 (d, J=9.0 Hz, 2H), 7.02 (d, J=4.9 Hz, 1H), 5.21 (s, 2H), 2.58 (s, 3H). LCMS-B rt 3.09 min, m/z (positive ion) 316.2 [M+H]⁺.

Example 6: Synthesis of 7-methyl-2-(4-(phenoxymethyl)phenyl)-3H-imidazo[4,5-b]pyridine (6)

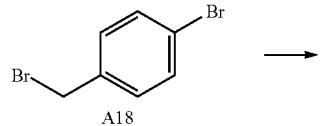

a) 1-Bromo-4-(phenoxymethyl)benzene (A19)

Phenol A1 (1.76 g, 18.7 mmol), DMF (50 mL), Cs$_2$CO$_3$ (6.647 g, 20.4 mmol) and 1-bromo-4-(bromomethyl)benzene A18 (4.429 g, 17.0 mmol) were stirred at room temperature. After 17 hours the mixture was diluted with water (200 mL) and stirred for a further hour. The mixture was filtered, the collected solid washed with water (200 mL) and air dried to give the title compound (3.975 g, 89%) as a white solid. ¹H NMR (400 MHz, CDCl$_3$) δ 7.55-7.48 (m, 2H), 7.33-7.27 (m, 4H), 7.01-6.92 (m, 3H), 5.02 (s, 2H). LCMS-A: rt 6.59 min; no product ions detected.

b) 4-(Phenoxymethyl)benzaldehyde (A20)

1-Bromo-4-(phenoxymethyl)benzene A19 (350 mg, 1.33 mmol) in THF (10 mL) was cooled to −78° C. under nitrogen, and n-butyllithium (1.5 M solution, 1.33 mL, 2.0 mmol) was added. After 30 minutes, DMF (1.03 mL, 13.3 mmol) was added and the mixture stirred at −78° C. for one hour. The cooling bath was removed and the mixture allowed to come to room temperature. The mixture was quenched with 1 M HCl (5 mL) and concentrated on a rotary evaporator. The aqueous residue was diluted with water (20 mL) and extracted with chloroform (2×20 mL). The combined chloroform extracts were washed with water (3×20 mL), brine (20 mL), dried over Na$_2$SO$_4$ and evaporated. Column chromatography (12 g silica cartridge, 0-100% chloroform/hexane) gave the title compound (198 mg, 70%)

as a white solid. ¹H NMR (400 MHz, CDCl₃) δ 10.03 (s, 1H), 7.93-7.88 (m, 2H), 7.61 (d, J=8.1 Hz, 2H), 7.34-7.27 (m, 2H), 7.02-6.95 (m, 3H), 5.16 (s, 2H). LCMS-A rt 6.61 min; no product ions detected.

c) 4-Methylpyridine-2,3-diamine (A21)

Iron powder (0.365 g, 6.53 mmol) and NH₄Cl (0.349 g, 6.53 mmol) were added to a stirred suspension of 4-methyl-3-nitropyridin-2-amine A17 (0.200 g, 1.31 mmol) in i-PrOH (10 mL) and water (5 mL). The reaction was heated to 70° C. and stirred for 2 hours. The reaction was then cooled and filtered through a plug of celite, which was washed with EtOAc (75 mL). The filtrate was washed with saturated aqueous NaHCO₃ (75 mL), brine (75 mL), dried (Na₂SO₄), filtered and concentrated in vacuo to give the title compound (0.060 g, 37%) as a dark purple solid. ¹H NMR (400 MHz, CDCl₃): δ 7.55 (d, J=5.1 Hz, 1H), 6.53 (d, J=5.1 Hz, 1H), 4.19 (br s, 2H), 3.26 (brs, 2H), 2.16 (s, 3H). LCMS-B: rt 0.74 min, m/z (positive ion) 124.1 [M+H]⁺.

d) 7-Methyl-2-(4-(phenoxymethyl)phenyl)-3H-imidazo[4,5-b]pyridine (6)

A solution of 4-methylpyridine-2,3-diamine A21 (0.060 g, 0.49 mmol) and 4-(phenoxymethyl)benzaldehyde A20 (0.114 g, 0.556 mmol) in MeOH (6 mL) was irradiated in a microwave reactor for 20 minutes at 110° C., then 20 minutes at 130° C. and finally 60 minutes at 130° C. The MeOH was evaporated in vacuo and the resulting gum was dissolved in THF (6 mL). (Diacetoxyiodo)benzene (0.204 g, 0.633 mmol) was added and the reaction stirred under an atmosphere of nitrogen for 3 hours. The reaction was concentrated, then diluted with EtOAc (100 mL) and saturated aqueous NaHCO₃ (100 mL). The layers were separated and the aqueous layer was extracted with EtOAc (100 mL). The combined organics were washed with brine (100 mL), dried (Na₂SO₄), filtered and concentrated in vacuo to give the crude product which was purified by silica gel chromatography (12 g silica Cartridge, 0-100% EtOAc in petroleum benzine 40-60° C., then 0-20% MeOH in EtOAc) to give the title compound (0.011 g, 7%) as a pale yellow solid. ¹H NMR (400 MHz, d₆-DMSO): δ 13.40 (br s, 1H), 8.26 (d, J=8.3 Hz, 2H), 8.19 (d, J=4.8 Hz, 1H), 7.63 (d, J=7.9 Hz, 2H), 7.31 (tt, J=7.4, 2.3 Hz, 2H), 7.08-7.02 (m, 3H), 6.96 (tt, J=7.2, 1.0 Hz, 1H), 5.20 (s, 2H), 2.60 (s, 3H). LCMS-B: rt 3.08 min, m/z (positive ion) 316.2 [M+H]⁺.

Example 7: Synthesis of 2-(4-(benzyloxy)phenyl)-7-methoxy-3H-imidazo[4,5-b]pyridine (7)

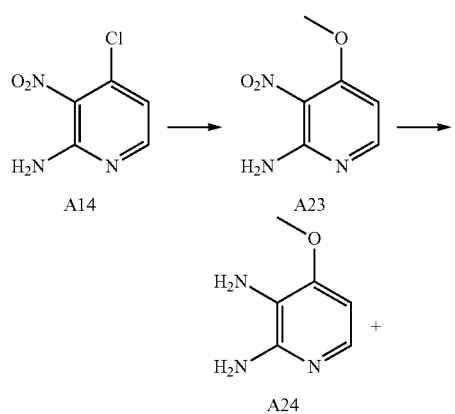

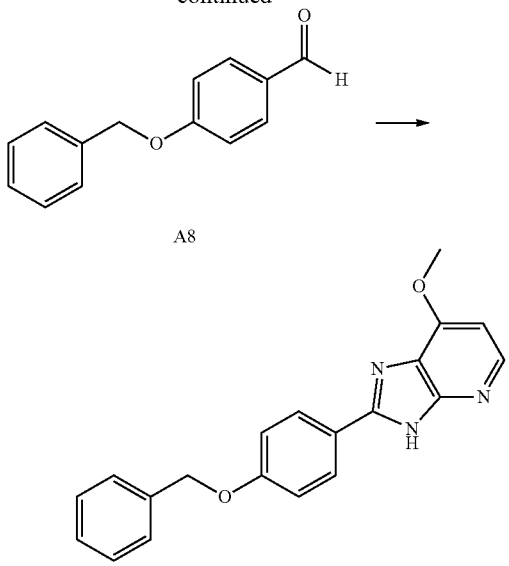

a) 4-Methoxy-3-nitropyridin-2-amine (A23)

4-Chloro-3-nitropyridin-2-amine A14 (0.600 g, 3.46 mmol) was dissolved in dry MeOH (40 mL) under an atmosphere of nitrogen and NaOMe (0.467 g, 8.64 mmol) was added. The reaction was heated at reflux for 18 hours, cooled and quenched with water (5 mL) and then concentrated in vacuo. The resulting residue was diluted with EtOAc (150 mL) and saturated aqueous NaHCO₃ (100 mL), the layers were separated and the aqueous layer was extracted with EtOAc (2×100 mL). The combined organics were washed with brine (100 mL), dried (Na₂SO₄), filtered and concentrated in vacuo to give the crude product which was purified by silica gel chromatography (40 g silica cartridge, 0-100% EtOAc in cyclohexane) to give the title compound (0.457 g, 78%) as a yellow solid. ¹H NMR (400 MHz, d₆-DMSO) δ 8.04 (d, J=5.8 Hz, 1H), 6.90 (s, 2H), 6.51 (d, J=5.8 Hz, 1H), 3.87 (s, 3H). LCMS-B rt 1.82 min, m/z (positive ion) 170.1 [M+H]⁺.

b) 4-Methoxypyridine-2,3-diamine (A24)

Iron powder (0.751 g, 13.5 mmol) followed by NH₄Cl (0.719 g, 13.5 mmol) were added to a stirred suspension of 4-methoxy-3-nitropyridin-2-amine A23 (0.455 g, 2.69 mmol) in isopropanol (20 mL) and water (10 mL) at room temperature. The reaction was heated to 70° C. and stirred at this temperature for 2 hours then cooled and filtered through a plug of celite which was washed with EtOAc (100 mL). The filtrate was washed with saturated aqueous NaHCO₃ (100 mL), brine (100 mL), dried (Na₂SO₄), filtered and concentrated in vacuo to give the title compound (0.143 g, 38%) as a purple solid. ¹H NMR (400 MHz, d₆-DMSO) δ 7.30 (d, J=5.7 Hz, 1H), 6.31 (d, J=5.7 Hz, 1H), 5.23 (s, 2H), 4.06 (s, 2H), 3.76 (s, 3H). LCMS-B rt 0.65 min, m/z (positive ion) 140.2 [M+H]⁺.

c) 2-(4-(Benzyloxy)phenyl)-7-methoxy-3H-imidazo[4,5-b]pyridine (7)

4-Methoxypyridine-2,3-diamine A24 (0.070 g, 0.50 mmol) and 4-(benzyloxy)benzaldehyde A8 (0.117 g, 0.55 mmol) were dissolved in MeOH (6 mL) and heated in the microwave for 20 minutes at 110° C. then 30 minutes at 130° C. and finally 60 minutes at 140° C. The MeOH was evaporated in vacuo and the resulting gum was dissolved in THF (6 mL). (Diacetoxyiodo)benzene (0.211 g, 0.654 mmol) was added and the mixture was stirred under an atmosphere of nitrogen at room temperature for 20 hours. The reaction was concentrated and diluted with EtOAc (100 mL) and saturated aqueous NaHCO$_3$ (100 mL), the layers were separated and the aqueous layer was extracted with EtOAc (100 mL). The combined organics were washed with brine (100 mL), dried (Na$_2$SO$_4$), filtered and concentrated in vacuo to give the crude product which was purified by silica gel chromatography (12 g silica cartridge, 0-100% EtOAc in petroleum benzine 40-60° C., then 0-15% MeOH in EtOAc) to give the title compound (0.035 g, 21%) as a yellow solid. $^1$H NMR (400 MHz, d$_6$-DMSO) δ 13.26 (br s, 1H), 8.15 (d, J=7.8 Hz, 3H), 7.51-7.45 (m, 2H), 7.44-7.38 (m, 2H), 7.38-7.32 (m, 1H), 7.20-7.15 (m, 2H), 6.82 (d, J=5.5 Hz, 1H), 5.20 (s, 2H), 4.05 (s, 3H). LCMS-A rt 4.82 min, m/z (positive ion) 332.2 [M+H]$^+$.

Example 8: Synthesis of 2-(4-(benzyloxy)phenyl)-7-(piperidin-4-yl)-3H-imidazo[4,5-b]pyridine (8)

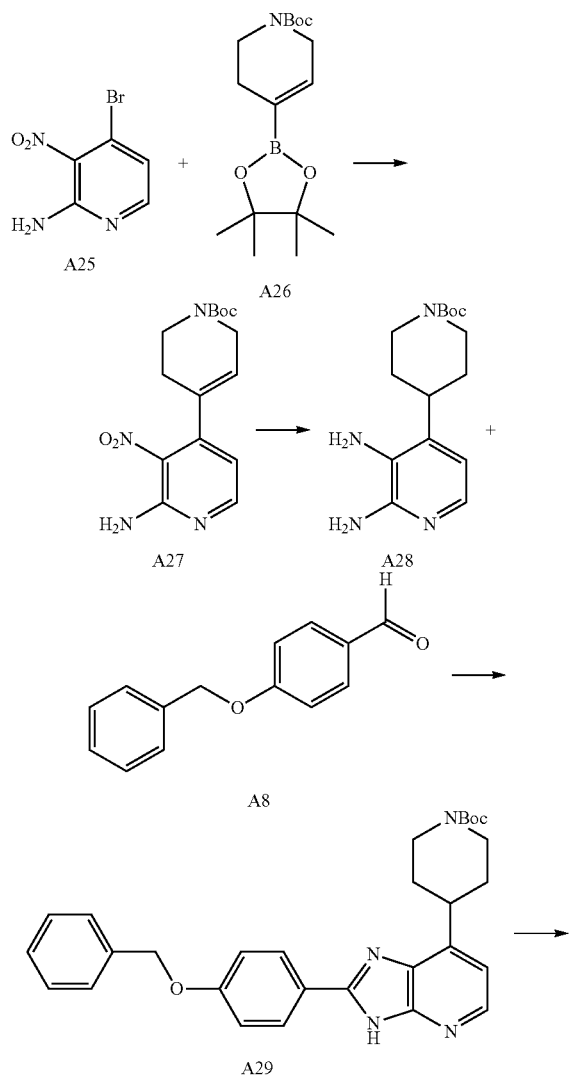

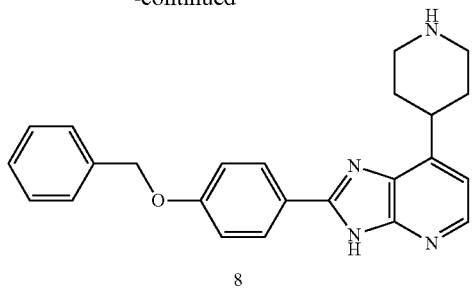

8 a) tert-Butyl 2'-amino-3'-nitro-5,6-dihydro-[4,4'-bipyridine]-1 (2H)-carboxylate (A27)

An aqueous solution of 2 M Na$_2$CO$_3$ (3.44 mL, 6.88 mmol) was added to a degassed mixture of tert-butyl 4-(4,4,5,5-tetramethyl-1,3,2-dioxaborolan-2-yl)-5,6-dihydropyridine-1 (2H)-carboxylate A26 (1.42 g, 4.59 mmol), 2-amino-4-bromo-3-nitropyridine A25 (0.500 g, 2.29 mmol) and PdCl$_2$(PPh$_3$)$_2$ (0.080 g, 0.12 mmol) in 1,4-dioxane (30 mL). The reaction mixture was stirred at 80-90° C. for 20 hours. The resulting mixture was concentrated in vacuo and partitioned between EtOAc (50 mL) and water (30 mL), then filtered through a pad of Celite. The layers were separated and the aqueous layer was extracted with EtOAc (15 mL). The combined organic layers were washed with 1:1 water: saturated brine (30 mL), dried (MgSO$_4$), filtered and concentrated in vacuo. The residue was purified by column chromatography (silica cartridge, 0-80% EtOAc in petroleum benzine 40-60° C.) to give the title compound (0.583 g, 79%) as a bright yellow solid. $^1$H NMR (400 MHz, d$_6$-DMSO) δ 8.15 (d, J=4.9 Hz, 1H), 7.23-6.93 (s, 2H), 6.54 (d, J=4.9 Hz, 1H), 5.68 (s, 1H), 3.97-3.75 (m, 2H), 3.58-3.40 (t, J=5.5 Hz, 2H), 2.29-2.14 (td, J=5.5, 2.5 Hz, 2H), 1.42 (s, 9H), LCMS-A rt 5.51 min, m/z (positive ion) 321 [M+H]$^+$.

b) tert-Butyl 4-(2, 3-diaminopyridin-4-yl)piperidine-1-carboxylate (A28)

A suspension of tert-butyl 2'-amino-3'-nitro-5,6-dihydro-[4,4'-bipyridine]-1(2H)-carboxylate A27 (400 mg, 1.25 mmol) and 10% Pd/C (54% water wet, 12.5 mg Pd) in 96% EtOH (125 mL) and EtOAc (125 mL) was stirred under hydrogen (5 bar) for 22 hours. The reaction mixture was filtered through celilte and washed with EtOH (30 mL) and the resulting solution was concentrated in vacuo. The residue was dissolved in EtOAc and filtered through celite again. The filtrate was concentrated in vacuo to give the title compound (340 mg, 93%) as a light brown solid. $^1$H NMR (400 MHz, d$_6$-DMSO) δ 7.25 (d, J=5.3 Hz, 1H), 6.30 (d, J=5.3 Hz, 1H), 5.28 (s, 2H), 4.48 (s, 2H), 4.12-4.00 (m, 2H), 2.96-2.69 (m, 2H), 1.67 (d, J=12.8 Hz, 2H), 1.41 (s, 9H+1H hidden underneath), 1.36-1.27 (m, 2H), LCMS-A rt 4.30 min; m/z (positive ion) 293 [M+H]$^+$.

c) tert-Butyl 4-(2-(4-(benzyloxy)phenyl)-3H-imidazo[4,5-b]pyridin-7-yl)piperidine-1-carboxylate (A29)

4-(Benzyloxy)benzaldehyde A8 (66.0 mg, 0.31 mmol) and tert-butyl 4-(2,3-diaminopyridin-4-yl)piperidine-1-carboxylate A28 (100 mg, 0.342 mmol) were heated at reflux in water (1 mL) for 17 hours. A brown solid formed and was collected by filtration, the solid was washed with water (3 mL) and then dissolved in DCM (10 mL), dried (MgSO₄) and filtered. The filtrate was concentrated in vacuo and the residue dissolved in DCM (2 mL), PhI(OAc)₂ (100 mg, 0.311 mmol) was added and the reaction was stirred for one hour. The mixture was concentrated in vacuo and the residue dissolved in MeOH (2 mL). The solution was loaded onto an SCX cartridge (10 g) which was eluted with MeOH (3×10 mL) then 9:1 MeOH:aqueous ammonia (3×10 mL). Fractions containing product were combined and concentrated to dryness and the resulting material was purified by chromatography (25 g silica cartridge, 1% MeOH in CHCl₃). Fractions containing impure material were concentrated and further purified by column chromatography (silica cartridge; 15%-100% EtOAc in petroleum benzine 40-60° C.). The fractions containing pure material from both columns were combined and concentrated in vacuo to give the title compound (9.3 mg, 6%) as a pale yellow powder; LCMS-A 5.33 min, m/z (positive ion) 485 [M+H]⁺ m/z (negative ion) 483 [M−H]⁺.

d) 2-(4-(Benzyloxy)phenyl)-7-(piperidin-4-yl)-3H-imidazo[4,5-b]pyridine (8)

tert-Butyl 4-(2-(4-(benzyloxy)phenyl)-3H-imidazo[4,5-b]pyridin-7-yl)piperidine-1-carboxylate A29 (9.3 mg, 0.019 mmol) in CDCl₃ (1 mL) was treated with TFA (37 μL). The solution was stirred for 2 hours and 1 M aqueous NaOH (1 mL) was added and the layers separated. The aqueous layer was extracted with CHCl₃ (2×5 mL), the combined organic layers were washed with 1:1 water: saturated brine (10 mL) dried (MgSO₄) and filtered. The reaction had not gone to completion by TLC. The organic layer was treated with TFA (1 mL) and stirred overnight. 1 M NaOH (5 mL) was added and the resulting precipitate was collected by vacuum filtration. The solid was dissolved in chloroform and evaporated to dryness to give the title compound (3.4 mg, 46%) as a pale golden coloured solid. ¹H NMR (400 MHz, d₆-DMSO) δ 7.55 (d, J=5.1 Hz, 1H), 7.38 (dt, J=8.8, 3.2 Hz, 2H), 6.68 (s, 2H), 6.65-6.57 (m, 2H), 6.58-6.53 (s, 1H), 6.53-6.47 (s, 1H), 6.49-6.39 (m, 2H), 4.43 (s, 2H), 3.04-2.75 (m, 4H), 1H obscured by solvent peaks, 1.54-1.45 (m, 2H) 1.54-1.45 (m, 2H). NH protons not observed. LCMS-A rt 4.21 min, m/z (positive ion) 385 [M+H]⁺.

Example 9: Synthesis of 2-(4-(phenoxymethyl)phenyl)-6-(piperidin-4-yl)-3H-imidazo[4,5-b]pyridine (9)

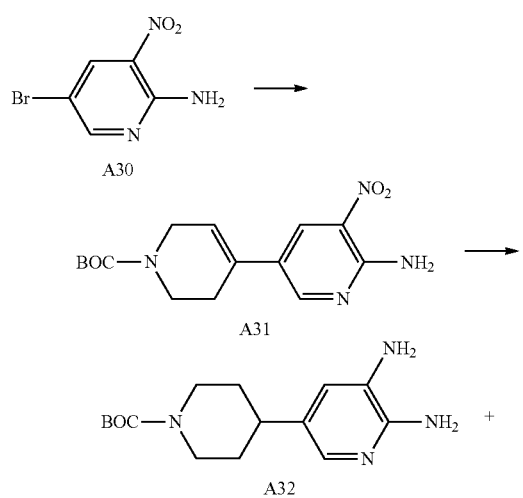

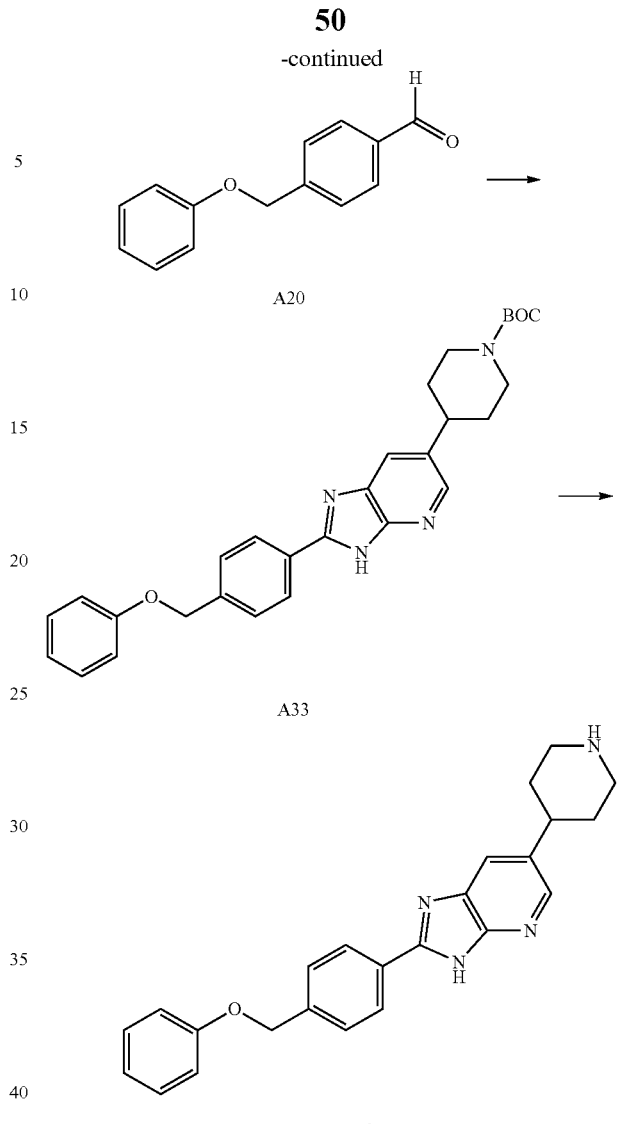

a) tert-Butyl 6-amino-5-nitro-5',6'-dihydro-[3, 4'-bipyridine]-1'(2'H)-carboxylate (A31)

5-Bromo-3-nitropyridin-2-amine A30 (2.50 g, 11.5 mmol), tert-butyl 4-(4,4,5,5-tetramethyl-1,3,2-dioxaborolan-2-yl)-5,6-dihydropyridine-1(2H)-carboxylate (3.90 g, 12.6 mmol) and PdCl₂(dppf) DCM solvate (474 mg, 5 mol %) were loaded into a flask, the flask was sealed and flushed with nitrogen. Dioxane (100 mL) was added, followed by a solution of K₂CO₃ (4.76 g, 34.4 mmol) in water (50 mL). The mixture was degassed with three vacuum/nitrogen cycles, heated to 80° C. for 16 hours, and allowed to cool. The mixture was concentrated, the aqueous residue diluted with water (400 mL) and chloroform (250 mL). The aqueous phase was extracted with chloroform (2×150 mL), the combined chloroform extracts washed with brine (200 mL), dried over Na₂SO₄, filtered and evaporated. Column chromatography (0-80% EtOAc/hexanes) gave the title compound (3.058 g, 83%) as a yellow-orange solid. ¹H NMR (400 MHz, CDCl₃) δ 8.45 (d, J=2.3 Hz, 1H), 8.37 (d, J=2.2 Hz, 1H), 6.73 (br s, 2H), 6.06 (s, 1H), 4.13-4.04 (m, 2H), 3.65 (t, J=5.7 Hz, 2H), 2.48 (s, 2H), 1.49 (s, 9H). LCMS-A: rt 5.58 min; m/z (positive ion) 321.2 [M+H]⁺, 265.1 [M−tBu+2H]⁺.

b) tert-Butyl 4-(5,6-diaminopyridin-3-yl)piperidine-1-carboxylate (A32)

tert-Butyl 6-amino-5-nitro-5',6'-dihydro-[3,4'-bipyridine]-1'(2'H)-carboxylate A31 (3.05 g, 9.52 mmol), 10% Pd/C (50% wet with water, 1.5 g), EtOAc (200 mL) and 96% EtOH (200 mL) were stirred under hydrogen at a pressure of 4 bar. After 16 hours the mixture was filtered through celite, and the celite washed with 96% EtOH (400 mL). The combined filtrates were evaporated, and the syrupy residue suspended in toluene and the mixture concentrated in vacuo. The residue was suspended in diethyl ether and the mixture concentrated in vacuo to give the title compound (2.76 g, 99%) as a brown solid. ¹H NMR (400 MHz, CDCl₃) δ 7.49 (d, J=1.7 Hz, 1H), 6.73 (d, J=1.8 Hz, 1H), 4.20 (br, 4H), 3.39 (br, 2H), 2.76 (t, J=11.9 Hz, 2H), 2.50 (tt, J=12.1, 3.4 Hz, 1H), 1.75 (d, J=12.9 Hz, 2H), 1.60-1.48 (m, 2H), 1.47 (s, 9H). LCMS-A: rt 4.22 min; m/z (positive ion) 293.3 [M+H]⁺.

c) tert-Butyl 4-(2-(4-(phenoxymethyl)phenyl)-3H-imidazo[4,5-b]pyridin-6-yl)piperidine-1-carboxylate A33 tert-Butyl 4-(5,6-diaminopyridin-3-yl)piperidine-1-carboxylate A32 (250 mg, 0.86 mmol), 4-(phenoxymethyl) benzaldehyde A20 (181 mg, 0.86 mmol), activated 3 Å molecular sieves (2 mm beads, 500 mg) and MeOH (5 mL) were stirred at 60° C. After 18 hours the mixture was decanted from the molecular sieves, the sieves washed with MeOH (5 mL) and the combined MeOH solutions concentrated in vacuo. The residue was dissolved in THF (5 mL), PhI(OAc)₂ (303 mg, 0.94 mmol) was added and the mixture stirred for two hours. The solvent was removed in vacuo, the residue partitioned between water (25 mL) and EtOAc (25 mL). The aqueous phase was extracted with further EtOAc (2×25 mL), the combined EtOAc phases washed with brine (50 mL), dried over Na₂SO₄, filtered and evaporated. Column chromatography (12 g silica cartridge, 0-100% EtOAc/petroleum benzine 40-60° C.) gave the title compound (200 mg, 48%) as a yellow solid ¹H NMR (400 MHz, d₆-DMSO) δ 13.35 (br s, 1H), 8.26 (d, J=1.8 Hz, 1H), 8.23 (d, J=8.3 Hz, 2H), 7.85 (s, 1H), 7.63 (d, J=8.3 Hz, 2H), 7.34-7.28 (m, 2H), 7.07-7.02 (m, 2H), 6.99-6.92 (m, 1H), 5.20 (s, 2H), 4.11 (d, J=12.0 Hz, 2H), 2.93-2.74 (m, 3H), 1.82 (d, J=12.5 Hz, 2H), 1.61 (qd, J=12.5, 4.1 Hz, 2H), 1.43 (s, 9H). LCMS-A: 6.24 min; m/z (positive ion) 485.3 [M+H]⁺; m/z (negative ion) 483.3 [M−H]⁻.

d) 2-(4-(Phenoxymethyl)phenyl)-6-(piperidin-4-yl)-3H-imidazo[4,5-b]pyridine (9)

tert-Butyl 4-(2-(4-(phenoxymethyl)phenyl)-3H-imidazo[4,5-b]pyridin-6-yl)piperidine-1-carboxylate A33 (200 mg, 0.41 mmol), DCM (8 mL) and TFA (2 mL) were stirred at room temperature for 18 hours. The mixture was quenched with 20% w/v aqueous NaOH (20 mL) and the volatile solvents removed in vacuo. The aqueous residue was diluted with water (30 mL) and the aqueous phase was extracted with EtOAc (3×50 mL), the combined organic extracts washed with brine (50 mL), dried over Na₂SO₄, filtered and concentrated in vacuo to give the title compound (160 mg, quant) as an off-white solid. ¹H NMR (400 MHz, d₆-DMSO) δ 8.26-8.19 (m, 3H), 7.81 (s, 1H), 7.63 (d, J=8.3 Hz, 2H), 7.34-7.27 (m, 2H), 7.04 (d, J=7.8 Hz, 2H), 6.95 (t, J=7.3 Hz, 1H), 5.20 (s, 2H), 3.07 (d, J=12.0 Hz, 2H), 2.81-2.72 (m, 1H), 2.69-2.59 (m, 2H), 1.81-1.72 (m, 2H), 1.62 (qd, J=12.3, 3.9 Hz, 2H). LCMS-A: rt 4.64 min; m/z (positive ion): 385.2 [M+H]⁺; m/z (negative ion): 383.2 [M−H]⁻.

Example 10: Synthesis of 1-(4-(2-(4-(phenoxymethyl)phenyl)-3H-imidazo[4,5-b]pyridin-6-yl)piperidin-1-yl)ethanone (10)

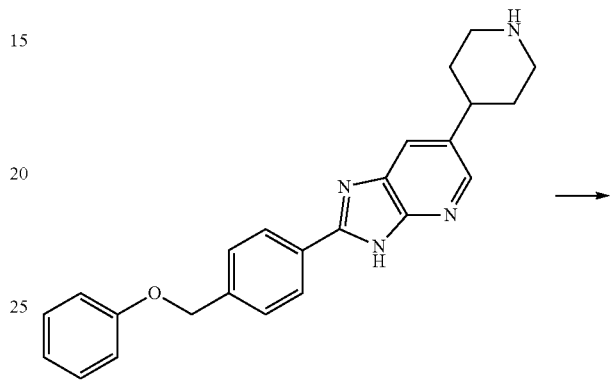

9

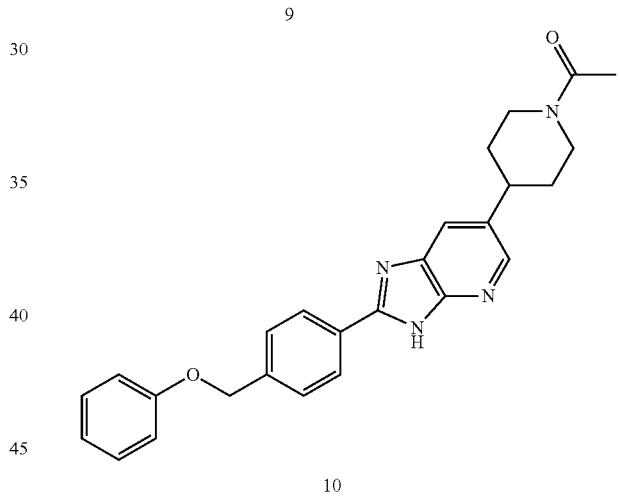

10

1-(4-(2-(4-(Phenoxymethyl)phenyl)-3H-imidazo[4,5-b]pyridin-6-yl)piperidin-1-yl)ethanone (10)

2-(4-(Phenoxymethyl)phenyl)-6-(piperidin-4-yl)-3H-imidazo[4,5-b]pyridine 9 (0.070 g, 0.182 mmol) was dissolved in DCM (7 mL) under an atmosphere of nitrogen and DIPEA (0.095 mL, 0.546 mmol) followed by acetyl chloride (0.019 mL, 0.273 mmol) were added and the resulting mixture was stirred at room temperature for 20 hours. The reaction mixture was diluted with EtOAc (100 mL) and saturated aqueous NaHCO₃ (100 mL), the layers were separated and the aqueous layer was extracted with EtOAc (70 mL). The combined organic layers were washed with water (70 mL), brine (70 mL), dried (Na₂SO₄), filtered and concentrated in vacuo to give the title compound (0.070 g, 90%) as a pale yellow solid. ¹H NMR (400 MHz, d₆-DMSO) δ 13.32 (brs, 1H), 8.29-8.18 (m, 3H), 7.84 (s, 1H), 7.63 (d, J=8.0 Hz, 2H), 7.36-7.24 (m, 2H), 7.07-6.99 (m, 2H), 6.95 (t, J=7.3 Hz, 1H), 5.20 (s, 2H), 4.62-4.52 (m, 1H), 3.99-3.91 (m, 1H), 3.16 (td, J=13.4, 13.0, 2.6 Hz, 1H), 2.95 (tt, J=12.2, 3.5 Hz, 1H), 2.62 (td, J=13.1, 2.8 Hz, 1H), 2.05 (s, 3H), 1.91-1.79 (m, 2H), 1.71 (qd, J=12.7, 4.2 Hz, 1H), 1.56 (qd, J=12.7, 4.3 Hz, 1H). LCMS-A rt 5.28 min; m/z (positive ion) 427.2 [M+H]⁺.

Example 11: Synthesis of 6-(1-methylpiperidin-4-yl)-2-(4-(phenoxymethyl)phenyl)-3H-imidazo[4,5-b]pyridine (11)

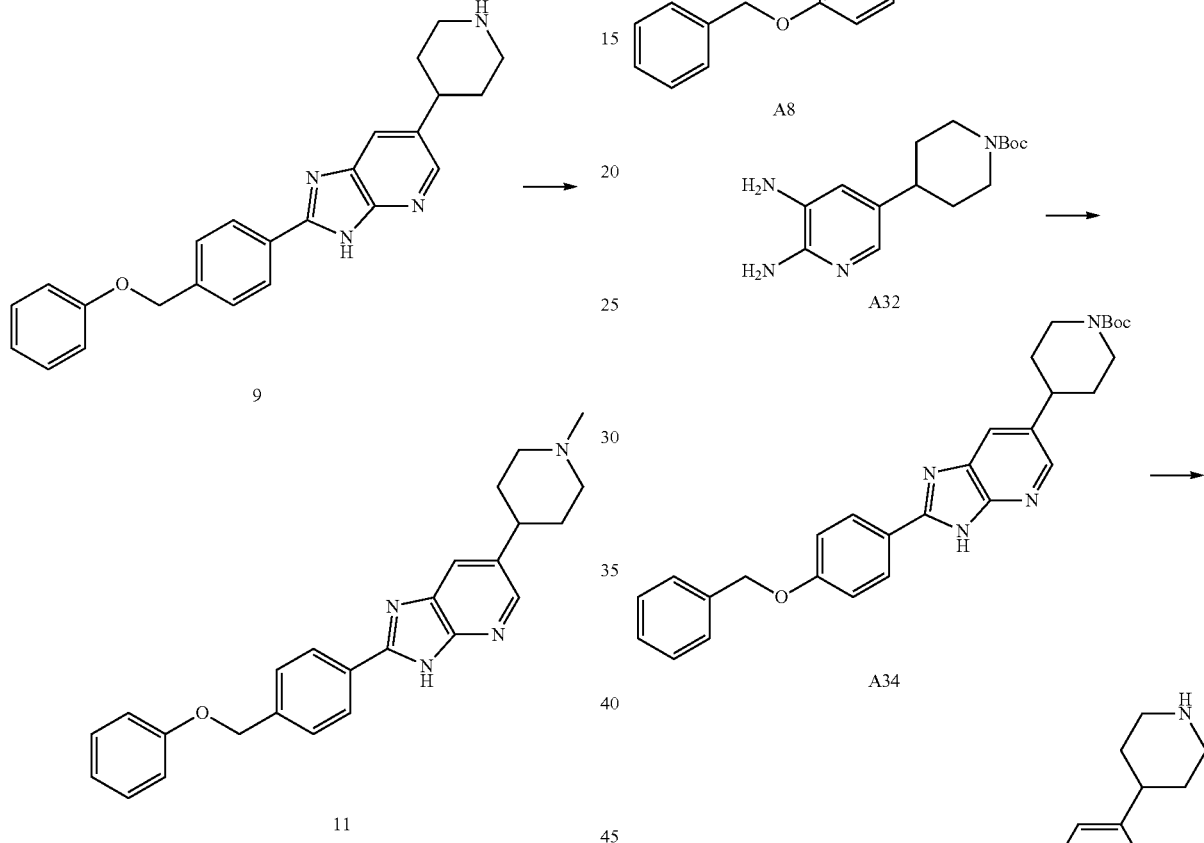

6-(1-Methylpiperidin-4-yl)-2-(4-(phenoxymethyl)phenyl)-3H-imidazo[4,5-b]pyridine (11)

To a solution of 2-(4-(phenoxymethyl)phenyl)-6-(piperidin-4-yl)-3H-imidazo[4,5-b]pyridine 9 (0.009 g, 0.023 mmol) in anhydrous MeOH (2 mL) was added a 37% aqueous solution of formaldehyde (0.005 mL, 0.070 mmol) under an atmosphere of nitrogen followed by NaBH(OAc)₃ (0.020 g, 0.094 mmol) and the reaction was stirred at room temperature for 18 hours. Volatiles were removed in vacuo and the residue was diluted with EtOAc (20 mL) and saturated aqueous NaHCO₃ (20 mL), the layers were separated and the aqueous layer was extracted with EtOAc (20 mL). The combined organic layers were washed with brine (30 mL), dried (Na₂SO₄), filtered and concentrated in vacuo to give a gum which was dissolved in DCM (~1 mL) and concentrated in vacuo to give the title compound (0.008 g, 80%) as an off-white solid. ¹H NMR (400 MHz, d₆-DMSO) δ 13.30 (brs, 1H), 8.28-8.17 (m, 3H), 7.84 (s, 1H), 7.66-7.57 (m, 2H), 7.36-7.27 (m, 2H), 7.08-7.01 (m, 2H), 6.95 (tt, J=7.2, 1.0 Hz, 1H), 5.20 (s, 2H), 2.93-2.85 (m, 2H), 2.70-2.57 (m, 1H), 2.21 (s, 3H), 2.04-1.95 (m, 2H), 1.84-1.71 (m, 4H). LCMS-A rt 4.64 min; m/z (positive ion) 399.2 [M+H]⁺.

Example 12: Synthesis of 2-(4-(benzyloxy)phenyl)-6-(piperidin-4-yl)-3H-imidazo[4,5-b]pyridine (12)

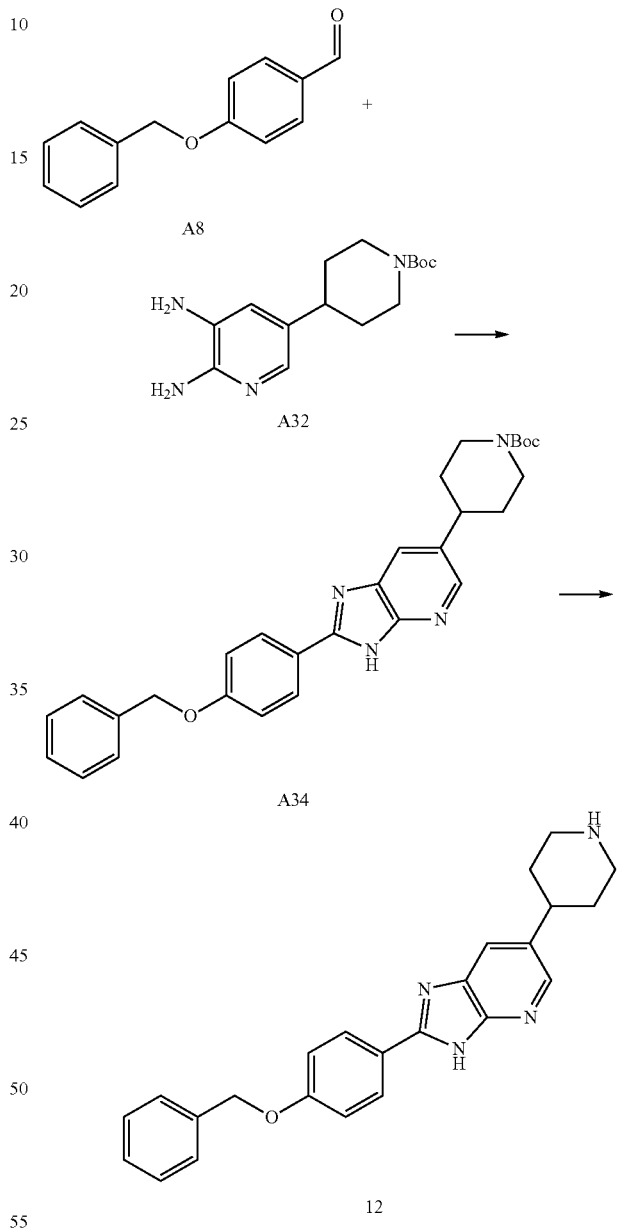

a) tert-Butyl 4-(2-(4-(benzyloxy)phenyl)-3H-imidazo[4,5-b]pyridin-6-yl)piperidine-1-carboxylate (A34)

4-(Benzyloxy)benzaldehyde A8 (0.200 g, 0.942 mmol) and tert-butyl 4-(5,6-diaminopyridin-3-yl)piperidine-1-carboxylate A32 (0.276 g, 0.942 mmol) were dissolved in MeOH (10 mL) and activated 3 Å sieves (0.500 g) were added. The reaction mixture was heated at reflux for 3 days. The resulting suspension was cooled to room temperature, decanted from the sieves and the solvent was removed in vacuo. Tetrahydrofuran (10 mL) followed by (Diacetoxyiodo)benzene (0.364 g, 1.131 mmol) were added under an atmosphere of nitrogen and the reaction was stirred at room temperature for 2 hours. The reaction was concentrated in vacuo and diluted with EtOAc (100 mL) and saturated aqueous NaHCO$_3$ (100 mL). The layers were separated and the aqueous layer was extracted with EtOAc (100 mL), the combined organics were washed with brine (100 mL), dried (Na$_2$SO$_4$), filtered and concentrated in vacuo to give the crude product which was purified by silica gel chromatography (40 g silica Cartridge, 0-100% EtOAc in petroleum benzine 40-60° C.) to give the title compound (0.210 g, 46%) as a pale yellow solid. $^1$H NMR (400 MHz, d$_6$-DMSO) δ 13.16 (br s, 1H), 8.25-8.09 (m, 3H), 7.80 (s, 1H), 7.52-7.29 (m, 5H), 7.27-7.14 (m, 2H), 5.21 (s, 2H), 4.11 (d, J=12.3 Hz, 2H), 2.93-2.72 (m, 3H), 1.82 (d, J=12.3 Hz, 2H), 1.61 (qd, J=12.5, 4.3 Hz, 2H), 1.43 (s, 9H). LCMS-A rt 5.91 min, m/z (positive ion) 485.3 [M+H]$^+$.

b) 2-(4-(Benzyloxy)phenyl)-6-(piperidin-4-yl)-3H-imidazo[4,5-b]pyridine (12)

tert-Butyl 4-(2-(4-(benzyloxy)phenyl)-3H-imidazo[4,5-b]pyridin-6-yl)piperidine-1-carboxylate A34 (0.205 g, 0.423 mmol) was dissolved in DCM (15 mL) under an atmosphere of nitrogen and trifluoroacetic acid (0.972 mL, 12.7 mmol) was added and the resulting mixture was stirred at room temperature for 20 hours. The reaction mixture was concentrated in vacuo and the resulting solid was dissolved in EtOAc (100 mL) and 2 M aqueous NaOH (100 mL), the layers were separated and the aqueous layer was extracted with EtOAc (70 mL), the combined organics were washed with brine (100 mL), dried (Na$_2$SO$_4$), filtered and concentrated in vacuo to give the title compound (0.142 g, 87%) as a pale yellow solid. $^1$H NMR (400 MHz, d$_6$-DMSO) δ 8.24-8.11 (m, 3H), 7.75 (s, 1H), 7.52-7.47 (m, 2H), 7.45-7.32 (m, 3H), 7.24-7.14 (m, 2H), 5.21 (s, 2H), 3.08-2.99 (m, 2H), 2.78-2.69 (m, 1H), 2.61 (td, J=12.0, 2.4 Hz, 2H), 1.78-1.69 (m, 2H), 1.60 (qd, J=12.1, 4.1 Hz, 2H). NH protons not observed. LCMS-A rt 4.56 min, m/z (positive ion) 385.2 [M+H]$^+$.

Example 13: 1-(4-(2-(4-(Benzyloxy)phenyl)-3H-imidazo[4,5-b]pyridin-6-yl)piperidin-1-yl)ethanone (13)

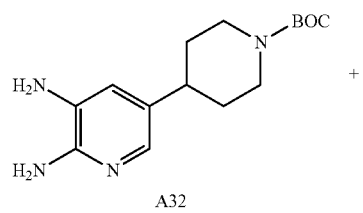

A32

+

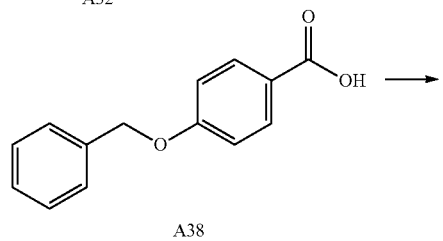

A38

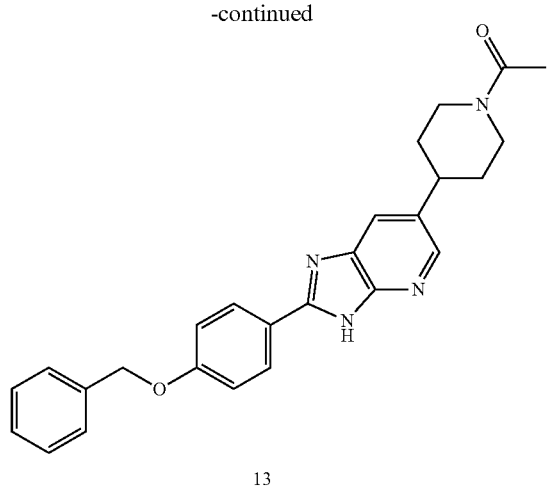

13 tert-Butyl 4-(5,6-diaminopyridin-3-yl)piperidine-1-carboxylate A32 (530 mg, 1.81 mmol), 4-(benzyloxy)benzoic acid A38 (414 mg, 1.81 mmol), MeCN (10 mL), DIPEA (0.947 mL, 5.44 mmol) and HATU (758 mg, 1.99 mmol) were stirred at room temperature for 19 hours. The mixture was poured into water (100 mL) and extracted with EtOAc (3×100 mL). The combined EtOAc phases were washed with brine (100 mL), dried over Na$_2$SO$_4$, filtered and evaporated. The residue was dissolved in acetic acid (20 mL) and heated in the microwave (140° C./1 hour). The cooled mixture was concentrated in vacuo, the residue dissolved in MeOH and applied to a 10 g SCX cartridge. The cartridge was eluted with MeOH (150 mL), followed by elution with 95:5 MeOH: concentrated aqueous ammonia (100 mL). The basic eluent was concentrated, and the residue concentrated in vacuo twice from absolute EtOH. Column chromatography (12 g silica cartridge, 0-20% MeOH/DCM) and collection of the major product containing fractions gave a yellow solid. The solid was suspended in ether (10 mL), the solvent decanted and the remaining solid dried under vacuum to give the title compound (151 mg, 20%) as a yellow solid. $^1$H NMR (400 MHz, d$_6$-DMSO) δ 13.19 (br s, 1H), 8.22 (d, J=1.6 Hz, 1H), 8.17-8.12 (m, 2H), 7.79 (s, 1H), 7.51-7.46 (m, 2H), 7.45-7.38 (m, 2H), 7.38-7.32 (m, 1H), 7.23-7.17 (m, 2H), 5.21 (s, 2H), 4.61-4.53 (m, 1H), 3.99-3.91 (m, 1H), 3.20-3.11 (m, 1H), 2.93 (tt, J=12.0, 3.3 Hz, 1H), 2.66-2.56 (m, 1H), 2.05 (s, 3H), 1.90-1.79 (m, 2H), 1.70 (qd, J=12.6, 4.1 Hz, 1H), 1.55 (qd, J=12.6, 4.2 Hz, 1H). LCMS-A: 4.79 min; m/z (positive ion) 427.3 [M+H]$^+$; m/z (negative ion): 425.1 [M–H]$^-$.

Example 14: Synthesis of 6-(piperidin-4-yl)-2-(4-((4-(trifluoromethyl)benzyl)oxy)phenyl)-3H-imidazo[4,5-b]pyridine (14)

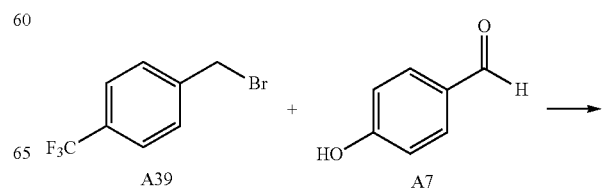

A39    A7

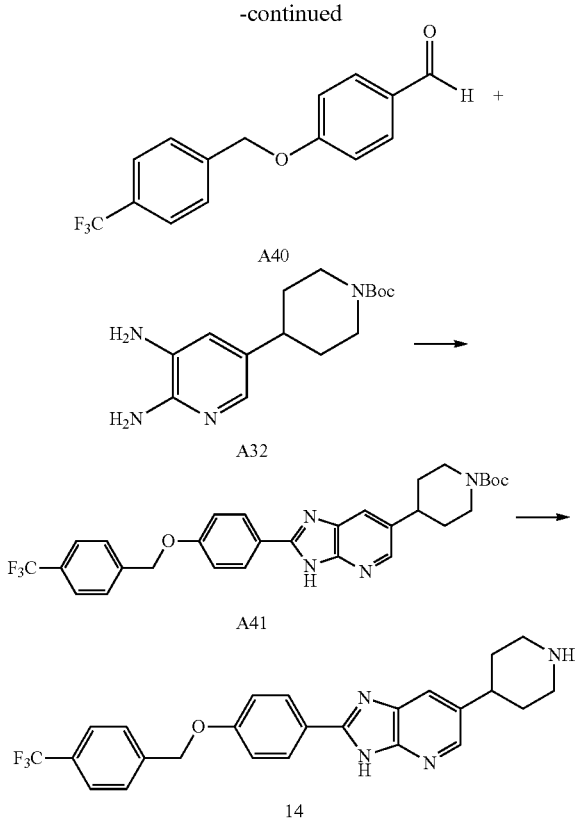

a) 4-((4-(Trifluoromethyl)benzyl)oxy)benzaldehyde (A40)

1-(Bromomethyl)-4-(trifluoromethyl)benzene (2.50 g, 10.4 mmol) was added to a suspension of 4-hydroxybenzaldehyde A7 (1.25 g, 10.2 mmol) and $K_2CO_3$ (2.12 g, 15.4 mmol) in acetonitrile (50 mL). The resulting mixture was stirred at room temperature for 18 hours. After this time, the suspension was filtered and the collected solids washed with acetonitrile (40 mL). The combined filtrates were evaporated in vacuo to give a solid residue which was suspended in petroleum benzine 40-60° C. (100 mL), the solid was collected via filtration, washed with petroleum benzine 40-60° C. (50 mL) and air dried to give the title compound (2.35 g, 82%) as an off-white solid. $^1$H NMR (400 MHz, CDCl$_3$) δ 9.90 (s, 1H), 7.92-7.79 (m, 2H), 7.67 (d, J=8.2 Hz, 2H), 7.56 (d, J=8.0 Hz, 2H), 7.13-7.04 (m, 2H), 5.22 (s, 2H). LCMS-A rt 6.87 min, m/z (positive ion) 281 [M+H].

b) tert-Butyl 4-(2-(4-((4-(trifluoromethyl)benzyl)oxy)phenyl)-3H-imidazo[4,5-b]pyridin-6-yl)piperidine-1-carboxylate (A41)

4-((4-(Trifluoromethyl)benzyl)oxy)benzaldehyde A40 (200 mg, 0.714 mmol) and tert-butyl 4-(5,6-diaminopyridin-3-yl)piperidine-1-carboxylate A32 (200 mg, 0.684 mmol) were heated at reflux in water (4 mL) for 17 hours. The reaction was evaporated to dryness and the residue dissolved in THF (4 mL). PhI(OAc)$_2$ (220 mg, 0.684 mmol) was added and stirred for 17 hours. The reaction mixture was concentrated in vacuo and the crude material was purified by column chromatography (silica cartridge, 15%-100% EtOAc in petroleum benzine 40-60° C.) to give the title compound (156 mg, 41%) as a pale yellow powder. $^1$H NMR (400 MHz, CDCl$_3$) δ 8.27 (d, J=1.9 Hz, 1H), 8.24 (d, J=1.9 Hz, 2H), 7.99 (d, J=1.9 Hz, 1H), 7.71 (d, J=8.1 Hz, 2H), 7.63 (d, J=8.0 Hz, 2H), 7.20 (d, J=8.9 Hz, 2H), 5.27 (s, 2H), 4.33 (s, 2H), 2.89 (m, 3H), 1.96 (d, J=12.0 Hz, 2H), 1.74 (s, 3H), 1.52 (s, 9H). LCMS-A rt 6.25 min, m/z (positive ion) 553 [M+H]$^+$.

c) 6-(Piperidin-4-yl)-2-(4-((4-(trifluoromethyl)benzyl)oxy)phenyl)-3H-imidazo[4,5-b]pyridine (14)

tert-Butyl 4-(2-(4-((4-(trifluoromethyl)benzyl)oxy)phenyl)-3H-imidazo[4,5-b]pyridin-6-yl)piperidine-1-carboxylate A41 (146 mg, 0.269 mmol) in DCM (4 mL) was treated with TFA (500 µL) and the resulting solution was stirred for 2 hours. 1 M aqueous NaOH (20 mL) and water (10 mL) were added and the mixture was extracted with EtOAc (2×50 mL). The combined organic layers were washed with water (25 mL), brine (25 mL), dried (Na$_2$SO$_4$), filtered and concentrated in vacuo. The crude material was dissolved in MeOH (3 mL) and loaded onto an SCX cartridge (10 g) which was washed with MeOH and the product eluted with 9:1 MeOH: aqueous NH$_4$OH. The product containing fractions were concentrated in vacuo to give the title compound (38 mg, 31%) as a colourless solid. $^1$H NMR (400 MHz, d$_6$-DMSO) δ 8.20 (br s, 1H), 8.15 (d, J=8.5 Hz, 2H), 7.78 (d, J=8.1 Hz, 2H), 7.76 (br s, 1H) 7.70 (d, J=8.0 Hz, 2H), 7.21 (d, J=8.4 Hz, 2H), 5.53 (s, 2H), 3.08 (d, J=12.0 Hz, 2H), 2.83-2.68 (m, 1H), 2.73-2.56 (m, 1H), 1.85-1.69 (d, J=12.1 Hz, 2H), 1.69-1.52 (m, 2H). LCMS-A rt 4.77 min, 94% purity; m/z (positive ion) 453 [M+H]$^+$, m/z (negative ion) 451 [M−H]$^-$.

Example 15: Synthesis of tert-butyl 3-(2-(4-(phenoxymethyl)phenyl)-3H-imidazo[4,5-b]pyridin-6-yl)piperidine-1-carboxylate (15)

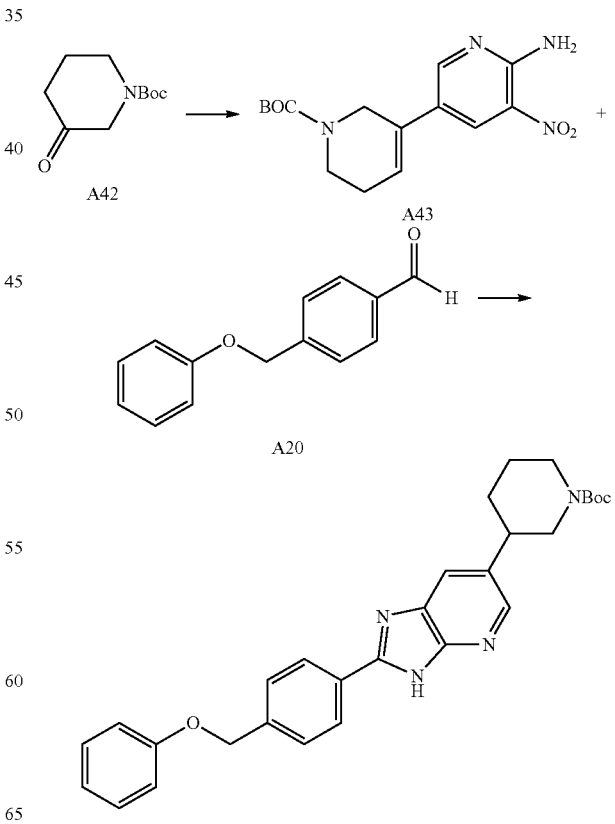

a) tert-Butyl 6'-amino-5'-nitro-5,6-dihydro-[3,3'-bipyridine]-(2H)-carboxylate (A43)

A solution of LiHMDS (1 M in toluene, 15.8 mL, 15.8 mmol) was added dropwise to a solution of 1-Boc-3-piperidone (3.00 g, 15.1 mmol) in dry THF (100 mL) at −78° C. under an atmosphere of nitrogen. The solution was then stirred at this temperature for 30 minutes, N-phenyl-bis(trifluoromethanesulfonimide) (5.92 g, 16.6 mmol) in dry THF (20 mL) was added and the reaction mixture was stirred at −78° C. for additional 15 minutes, and then at 0° C. for 2 hours. The reaction mixture was quenched with saturated aqueous NH$_4$Cl (10 mL), volatiles were removed in vacuo, EtOAc (200 mL) and saturated aqueous NH$_4$Cl (100 mL) were added, the layers were separated and the organic layer was washed with brine (100 mL), dried (Na$_2$SO$_4$), filtered and concentrated in vacuo to give a yellow gum. The residue was purified by silica gel chromatography (120 g silica Cartridge, 0-10% EtOAc in petroleum benzine 40-60° C.), fractions were combined and concentrated in vacuo to give the product (2.910 g, impure) as a pale yellow oil which solidified upon standing. The product was taken into next reaction without further purification.

To a solution of above intermediate (2.900 g) in dry 1,4-dioxane (40 mL) was added KOAc (1.804 g, 18.38 mmol), bis(pinacolato)diboron (2.334 g, 9.191 mmol) and the suspension was de-gassed with nitrogen gas. Dppf (0.173 g, 0.306 mmol) followed by PdCl$_2$(dppf) DCM solvate (0.253 g, 0.306 mmol) were added and the reaction was sealed and heated to 80° C. for 18 hours. The reaction was filtered through celite, which was washed with MeOH and EtOAc, the filtrates were combined and concentrated in vacuo to give a brown oil. The crude material was purified by silica gel chromatography (120 g silica Cartridge, 0-20% EtOAc in petroleum benzine 40-60° C.), fractions were combined and concentrated in vacuo to give the product (2.38 g, impure). A part of this material (0.711 g) and 5-bromo-3-nitropyridin-2-amine (0.167 g, 0.766 mmol) were dissolved in dry 1,4-dioxane (7 mL) and PdCl$_2$(dppf) DCM solvate (0.032 g, 0.038 mmol) followed by a solution of K$_2$CO$_3$ (0.318 g, 2.30 mmol) in water (0.766 mL) were added. The reaction mixture was then heated at 80° C. for 18 hours. The reaction mixture was filtered through celite, washed with EtOAc (5×20 mL) and then concentrated in vacuo to give a brown solid. The crude material was purified by silica gel chromatography (40 g silica Cartridge, 0-40% EtOAc in petroleum benzine 40-60° C.) to give the title compound (0.095 g, 7% over 3 steps) as a yellow solid. $^1$H NMR (400 MHz, d-DMSO) δ 8.56 (d, J=2.4 Hz, 1H), 8.23 (d, J=2.4 Hz, 1H), 7.96 (s, 2H), 6.38-6.30 (m, 1H), 4.17 (q, J=2.2 Hz, 2H), 3.45 (t, J=5.7 Hz, 2H), 2.28-2.19 (m, 2H), 1.43 (s, 9H). LCMS-A rt 6.48 min, m/z (positive ion) 321.2 [M+H]$^+$.

b) tert-Butyl 3-(2-(4-(phenoxymethyl)phenyl)-3H-imidazo[4,5-b]pyridin-6-yl)piperidine-1-carboxylate (15)

To tert-butyl 6'-amino-5'-nitro-5,6-dihydro-[3,3'-bipyridine]-1(2H)-carboxylate A43 (0.093 g, 0.29 mmol) and platinum(IV) oxide (0.010 g) under an atmosphere of nitrogen was added DIPEA (5 mL) followed by EtOH (2 mL). The reaction was stirred under an atmosphere of hydrogen (balloon) for 40 hours. The mixture was filtered through celite, and the celite was washed with EtOAc (5×20 mL). The combined filtrates were evaporated to give a grey solid. This material (0.103 g) and 4-(phenoxymethyl)-benzaldehyde A20 (0.060 g, 0.28 mmol) were dissolved in dry MeOH (5 mL) and activated 3 Å molecular sieves (0.200 g) were added. The reaction mixture was heated at reflux for 20 hours, cooled to room temperature, the solution was decanted from the sieves and the solvent was removed in vacuo. Tetahydrofuran (5 mL) followed by (diacetoxyiodo)benzene (0.208 g, 0.646 mmol) were added under an atmosphere of nitrogen and the reaction was stirred at room temperature for 3 hours. The reaction was concentrated in vacuo and diluted with EtOAc (100 mL) and saturated aqueous NaHCO$_3$ (100 mL). The layers were separated and the aqueous layer was extracted with EtOAc (100 mL), the combined organics were washed with brine (100 mL), dried (Na$_2$SO$_4$), filtered and concentrated in vacuo to give the crude product which was purified by silica gel chromatography (24 g silica Cartridge, 0-100% EtOAc in petroleum benzine 40-60° C.) to give the title compound (0.063 g, 46%) as a pale yellow solid. $^1$H NMR (400 MHz, d$_6$-DMSO) δ 13.40 (br s, 1H), 8.28 (d, J=2.0 Hz, 1H), 8.26-8.19 (m, 2H), 7.90 (s, 1H), 7.63 (d, J=8.1 Hz, 2H), 7.35-7.26 (m, 2H), 7.04 (d, J=8.0 Hz, 2H), 6.95 (t, J=7.3 Hz, 1H), 5.20 (s, 2H), 4.06-3.92 (m, 2H), 3.04-2.72 (m, 3H), 1.95 (d, J=12.1 Hz, 1H), 1.83-1.67 (m, 2H), 1.56-1.35 (m, 10H). LCMS-A rt 6.33 min, m/z (positive ion) 485.3 [M+H]$^+$.

Example 16: Synthesis of 2-(4-(phenoxymethyl)phenyl)-6-(piperidin-3-yl)-3H-imidazo[4,5-b]pyridine (16)

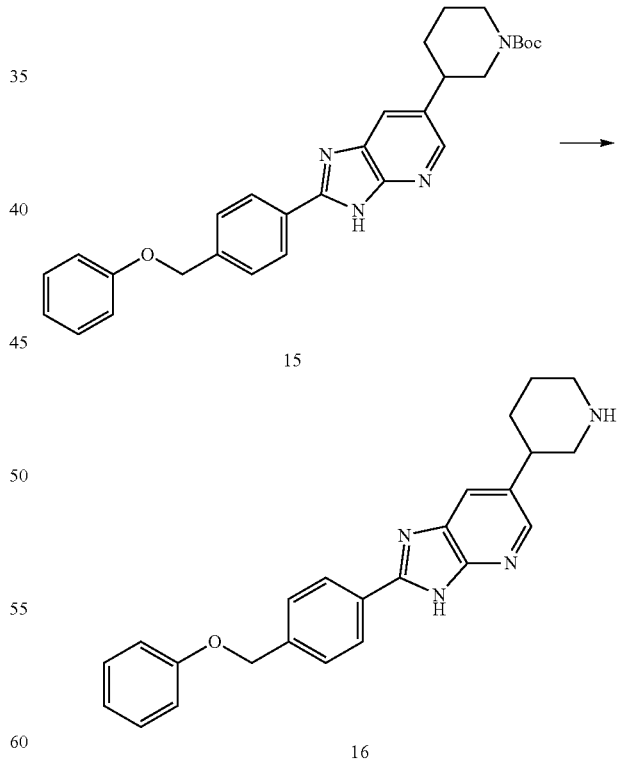

tert-Butyl 3-(2-(4-(phenoxymethyl)phenyl)-3H-imidazo[4,5-b]pyridin-6-yl)piperidine-1-carboxylate 15 (0.060 g, 0.12 mmol) was dissolved in DCM (10 mL) under an atmosphere of nitrogen and trifluoroacetic acid (0.284 mL, 3.71 mmol) was added and the resulting mixture was stirred at room temperature for 18 hours. The reaction mixture was concentrated in vacuo and the resulting solid was dissolved in EtOAc (70 mL) and 2 M aqueous NaOH (70 mL), the layers were separated and the aqueous layer was extracted with EtOAc (50 mL), the combined organics were washed with water (50 mL), brine (50 mL), dried ($Na_2SO_4$), filtered and concentrated in vacuo. The solid was suspended in DCM (~5 mL) and the solution was concentrated in vacuo to give the title compound (0.037 g, 78%) as a pale yellow solid. $^1$H NMR (400 MHz, $d_6$-DMSO) δ 8.28-8.15 (m, 3H), 7.83 (s, 1H), 7.63 (d, J=8.0 Hz, 2H), 7.31 (t, J=7.8 Hz, 2H), 7.04 (d, J=8.1 Hz, 2H), 6.95 (t, J=7.3 Hz, 1H), 5.19 (s, 2H), 3.05-2.91 (m, 2H), 2.77 (tt, J=10.7, 3.0 Hz, 1H), 2.66-2.52 (m, 2H, obscured by DMSO signal), 1.96-1.88 (m, 1H), 1.76-1.61 (m, 2H), 1.59-1.44 (m, 1H). NH protons not observed. LCMS-A rt 4.68 min, m/z (positive ion) 385.2 [M+H]$^+$.

Example 17: Synthesis 2-(4-(benzyloxy)phenyl)-5-chloro-3H-imidazo[4,5-b]pyridine (17)

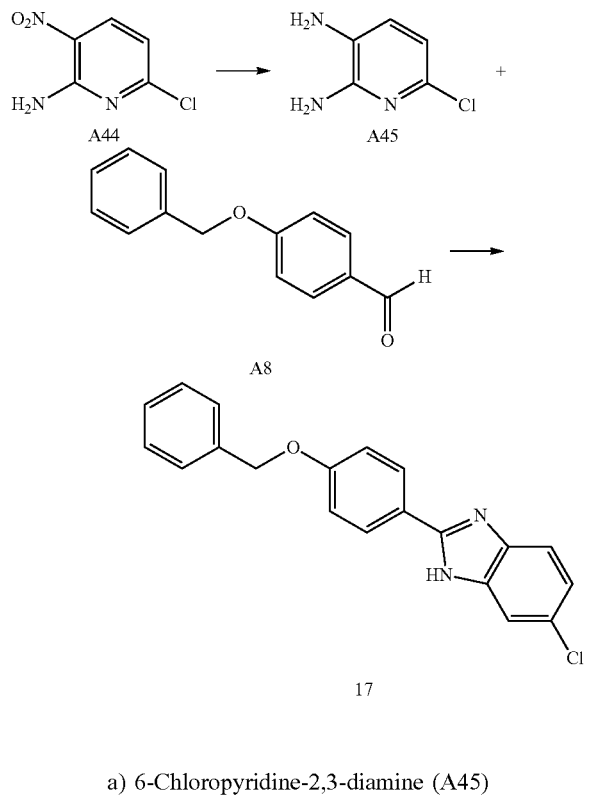

a) 6-Chloropyridine-2,3-diamine (A45)

Iron powder (9.65 g, 173 mmol) was added to a suspension of 6-chloro-3-nitropyridin-2-amine A44 (10.0 g, 57.6 mmol) and $NH_4Cl$ (6.16 g, 115 mmol) in isopropanol (180 mL) and water (90 mL). The resulting mixture was heated at 90° C. for one hour. After this time, the suspension was left to cool to room temperature, then diluted with EtOAc (100 mL), filtered through Celite and the residues washed with further EtOAc (2×150 mL). The filtrate was washed with water (3×100 mL), brine (100 mL), dried over $Na_2SO_4$ and the volatiles removed under reduced pressure to give the title compound (7.50 g, 91%) as a dark brown solid. $^1$H NMR (400 MHz, $d_6$-DMSO) δ 6.68 (d, J=7.8 Hz, 1H), 6.35 (d, J=7.8 Hz, 1H), 5.78 (s, 2H), 4.76 (s, 2H).

b) (4-(5-Chloro-3H-imidazo[4,5-b]pyridin-2-yl)phenyl)(phenyl)methanone (17)

A suspension of 6-chloropyridine-2,3-diamine A45 (1.00 g, 6.97 mmol) and 4-(benzyloxy)benzaldehyde A8 (1.48 g, 6.97 mmol) in MeOH (25 mL) was heated under microwave irradiation at 120° C. for 15 minutes. The volatiles were removed in vacuo and the residue dissolved in THF (50 mL). PhI(OAc)$_2$ (2.24 g, 6.97 mmol) was added and the resulting mixture stirred for 18 hours at room temperature. The volatiles were removed in vacuo, the residue suspended in saturated aqueous $NaHCO_3$ (100 mL) and filtered giving a brown solid which was washed with saturated aqueous $NaHCO_3$ (100 mL), water (100 mL) and diethyl ether (100 mL). The resulting solid was allowed to air dry for approx 72 hours to give the title compound (1.71 g, 73%) as a brown solid. $^1$H NMR (400 MHz, $d_6$-DMSO) b 8.15 (d, J=8.8 Hz, 2H), 7.97 (d, J=8.3 Hz, 1H), 7.52-7.47 (m, 2H), 7.45-7.39 (m, 2H), 7.38-7.32 (m, 1H), 7.24-7.19 (m, 3H), 5.21 (s, 2H).

Example 18: Synthesis of 2-(4-(benzyloxy)phenyl)-5-(piperidin-4-yloxy)-3H-imidazo[4,5-b]pyridine (18)

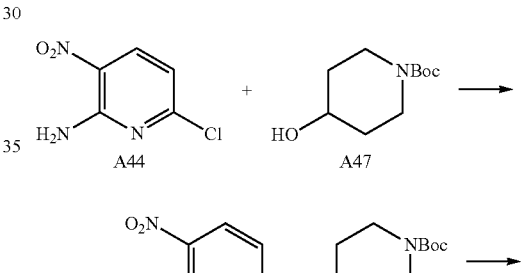

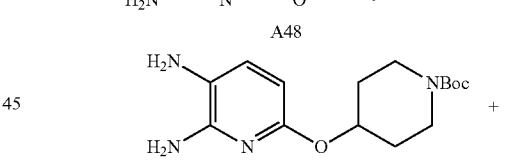

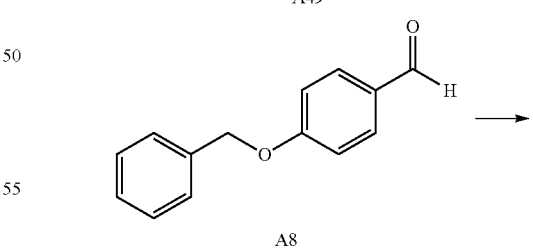

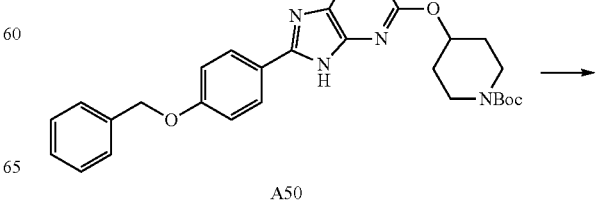

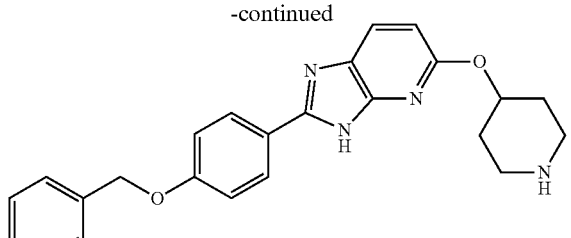

18 a) tert-Butyl 4-((6-amino-5-nitropyridin-2-yl)oxy)piperidine-1-carboxylate (A48)

tert-Butyl 4-hydroxypiperidine-1-carboxylate A47 (0.290 g, 1.44 mmol) was dissolved in dry DMF (7 mL) and NaH (60% dispersion in mineral oil, 0.086 g, 2.2 mmol) was added in one portion. After 10 minutes, 2-amino-6-chloro-3-nitropyridine A44 (0.250 g, 1.44 mmol) was added and the reaction mixture was stirred at room temperature for 18 hours. The reaction was quenched by addition of water (4 mL) and the mixture was diluted with saturated aqueous NaHCO$_3$ (30 mL) and EtOAc (50 mL). The layers were separated and the aqueous layer was extracted with EtOAc (3×40 mL), the combined organics were washed with brine (50 mL), dried (Na$_2$SO$_4$), filtered and concentrated in vacuo to give a yellow oily solid. The crude material was purified by silica gel chromatography (40 g silica cartridge, 0-40% EtOAc in petroleum benzine 40-60° C.) to give the title compound (0.157 g, 32%) as a yellow solid. $^1$H NMR (400 MHz, d$_6$-DMSO) δ 8.25 (d, J=9.1 Hz, 1H), 8.11 (s, 2H), 6.12 (d, J=9.1 Hz, 1H), 5.25-5.14 (m, 1H), 3.71-3.62 (m, 2H), 3.22-3.11 (m, 2H), 2.01-1.92 (m, 2H), 1.62-1.51 (m, 2H), 1.40 (s, 9H). LCMS-A rt 6.75 min; no product ions detected.

b) tert-Butyl 4-((5,6-diaminopyridin-2-yl)oxy)piperidine-1-carboxylate (A49)

Iron powder (0.128 g, 2.29 mmol) followed by NH$_4$Cl (0.123 g, 2.29 mmol) were added to a stirred suspension of tert-butyl 4-((6-amino-5-nitropyridin-2-yl)oxy)piperidine-1-carboxylate A48 (0.155 g, 0.458 mmol) in isopropanol (6 mL) and water (3 mL) at room temperature. The reaction was heated to 70° C. and stirred at this temperature for 2 hours, then cooled and filtered through a plug of celite which was washed with EtOAc (100 mL). The filtrate was washed with saturated aqueous NaHCO$_3$ (50 mL), brine (100 mL), dried (Na$_2$SO$_4$), filtered and concentrated in vacuo to give the title compound (0.130 g, 92%) as a brown glassy solid. $^1$H NMR (400 MHz, d$_6$-DMSO) δ 6.72 (d, J=7.9 Hz, 1H), 5.77 (d, J=7.9 Hz, 1H), 5.29 (s, 2H), 4.88-4.78 (m, 1H), 4.09 (s, 2H), 3.66-3.57 (m, 2H), 3.18-3.06 (m, 2H), 1.89-1.78 (m, 2H), 1.52-1.35 (m, 11H). LCMS-A rt 4.90 min, m/z (positive ion) 309.2 [M+H]$^+$.

c) tert-Butyl 4-((2-(4-(benzyloxy)phenyl)-3H-imidazo[4,5-b]pyridin-5-yl)oxy)piperidine-1-carboxylate (A50)

tert-Butyl 4-((5,6-diaminopyridin-2-yl)oxy)piperidine-1-carboxylate A49 (0.126 g, 0.409 mmol) and 4-(benzyloxy)benzaldehyde A8 (0.104 g, 0.490 mmol) were suspended in water (10 mL) and MeOH (2 mL) and the reaction mixture was heated at reflux for 20 hours then cooled to room temperature and the solvent was removed in vacuo. Tetrahydrofuran (10 mL) followed by (Diacetoxyiodo)benzene (0.132 g, 0.409 mmol) were added under an atmosphere of nitrogen and the mixture was stirred at room temperature for 3 hours. The reaction was concentrated in vacuo and diluted with EtOAc (100 mL) and saturated aqueous NaHCO$_3$ (100 mL). The layers were separated and the aqueous layer was extracted with EtOAc (100 mL), the combined organics were washed with brine (100 mL), dried (Na$_2$SO$_4$), filtered and concentrated in vacuo to give the crude product which was purified by silica gel chromatography (40 g silica cartridge, 0-40% EtOAc in petroleum benzine 40-60° C.) to give the title compound (0.106 g, 52%) as a pale yellow foam. $^1$H NMR (400 MHz, d$_6$-DMSO) δ 13.21 (brs, 1H), 8.10 (d, J=8.9 Hz, 2H), 7.99-7.78 (m, 1H), 7.49 (d, J=7.0 Hz, 2H), 7.46-7.38 (m, 2H), 7.38-7.32 (m, 1H), 7.17 (d, J=8.6 Hz, 2H), 6.63 (d, J=8.5 Hz, 1H), 5.20 (s, 3H), 3.75 (dt, J=9.5, 4.4 Hz, 2H), 3.19 (s, 2H), 2.08-1.96 (m, 2H), 1.66-1.53 (m, 2H), 1.42 (s, 9H). LCMS-A rt 6.23 min, m/z (positive ion) 501.3 [M+H]$^+$.

d) 2-(4-(Benzyloxy)phenyl)-5-(piperidin-4-yloxy)-3H-imidazo[4,5-b]pyridine (18)

tert-Butyl 4-((2-(4-(benzyloxy)phenyl)-3H-imidazo[4,5-b]pyridin-5-yl)oxy)piperidine-1-carboxylate A50 (0.106 g, 0.212 mmol) was dissolved in DCM (7 mL) under an atmosphere of nitrogen, trifluoroacetic acid (0.486 mL, 6.35 mmol) was added and the resulting mixture was stirred at room temperature for 20 hours. The reaction mixture was concentrated in vacuo and the resulting solid was dissolved in EtOAc (70 mL) and 2 M aqueous NaOH (70 mL), the layers were separated and the aqueous layer was extracted with EtOAc (50 mL), the combined organics were washed with brine (50 mL), dried (Na$_2$SO$_4$), filtered and concentrated in vacuo. The solid was dissolved in DCM (~5 mL) and MeOH (~2 mL) and the solution was concentrated in vacuo to give the title compound (0.075 g, 88%) as a pale yellow solid. $^1$H NMR (400 MHz, d$_6$-DMSO) δ 8.12-8.03 (m, 2H), 7.85 (d, J=7.0 Hz, 1H), 7.51-7.45 (m, 2H), 7.45-7.38 (m, 2H), 7.38-7.31 (m, 1H), 7.16 (d, J=8.7 Hz, 2H), 6.59 (d, J=8.5 Hz, 1H), 5.19 (s, 2H), 5.10-4.98 (m, 1H), 2.98 (dt, J=12.4, 3.8 Hz, 2H), 2.63-2.54 (m, 2H), 2.05-1.94 (m, 2H), 1.57-1.43 (m, 2H). LCMS-A rt 4.67 min, m/z (positive ion) 401.3 [M+H]$^+$.

Example 19: Synthesis of 4-(2-(4-(benzyloxy)phenyl)-3H-imidazo[4,5-b]pyridin-5-yl)morpholine (19)

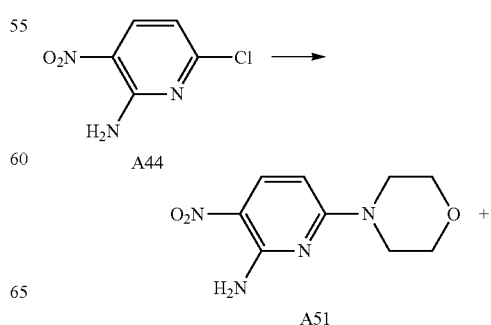

-continued

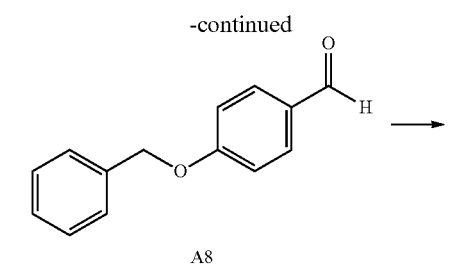

A8

19 a) 6-Morpholino-3-nitropyridin-2-amine (A51)

Potassium tert-butoxide (178 mg, 1.58 mmol), THF (10 mL) and morpholine (0.150 mL, 1.73 mmol) were stirred at room temperature for five minutes, then 6-chloro-3-nitropyridin-2-amine A44 (250 mg, 1.44 mmol) was added and the orange-red mixture stirred at room temperature for 18 hours. The mixture was poured into water (140 mL), the precipitate collected by filtration and air dried. Purification by column chromatography (40 g silica cartridge, 5-100% EtOAc/hexanes) gave the title compound (166 mg, 51%) as a yellow solid. $^1$H NMR (400 MHz, CDCl$_3$) δ 8.20 (d, J=9.4 Hz, 1H), 7.95 (br s, 1H), 6.05 (d, J=9.4 Hz, 1H), 5.57 (br s, 1H), 3.80-3.74 (m, 4H), 3.73-3.66 (m, 4H). LCMS-A: rt 5.38 min; m/z (positive ion) 225.2 [M+H]$^+$.

b) 4-(2-(4-(Benzyloxy)phenyl)-3H-imidazo[4,5-b]pyridin-5-yl)morpholine (19)

A mixture of 6-morpholino-3-nitropyridin-2-amine A51 (165 mg, 0.74 mmol) and 2:1 MeOH:THF (9 mL) was cooled to 0° C. and NiCl$_2$.6H$_2$O (18 mg, 10 mol %) was added. NaBH$_4$ (139 mg, 3.68 mmol) was added in portions (3 portions, 5 minutes apart). After all the NaBH$_4$ was added, stirring was continued at 0° C. for ten minutes, and the mixture was quenched with saturated aqueous NH$_4$Cl (10 mL). The volatile solvents were removed in vacuo, the residue diluted with water (20 mL) and extracted with EtOAc (3×30 mL). The combined EtOAc phases were washed with 5% w/v tetrasodium EDTA solution (50 mL), brine (50 mL) dried over Na$_2$SO$_4$, filtered and evaporated to give a dark solid residue (97 mg). The dark solid residue, 4-(benzyloxy)benzaldehyde A8 (106 mg, 0.50 mmol) and EtOH (20 mL) were heated at reflux under air. After 18 hours the mixture was concentrated and the residue purified by chromatography (12 g silica cartridge, 0-100% EtOAc/hexanes) to give the title compound (31 mg, 16%) as an off-white solid. $^1$H NMR (400 MHz, d$_6$-DMSO) δ 12.89 (br s, 1H), 8.09-8.04 (m, 2H), 7.78 (d, J=8.7 Hz, 1H), 7.50-7.45 (m, 2H), 7.44-7.38 (m, 2H), 7.37-7.32 (m, 1H), 7.14 (d, J=8.9 Hz, 2H), 6.76 (d, J=8.9 Hz, 1H), 5.18 (s, 2H), 3.78-3.71 (m, 4H), 3.47-3.43 (m, 4H). LCMS-A: 4.96 min; m/z (positive ion) 387.2 [M+H]; 385.2 [M−H]$^−$.

Example 20: Synthesis of 2-(4-(benzyloxy)phenyl)-N-(1H-pyrazol-4-yl)-3H-imidazo[4,5-b]pyridin-5-amine (20)

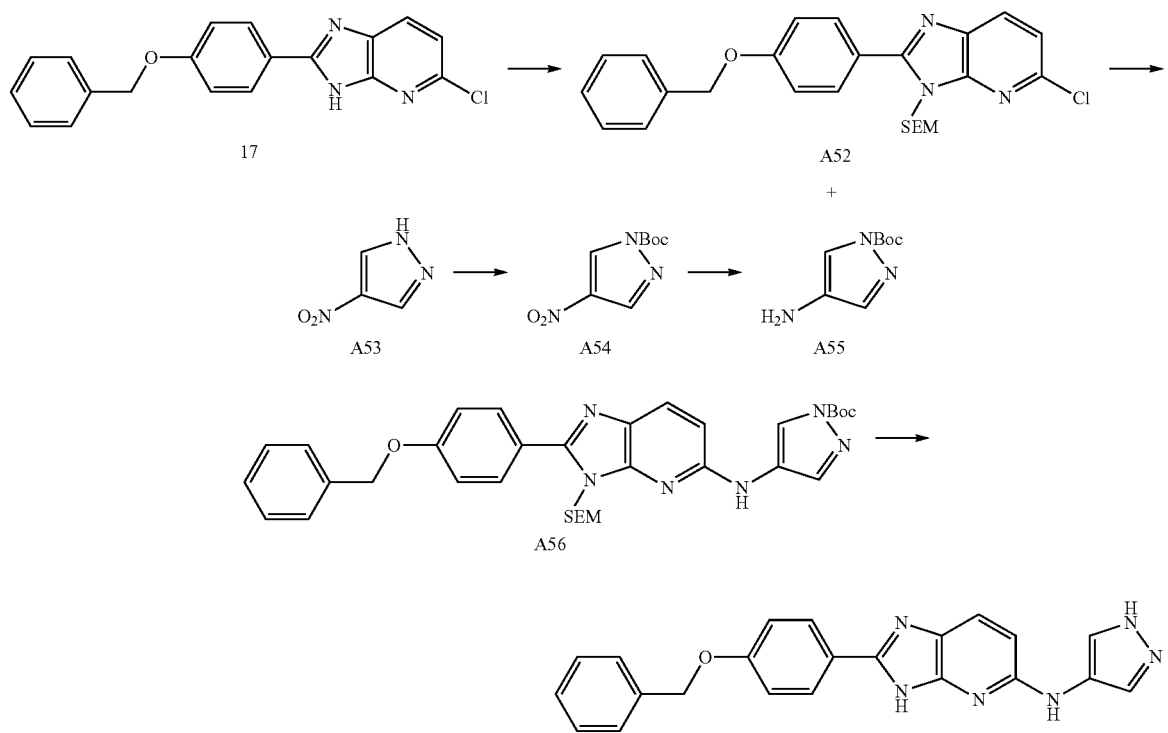

a) 2-(4-(Benzyloxy)phenyl)-5-chloro-3-((2-(trimethylsilyl)ethoxy)methyl)-3H-imidazo[4,5-b]pyridine (A52)

NaH (60% dispersion in oil, 71 mg, 1.8 mmol) was added to a stirred solution of 2-(4-(benzyloxy)phenyl)-5-chloro-3H-imidazo[4,5-b]pyridine 17 (500 mg, 1.49 mmol) in THF (6 mL) and DMF (3 mL) at room temperature under nitrogen. The resulting brown solution was stirred for 30 minutes, SEM-Cl (395 µL, 2.23 mmol) was added dropwise and the solution was stirred for 1 hour. Water (20 mL) and EtOAc (50 mL) were added and the layers were separated. The aqueous layer was extracted with DCM (50 mL). The combined organic layers were washed with water (25 mL): saturated brine (25 mL), dried over $MgSO_4$, filtered and concentrated in vacuo. The crude material was purified by column chromatography (40 g silica cartridge, 5%-50% EtOAc in petroleum benzine 40-60° C.) to give the title compound (330 mg, 47%) as a pale yellow solid. $^1$H NMR (400 MHz, $CDCl_3$) δ 8.08 (d, J=8.8 Hz, 2H), 7.98 (d, J=8.3 Hz, 1H), 7.49-7.44 (m, 2H), 7.44-7.38 (m, 2H), 7.38-7.34 (m, 1H), 7.26 (d, J=8.3 Hz, 1H), 7.13 (d, J=8.8 Hz, 2H), 5.64 (s, 2H), 5.16 (s, 2H), 3.97-3.79 (m, 2H), 1.16-0.87 (m, 2H), 0.00 (s, 9H).

b) tert-Butyl 4-nitro-1H-pyrazole-1-carboxylate (A54)

DMAP (0.540 g, 4.42 mmol) was added to a suspension of 4-nitro-1H-pyrazole A53 (2.50 g, 22.1 mmol) and Boc anhydride (4.83 g, 22.1 mmol) in DCM (150 mL). The resulting reaction mixture slowly went into solution and was allowed to stir for 20 hours at room temperature. The reaction mixture was washed with water (100 mL), brine (100 mL), dried (phase separation cartridge) and concentrated under reduced pressure to give a pale yellow foam. This residue was purified by silica gel chromatography (2×40 g silica cartridges eluting with 0-75% EtOAc in petroleum benzine 40-60° C.) to give the title compound (3.72 g, 79%) as a white solid. $^1$H NMR (400 MHz, $CDCl_3$) δ 8.78 (d, J=0.6 Hz, 1H), 8.22 (d, J=0.4 Hz, 1H), 1.68 (s, 9H). LCMS-A rt 5.30 min; no product ions detected.

c) tert-Butyl 4-amino-1H-pyrazole-1-carboxylate (A55)

A suspension of tert-butyl 4-nitro-1H-pyrazole-1-carboxylate A54 (3.70 g, 17.4 mmol) and 10% Pd/C wetted with ca. 53% water (0.300 g) in EtOH (150 mL) were stirred under hydrogen (1 atm) at room temperature for 20 hours. The reaction mixture was then filtered through celite, the plug was washed with EtOAc (ca. 100 mL) and the filtrate concentrated under reduced pressure to give the title compound (3.09 g, 97%) as a pale brown solid. $^1$H NMR (400 MHz, $CDCl_3$) δ 7.54 (d, J=0.6 Hz, 1H), 7.40 (d, J=0.8 Hz, 1H), 3.10 (s, 2H), 1.62 (s, 9H). LCMS-A rt 3.75 min; no product ions detected.

d) tert-Butyl 4-((2-(4-(benzyloxy)phenyl)-3-((2-(trimethylsilyl)ethoxy)methyl)-3H-imidazo[4,5-b]pyridin-5-yl)amino)-1H-pyrazole-1-carboxylate (A56)

A flask containing a suspension of 2-(4-(benzyloxy)phenyl)-5-chloro-3-((2-(trimethylsilyl)ethoxy)methyl)-3H-imidazo[4,5-b]pyridine A52 (51.3 mg, 133 µmol), tert-butyl 4-amino-1H-pyrazole-1-carboxylate A55 (24.5 mg, 133 µmol), chloro[2-(dicyclohexylphosphino)-3,6-dimethoxy-2',4',6'-triisopropyl-1,1'-biphenyl][2-(2-aminoethyl)phenyl]palladium(II) (10.4 mg, 13 µmol) and $K_2CO_3$ (36.5 mg, 264 µmol) in t-BuOH (1 mL) was evacuated and purged with nitrogen three times. The suspension was heated at 85° C. for 3 hours and then cooled to room temperature. EtOAc (10 mL) and water (5 mL) were added and the layers separated. The aqueous layer was extracted with EtOAc (5 mL), the combined organic layers were dried with $Na_2SO_4$, filtered and concentrated in vacuo. The crude reaction mixture was purified by column chromatography (12 g silica cartridge, 10-100% EtOAc in petroleum benzine 40-60° C.) to give the title compound (48.5 mg, 71%) as a pale yellow oil. $^1$H NMR (400 MHz, $CDCl_3$) δ 8.73 (d, J=0.9 Hz, 1H), 8.06 (d, J=8.8 Hz, 2H), 7.86 (d, J=8.5 Hz, 1H), 7.80 (d, J=0.9 Hz, 1H), 7.46 (m, 2H), 7.44-7.37 (ddd, J=8.0, 6.9, 1.0 Hz, 2H), 7.35 (d, J=7.2 Hz, 1H), 7.11 (d, J=8.8 Hz, 2H), 6.83 (s, 1H), 6.61 (d, J=8.6 Hz, 1H), 5.64 (s, 2H), 5.14 (s, 2H), 4.01-3.83 (m, 2H), 1.68 (s, 9H), 1.19-0.92 (m, 2H), −0.09 (s, 9H). LCMS-B rt 4.01 min; no product ions detected.

e) 4-((2-(4-(Benzyloxy)phenyl)-3-((2-(trimethylsilyl)ethoxy)methyl)-3H-imidazo[4,5-b]pyridin-5-yl)amino)-1H-pyrazole (20)

tert-Butyl 4-((2-(4-(benzyloxy)phenyl)-3-((2-(trimethylsilyl)ethoxy)methyl)-3H-imidazo[4,5-b]pyridin-5-yl)amino)-1H-pyrazole-1-carboxylate A56 (48.5 mg, 79.1 µmol) was dissolved in $CDCl_3$ (2 mL) and TFA (1 mL) and was stirred for 18 hours at room temperature. The reaction mixture was concentrated in vacuo and purified by column chromatography (12 g silica cartridge, 2-10% (10% $Et_3N$ in MeOH) in EtOAc) to give the title compound (10.5 mg, 34%) as a pale yellow solid. $^1$H NMR (400 MHz, $CD_3OD$) δ 8.07-7.80 (m, 4H), 7.69 (d, J=8.7 Hz, 1H), 7.46 (d, J=7.0 Hz, 2H), 7.39 (t, J=7.5 Hz, 2H), 7.33 (d, J=5.9 Hz, 1H), 7.13 (d, J=8.9 Hz, 2H), 6.61 (d, J=8.7 Hz, 1H), 5.17 (s, 2H); LCMS-B rt 2.99 min, m/z (positive ion) 383 [M+H]$^+$, m/z (negative ion) 381 [M−H]$^−$.

Example 21: Synthesis of 1-(2-(4-(benzyloxy)phenyl)-3H-imidazo[4,5-b]pyridin-5-yl)piperazin-2-one (21)

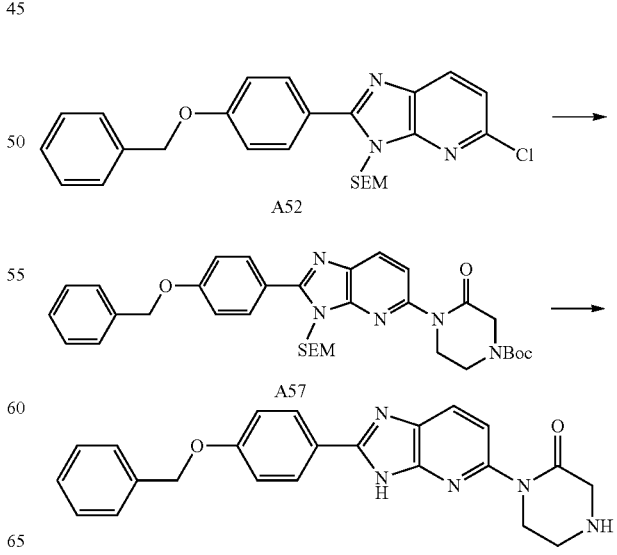

a) tert-Butyl 4-(2-(4-(benzyloxy)phenyl)-3-((2-(trimethylsilyl)ethoxy)methyl)-3H-imidazo[4,5-b]pyridin-5-yl)-3-oxopiperazine-1-carboxylate (A57)

A suspension of 2-(4-(benzyloxy)phenyl)-5-chloro-3-((2-(tri methylsilyl)ethoxy)methyl)-3H-imidazo[4,5-b]pyridine A52 (50 mg, 0.11 mmol), N-Boc-3-oxopiperazine (43 mg, 0.22 mmol), Ruphos (2.5 mg, 0.0054 mmol), chloro-(2-dicyclohexylphosphino-2',6'-diisopropoxy-1, 1'-biphenyl)[2-(2-aminoethyl)phenyl]palladium(II)-methyl-t-butyl ether adduct (4.4 mg, 0.0054 mmol) and Cs$_2$CO$_3$ (42 mg, 0.13 mmol) in t-BuOH (1 mL) was evacuated and purged with nitrogen three times. The suspension was heated at 85° C. for 3 hours. The reaction was cooled to room temperature and left overnight. The reaction mixture was filtered and the residue purified by column chromatography twice (4 g silica cartridge, then 12 g silica cartridge, 12-100% EtOAc in petroleum benzine 40-60° C.) to give the title compound (5.0 mg, 7%) as a pale colourless oil. $^1$H NMR (400 MHz, CDCl$_3$) δ 8.14-8.01 (m, 3H), 7.84 (d, J=8.5 Hz, 1H), 7.49-7.44 (m, 2H), 7.44-7.38 (m, 2H), 7.38-7.32 (m, 1H), 7.13 (d, J=8.8 Hz, 2H), 5.61 (s, 2H), 5.16 (s, 2H), 4.32 (s, 2H), 4.23-4.04 (m, 2H), 3.96-3.65 (m, 4H), 1.51 (s, 9H), 1.02 (dd, J=8.8, 7.7 Hz, 2H), −0.01 (s, 9H); LCMS-A rt 7.65 min; m/z (positive ion) 630 [M+H]$^+$.

b) 1-(2-(4-(Benzyloxy)phenyl)-3H-imidazo[4,5-b]pyridin-5-yl)piperazin-2-one (21)

tert-Butyl 4-(2-(4-(benzyloxy)phenyl)-3-((2-(trimethylsilyl)ethoxy)methyl)-3H-imidazo[4,5-b]pyridin-5-yl)-3-oxopiperazine-1-carboxylate A57 (5.0 mg, 7.9 μmol) was dissolved in DCM (400 μL) and TFA (200 μL) for 18 hours at room temperature. The reaction mixture was treated with 2% NaOH (3 mL) and the volatiles removed in vacuo. The aqueous layer was extracted with EtOAc (3×5 mL). The combined organic layers were washed with brine (3 mL), dried over Na$_2$SO$_4$, filtered and concentrated in vacuo to give the title compound (2.0 mg, 63%) as a colourless solid. $^1$H NMR (400 MHz, CD$_3$OD) δ 8.07 (d, J=8.9 Hz, 2H), 8.00-7.90 (m, 1H), 7.54 (d, J=8.4 Hz, 1H), 7.51-7.44 (m, 2H), 7.44-7.36 (m, 2H), 7.36-7.29 (m, 1H), 7.18 (d, J=8.9 Hz, 2H), 5.20 (s, 2H), 4.00 (t, J=5.5 Hz, 2H), 3.63 (s, 2H), 3.23 (t, J=5.5 Hz, 2H). LCMS-B rt 2.94 min; m/z (positive ion) 400 [M+H]$^+$; m/z (negative ion) 398 [M−H]$^−$.

General Method A:

A solution of 2-amino-6-chloro-3-nitropyridine A44 (1 equiv), amine (1.2 equiv) and diisopropylethylamine (2 equiv) in DMF (10 mL/g) was heated at 80° C. for 45 minutes or until the reaction had gone to completion as judged by TLC or LCMS. The reaction was cooled to room temperature and treated with water (20 mL/g). The product was collected by vacuum filtration and washed with water until the liquors ran clear. The product was dried under vacuum.

General Method B:

1 M Na$_2$S$_2$O$_4$ solution (3 equiv.) was added to a suspension of 4-(benzyloxy)benzaldehyde A8 (1.1 equiv) and the 2-amino-3-nitropyridine (1 equiv) in EtOH (40 mL/g). The resulting yellow suspension was heated to 70° C. or 110° C. for 15 minutes in a microwave. The reaction was cooled to room temperature, 5 M aqueous NH$_4$OH (10 mL/g) was added and the reaction mixture was stirred for 5 minutes at room temperature. The suspension was filtered to give the desired product or partitioned between water (50 mL) and EtOAc (50 mL). The aqueous layer was extracted with EtOAc (50 mL). The combined organic layers were washed with water (30 mL), saturated brine (30 mL), dried over Na$_2$SO$_4$, filtered and concentrated in vacuo. The crude product was further purified by column chromatography (silica cartridge) if necessary.

Example 22: Synthesis of N-(2-((2-(4-(benzyloxy)phenyl)-3H-imidazo[4,5-b]pyridin-5-yl)amino)ethyl)acetamide (22)

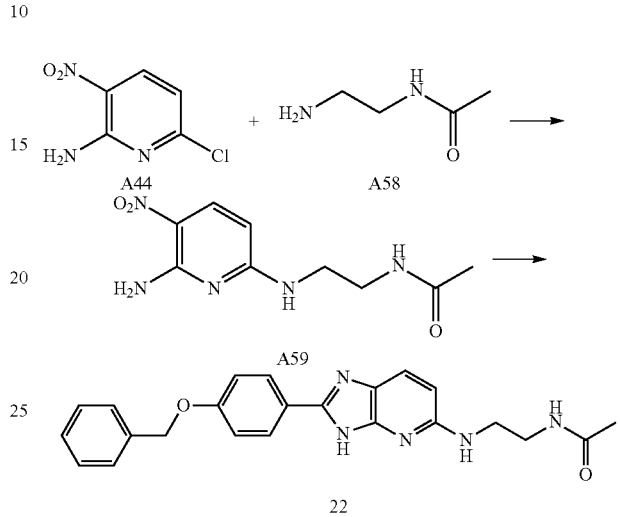

a) N-(2-((6-Amino-5-nitropyridin-2-yl)amino)ethyl)acetamide (A59)

General Method A: 2-amino-6-chloro-3-nitropyridine A44 (500 mg, 2.88 mmol), N-(2-aminoethyl)acetamide (346 mg, 3.46 mmol). The title compound (530 mg, 77%) was isolated as a yellow solid. LCMS-B rt 2.69 min, m/z (positive ion) 240 [M+H]$^+$.

b) N-(2-((2-(4-(Benzyloxy)phenyl)-3H-imidazo[4,5-b]pyridin-5-yl)amino)ethyl)acetamide (22)

General Method B: N-(2-((6-amino-5-nitropyridin-2-yl)amino)ethyl)acetamide A59 (100 mg, 0.418 mmol). Isolated the title compound (12.0 mg, 7%) as a colourless powder. $^1$H NMR (400 MHz, CD$_3$OD) δ 7.95 (d, J=8.3 Hz, 2H), 7.61 (d, J=8.6 Hz, 1H), 7.52-7.43 (m, 2H), 7.43-7.35 (m, 2H), 7.35-7.28 (m, 1H), 7.13 (d, J=8.9 Hz, 2H), 6.45 (d, J=8.7 Hz, 1H), 5.17 (s, 2H), 3.53 (t, J=5.9 Hz, 2H), 3.3.43 (t, J=6.0 Hz, 2H), 1.94 (s, 3H); LCMS-B rt 2.97 min; m/z (positive ion) 402; m/z (negative ion) 400.

Example 23: Synthesis of 4-(2-(4-(benzyloxy)phenyl)-3H-imidazo[4,5-b]pyridin-5-yl)thiomorpholine (23)

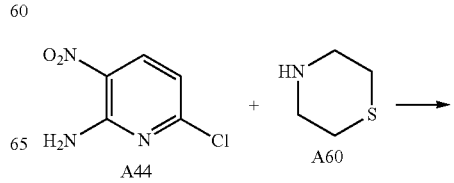

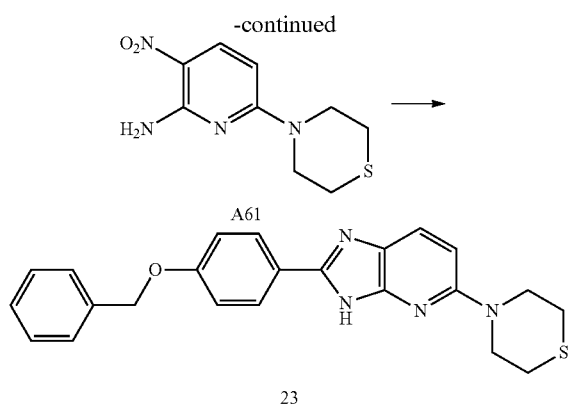

a) 3-Nitro-6-thiomorpholinopyridin-2-amine (A61)

General Method A: 2-amino-6-chloro-3-nitropyridine A44 (500 mg, 2.88 mmol), thiomorpholine A60 (356 mg, 3.46 mmol). Isolated the title compound (615 mg, 88%) as a yellow powder. LCMS-B rt 3.24 min, m/z (positive ion) 241 [M+H]$^+$.

b) 4-(2-(4-(Benzyloxy)phenyl)-3H-imidazo[4,5-b]pyridin-5-yl)thiomorpholine (23)

General Method B: 3-nitro-6-thiomorpholinopyridin-2-amine A61 (200 mg, 0.832 mmol). Isolated the title compound (145 mg, 44%) as a colourless powder. $^1$H NMR (400 MHz, d$_6$-DMSO) δ 8.06 (d, J=8.9 Hz, 2H), 7.89-7.67 (br, d, J=8.8 Hz, 1H), 7.52-7.45 (m, 2H), 7.41 (t, J=7.3 Hz, 2H), 7.37-7.29 (m, 1H), 7.19-7.08 (d, J=8.3 Hz, 3H), 6.75 (d, J=8.8 Hz, 1H), 5.18 (s, 2H), 4.04-3.79 (m, 4H), 2.72-2.57 (m, 4H). LCMS-B rt 3.18 min; m/z (positive ion) 403 [M+H]$^+$; m/z (negative ion) 401 [M-H]$^-$.

Example 24: Synthesis of 4-(2-(4-(benzyloxy)phenyl)-3H-imidazo[4,5-b]pyridin-5-yl)thiomorpholine 1-oxide (24)

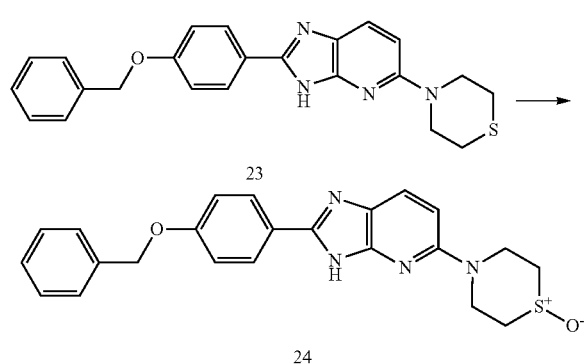

4-(2-(4-(benzyloxy)phenyl)-3H-imidazo[4,5-b]pyridin-5-yl)thiomorpholine 23 (44.2 mg, 0.110 mmol) was dissolved in DCM (5 mL) and mCPBA (25 mg, 0.10 mmol) was added at room temperature. The solution was stirred for 10 minutes, Ca(OH)$_2$ (13 mg, 0.18 mmol) was added to give a light, cloudy suspension. The suspension was stirred for 1 hour. The mixture was filtered and the residue washed with DCM (3×10 mL) and the filtrate concentrated in vacuo. The crude material was purified by column chromatography (4 g silica cartridge, 80-100% EtOAc:petroleum benzine 40-60° C. then 0-20% MeOH:EtOAc) to give a 2:1 mixture of products. Water (10 mL) was added to the NMR sample (in d$_6$-DMSO) which was extracted with DCM (2×10 mL) to remove the minor impurity. The product was extracted from the cloudy aqueous layer using EtOAc (2×20 mL). The combined EtOAc organic layers were washed with water (20 mL), brine (20 mL), dried over MgSO$_4$ and concentrated to give the title compound (1.4 mg, 3%) as a pale yellow solid. $^1$H NMR (400 MHz, CD$_3$OD) δ 7.98 (d, J=8.8 Hz, 2H), 7.79 (d, J=8.8 Hz, 1H), 7.51-7.44 (m, 2H), 7.42-7.35 (m, 2H), 7.35-7.30 (m, 1H), 7.14 (d, J=8.9 Hz, 2H), 6.91 (d, J=8.9 Hz, 1H), 5.18 (s, 2H), 4.44-3.93 (m, 4H), 3.19-2.94 (ddd, J=13.7, 9.4, 4.2 Hz, 2H), 2.91-2.70 (dt, J=14.2, 2.7 Hz, 2H); LCMS-B rt 2.97 min; m/z (positive ion) 419 [M+H]$^+$; m/z (negative ion) 417 [M-H]$^-$.

Example 25: Synthesis of 4-(2-(4-(benzyloxy)phenyl)-3H-imidazo[4,5-b]pyridin-5-yl)thiomorpholine 1,1-dioxide (25)

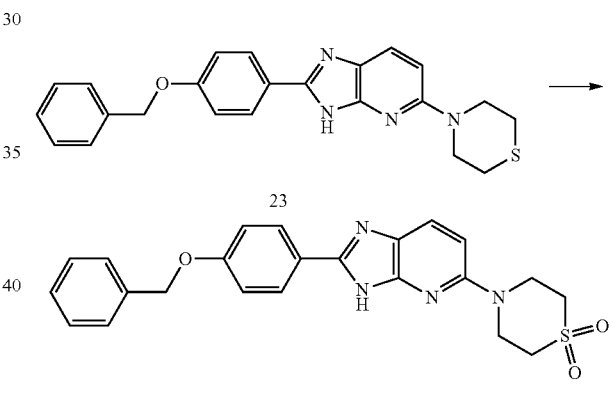

4-(2-(4-(Benzyloxy)phenyl)-3H-imidazo[4,5-b]pyridin-5-yl)thiomorpholine 23 (50 mg, 0.12 mmol) was dissolved in DCM (5 mL). mCPBA (67 mg, 0.27 mmol) was added at 0° C. and warmed to room temperature. The solution was stirred for 5 minutes, Ca(OH)$_2$ (20 mg, 0.27 mmol) was added to give a light, cloudy suspension. The mixture was filtered and the residue washed with DCM (3×10 mL). The combined filtrates were washed with 2 M aqueous Na$_2$CO$_3$ (2×20 mL), brine (20 mL) and concentrated in vacuo to give a cream coloured solid. The crude material was purified by column chromatography (12 g silica cartridge, 50%-100% EtOAc: petroleum benzine 40-60° C.) to give the title compound as a colourless solid (2.3 mg, 4%); $^1$H NMR (400 MHz, CD$_3$OD) (8.00 (d, J=8.9 Hz, 2H), 7.83 (d, J=8.7 Hz, 1H), 7.55-7.45 (m, 2H), 7.44-7.37 (ddd, J=7.9, 7.0, 1.0 Hz, 2H), 7.37-7.30 (d, J=7.2 Hz, 1H), 7.16 (d, J=8.9 Hz, 2H), 6.95 (d, J=8.8 Hz, 1H), 5.19 (s, 2H), 4.23 (d, J=5.0 Hz, 4H), 3.16 (m, 4H); LCMS-B rt 3.05 min; m/z (positive ion) 435 [M+H]$^+$.

Example 26: Synthesis of 2-(4-(benzyloxy)phenyl)-5-(4-methylpiperazin-1-yl)-3H-imidazo[4,5-b]pyridine (26)

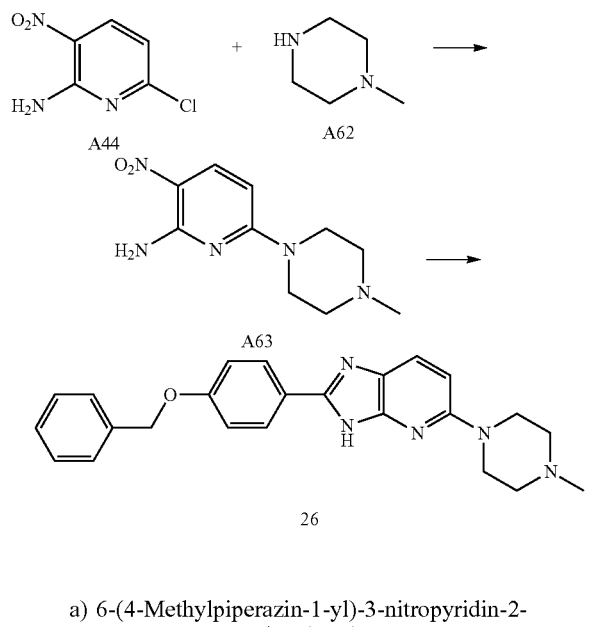

a) 6-(4-Methylpiperazin-1-yl)-3-nitropyridin-2-amine (A63)

General Method A: 2-amino-6-chloro-3-nitropyridine A44 (200 mg, 1.15 mmol), N-methylpiperidine (179 mg, 0.754 mmol). Isolated the title compound (179 mg, 65%) as a yellow solid. LCMS-B rt 2.09 min, m/z (positive ion) 238 [M+H]$^+$.

b) 2-(4-(Benzyloxy)phenyl)-5-(4-methylpiperazin-1-yl)-3H-imidazo[4,5-b]pyridine (26)

General Method B: 6-(4-methylpiperazin-1-yl)-3-nitropyridin-2-amine A63 (95.0 mg, 0.400 mmol). The reaction was filtered, the residue dissolved in MeOH and loaded onto a SCX cartridge. The SCX cartridge was washed with MeOH (3×10 mL), the product was eluted with 10% NH$_4$OH in MeOH (50 mL) and concentrated to give the title compound (17.5 mg, 11%) as a colourless solid. $^1$H NMR (400 MHz, CD$_3$OD) δ 7.97 (d, J=8.8 Hz, 2H), 7.74 (d, J=8.8 Hz, 1H), 7.50-7.43 (m, 2H), 7.38 (t, J=7.4 Hz, 2H), 7.35-7.28 (m, 1H), 7.12 (d, J=8.8 Hz, 2H), 6.78 (d, J=8.8 Hz, 1H), 5.16 (s, 2H), 3.60 (d, J=4.9 Hz, 4H), 2.61 (t, J=5.1 Hz, 4H), 2.36 (s, 3H); LCMS-B rt 2.86 min, m/z (positive ion) 400 [M+H]$^+$; m/z (negative ion) 398 [M–H]$^-$.

Example 27: Synthesis of 2-(4-(benzyloxy)phenyl)-5-(4-(ethylsulfonyl)piperazin-1-yl)-3H-imidazo[4,5-b]pyridine (27)

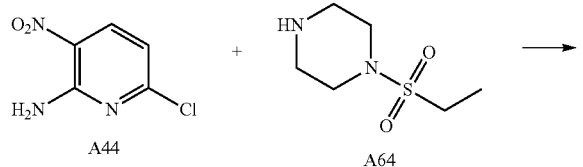

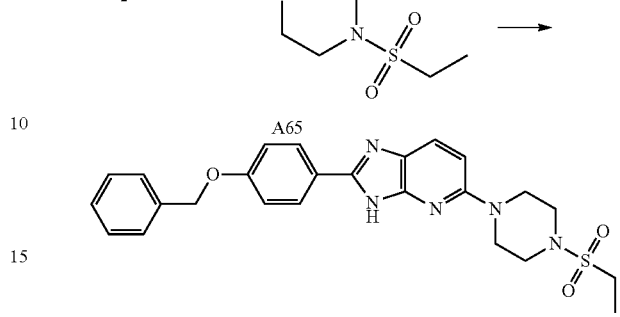

a) 6-(4-(Ethylsulfonyl)piperazin-1-yl)-3-nitropyridin-2-amine (A65)

General Method A: 2-amino-6-chloro-3-nitropyridine A44 (200 mg, 1.15 mmol), 1-(ethylsulfonyl)piperazine A64 (179 mg, 0.754 mmol). Isolated the title compound (110 mg, 30%) as a yellow solid. LCMS-B rt 3.09 min, m/z (positive ion) 316 [M+H]$^+$.

b) 2-(4-(Benzyloxy)phenyl)-5-(4-(ethylsulfonyl)piperazin-1-yl)-3H-imidazo[4,5-b]pyridine (27)

General Method B: 6-(4-(ethylsulfonyl)piperazin-1-yl)-3-nitropyridin-2-amine A65 (126.1 mg, 0.400 mmol). The reaction was filtered, the residue dissolved in MeOH and loaded onto a SCX cartridge. The SCX was washed with MeOH (3×10 mL), the product was eluted with 10% NH4OH in MeOH (50 mL) and concentrated to give the title compound (100 mg, 52%) as a colourless solid. 1H NMR (400 MHz, d6-DMSO) δ 8.21-7.96 (d, J=8.9 Hz, 2H), 7.92-7.75 (d, J=8.8 Hz, 1H), 7.52-7.44 (d, J=6.8 Hz, 2H), 7.45-7.37 (m, 2H), 7.37-7.31 (m, 1H), 7.17-7.10 (d, J=8.6 Hz, 2H), 6.86-6.77 (d, J=8.8 Hz, 1H), 5.42-4.96 (s, 2H), 3.69-3.55 (s, 4H), 3.34-3.22 (d, J=4.9 Hz, 4H), 3.15-2.96 (q, J=7.3 Hz, 2H), 1.41-1.01 (t, J=7.3 Hz, 3H); LCMS-B rt 3.17 min, m/z (positive ion) 478 [M+H]$^+$; m/z (negative ion) 476 [M–H]$^-$.

Example 28: Synthesis of tert-butyl ((1-(2-(4-(benzyloxy)phenyl)-3H-imidazo[4,5-b]pyridin-5-yl)piperidin-3-yl)methyl)carbamate (28)

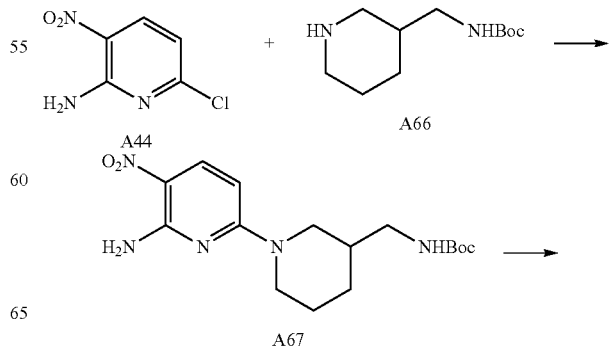

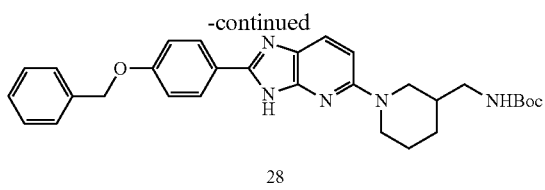

28 a) tert-Butyl ((1-(6-amino-5-nitropyridin-2-yl)piperidin-3-yl)methyl)carbamate (A67)

General Method A: 2-amino-6-chloro-3-nitropyridine A44 (174 mg, 1.00 mmol), tert-butyl (piperidin-3-ylmethyl)carbamate (258 mg, 1.20 mmol). The reaction was cooled to room temperature, treated with water (20 mL/g) and filtered. The filtrate was extracted with EtOAc (2×5 mL), the combined organics were washed with brine (5 mL) and concentrated to give the title compound (305 mg, 87%) as a yellow powder. LCMS-B rt 3.41 min, m/z (positive ion) 352 [M+H]$^+$; m/z (negative ion) 350 [M−H]$^-$.

b) tert-Butyl ((1-(2-(4-(benzyloxy)phenyl)-3H-imidazo[4,5-b]pyridin-5-yl)piperidin-3-yl)methyl)carbamate (28)

General Method B: A67 (175 mg, 0.500 mmol). Isolated the title compound (80.4 mg, 32%) as a colourless powder. $^1$H NMR (400 MHz, CDCl$_3$) δ 7.90 (d, J=8.3 Hz, 2H), 7.74 (br, s, 1H), 7.43 (m, 2H), 7.39 (d, J=7.8 Hz, 2H), 7.35 (d, J=6.9 Hz, 1H), 7.06 (d, J=8.8 Hz, 2H), 6.33 (d, J=8.6 Hz, 1H), 5.11 (s, 2H), 4.62 (br, s, 1H), 3.93 (br, s, 1H), 3.76 (d, J=13.1 Hz, 1H), 3.41-3.16 (m, 2H), 3.08-2.87 (m, 1H), 2.87-2.67 (m, 1H), 1.93-1.73 (m, 4H), 1.73-1.56 (m, 2H), 1.44 (s, 9H); LCMS-B rt 3.36 min, m/z (positive ion) 514 [M+H]$^+$, m/z (negative ion) 512 [M−H]$^-$.

Example 29: Synthesis of tert-butyl 2-(((2-(4-(benzyloxy)phenyl)-3H-imidazo[4,5-b]pyridin-5-yl)amino)methyl)piperidine-1-carboxylate (29)

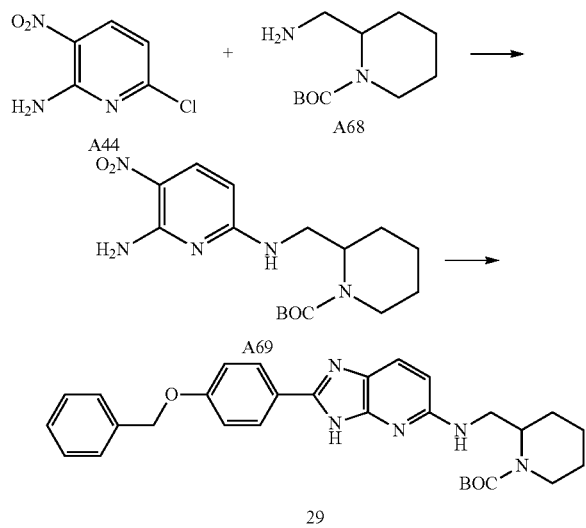

a) tert-Butyl 2-(((6-amino-5-nitropyridin-2-yl)amino)methyl)piperidine-1-carboxylate (A69)

General Method A: 2-amino-6-chloro-3-nitropyridine A44 (174 mg, 1.00 mmol), tert-butyl 2-(aminomethyl)piperidine-1-carboxylate A68 (258 mg, 1.20 mmol). Isolated the title compound as a yellow powder (258 mg, 73%) LCMS-B rt 3.39 min, m/z (positive ion) 352 [M+H]$^+$; m/z (negative ion) 350 [M−H]$^-$.

b) tert-Butyl 2-(((2-(4-(benzyloxy)phenyl)-3H-imidazo[4,5-b]pyridin-5-yl)amino)methyl)piperidine-1-carboxylate (29)

General Method B: tert-butyl 2-(((6-amino-5-nitropyridin-2-yl)amino)methyl)piperidine-1-carboxylate A69 (66 mg, 0.31 mmol). Isolated the title compound as a colourless powder (56 mg, 42%); $^1$H NMR (400 MHz, CDCl$_3$) δ 7.93 (d, J=8.2 Hz, 2H), 7.75 (br, s, 1H), 7.48-7.42 (m, 2H), 7.42-7.37 (m, 2H), 7.37-7.30 (m, 1H), 7.06 (d, J=8.8 Hz, 2H), 6.32 (d, J=8.7 Hz, 1H), 5.34-5.16 (br, s, 1H), 5.12 (s, 2H), 4.70-4.42 (m, 1H), 4.07-3.88 (br, s, 1H), 3.85-3.65 (br, s, 1H), 3.40-3.20 (br s, 1H), 2.78 (t, J=12.9 Hz, 1H), 1.95-1.75 (br, s, 2H), 1.71-1.61 (m, 2H), 1.61-1.52 (m, 2H), 1.50-1.39 (m, 1H), 1.37 (s, 9H); LCMS-B rt 3.36 min, m/z (positive ion) 514 [M+H]$^+$, m/z (negative ion) 512 [M−H]$^-$.

Example 30: Synthesis of tert-butyl 3-((2-(4-(benzyloxy)phenyl)-3H-imidazo[4,5-b]pyridin-5-yl)(methyl)amino)piperidine-1-carboxylate (30)

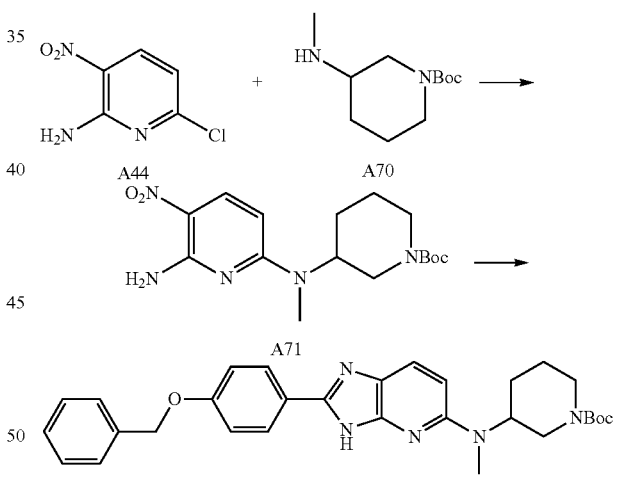

a) tert-Butyl 3-((6-amino-5-nitropyridin-2-yl)(methyl)amino)piperidine-1-carboxylate (A71)

General Method A: 2-amino-6-chloro-3-nitropyridine A44 (174 mg, 1.00 mmol), tert-butyl 3-(methylamino)piperidine-1-carboxylate A70 (258 mg, 1.20 mmol). The reaction was cooled to room temperature, treated with water (20 mL/g) and filtered. The filtrate was extracted with EtOAc (2×5 mL), the combined organics were washed with brine (5 mL) and concentrated to give the title compound as a yellow powder (317 mg, 90%). LCMS-B rt 3.50 min m/z (positive ion) 352 [M+H]$^+$, m/z (negative ion) 350 [M−H]$^-$.

b) tert-Butyl 3-((2-(4-(benzyloxy)phenyl)-3H-imidazo[4,5-b]pyridin-5-yl)(methyl)amino)piperidine-1-carboxylate (30)

General Method B: tert-butyl 3-((6-amino-5-nitropyridin-2-yl)(methyl)amino)piperidine-1-carboxylate A71 (148 mg, 0.420 mmol). Isolated the title compound as a colourless powder (90 mg, 42%); ¹H NMR (400 MHz, CDCl₃) δ 7.90 (d, J=8.3 Hz, 2H), 7.81 (br, s, 1H), 7.48-7.42 (m, 2H), 7.42-7.37 (m, 2H), 7.37-7.30 (m, 1H), 7.05 (d, J=8.8 Hz, 2H), 6.54 (d, J=8.9 Hz, 1H), 5.12 (s, 2H), 4.50-4.18 (br, s, 1H), 4.50-4.18 (br, s, 1H, hidden under solvent peak), 3.06-2.88 (s, 3H), 2.87-2.69 (br, s, 1H), 2.69-2.54 (t, J=12.5 Hz, 1H), 1.97-1.55 (m, 6H), 1.47 (s, 9H); LCMS-B rt 3.45 min, m/z (positive ion) 514 [M+H]⁺, m/z (negative ion) 512 [M−H]⁻.

Example 31: Synthesis of tert-butyl 4-(((2-(4-(benzyloxy)phenyl)-3H-imidazo[4,5-b]pyridin-5-yl)amino)methyl)piperidine-1-carboxylate (31)

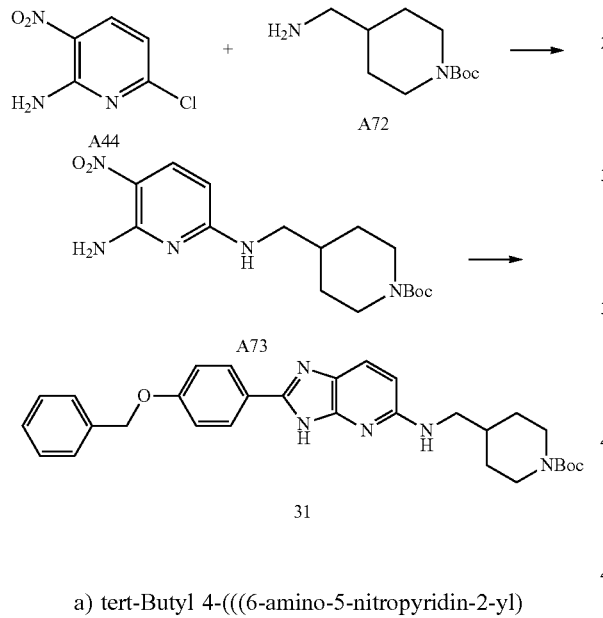

a) tert-Butyl 4-(((6-amino-5-nitropyridin-2-yl)amino)methyl)piperidine-1-carboxylate (A73)

General Method A: 2-amino-6-chloro-3-nitropyridine A44 (174 mg, 1.00 mmol), tert-butyl 4-(aminomethyl)piperidine-1-carboxylate A72 (258 mg, 1.20 mmol). The reaction was cooled to room temperature, treated with water (20 mL/g) and filtered. The filtrate was extracted with EtOAc (2×5 mL), washed with brine (5 mL) and concentrated to give the title compound as a yellow powder (286 mg, 81%). LCMS-B rt 3.37 min m/z (positive ion) 352 [M+H]⁺, m/z (negative ion) 350 [M−H]⁻.

b) tert-Butyl 4-(((2-(4-(benzyloxy)phenyl)-3H-imidazo[4,5-b]pyridin-5-yl)amino)methyl)piperidine-1-carboxylate (31)

General Method B: tert-butyl 4-(((6-amino-5-nitropyridin-2-yl)amino)methyl)piperidine-1-carboxylate A73 (123 mg, 0.350 mmol). Isolated the title compound as a colourless powder (50 mg, 28%); ¹H NMR (400 MHz, CDCl₃) δ 10.82-10.40 (br, s, 1H), 7.97-7.83 (m, 2H), 7.78 (br, s, 1H), 7.47-7.42 (m, 2H), 7.42-7.36 (m, 2H), 7.36-7.30 (m, 1H), 7.14-6.93 (m, 2H), 6.34 (d, J=8.7 Hz, 1H), 5.10 (s, 2H), 452 (t, J=6.0 Hz, 1H), 4.23-3.87 (1H hidden under solvent peak), 3.21 (t, J=6.1 Hz, 2H), 2.80-2.51 (m, 2H), 1.92-1.59 (m, 4H), 1.55-1.36 (s, 9H), 1.19-1.03 (m 2H); LCMS-B rt 3.30 min, m/z (positive ion) 514 [M+H]⁺, m/z (negative ion) 512 [M−H]⁻.

Example 32: Synthesis of tert-butyl 4-((2-(4-(benzyloxy)phenyl)-3H-imidazo[4,5-b]pyridin-5-yl)amino)piperidine-1-carboxylate (32)

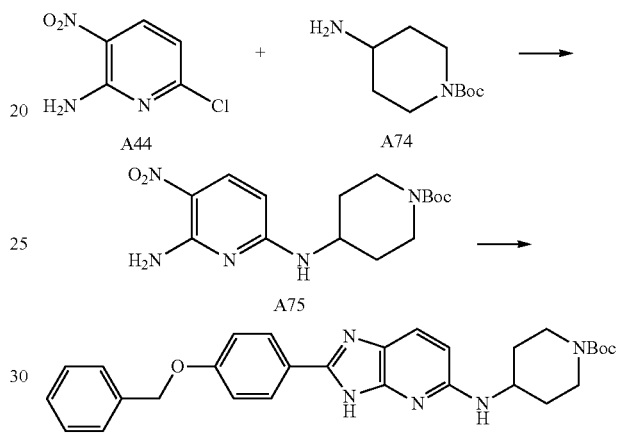

a) tert-Butyl 4-((6-amino-5-nitropyridin-2-yl)amino)piperidine-1-carboxylate (A75)

General Method A: 2-amino-6-chloro-3-nitropyridine A44 (174 mg, 1.00 mmol), tert-butyl 4-aminopiperidine-1-carboxylate (240 mg, 1.20 mmol). Isolated the title compound as a yellow powder (253 mg, 75%). LCMS-B rt 3.34 min, m/z (positive ion) 360 [M+Na]⁺, m/z (negative ion) 336 [M−H]⁻.

b) tert-Butyl 4-((2-(4-(benzyloxy)phenyl)-3H-imidazo[4,5-b]pyridin-5-yl)amino)piperidine-1-carboxylate (32)

General Method B: tert-Butyl 4-((6-amino-5-nitropyridin-2-yl)amino)piperidine-1-carboxylate A75 (87.7 mg, 0.260 mmol). Isolated the title compound as a colourless powder (65 mg, 50%); ¹H NMR (400 MHz, CDCl₃) (10.67-10.25 (br, s, 1H), 7.91 (d, J=8.2 Hz, 2H), 7.84-7.66 (br, s, 1H), 7.46-7.42 (m, 2H), 7.42-7.37 (m, 2H), 7.37-7.30 (m, 1H), 7.04 (d, J=8.8 Hz, 2H), 6.33 (d, J=8.6 Hz, 1H), 5.11 (s, 2H), 4.30 (d, J=8.1 Hz, 1H), 4.14-3.93 (br, s, 2H), 3.93-3.74 (br, s, 1H), 3.05-2.67 (t, J=12.0 Hz, 2H), 2.14-1.93 (m, 2H), 1.49 (s, 9H), 1.91-1.64 (br s, 1H) 1.42-1.18 (m, 2H); LCMS-B rt 3.28 min, m/z (positive ion) 500 [M+H]⁺, m/z (negative ion) 498 [M−H]⁻.

Example 33: Synthesis of 4-(2-(4-(benzyloxy)phenyl)-3H-imidazo[4,5-b]pyridin-5-yl)piperazin-2-one (33)

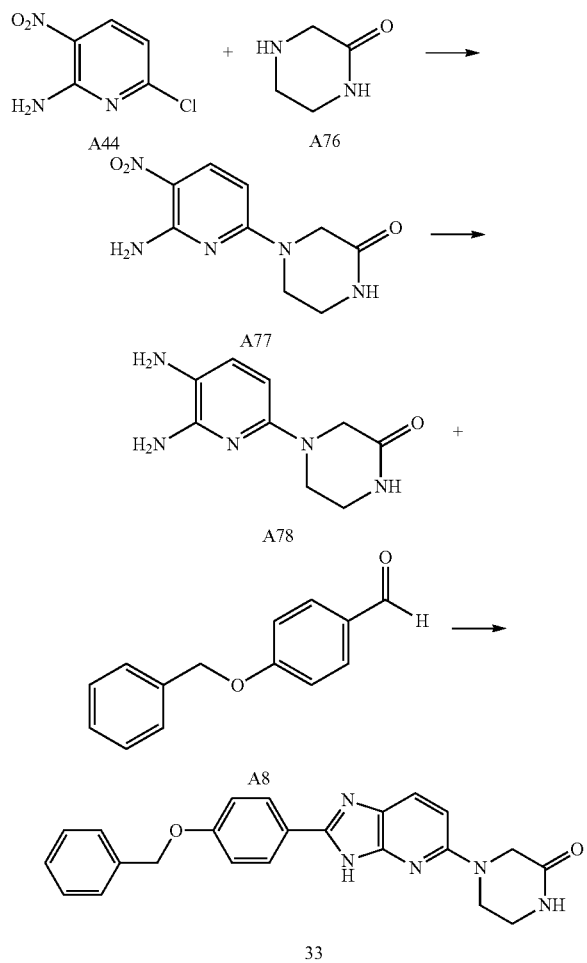

a) 4-(6-Amino-5-nitropyridin-2-yl)piperazin-2-one (A77)

General Method A: 2-amino-6-chloro-3-nitropyridine A44 (500 mg, 2.88 mmol), piperazine-2-one A76 (346 mg, 3.46 mmol). Isolated the title compound as a yellow solid (567 mg, 83%); $^1$H NMR (400 MHz, $d_6$-DMSO) δ 8.20 (s, 1H), 8.10 (d, J=9.5 Hz, 1H), 8.03-7.65 (s, 2H), 6.30 (d, J=9.5 Hz, 1H), 4.21 (s, 2H), 3.84 (s, 2H), 3.31-3.26 (m, 2H); LCMS-B rt 2.78 min, m/z (positive ion) 260 [M+Na]$^+$; 238 [M+H]$^+$.

b) 4-(5,6-Diaminopyridin-2-yl)piperazin-2-one (A78)

A suspension of 4-(6-amino-5-nitropyridin-2-yl)piperazin-2-one A77 (550 mg, 2.32 mmol) and 10% Pd on C (53% water wet, 112 mg, 5.6 mg Pd) in MeOH (30 mL) was stirred under hydrogen (1 atm) for 17 hours. The suspension was filtered through celite and concentrated in vacuo give the title compound as a brown solid (379 mg, 79%). $^1$H NMR (400 MHz, $d_6$-DMSO) δ 7.89 (s, 1H), 6.69 (d, J=8.0 Hz, 1H), 5.81 (d, J=8.0 Hz, 1H), 5.21 (s, 2H), 4.01 (s, 2H), 3.68 (s, 2H), 3.56-3.40 (m, 2H), 3.26-3.18 (m, 2H).

c) 4-(2-(4-(Benzyloxy)phenyl)-3H-imidazo[4,5-b]pyridin-5-yl)piperazin-2-one (33)

A suspension of 4-(5,6-diaminopyridin-2-yl)piperazin-2-one A78 (200 mg, 0.965 mmol) and 4-(benzyloxy)benzaldehyde A8 (205 mg, 0.965 mmol) in MeOH (5 mL) was heated under microwave irradiation at 120° C. for 20 minutes. The volatiles were removed in vacuo and the residue dissolved in THF (30 mL). PhI(OAc)$_2$ (311 mg, 0.965 mmol) was added and the resulting mixture stirred for 18 hours at room temperature. The reaction mixture was diluted with DCM (50 mL), washed with 0.5 M aqueous citric acid (30 mL); saturated aqueous Na$_2$CO$_3$ (30 mL) and filtered to give the crude compound (175 mg) as a green powder. The residue was dissolved in MeOH (1 mL) and purified by column chromatography (40 g silica, EtOAc:petroleum benzine) to give the title compound as a colourless solid (40.4 mg, 10%); $^1$H NMR (400 MHz, $d_6$-DMSO) δ 8.11-8.00 (m, 3H), 7.81 (s, 1H), 7.51-7.45 (m, 2H), 7.45-7.38 (m, 2H), 7.37-7.31 (m, 1H), 7.20-7.06 (m, 2H), 6.75 (d, J=8.9 Hz, 1H), 5.19 (s, 2H), 4.03 (s, 2H), 3.83-3.62 (m 2H), 3.48-3.31 (m, 2H)—hidden under solvent peak; LCMS-B rt 2.98 min; m/z (positive ion) 400 [M+H]$^+$; m/z (negative ion) 398 [M−H]$^-$.

Example 34: Synthesis of tert-butyl 3-(2-(4-(phenoxymethyl)phenyl)-3H-imidazo[4,5-b]pyridin-5-yl)piperidine-1-carboxylate (34)

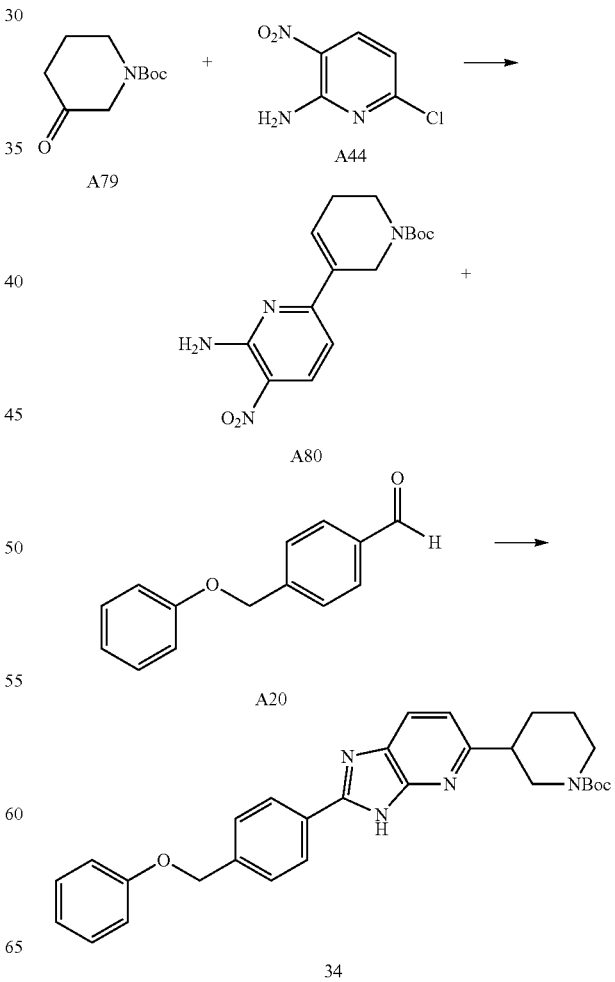

a) tert-Butyl 6-amino-5-nitro-5',6'-dihydro-[2,3'-bipyridine]-1'(2'H)-carboxylate (A80)

A solution of LiHMDS (1 M in toluene, 15.8 mL, 15.8 mmol) was added dropwise to a solution of 1-Boc-3-piperidone A79 (3.00 g, 15.1 mmol) in dry THF (100 mL) at −78° C. under an atmosphere of nitrogen. The solution was then stirred at this temperature for 30 minutes, N-phenyl-bis (trifluoromethanesulfonimide) (5.92 g, 16.6 mmol) in dry THF (20 mL) was added and the reaction mixture was stirred at −78° C. for additional 15 minutes, and then at 0° C. for 2 hours. The reaction mixture was quenched with saturated aqueous NH$_4$Cl (10 mL), volatiles were removed in vacuo, EtOAc (200 mL) and saturated aqueous NH$_4$Cl (100 mL) were added, the layers were separated and the organic layer was washed with brine (100 mL), dried (Na$_2$SO$_4$), filtered and concentrated in vacuo to give a yellow gum. The residue was purified by silica gel chromatography (120 g silica Cartridge, 0-10% EtOAc in petroleum benzine 40-60° C.), fractions were combined and concentrated in vacuo to give the product (2.910 g, impure) as a pale yellow oil which solidified upon standing. The product was taken into next reaction without further purification.

To a solution of above intermediate (2.900 g) in dry 1,4-dioxane (40 mL) was added KOAc (1.804 g, 18.38 mmol), bis(pinacolato)diboron (2.334 g, 9.191 mmol) and the suspension was de-gassed with nitrogen. Dppf (0.173 g, 0.306 mmol) followed by PdCl$_2$(dppf) DCM solvate (0.253 g, 0.306 mmol) were added and the reaction vessel was sealed and heated to 80° C. for 18 hours. The reaction mixture was filtered through celite, which was washed with MeOH and EtOAc, the filtrates were combined and concentrated in vacuo to give a brown oil. The crude material was purified by silica gel chromatography (120 g silica cartridge, 0-20% EtOAc in petroleum benzine 40-60° C.), fractions were combined and concentrated in vacuo to give the product (2.38 g, impure). A part of this material (1.670 g) and 2-amino-6-chloro-3-nitropyridine A44 (0.250 g, 1.44 mmol) were dissolved in dry 1,4-dioxane (10 mL); tetrabutylammonium bromide (0.046 g, 0.144 mmol) and Pd(PPh$_3$)$_2$Cl$_{1-2}$ (0.051 g, 0.072 mmol) followed by a solution of Na$_2$CO$_3$ (0.458 g, 4.32 mmol) in water (1.440 mL) were added. The reaction mixture was then heated at 80° C. for 18 hours. The reaction mixture was filtered through celite, which was washed with EtOAc (5×20 mL) and the combined organics were concentrated in vacuo to give a brown solid which was purified by silica gel chromatography (40 g silica Cartridge, 0-40% EtOAc in petroleum benzine 40-60° C.) to give the title compound (0.225 g, 7% over 3 steps) as a yellow solid. $^1$H NMR (400 MHz, CDCl$_3$) b 8.36 (d, J=8.7 Hz, 1H), 6.92-6.82 (m, 2H), 4.36 (s, 2H), 3.56 (t, J=5.7 Hz, 2H), 2.43-2.34 (m, 2H), 1.47 (s, 9H). LCMS-A rt 6.64 min.

b) tert-Butyl 3-(2-(4-(phenoxymethyl)phenyl)-3H-imidazo[4,5-b]pyridin-5-yl)piperidine-1-carboxylate (34)

tert-Butyl 6-amino-5-nitro-5',6'-dihydro-[2,3'-bipyridine]-1'(2'H)-carboxylate A80 (0.221 g, 0.690 mmol) was suspended in DIPEA (6.5 mL) under an atmosphere of nitrogen and platinum(IV) oxide (0.050 g) was added suspended in EtOAc (2 mL). EtOH (2 mL) was added and the reaction was then stirred under an atmosphere of hydrogen (balloon) for 18 hours. The mixture was filtered through celite, and the celite was washed with EtOAc (5×20 mL). The combined filtrates were concentrated in vacuo, toluene was added to the resulting gum and then concentrated in vacuo to give to give a brown solid. This material (0.236 g) and 4-(phenoxymethyl)-benzaldehyde A20 (0.114 g, 0.539 mmol) were dissolved in MeOH (10 mL) and activated 3 Å sieves (0.526 g) were added. The reaction mixture was then heated at reflux for 20 hours. The mixture was then cooled to room temperature, the solution was decanted from the sieves and the solvent was removed in vacuo. Tetrahydrofuran (10 mL) followed by (Diacetoxyiodo)benzene (0.208 g, 0.646 mmol) were added under an atmosphere of nitrogen and the reaction was stirred at room temperature for 3 hours. The reaction was concentrated in vacuo and diluted with EtOAc (100 mL) and saturated aqueous NaHCO$_3$ (100 mL). The layers were separated and the aqueous layer was extracted with EtOAc (100 mL), the combined organics were washed with brine (100 mL), dried (Na$_2$SO$_4$), filtered and concentrated in vacuo to give the crude product which was purified by silica gel chromatography (24 g silica Cartridge, 0-40% EtOAc in petroleum benzine 40-60° C.) to give the title compound (0.095 g, 28% over 2 steps) as a yellow solid. $^1$H NMR (400 MHz, d$_6$-DMSO) δ 13.50 (br s, 1H), 8.26-8.15 (m, 2H), 7.96 (d, J=7.9 Hz, 1H), 7.62 (d, J=8.0 Hz, 2H), 7.37-7.26 (m, 2H), 7.20 (d, J=8.2 Hz, 1H), 7.09-7.00 (m, 2H), 6.95 (tt, J=7.3, 1.1 Hz, 1H), 5.19 (s, 2H), 4.15 (br s, 1H), 4.04-3.95 (m, 1H), 3.08-2.70 (m, 3H), 2.06-1.99 (m, 1H), 1.83-1.69 (m, 2H), 1.56-1.32 (m, 10H). LCMS-A rt 6.55 min, m/z (positive ion) 485.3 [M+H]$^+$.

Example 35: Synthesis of 2-(4-(phenoxymethyl)phenyl)-5-(piperidin-3-yl)-3H-imidazo[4,5-b]pyridine (35)

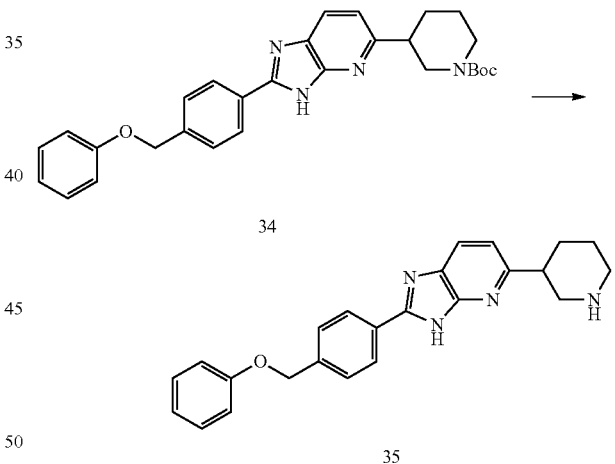

34

35 tert-Butyl 3-(2-(4-(phenoxymethyl)phenyl)-3H-imidazo[4,5-b]pyridin-5-yl)piperidine-1-carboxylate 34 (0.088 g, 0.18 mmol) was dissolved in DCM (7 mL) under an atmosphere of nitrogen and trifluoroacetic acid (0.348 mL, 4.54 mmol) was added and the resulting mixture was stirred at room temperature for 20 hours. The reaction mixture was concentrated in vacuo and the resulting solid was dissolved in EtOAc (70 mL) and 2 M aqueous NaOH (70 mL), the layers were separated and the aqueous layer was extracted with EtOAc (50 mL), the combined organics were washed with brine (50 mL), dried (Na$_2$SO$_4$), filtered and concentrated in vacuo. The solid was dissolved in DCM (~5 mL) and the solution was concentrated in vacuo to give the title compound (0.064 g, 92%) as a beige solid. $^1$H NMR (400 MHz, d$_6$-DMSO) δ 8.25-8.18 (m, 2H), 7.91 (d, J=8.2 Hz, 1H), 7.62 (d, J=8.1 Hz, 2H), 7.34-7.27 (m, 2H), 7.14 (d, J=8.2 Hz, 1H), 7.07-7.01 (m, 2H), 6.95 (tt, J=7.3, 1.1 Hz, 1H), 5.19 (s, 2H), 3.13-3.04 (m, 1H), 3.00-2.91 (m, 1H), 2.86 (tt, J=11.1, 3.6 Hz, 1H), 2.75-2.63 (m, 1H), 2.55-2.44 (m, 1H, obscured by DMSO peak), 2.02-1.93 (m, 1H), 1.84-1.64 (m, 2H), 1.50 (qt, J=12.8, 3.9 Hz, 1H). NH protons not observed. LCMS-A rt 4.72 min, m/z (positive) 385.2 [M+H]$^+$.

Example 36: Synthesis of 2-(4-(benzyloxy)phenyl)-5-(pyridin-3-yl)-3H-imidazo[4,5-b]pyridine (36)

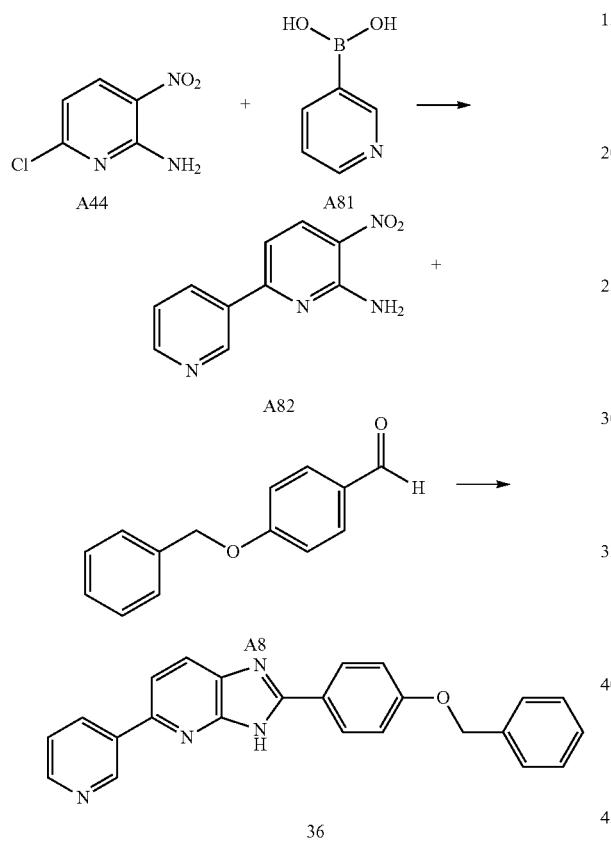

a) 5-Nitro-[2,3'-bipyridin]-6-amine (A82)

A mixture of 2-amino-3-nitro-6-chloropyridine A44 (0.10 g, 0.58 mmol), Na$_2$CO$_3$ (0.244 g, 2.31 mmol), pyridin-3-ylboronic acid A81 (0.092 g, 0.75 mmol) and PdCl$_2$(dppf) DCM solvate (0.036 g, 0.043 mmol) in dioxane (4.75 mL) and H$_2$O (0.25 mL) was degassed for 10 mins under a stream of nitrogen. The mixture was irradiated in the microwave at 120° C. for 20 minutes. The cooled mixture was concentrated under reduced pressure and purified by silica gel chromatography (silica 24 g cartridge, 0-100% EtOAc in petroleum benzine 40-60° C.) to give the title compound as a yellow-brown solid (0.053 g, 43%); $^1$H NMR (400 MHz, d$_6$-DMSO) δ 9.29 (dd, J=2.4, 0.9 Hz, 1H), 8.70 (dd, J=4.7, 1.6 Hz, 1H), 8.49 (d, J=8.7 Hz, 1H), 8.45 (ddd, J=8.0, 2.3, 1.6 Hz, 1H), 8.03 (brs, 2H), 7.56 (ddd, J=8.0, 4.8, 0.9 Hz, 1H), 7.42 (d, J=8.7 Hz, 1H). LCMS-A rt 4.69 min, m/z (positive ion) 217.2 [M+H]$^+$.

b) 2-(4-(Benzyloxy)phenyl)-5-(pyridin-3-yl)-3H-imidazo[4,5-b]pyridine (36)

A mixture of 4-(benzyloxy)benzaldehyde A8 (0.052 g, 0.25 mmol), 5-nitro-[2,3'-bipyridin]-6-amine A82 (0.053 g, 0.25 mmol), Na$_2$S$_2$O$_4$ (0.128 g, 0.734 mmol) in MeOH (4 mL) and H$_2$O (0.73 mL) in a sealed tube was irradiated in the microwave at 110° C. for 15 minutes. The reaction mixture was cooled to room temperature, aqueous ammonia added (0.4 mL), then filtered. The filtrate was evaporated under reduced pressure, then purified by silica gel chromatography (silica 24 g cartridge, 0-10% MeOH in EtOAc) to give the title compound as a yellow solid (0.009 g, 10%); $^1$H NMR (400 MHz, d$_6$-DMSO) δ 9.30 (d, J=2.3 Hz, 1H), 8.62-8.57 (m, 1H), 8.47-8.42 (m, 1H), 8.23-8.18 (m, 2H), 8.06-8.00 (m, 1H), 7.84 (d, J=8.4 Hz, 1H), 7.55-7.32 (m, 6H), 7.20 (d, J=8.4 Hz, 2H), 5.21 (s, 2H). Amine proton not seen. LCMS-A: rt 5.03 min, m/z (positive ion) 379.2 [M+H]$^+$.

Example 37: Synthesis of 2-(4-(benzyloxy)phenyl)-5-(pyridin-4-yl)-3H-imidazo[4,5-b]pyridine (37)

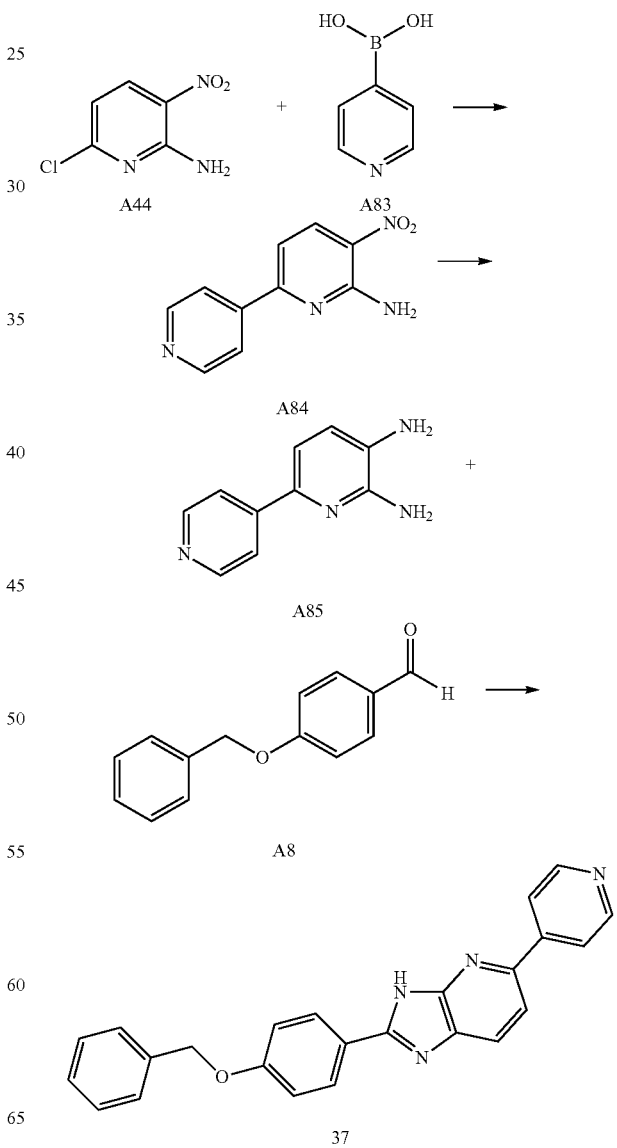

a) 5-Nitro-[2,4'-bipyridin]-6-amine (A84)

A mixture of 2-amino-3-nitro-6-chloropyridine A44 (0.20 g, 1.1 mmol), Na$_2$CO$_3$ (0.489 g, 4.61 mmol), pyridin-4-ylboronic acid A83 (0.184 g, 1.50 mmol) and PdCl$_2$(dppf) DCM solvate (0.071 g, 0.086 mmol) in dioxane (9.5 mL) and H$_2$O (0.5 mL) was degassed for 10 minutes under a stream of nitrogen. The mixture was irradiated in the microwave at 120° C. for 50 minutes. The cooled mixture was diluted with EtOAc, adsorbed onto silica gel then purified by silica gel chromatography (silica 40 g cartridge, 0-100% EtOAc in petroleum benzine 40-60° C.), to give the title compound as a yellow-brown solid (0.161 g, 65%); $^1$H NMR (400 MHz, d$_6$-DMSO) δ 8.77-8.72 (m, 2H), 8.52 (d, J=8.6 Hz, 1H), 8.07-7.97 (m, 4H), 7.45 (d, J=8.6 Hz, 1H). LCMS-A: rt 4.33 min, m/z (positive ion) 217.1 [M+H]$^+$.

b) [2,4'-Bipyridine]-5,6-diamine (A85)

A suspension of 10% Pd/C (0.020 g, 0.19 mmol) in EtOH (35 mL) and 5-nitro-[2,4'-bipyridin]-6-amine A84 (0.161 g, 0.75 mmol) in EtOAc (35 mL) was stirred under hydrogen (1 atm) at room temperature for 5 hours. The resulting mixture was filtered through celite, washing with EtOH and EtOAc. The filtrate was evaporated to dryness to give the title compound as lilac crystals (0.141 g, quant); $^1$H NMR (400 MHz, CD$_3$OD) δ 8.52-8.41 (m, 2H), 7.93-7.81 (m, 2H), 7.22 (d, J=7.9 Hz, 1H), 6.96 (d, J=7.8 Hz, 1H). Amine proton not seen. LCMS-A: rt 1.11 min, m/z (positive ion) 187.2 [M+H]$^+$.

c) 2-(4-(Benzyloxy)phenyl)-5-(pyridin-4-yl)-3H-imidazo[4,5-b]pyridine (37)

A mixture of 4-(benzyloxy)benzaldehyde A8 (0.161 g, 0.757 mmol), [2,4'-bipyridine]-5,6-diamine A85 (0.141 g, 0.757 mmol), activated molecular sieves 3 Å (400 mg) and acetic acid (26 drops) in dry MeOH (10 mL) under an atmosphere of nitrogen was stirred at 60° C. for 20 hours. The volatiles were removed in vacuo, and the residue dissolved in THF (6 mL). PhI(OAc)$_2$ (0.244 g, 0.757 mmol) was added then stirred at room temperature for 4.5 hours. The volatiles were removed in vacuo, the residue dissolved in EtOAc, washed with saturated aqueous NaHCO$_3$, extracted with EtOAc. The organic layers were combined then washed with saturated aqueous NaCl. The organic layer was dried over Na$_2$SO$_4$, filtered, evaporated under reduced pressure, then purified using silica gel chromatography (24 g silica cartridge, 0-100% EtOAc in petroleum benzine 40-60° C.), to give the title compound as a peach powder (0.038 g, 13%); $^1$H NMR (400 MHz, CD$_3$OD) δ 8.65-8.59 (m, 2H), 8.17-8.14 (m, 2H), 8.11-8.06 (m, 2H), 8.03 (d, J=8.4 Hz, 1H), 7.94 (d, J=8.4 Hz, 1H), 7.49-7.44 (m, 2H), 7.39 (ddd, J=7.9, 7.0, 1.0 Hz, 2H), 7.36-7.29 (m, 1H), 7.20-7.15 (m, 2H), 5.18 (s, 2H). Amine proton not seen. LCMS-A: rt 4.86 min, m/z (positive ion) 379.2[M+H]$^+$, m/z (negative ion) 377.2 [M–H]$^-$.

Example 38: Synthesis of 5-(1-methyl-1H-pyrazol-3-yl)-2-(4-(phenoxymethyl)phenyl)-3H-imidazo[4,5-b]pyridine (38)

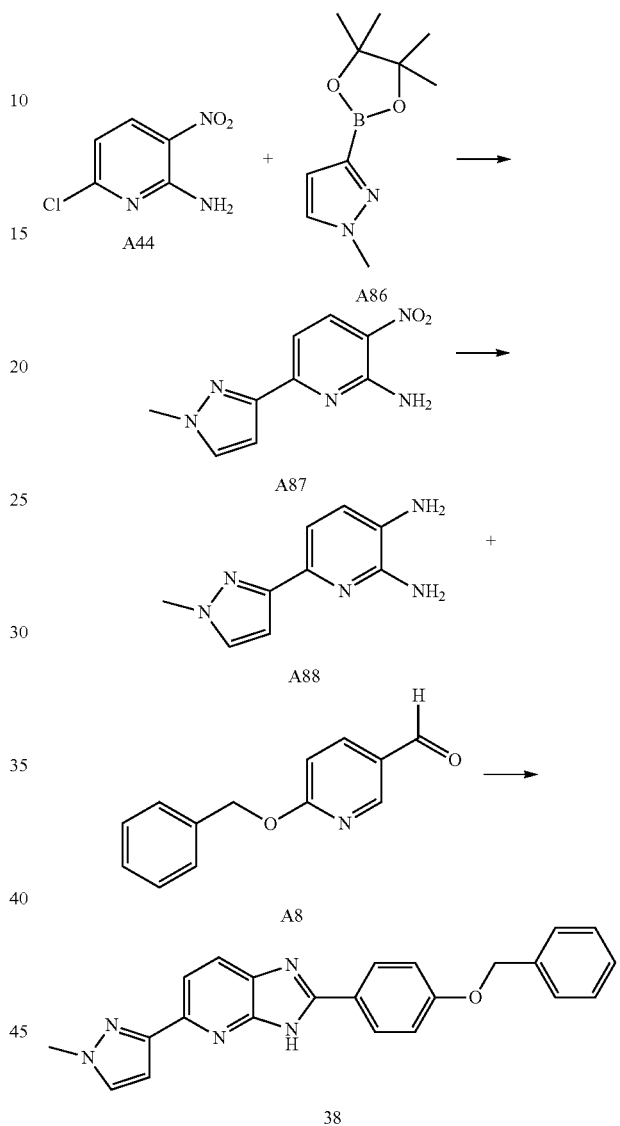

a) 6-(1-Methyl-1H-pyrazol-3-yl)-3-nitropyridin-2-amine (A87)

A mixture of 2-amino-3-nitro-6-chloropyridine A44 (0.20 g, 1.1 mmol), Na$_2$CO$_3$ (0.489 g, 4.61 mmol), 1-methyl-3-(4,4,5,5-tetramethyl-1,3,2-dioxaborolan-2-yl)-1H-pyrazole A86 (0.312 g, 1.50 mmol) and PdCl$_2$(dppf) DCM solvate (0.072 g, 0.086 mmol) in dioxane (9.5 mL) and H$_2$O (0.5 mL) was degassed for 10 minutes under a stream of nitrogen. The mixture was irradiated in the microwave at 120° C. for 50 minutes. The cooled mixture was evaporated under reduced pressure, then purified by silica gel chromatography (40 g silica cartridge, 0-100% EtOAc in petroleum benzine 40-60° C.) to give the title compound as a yellow solid (0.155 g, 61%); $^1$H NMR (400 MHz, d$_6$-DMSO) δ 8.42 (d, J=8.8 Hz, 1H), 8.09 (br. s, 2H), 7.52 (d, J=2.0 Hz, 1H), 7.16

(d, J=8.8 Hz, 1H), 7.00 (d, J=2.0 Hz, 1H), 4.23 (s, 3H). LCMS-A: rt 5.63 min, m/z (positive ion) 220.1 [M+H]⁺.

b) 6-(1-Methyl-1H-pyrazol-3-yl)pyridine-2,3-diamine (A88)

A suspension of 10% Pd/C (0.020 g) and 6-(1-methyl-1H-pyrazol-3-yl)-3-nitropyridin-2-amine A87 (0.155 g, 0.707 mmol) in EtOAc (35 mL) and EtOH (35 mL) was stirred under hydrogen (1 atm) at room temperature for 5 hours. The resulting mixture was filtered through celite, washing with EtOAc. The filtrate was evaporated to dryness to give the title compound as purple crystals (0.138 g, quant). ¹H NMR (400 MHz, d₆-DMSO) δ 7.31 (d, J=1.8 Hz, 1H), 6.74 (s, 2H), 6.36 (d, J=1.9 Hz, 1H), 5.56 (s, 2H), 4.92 (s, 2H), 4.05 (s, 3H). LCMS-A: rt 2.20 min, m/z (positive ion) 190.2 [M+H]⁺.

c) 5-(1-Methyl-1H-pyrazol-3-yl)-2-(4-(phenoxymethyl)phenyl)-3H-imidazo[4,5-b]pyridine (38)

A mixture of 4-(benzyloxy)benzaldehyde A8 (0.155 g, 0.729 mmol), 6-(1-methyl-1H-pyrazol-3-yl)pyridine-2,3-diamine A88 (0.138 g, 0.729 mmol), activated 3 Å molecular sieves (400 mg) in dry MeOH (8 mL) under an atmosphere of N₂ was stirred at 60° C. for 18 hours, acetic acid (0.4 mL) was added, then stirred for a further 7 hours. The volatiles were removed in vacuo, and the residue dissolved in THF (6 mL). PhI(OAc)₂ (0.235 g, 0.729 mmol) was added and the mixture stirred at room temperature for 22 hours. The volatiles were removed in vacuo, the residue dissolved in EtOAc, washed with saturated aqueous NaHCO₃, which was then extracted with EtOAc. The organic layers were combined then washed with saturated aqueous NaCl. The organic layer was dried over Na₂SO₄, filtered, evaporated under reduced pressure, then purified using silica gel chromatography (24 g silica cartridge, 0-100% EtOAc in petroleum benzine 40-60° C.), to give a yellow oil. The residue was dissolved in DCM and evaporated under reduced pressure to give the title compound as a pale yellow solid (0.133 g, 48%). ¹H NMR (400 MHz, CD₃OD) δ 8.14-8.06 (m, 2H), 8.00 (d, J=8.3 Hz, 1H), 7.65 (d, J=8.3 Hz, 1H), 7.51 (d, J=2.1 Hz, 1H), 7.49-7.45 (m, 2H), 7.39 (ddd, J=8.0, 7.0, 1.0 Hz, 2H), 7.36-7.30 (m, 1H), 7.22-7.15 (m, 2H), 6.72 (d, J=2.1 Hz, 1H), 5.20 (s, 2H), 4.27 (s, 3H). Amine proton not seen. LCMS-A: rt 5.94 min, m/z (positive ion) 382.2 [M+H]⁺.

Example 39: Synthesis of tert-butyl 4-(2-(4-(benzyloxy)phenyl)-3H-imidazo[4,5-b]pyridin-5-yl)piperidine-1-carboxylate (39)

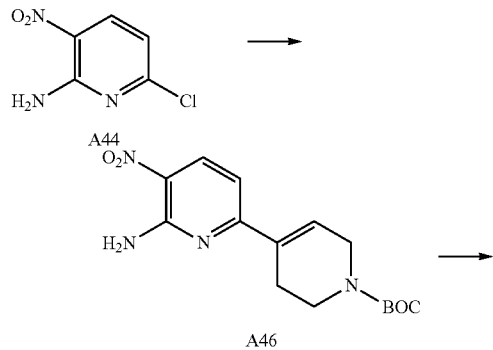

a) tert-Butyl 6-amino-5-nitro-5',6'-dihydro-[2,4'-bipyridine]-1'(2'H)-carboxylate (A46)

tert-Butyl 4-(4,4,5,5-tetramethyl-1,3,2-dioxaborolan-2-yl)-5,6-dihydropyridine-1(2H)-carboxylate (2.333 g, 7.490 mmol) and 2-amino-6-chloro-3-nitropyridine A44 (1.00 g, 5.762 mmol) were dissolved in dry 1,4-dioxane (50 mL), then nitrogen gas was bubbled through the solution for 10 minutes. TBAB (0.186 g, 0.576 mmol), Pd(dppf)Cl₂.DCM (0.238 g, 0.288 mmol) followed by a 3M solution of Na₂CO₃ (1.527 g, 14.404 mmol) in water (4.801 mL) were added and the reaction mixture was heated at 80° C. for 66 hours. The reaction mixture was filtered through celite, washed with EtOAc (5×20 mL) then concentrated in vacuo to give a brown solid. The crude material was purified by silica gel chromatography (120 g silica cartridge, 0-16% EtOAc in DCM) to give the title compound (1.653 g, 90%) as a yellow solid. ¹H NMR (400 MHz, d₆-DMSO) δ 8.33 (d, J=8.8 Hz, 1H), 7.87 (s, 2H), 6.96 (d, J=8.8 Hz, 1H), 6.85 (s, 1H), 4.07 (s, 2H), 3.50 (t, J=5.7 Hz, 2H), 2.56-2.50 (m, 2H), 1.42 (s, 9H). LCMS-A rt 6.596 min, m/z (positive ion) 265.1 [M-C₄H₉+2H]⁺ b) tert-Butyl 4-(5,6-diaminopyridin-2-yl)piperidine-1-carboxylate (A89)

tert-Butyl 6-amino-5-nitro-5',6'-dihydro-[2,4'-bipyridine]-1'(2'H)-carboxylate (A46) (0.364 g, 1.136 mmol) was dissolved in EtOH (150 mL) and EtOAc (150 mL) and 10% Pd/C (50% wet with water, 0.365 g) was added and the suspension was stirred under an atmosphere of hydrogen (5 bar) for 18 hours. The mixture was filtered through celite, and the celite was washed with EtOAc (200 mL). The pooled filtrates were evaporated to give the title compound (0.350 g, >99%) as a brown solid. ¹H NMR (400 MHz, CDCl₃) δ

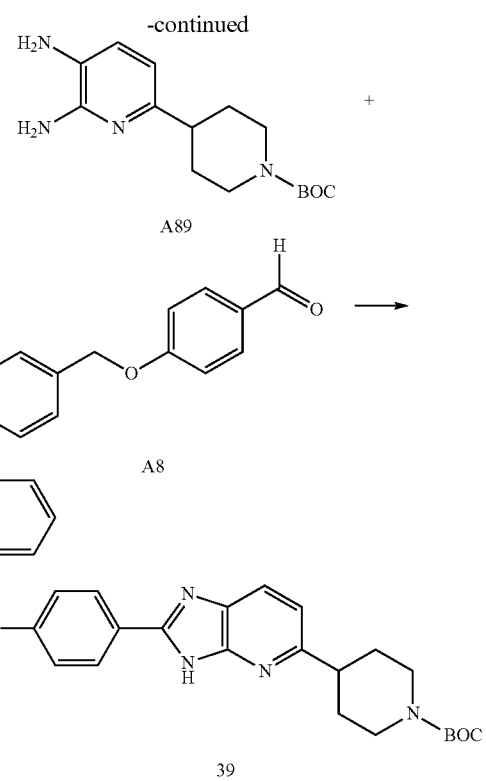

6.85 (d, J=7.7 Hz, 1H), 6.45 (d, J=7.7 Hz, 1H), 4.20 (br s, 4H), 2.79 (t, J=11.6 Hz, 2H), 2.64-2.50 (m, 1H), 1.86 (d, J=13.4 Hz, 2H), 1.73-1.54 (m, overlaps with water signal, 4H), 1.47 (s, 9H). LCMS-A rt 4.181 min, m/z (positive ion) 237.2 [M-tBu+2H]$^+$ (c) tert-butyl 4-(2-(4-(benzyloxy)phenyl)-3H-imidazo[4,5-b]pyridin-5-yl)piperidine-1-carboxylate (39)

tert-Butyl 4-(5,6-diaminopyridin-2-yl)piperidine-1-carboxylate A89 (261 mg, 0.89 mmol), 4-(benzyloxy)benzaldehyde A8 (208 mg, 0.98 mmol) and water (20 mL) were heated at reflux under air. After 66 hours the mixture was cooled and diluted with EtOAc (20 mL) and brine (10 mL). The aqueous phase was extracted with further EtOAc (2×20 mL), the combined organic extracts washed with brine (50 mL), dried over Na$_2$SO$_4$, filtered and evaporated. The mixture was dissolved in DCM (10 mL) and treated with PhI(OAc)$_2$ (288 mg, 0.89 mmol). After 19 hours the mixture was diluted with MeOH (10 mL) and loaded onto a 5 g SCX cartridge. The cartridge was washed with DCM (20 mL), 1:1 DCM:MeOH (20 mL), and MeOH (40 mL). The cartridge was eluted with 1:9 concentrated aqueous ammonia:MeOH (60 mL), and the basic eluent evaporated. Column chromatography (4 g silica cartridge, 5-100% EtOAc/hexanes) gave the title compound as a pale yellow solid (44 mg, 10%). $^1$H NMR (400 MHz, CDCl$_3$) δ 10.16 (s, 1H), 8.01-7.94 (m, 3H), 7.47-7.32 (m, 5H), 7.10 (dd, J=8.5, 3.5 Hz, 3H), 5.14 (s, 2H), 4.27 (br s, 2H), 2.95-2.75 (m, 3H), 1.93 (d, J=12.5 Hz, 2H), 1.78 (qd, J=12.8, 4.2 Hz, 2H), 1.49 (s, 9H). LCMS-A: rt 5.24 min, m/z (positive ion) 485.3 [M+H]$^+$, 429.2 [M-tBu+2H]$^+$, m/z (negative ion) 483.2 [M-H]$^-$.

Example 40: Synthesis of 2-(4-(benzyloxy)phenyl)-5-(piperidin-4-yl)-3H-imidazo[4,5-b]pyridine (40)

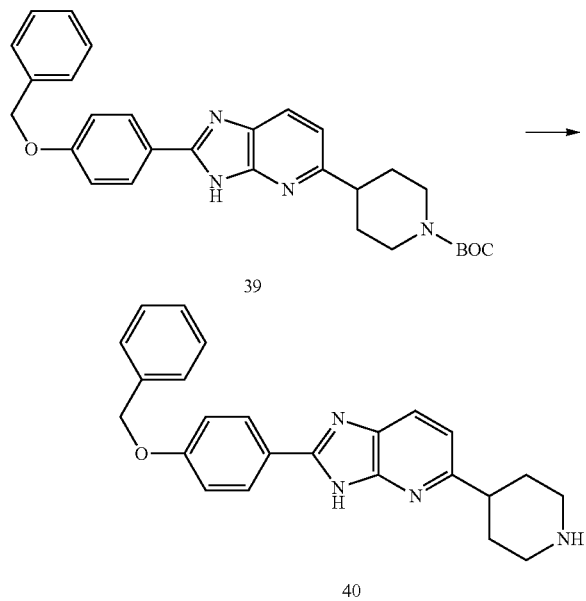

tert-Butyl 4-(2-(4-(benzyloxy)phenyl)-3H-imidazo[4,5-b]pyridin-5-yl)piperidine-1-carboxylate 39 (42 mg, 0.09 mmol), DCM (4 mL) and TFA (1 mL) were stirred at room temperature. After 4 hours the mixture was diluted with saturated aqueous NaHCO$_3$ (20 mL) and the pH brought to 10 with NaOH. The mixture was extracted with EtOAc (3×30 mL), and the combined EtOAc phases washed with brine (50 mL), dried over Na$_2$SO$_4$, filtered and evaporated. The residue was sonicated in ether (2 mL), the ether decanted and the solid dried under vacuum to give the title compound as a yellow solid (26 mg, 78%). $^1$H NMR (400 MHz, d$_6$-DMSO) δ 13.07 (br s, 1H), 8.18-8.12 (m, 2H), 7.92 (s, 1H), 7.52-7.45 (m, 2H), 7.44-7.39 (m, 2H), 7.38-7.32 (m, 1H), 7.19 (d, J=8.4 Hz, 2H), 7.12 (d, J=8.2 Hz, 1H), 5.21 (s, 2H), 3.10-2.93 (m, overlaps with water), 2.06-1.92 (m, 4H). LCMS-A: 4.30 min; m/z (positive ion): 385.3 [M+H]$^+$; m/z (negative ion) 383.1 [M-H]$^-$.

Example 41: Synthesis of 2-(4-(benzyloxy)phenyl)-5,7-dichloro-1H-imidazo[4,5-b]pyridine (41)

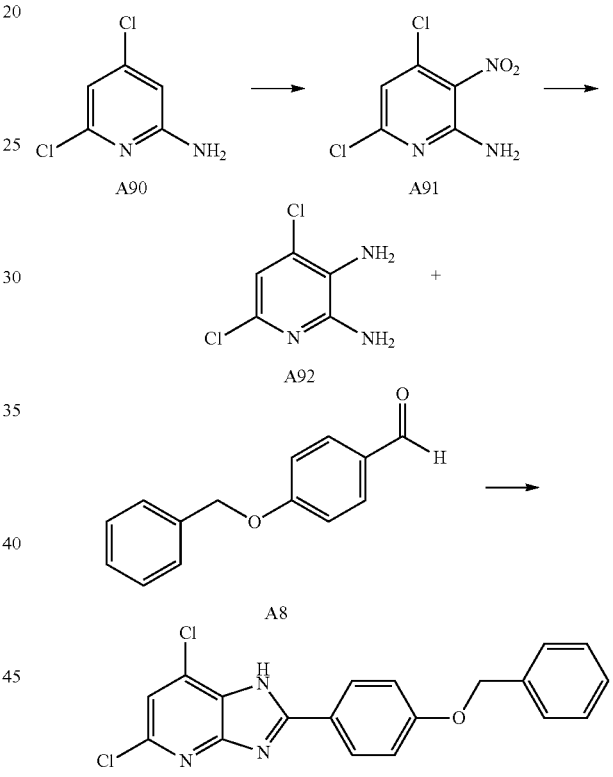

a) 4,6-Dichloro-3-nitropyridin-2-amine (A91)

To 2-amino-4,6-dichloropyridine (1.0 g, 6.1 mmol) was added concentrated H$_2$SO$_4$ (5.4 mL) dropwise at 0° C. and the mixture stirred for 10 minutes. To this stirring solution was added concentrated fuming HNO$_3$ (0.3 mL) dropwise, and the mixture stood at 4° C. for five days. The reaction mixture was poured onto crushed ice then neutralized with NaHCO$_3$. The resulting precipitate was filtered, washed with H$_2$O and dried to give the crude product as a yellow powder. The crude product was adsorbed onto silica gel then purified using silica gel chromatography twice (24 g silica cartridge, 0-10% MeOH in DCM then 0-5% MeOH in DCM), evaporated under reduced pressure, then dried to give the title compound as a bright yellow powder (0.744 g, 58%); $^1$H NMR (400 MHz, CDCl₃): δ 6.83 (s, 1H), 6.24 (br. s, 2H). LCMS-A: rt 6.21 min, m/z (positive ion) 208.1 [M+H]⁺.

b) 4,6-Dichloropyridine-2,3-diamine (A92)

To a stirred suspension of 4,6-dichloro-3-nitropyridin-2-amine A91 (0.51 g, 2.5 mmol) in a mixture of water (11 mL) and propan-2-ol (22 mL) was added iron powder (0.68 g, 12 mmol) followed by NH₄Cl (0.64 g, 12.2 mmol) at room temperature and the mixture was then heated to 70° C. for 2 hours. The cooled reaction mixture was filtered through celite and washed with EtOAc (150 mL). The resulting solution was washed with saturated aqueous NaHCO₃, brine, dried over Na₂SO₄, filtered and evaporated under reduced pressure then dried to give the title compound as light brown crystals (0.39 g, 89%); ¹H NMR (400 MHz, CDCl₃) δ 6.76 (s, 1H), 4.44 (s, 2H), 3.56 (s, 2H). LCMS-A: rt 5.53 min, m/z (positive ion) 178.1 [M+H]⁺.

c) 2-(4-(Benzyloxy)phenyl)-5, 7-dichloro-1H-imidazo[4,5-b]pyridine (41)

A suspension of 4,6-dichloropyridine-2,3-diamine A92 (0.39 g, 2.2 mmol) and 4-(benzyloxy)benzaldehyde A8 (0.465 g, 2.19 mmol) in MeOH (10 mL) was irradiated in the microwave at 120° C. for 15 minutes. The volatiles were removed in vacuo and the residue dissolved in THF (10 mL). PhI(OAc)₂ (0.706 g, 2.19 mmol) was added and the resulting mixture stirred for 18 hours at room temperature. The volatiles were removed in vacuo, the residue suspended in saturated aqueous NaHCO₃ (25 mL), extracted into DCM (~100 mL) then adsorbed onto silica gel and purified using silica gel chromatography (40 g silica cartridge, 0-100% EtOAc in cyclohexane), solvent evaporated under reduced pressure, then dried to give the title compound as a fawn coloured solid (0.083 g, 10%); ¹H NMR (400 MHz, d₆-DMSO) δ 8.18 (d, J=8.0 Hz, 2H), 7.53 (s, 1H), 7.51-7.44 (m, 2H), 7.45-7.31 (m, 3H), 7.25-7.13 (m, 2H), 5.22 (s, 2H). Amine proton not seen; LCMS-A: rt 6.79 min, m/z (positive ion) 370.0 [M+H]⁺; m/z (negative ion) 368.0 [M–H]⁻.

Example 42: Synthesis of 7-chloro-2-(4-(phenoxymethyl)phenyl)-5-(piperidin-4-yl)-1H-imidazo[4,5-b]pyridine (42)

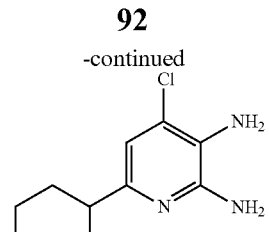

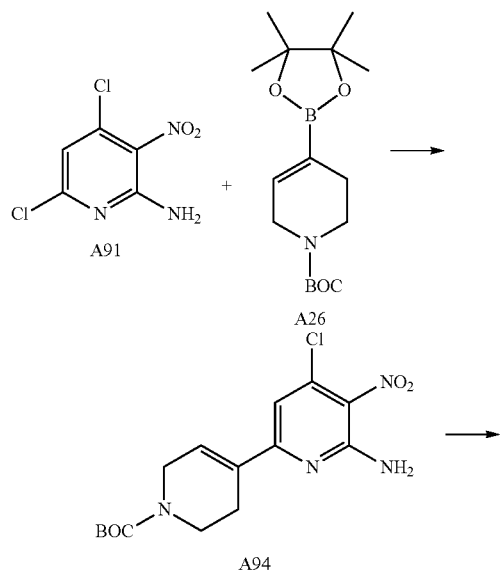

a) tert-Butyl 6-amino-4-chloro-5-nitro-5',6'-dihydro-[2,4'-bipyridine]-1'(2'H)-carboxylate (A94)

To a mixture of 4,6-dichloropyridine-2,3-diamine A91 (1.24 g, 5.96 mmol) in dioxane (36 mL) and H₂O (1.8 mL) was added Na₂CO₃ (2.527 g, 23.84 mmol) followed by tert-butyl 4-(4,4,5,5-tetramethyl-1,3,2-dioxaborolan-2-yl)-5,6-dihydropyridine-1(2H)-carboxylate A26 (2.393 g, 7.74 mmol). The resulting mixture was degassed for 10 mins under a stream of nitrogen. PdCl₂(dppf) DCM solvate (0.260 g, 0.447 mmol) was added, then the mixture was heated to 100° C. for 24 hours. The cooled mixture was evaporated under reduced pressure, the residue dissolved in DCM, adsorbed onto silica then purified by silica gel chromatography (40 g silica cartridge, 0-100% EtOAc in petroleum benzine 40-60° C.) gave the title compound as bright yellow crystals (0.225 g, 11%); ¹H NMR (400 MHz, CDCl₃) δ 6.53 (s, 1H), 6.45 (br. s, 2H), 5.65 (br. s, 1H), 4.03 (s, 2H), 3.62 (d, J=5.4 Hz, 2H), 2.26 (br. s, 2H), 1.49 (s, 9H). LCMS-A: rt 6.75 min, m/z (positive ion) 255.1 [M-Boc+2H]⁺; m/z (negative ion) 353.1 [M–H]⁻.

b) tert-Butyl 4-(5,6-diamino-4-chloropyridin-2-yl)piperidine-1-carboxylate (A95)

A suspension of tert-butyl 6-amino-4-chloro-5-nitro-5',6'-dihydro-[2,4'-bipyridine]-1'(2'H)-carboxylate A94 (0.225 g, 0.36 mmol) and platinum(IV) oxide (0.030 g, 0.64 mmol), in DIPEA (6.7 mL) and MeOH (1.4 mL) was stirred under

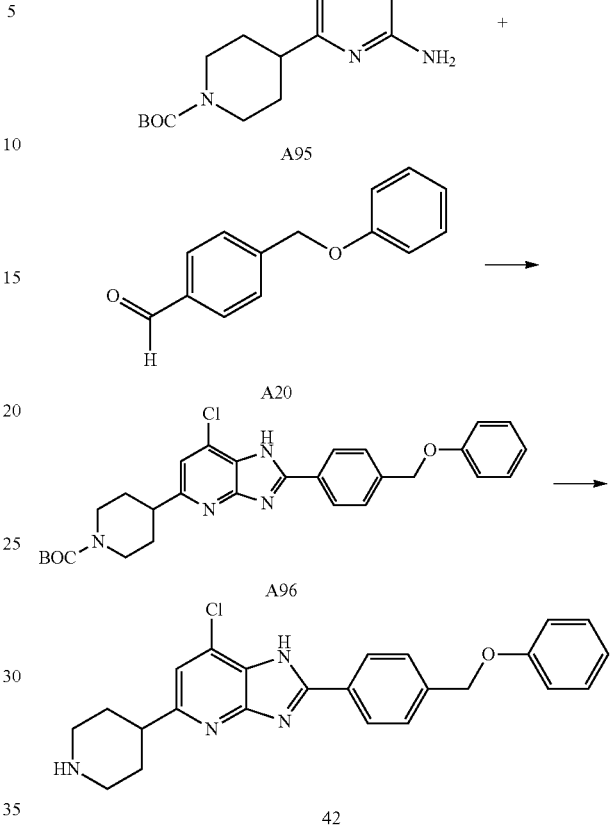

hydrogen (1 atm) for 18 hours. The reaction mixture was filtered through celite, washed with EtOAc, evaporated under reduced pressure, then placed on the freezedrier overnight to give the title compound as a brown solid (0.235 g, quant). LCMS-A rt 6.03 min, 327.2 [M+H]¹H NMR (400 MHz, d$_6$-DMSO) b 6.27 (s, 1H), 5.76 (s, 2H), 4.60 (s, 2H), 4.14-3.92 (m, 2H), 2.89-2.69 (m, 3H), 1.65 (d, J=12.7 Hz, 2H), 1.40 (s, 9H). Two protons obscured by solvent.

c) tert-Butyl 4-(7-chloro-2-(4-(phenoxymethyl)phenyl)-1H-imidazo[4,5-b]pyridin-5-yl)piperidine-1-carboxylate (A96)

A mixture of 4-(phenoxymethyl)benzaldehyde A20 (0.153 g, 0.719 mmol), tert-butyl 4-(5,6-diamino-4-chloropyridin-2-yl)piperidine-1-carboxylate A95 (0.235 g, 0.719 mmol) in MeOH (6 mL), activated 3 Å molecular sieves (400 mg) and acetic acid (9 drops) under an atmosphere of nitrogen was stirred at 60° C. for 18 hours. The volatiles were removed in vacuo, and the residue dissolved in THF (6 mL). PhI(OAc)$_2$ (0.232 g, 0.719 mmol) was added then stirred at room temperature for 22 hours. The volatiles were removed in vacuo, the residue dissolved in EtOAc, washed with saturated aqueous NaHCO$_3$, then extracted with EtOAc. The organic layers were combined then washed with saturated aqueous NaCl. The organic layer was dried over Na$_2$SO$_4$, filtered, evaporated under reduced pressure, the residue adsorbed onto silica gel then purified using silica gel chromatography (24 g silica cartridge, 0-100% EtOAc in petroleum benzine 40-60° C.) to give the title compound as an off-white powder (0.071 g, 19%); ¹H NMR (400 MHz, d$_6$-DMSO) δ 8.21 (d, J=8.4 Hz, 2H), 7.63 (d, J=8.0 Hz, 2H), 7.30 (dd, J=8.7, 7.3 Hz, 2H), 7.16 (s, 1H), 7.08-6.99 (m, 2H), 6.98-6.89 (m, 1H), 5.19 (s, 2H), 4.12 (d, J=12.5 Hz, 2H), 2.89 (br. s, 2H), 1.88 (d, J=9.2 Hz, 2H), 1.80 (br. s, 2H), 1.43 (s, 9H). One proton obscured by solvent, amine proton not observed. LCMS-A: rt 7.10 min, m/z (positive ion) 519.2 [M+H]$^+$.

d) 7-Chloro-2-(4-(phenoxymethyl)phenyl)-5-(piperidin-4-yl)-1H-imidazo[4,5-b]pyridine (42)

tert-Butyl 4-(7-chloro-2-(4-(phenoxymethyl)phenyl)-1H-imidazo[4,5-b]pyridin-5-yl)piperidine-1-carboxylate A96 (0.071 g, 0.14 mmol) was dissolved in DCM (6 mL) under an atmosphere of nitrogen and trifluoroacetic acid (0.32 mL, 4.1 mmol) was added. The resulting mixture was stirred at room temperature for 18 hours. The reaction mixture was concentrated in vacuo and the resulting solid was dissolved in EtOAc (50 mL) and 2 M aqueous NaOH (50 mL). The layers were separated and the aqueous layer was extracted with EtOAc (20 mL), the combined organics were washed with brine (20 mL), dried (Na$_2$SO$_4$), filtered and concentrated in vacuo to give the title compound as a pale yellow solid (0.053 g, 93%); ¹H NMR (400 MHz, d$_6$-DMSO) δ 8.23 (d, J=8.3 Hz, 2H), 7.61 (d, J=8.3 Hz, 2H), 7.30 (dd, J=8.7, 7.3 Hz, 2H), 7.07-7.01 (m, 3H), 6.99-6.87 (m, 1H), 5.18 (s, 2H), 3.08 (d, J=12.0 Hz, 2H), 2.69 (td, J=12.2, 2.9 Hz, 2H), 1.87-1.67 (m, 4H). One proton obscured by solvent, amine proton not observed. LCMS-A: rt 4.80 min, m/z (positive ion) 419.2 [M+H]$^+$, m/z (negative ion) 417.1 [M-H]$^-$.

Example 43: Synthesis of 7-methyl-2-(4-(phenoxymethyl)phenyl)-3H-imidazo[4,5-b]pyridin-5-amine (43)

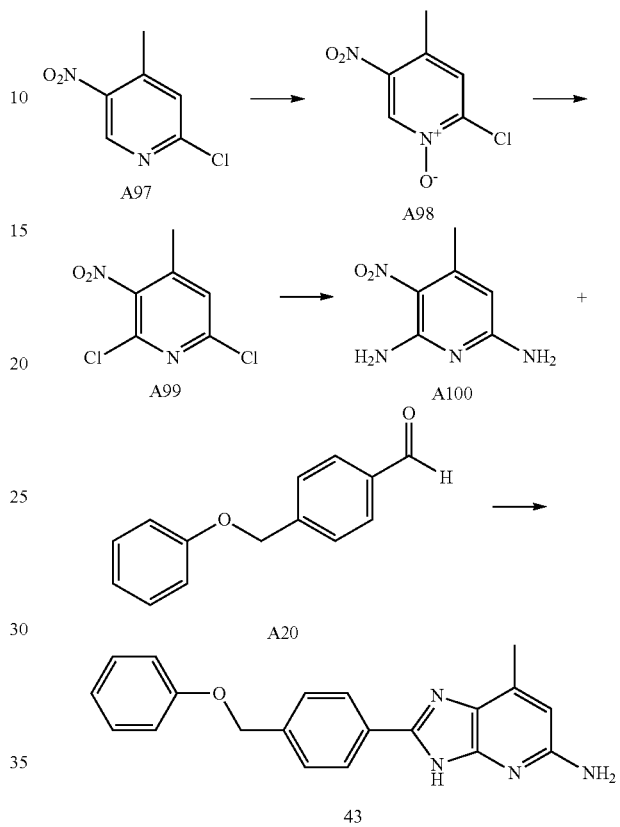

a) 2-Chloro-4-methyl-5-nitropyridine-1-oxide (A98)

A solution of 2-chloro-5-nitro-4-picoline A97 (2.50 g, 14.5 mmol) in DCM (25 mL) was cooled to 0° C. and urea hydrogen peroxide (2.86 g, 30.4 mmol) was added, followed by dropwise addition of trifluoroacetic anhydride (4.10 mL, 29.0 mmol). The mixture stirred at 0° C. for 10 minutes, then allowed to warm to r.t. and stirred for a further 20 hours. The reaction was quenched with water (25 mL), stirred for 20 minutes, then diluted with further water and DCM (50 mL each). The aqueous phase was separated and extracted with DCM (3×75 mL). The combined organic extracts were washed with saturated NaHCO$_3$ (100 mL), and the bicarbonate wash back extracted with further DCM (2×75 mL). The combined organic extracts were dried over Na$_2$SO$_4$, filtered and concentrated in vacuo. The solid residue was washed with diethyl ether (10 mL) and dried under vacuum to give the title compound as a bright yellow solid (2.53 g, 93%). ¹H NMR (400 MHz, CDCl$_3$): δ 9.02 (s, 1H), 7.51 (s, 1H), 2.63 (s, 3H). LCMS-B: 2.637 min; m/z (positive ion) 189.0 [M+H]$^+$.

b) 2,6-Dichloro-4-methyl-3-nitropyridine (A99)

2-Chloro-4-methyl-5-nitropyridine-1-oxide A98 (2.528 g, 13.4 mmol) was stirred in POCl$_3$ (12.5 mL) at 80° C. After 17 hours, the mixture was cooled and added slowly and cautiously to water (150 mL). Once the exothermic POCl₃ breakdown had finished, the mixture was diluted with ice (50 g), neutralised with solid NaHCO₃, diluted with further water (75 mL) and extracted with DCM (5×75 mL). The combined DCM extracts were dried over Na₂SO₄ then concentrated in vacuo. The crude material was purified by silica gel chromatography (40 g silica cartridge, 0-80% EtOAc in petroleum benzine 40-60° C.) to give the title compound as a yellow oil (778 mg, 28%). ¹H NMR (400 MHz, CDCl₃): δ 7.28 (q, J=0.8 Hz, 1H), 2.38 (d, J=0.7 Hz, 3H). LCMS-B: rt 3.44 min, no product ions detected.

c) 4-Methyl-3-nitropyridine-2,6-diamine (A100)

To 2,6-dichloro-4-methyl-3-nitropyridine A99 (100 mg, 0.483 mmol) was added 29% w/w aqueous ammonia (1.0 mL, 16 mmol). The mixture was irradiated in a microwave reactor at 130° C. for 30 minutes. The mixture was cooled, diluted with water (1.0 mL) and the precipitate filtered to give a brown solid. The solid was purified by silica gel chromatography (12 g silica cartridge, 0-100% EtOAc in petroleum benzine 40-60° C.) to give the title compound (0.035 g, 43%) as a yellow solid. ¹H NMR (400 MHz, d₆-DMSO): δ 7.64 (br s, 2H), 6.97 (brs, 2H), 5.74 (d, J=1.0 Hz, 1H), 2.39 (d, J=0.9 Hz, 3H). LC-MS: rt 2.67 min, m/z (positive ion) 168.2 [M+H]⁺.

d) 7-Methyl-2-(4-(phenoxymethyl)phenyl)-3H-imidazo[4,5-b]pyridin-5-amine (43)

To a suspension of 4-(phenoxymethyl)benzaldehyde A20 (0.015 g, 0.072 mmol) and 4-methyl-3-nitropyridine-2,6-diamine A100 (0.011 g, 0.065 mmol) in EtOH (0.325 mL) was added 1 M aqueous Na₂S₂O₄ solution (0.196 mL, 0.196 mmol). The resulting yellow suspension was irradiated in a microwave reactor at 110° C. for 15 minutes. The reaction was cooled to room temperature then 28% w/w aqueous NH₃ (1 mL) was added and the reaction mixture was stirred for 5 minutes. The solution was filtered to give a yellow solid. The solid was purified by silica gel chromatography (4 g silica Cartridge, 0-100% EtOAc in petroleum benzine 40-60° C., then 0-10% MeOH in EtOAc) to give the title compound (0.004 g, 19%) as a white solid. ¹H NMR (400 MHz, d₆-acetone): δ 11.64 (br s, 1H), 8.20 (d, J=8.3 Hz, 2H), 7.60 (d, J=8.0 Hz, 2H), 7.37-7.24 (m, 2H), 7.05 (d, J=8.2 Hz, 2H), 6.95 (t, J=7.3, 7.3 Hz, 1H), 6.33 (s, 1H), 5.24 (brs, 1H), 5.22 (br s, 1H), 5.19 (s, 2H), 2.48 (s, 3H). LCMS-B: rt 3.08 min, m/z (positive ion) 331.2 [M+H]⁺.

Example 44: Synthesis of (4-(5-chloro-3H-imidazo[4,5-b]pyridin-2-yl)phenyl)(phenyl)MeOH (44)

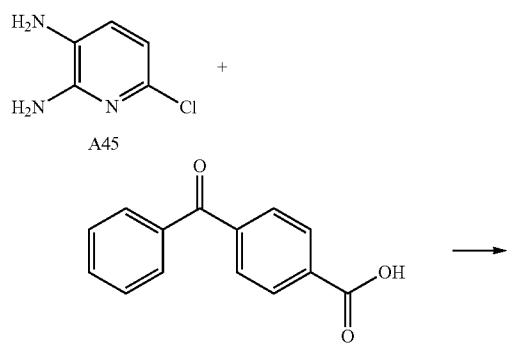

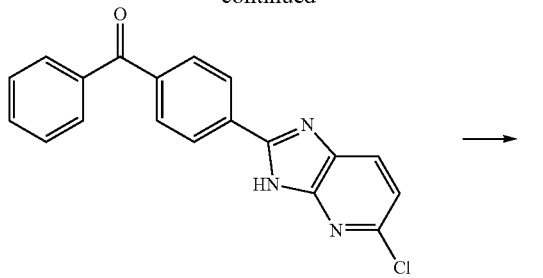

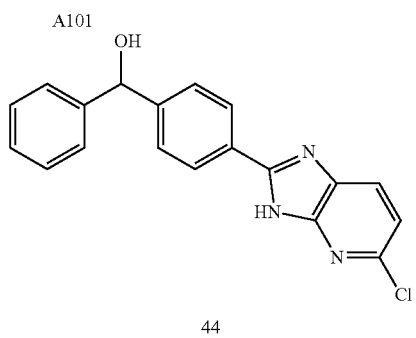

a) (4-(5-Chloro-3H-imidazo[4,5-b]pyridin-2-yl)phenyl)(phenyl)methanone (A101)

HATU (0.924 g, 2.43 mmol) was added to a solution of the 6-chloropyridine-2,3-diamine A45 (0.317 g, 2.21 mmol), 4-benzoylbenzoic acid (0.500 g, 2.21 mmol) and DIPEA (1.16 mL, 6.63 mmol) in MeCN (40 mL) and the resulting solution stirred at 40° C. for 18 hours. The mixture was diluted with saturated aqueous NaHCO₃ (100 mL) and extracted with EtOAc (3×100 mL). The combined organic extracts were washed with saturated brine (150 mL), dried (Na₂SO₄), filtered and the volatiles removed in vacuo to give a brown solid. The solid was dissolved in acetic acid (6 mL) and heated under microwave irradiation at 140° C. for 1 hour. The volatiles were removed in vacuo and the residue treated with saturated aqueous NaHCO₃ (100 mL) and extracted with EtOAc (3×100 mL). The combined organic extracts were washed with brine (150 mL), dried (Na₂SO₄), filtered and the volatiles removed in vacuo to give a brown semi-solid which was purified by silica gel chromatography (40 g silica cartridge eluting with 0-70% EtOAc in petroleum benzine 40-60° C.) to give a pale yellow solid which was sonicated in diethyl ether (15 mL) and the supernatant carefully removed and discarded. The resulting solid was dried in vacuo to give the title compound as a white solid (0.086 g, 12%). ¹H NMR (400 MHz, d₆-DMSO) δ 13.84 (s, 1H), 8.38 (d, J=8.5 Hz, 2H), 8.11 (d, J=8.3 Hz, 1H), 7.93 (d, J=8.4 Hz, 2H), 7.81-7.77 (m, 2H), 7.74-7.69 (m, 1H), 7.60 (t, J=7.6 Hz, 2H), 7.35 (d, J=8.3 Hz, 1H). LCMS-A rt 6.15 min, m/z (positive ion) 334, 336 [M+H]⁺.

b) (4-(5-Chloro-3H-imidazo[4,5-b]pyridin-2-yl)phenyl)(phenyl)MeOH (44)

NaBH₄ (0.024 g, 0.63 mmol) was added to a solution of (4-(5-chloro-3H-imidazo[4,5-b]pyridin-2-yl)phenyl)(phenyl)methanone A101 (0.070 g, 0.21 mmol) in MeOH (5 mL) and DCM (1 mL) and the resulting mixture stirred at room temperature for 2 hours. The volatiles were removed in vacuo and the residue dissolved in EtOAc (25 mL) and washed with 2 M aqueous HCl (25 mL), saturated aqueous NaHCO₃ (25 mL), brine (25 mL), dried (Na₂SO₄), filtered and concentrated under reduced pressure to give a white solid which was purified by silica gel chromatography (12 g silica cartridge, 0-100% EtOAc in petroleum benzine 40-60° C.) to give the title compound as a white solid (0.036 g, 51%); ¹H NMR (400 MHz, d₆-DMSO) δ 13.52 (s, 1H), 8.13 (d, J=8.3 Hz, 2H), 8.02 (d, J=8.2 Hz, 1H), 7.57 (d, J=8.3 Hz, 2H), 7.44-7.39 (m, 2H), 7.34-7.27 (m, 3H), 7.24-7.18 (m, 1H), 6.03 (d, J=4.0 Hz, 1H), 5.78 (d, J=3.7 Hz, 1H). LCMS-A rt 5.77 min, m/z (positive ion) 336, 338 [M+H]⁺.

Example 45: Synthesis of 2-(4-(benzyloxy)phenyl)-5-(1,2,3,6-tetrahydropyridin-4-yl)-3H-imidazo[4,5-b]pyridine (45)

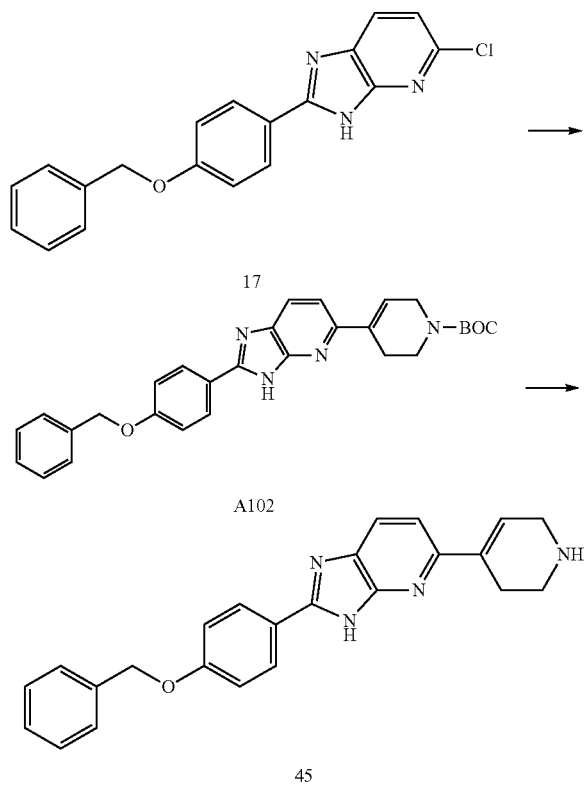

a) tert-Butyl 4-(2-(4-(benzyloxy)phenyl)-3H-imidazo[4,5-b]pyridin-5-yl)-5,6-dihydropyridine-1(2H)-carboxylate (A102)

2-(4-(benzyloxy)phenyl)-5-chloro-3H-imidazo[4,5-b]pyridine (17) (100 mg, 0.30 mmol), tert-butyl 4-(4,4,5,5-tetramethyl-1,3,2-dioxaborolan-2-yl)-5,6-dihydropyridine-1(2H)-carboxylate (276 mg, 0.89 mmol), PdCl₂(dppf) DCM solvate (62 mg, 25 mol %) and DMF (5 mL) were stirred under nitrogen. A solution of Na₂CO₃ (284 mg, 2.68 mmol) in water (1.5 mL) was added, the mixture degassed with bubbling nitrogen and heated to 80° C. under nitrogen. After 17 hours the mixture was cooled and added to EtOAc (50 mL). The mixture was filtered through celite, the celite washed with further EtOAc (50 mL) and the filtrate concentrated. Column chromatography (12 g silica cartridge, 0-100% EtOAc/hexanes) and collection of the suspected product fractions gave tert-butyl 4-(2-(4-(benzyloxy)phenyl)-3H-imidazo[4,5-b]pyridin-5-yl)-5,6-dihydropyridine-1(2H)-carboxylate as a white solid (93 mg, 64%). ¹H NMR (400 MHz, DMSO) δ 13.26 (br s, 1H), 8.19-8.12 (m, 2H), 7.91 (d, J=8.3 Hz, 1H), 7.52-7.31 (m, 5H), 7.22-7.16 (m, 2H), 6.64 (s, 1H), 5.21 (s, 2H), 4.07 (s, 2H), 3.57 (t, J=5.6 Hz, 2H), 2.69-2.62 (m, 2H), 1.44 (s, 9H). LCMS-A rt 6.25 min; m/z (positive ion) 483.3 [M+H]⁺; m/z (negative ion) 481.2 [M−H]⁻.

b) 2-(4-(Benzyloxy)phenyl)-5-(1,2,3,6-tetrahydropyridin-4-yl)-3H-imidazo[4,5-b]pyridine (45)

tert-Butyl 4-(2-(4-(benzyloxy)phenyl)-3H-imidazo[4,5-b]pyridin-5-yl)-5,6-dihydropyridine-1(2H)-carboxylate (92 mg, 0.19 mmol), DCM (4 mL) and TFA (1 mL) were stirred at room temperature for 18 hours. The mixture was quenched with saturated aqueous K₂CO₃ until pH 11 was reached, the volatiles were removed on a rotary evaporator and the residue diluted with water (10 mL). The precipitate was collected, dissolved in MeOH and applied to a 10 g SCX cartridge. The cartridge was washed with MeOH (100 mL) and eluted with 9:1 MeOH:concentrated aqueous ammonia. The basic eluent was concentrated, and the residue evaporated from absolute EtOH twice to give the title compound as an off-white solid (19 mg, 26%). ¹H NMR (400 MHz, DMSO) δ 8.16 (d, J=8.4 Hz, 2H), 7.91 (d, J=8.4 Hz, 1H), 7.51-7.33 (m, 5H), 7.19 (d, J=8.4 Hz, 2H), 6.68 (s, 1H), 5.20 (s, 2H), 3.53 (s, overlaps with water), 3.05 (s, 2H), 2.61 (s, 2H). NH protons not visible. LCMS-A: rt 4.66 min; m/z (positive ion) 383.2 [M+H]⁺; m/z (negative ion) 381.1 [M−H]⁻.

Example 46: Synthesis of (R)-2-amino-1-(4-(2-(4-(benzyloxy)phenyl)-3H-imidazo[4,5-b]pyridin-5-yl)piperidin-1-yl)propan-1-one (46)

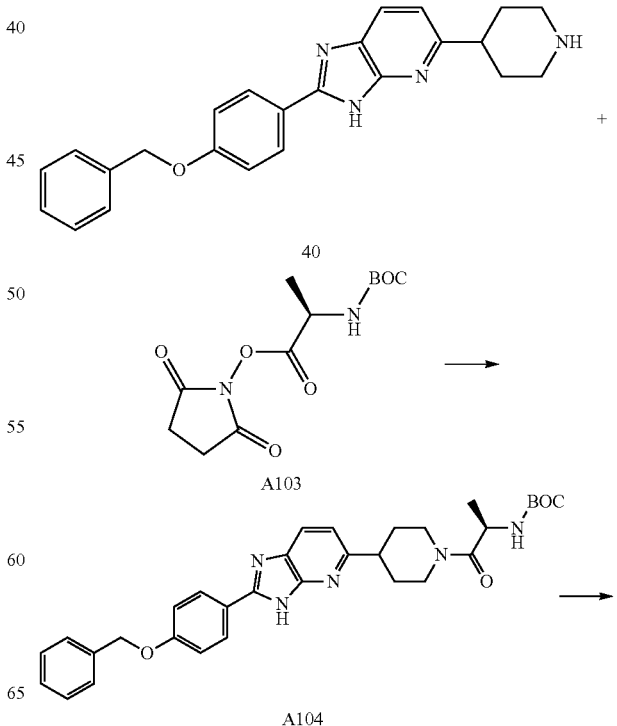

-continued

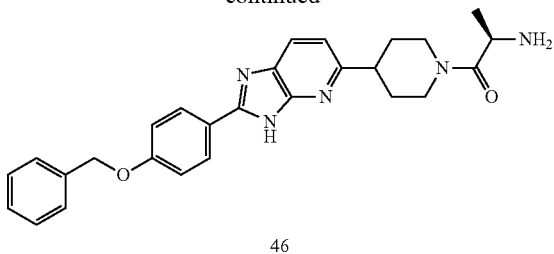

46 a) (R)-tert-Butyl (1-(4-(2-(4-(benzyloxy)phenyl)-3H-imidazo[4,5-b]pyridin-5-yl)piperidin-1-yl)-1-oxopropan-2-yl)carbamate (A104)

2-(4-(Benzyloxy)phenyl)-5-(piperidin-4-yl)-3H-imidazo[4,5-b]pyridine 40 (30 mg, 0.078 mmol), (R)-2,5-dioxopyrrolidin-1-yl 2-((tert-butoxycarbonyl)amino)propanoate A103 (34 mg, 0.12 mmol) and DMF (0.5 mL) were mixed and stood at room temperature. After 16 hours the mixture was added to water (20 mL) and extracted with EtOAc (3×20 mL). The combined EtOAc phases were washed with water (40 mL), brine (3×40 mL), dried over $Na_2SO_4$, filtered and evaporated. Column chromatography (4 g silica cartridge, 0-100% EtOAc/hexanes) and collection of the suspected product fractions gave (R)-tert-butyl (1-(4-(2-(4-(benzyloxy)phenyl)-3H-imidazo[4,5-b]pyridin-5-yl)piperidin-1-yl)-1-oxopropan-2-yl)carbamate as a colourless syrup (26 mg, 60%). LCMS: rt 5.60 min; m/z (positive ion) 556.3 $[M+H]^+$, 456.2 $[M-Boc+2H]^+$; m/z (negative ion) 554.3 $[M-H]$ $^1H$ NMR (400 MHz, $CDCl_3$) δ 10.48 (s, 1H), 8.11-7.91 (m, 3H), 7.48-7.31 (m, 5H), 7.14-7.02 (m, 3H), 5.80 (d, J=7.9 Hz, 1H), 4.81-4.62 (m, 2H), 4.01 (d, J=13.4 Hz, 1H), 3.28-3.11 (m, 1H), 3.09-2.95 (m, 1H), 2.76 (q, J=11.5 Hz, 1H), 2.11-1.95 (m, overlaps with trace solvent), 1.94-1.77 (m, overlaps with water), 1.42 (d, J=6.4 Hz, 9H), 1.35 (dd, J=15.5, 6.8 Hz, 3H).

b) (R)-2-Amino-1-(4-(2-(4-(benzyloxy)phenyl)-3H-imidazo[4,5-b]pyridin-5-yl)piperidin-1-yl)propan-1-one (46)

(R)-tert-butyl (1-(4-(2-(4-(benzyloxy)phenyl)-3H-imidazo[4,5-b]pyridin-5-yl)piperidin-1-yl)-1-oxopropan-2-yl)carbamate (25 mg, 0.045 mmol), DCM (4 mL) and TFA (2 mL) were stood for two hours. The mixture was quenched with saturated aqueous $K_2CO_3$ (20 mL) and the volatiles solvents removed on a rotary evaporator. The aqueous residue was diluted with water (10 mL) and extracted with EtOAc (3×20 mL). The combined organic extracts were dried over $Na_2SO_4$, filtered and evaporated to give (R)-2-amino-1-(4-(2-(4-(benzyloxy)phenyl)-3H-imidazo[4,5-b]pyridin-5-yl)piperidin-1-yl)propan-1-one as a colourless glass (36 mg).

LCMS: rt 4.58 min; m/z (positive ion) 456.3 $[M+H]^+$, 385.2 $[M-Ala+2H]^+$; m/z (negative ion) 454.3 $[M-H]$ $^1H$ NMR (400 MHz, DMSO) δ 8.17-8.12 (m, 2H), 7.86 (d, J=8.1 Hz, 1H), 7.51-7.46 (m, 2H), 7.45-7.39 (m, 2H), 7.38-7.33 (m, 1H), 7.18 (d, J=8.9 Hz, 2H), 7.10 (d, J=8.1 Hz, 1H), 5.21 (s, 2H), 4.61-4.49 (m, 1H), 4.11-3.99 (m, 1H), 3.80 (q, J=6.6 Hz, 1H), 3.23-3.11 (m, 2H), 3.09-2.99 (m, 1H), 2.75-2.64 (m, 1H), 1.91 (d, J=13.7 Hz, 2H), 1.86-1.50 (m, 3H), 1.15-1.06 (m, 3H).

Example 47: Synthesis of 2-(4-(benzyloxy)phenyl)-5-(piperazin-1-yl)-3H-imidazo[4,5-b]pyridine (47)

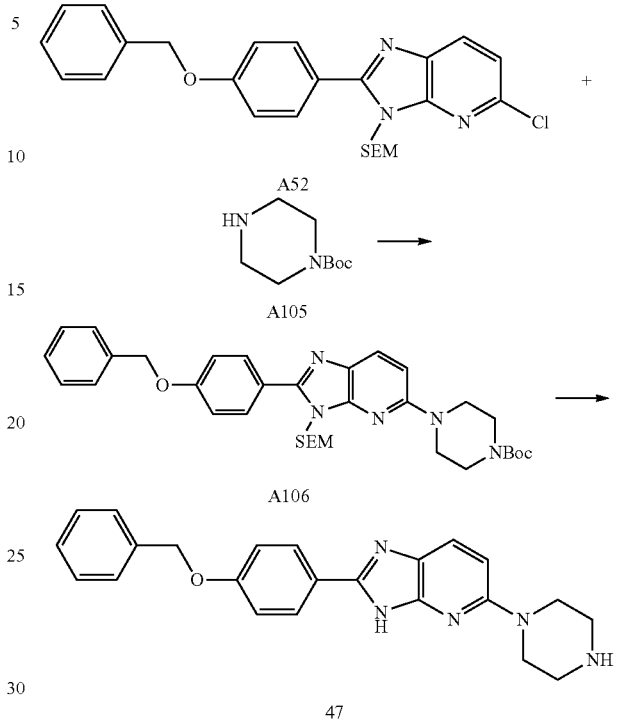

a) tert-Butyl 4-(2-(4-(benzyloxy)phenyl)-3-((2-(trimethylsilyl)ethoxy)methyl)-3H-imidazo[4, 5-b]pyridin-5-yl)piperazine-1-carboxylate (A106)

A solution of 2-(4-(benzyloxy)phenyl)-5-chloro-3-((2-(trimethylsilyl)ethoxy)methyl)-3H-imidazo[4,5-b]pyridine A52 (51.3 mg, 110 μmol), N-Boc piperazine A105 (24.6 mg, 132 μmol), RuPhos ligand (4.8 mg, 10 μmol), chloro-(2-dicyclohexylphosphino-2',6'-diisopropoxy-1,1'-biphenyl)[2-(2-aminoethyl)phenyl]palladium(II)-methyl-t-butyl ether adduct (11.3 mg, 13 μmol) and NaOt-Bu (12.6 mg, 131 μmol) in THF (1 mL) was evacuated and purged with nitrogen three times. The suspension was heated at 85° C. for 3 hours and then cooled to room temperature. EtOAc (10 mL) and water (5 mL) were added and the layers separated. The aqueous layer was extracted with EtOAc (5 mL). The combined organic layers were dried with $Na_2SO_4$, filtered and concentrated in vacuo. The crude reaction product was purified by column chromatography (4 g silica cartridge, 10-80% EtOAc in cyclohexane) to give the title compound as a pale yellow oil (24.7 mg, 36%). $^1H$ NMR (400 MHz, $CDCl_3$) δ 8.06-8.02 (m, 2H), 7.88 (d, J=8.7 Hz, 1H), 7.49-7.44 (m, 2H), 7.43-7.38 (m, 2H), 7.37-7.33 (m, 1H), 7.12-7.08 (m, 2H), 6.68 (d, J=8.8 Hz, 1H), 5.57 (s, 2H), 5.14 (s, 2H), 3.90-3.84 (m, 2H), 3.59 (s, 8H) 1.50 (s, 9H), 1.06-0.99 (m, 2H), −0.01 (s, 9H); LCMS-B rt 4.86 min.

b) 2-(4-(Benzyloxy)phenyl)-5-(piperazin-1-yl)-3H-imidazo[4,5-b]pyridine (47)

tert-Butyl 4-(2-(4-(benzyloxy)phenyl)-3-((2-(trimethylsilyl)ethoxy)methyl)-3H-imidazo[4,5-b]pyridin-5-yl)piperazine-1-carboxylate A106 (24.7 mg, 40.0 μmol) was dissolved in $CDCl_3$ (2 mL), TFA (1 mL) was added and the mixture stirred for 72 hours. The reaction mixture was concentrated and the residue dissolved in the minimum amount of MeOH. The solution was loaded onto an SCX cartridge (1 g) and washed with MeOH (20 mL). The product was eluted by treating with MeOH:NH₄OH 9:1 to give a pale yellow solid. The solid was further purified by mass-directed prep HPLC to give the title compound as a pale yellow solid (3.2 mg, 20%). ¹H NMR (400 MHz, DMSO) δ 8.27 (s, 1H), 8.06 (d, J=8.9 Hz, 2H), 7.76 (d, J=8.8 Hz, 1H), 7.51-7.45 (m, 2H), 7.45-7.37 (m, 2H), 7.37-7.31 (m, 1H), 7.14 (d, J=8.9 Hz, 1H), 6.75 (d, J=8.9 Hz, 1H), 5.18 (s, 2H), 3.66-3.38 (m, 4H), 2.96-2.87 (m, 4H); LCMS-C rt 4.08 min; m/z (positive ion) 386 [M+H]⁺.

Example 48: Synthesis of 2-(4-(benzyloxy)phenyl)-N,N-dimethyl-3H-imidazo[4,5-b]pyridin-5-amine (48)

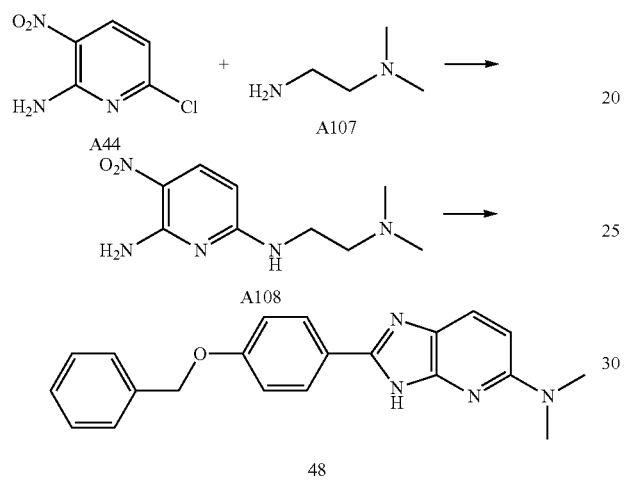

(a) N²-(2-(Dimethylamino)ethyl)-5-nitropyridine-2,6-diamine (A108)

General Method A: 2-amino-6-chloro-3-nitropyridine A44 (200 mg, 1.15 mmol), N¹,N¹-dimethylethane-1,2-diamine A107 (122 mg, 1.38 mmol). The orange solution was treated with water (5 mL) and the resulting suspension filtered. The filtrate was extracted with EtOAc (2×20 mL), washed with brine (5 mL) and concentrated to give the title compound as a yellow powder (114 mg, 44%); LCMS-B rt 1.77 min, m/z (positive ion) 226 [M+H]⁺ with impurities at 2.89 min, and 3.03 min.

(b) 2-(4-(Benzyloxy)phenyl)-N, N-dimethyl-3H-imidazo[4,5-b]pyridin-5-amine (48)

General Method B: N2-(2-(dimethylamino)ethyl)-5-nitropyridine-2,6-diamine A108 (289 mg, 1.28 mmol). The resulting yellow suspension was heated at 110° C. for 20 minutes in a microwave. The reaction was cooled to room temperature. The reaction mixture was treated with 28% w/w aqueous ammonia (1 mL) and extracted with EtOAc (3×10 mL). The combined organic layers were washed with water (2×10 mL), brine (5 mL), dried (MgSO₄) and concentrated in vacuo. The crude material was purified by column chromatography (24 g silica cartridge, 10-100% EtOAc in petroleum benzine 40-60° C.) to give the title compound as a colourless solid (1.8 mg, 0.4%); ¹H NMR (400 MHz, CD₃OD) δ 7.96 (d, J=8.9 Hz, 2H), 7.71 (d, J=8.8 Hz, 1H), 7.52-7.43 (m, 2H), 7.43-7.35 (m, 2H), 7.35-7.28 (m, 1H), 7.12 (d, J=8.9 Hz, 2H), 6.62 (d, J=8.9 Hz, 1H), 5.17 (s, 2H), 3.31 (s, 6H). LCMS-B rt 3.16 min, m/z (positive ion) 345 [M+H]⁺, m/z (negative ion) 343 [M−H]⁻.

Example 49: Synthesis of 2-(4-(benzyloxy)phenyl)-4-methyl-6-(piperidin-4-yl)-1H-benzo[d]imidazole (49)

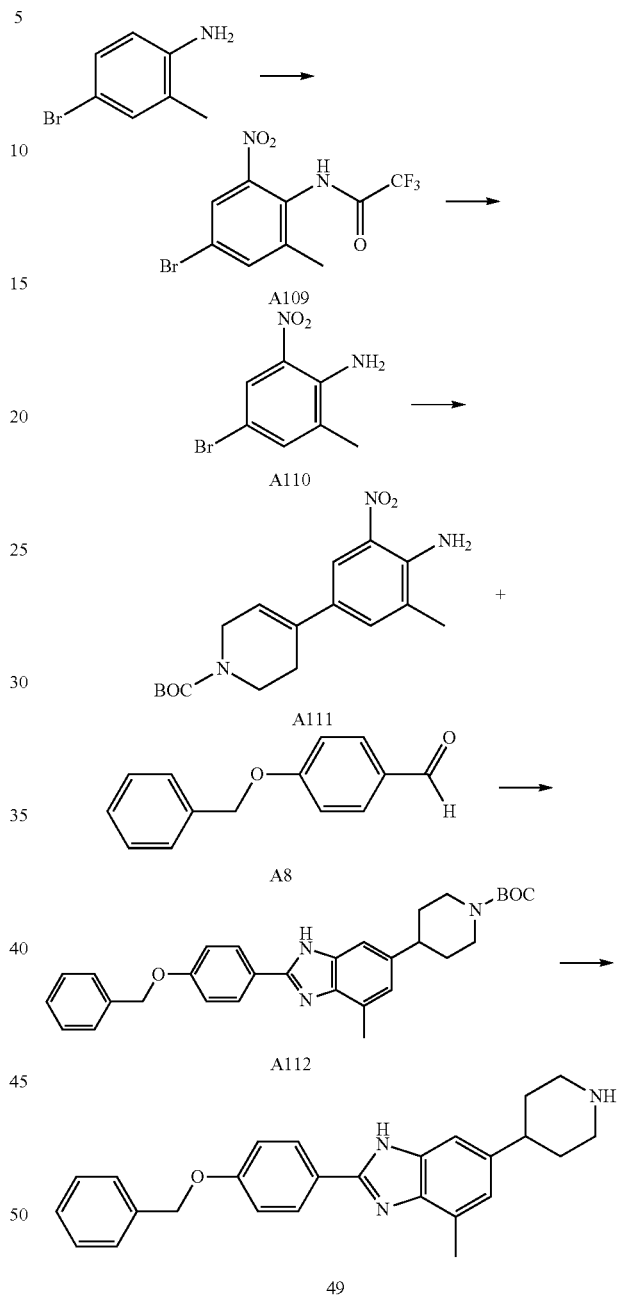

a) N-(4-Bromo-2-methyl-6-nitrophenyl)-2,2,2-trifluoroacetamide (A109)

4-Bromo-2-methylaniline (1.0 g, 5.4 mmol) was dissolved in DCM (4 mL) and cooled to 0° C. Trifluoroacetic anhydride (2 mL) was added, and the mixture stirred for 30 minutes at 0° C. Potassium nitrate (0.679 g, 6.72 mmol) was added, and the cooling bath removed. After 1 hour the mixture became thick and difficult to stir, the mixture was sonicated for 2 minutes and stirring resumed. After 4 hours the mixture was concentrated by evaporation, and the residue suspended in water (25 mL). The mixture was sonicated for 1 minute, filtered and the collected solid washed with water (3×30 mL). The solid was air dried to give the title compound as a lemon yellow solid (1.7 g, 96% yield). $^1$H NMR (400 MHz, CDCl$_3$) δ 9.03 (s, 1H), 8.11-8.09 (m, 1H), 7.76 (d, J=2.2 Hz, 1H), 2.33 (s, 3H). LCMS-B: rt 6.46 min, m/z (negative ion) 327.0 [M−H]$^-$ for $^{81}$Br b) 4-Bromo-2-methyl-6-nitroaniline (A110)

N-(4-Bromo-2-methyl-6-nitrophenyl)-2,2,2-trifluoroacetamide A109 (750 mg, 2.29 mmol), potassium carbonate (634 mg, 4.59 mmol), water (10 mL) and MeOH (20 mL) were stirred at 50° C. After 17 hours the mixture was heated to reflux for 1 hour then allowed to cool. The mixture was diluted with water to 100 mL, and the resultant precipitate collected, washed with water (50 mL) and air dried to give the title compound as a bright yellow solid (323 mg, 61% yield). $^1$H NMR (400 MHz, CDCl$_3$) δ 8.21 (d, J=2.2 Hz, 1H), 7.43-7.39 (m, 1H), 6.20 (br s, 2H), 2.26 (s, 3H). LCMS-B rt 6.56 min.

c) tert-Butyl 4-(4-amino-3-methyl-5-nitrophenyl)-3,6-dihydropyridine-1 (2H)-carboxylate (A111)

4-Bromo-2-methyl-6-nitroaniline A110 (320 mg, 1.39 mmol), tert-butyl 4-(4,4,5,5-tetramethyl-1,3,2-dioxaborolan-2-yl)-3,6-dihydropyridine-1(2H)-carboxylate (471 mg, 1.52 mmol) and PdCl$_2$(dppf) (57 mg, 5 mol %) were loaded into a flask. 1,4-Dioxane (10 mL) was added, followed by a solution of potassium carbonate (383 mg, 2.77 mmol) in water (5 mL). The mixture was degassed by bubbling nitrogen through the reaction mixture then stirred for 17 hours at 80° C. under nitrogen. The cooled mixture was concentrated, the aqueous residue diluted with water (50 mL) and extracted with CHCl$_3$ (3×50 mL). The pooled CHCl$_3$ extracts were washed with brine (50 mL), dried over Na$_2$SO$_4$ and evaporated. Column chromatography (12 g SiO$_2$ cartridge, 0-100% EtOAc in petroleum benzine 40-60° C.) gave the title compound as a viscous orange syrup (321 mg, 70% yield). $^1$H NMR (400 MHz, CDCl$_3$) δ 8.01 (s, 1H), 7.39 (s, 1H), 6.19 (s, 2H), 5.99 (s, 1H), 4.08-4.04 (m, 2H), 3.62 (t, J=5.7 Hz, 2H), 2.51-2.44 (m, 2H), 2.26 (s, 3H), 1.49 (s, 9H). LCMS-B: rt 6.87 min; m/z (positive ion) 278.2 [M-tBu+2H]$^+$; $^{234.1}$ [M-Boc+2H]

d) tert-Butyl 4-(2-(4-(benzyloxy)phenyl)-4-methyl-1H-benzo[d]imidazol-6-yl)piperidine-1-carboxylate (A112)

A mixture of tert-butyl 4-(4-amino-3-methyl-5-nitrophenyl)-3,6-dihydropyridine-1(2H)-carboxylate A111 (320 mg, 0.96 mmol) and 10% Pd/C (50% wet with water, 150 mg) in 1:1 EtOAc:96% EtOH (20 mL) was stirred at room temperature under hydrogen. After 90 hours the mixture was filtered through Celite, and the Celite washed with EtOH (50 mL). The filtrate was evaporated under reduced pressure to give a solid residue. A solution of the resultant solid residue and A8 (211 mg, 0.99 mmol) in EtOH (10 mL) was refluxed under air. After 20 hours the mixture was cooled and concentrated in vacuo. Column chromatography (12 g SiO$_2$ cartridge, 5-100% EtOAc in petroleum benzine 40-60° C., then 0-20% MeOH/EtOAc) then (12 g SiO$_2$ cartridge, 0-100% EtOAc in petroleum benzine 40-60° C.) to gave the title compound as a pale yellow syrup (42 mg, 9% yield). $^1$H NMR (400 MHz, CDCl$_3$) δ 9.64 (br s, 0.5H), 9.36 (br s, 0.5H), 7.98 (d, J=8.4 Hz, 2H), 7.48-7.31 (m, 5H), 7.07 (d, J=8.8 Hz, 2H), 6.91 (s, 1H), 5.13 (s, 2H), 4.26 (br s, 2H), 2.90-2.77 (m, 2H), 2.77-2.46 (m, 4H), 1.87 (d, J=13.0 Hz, 2H), 1.74-1.61 (m, 4H), 1.50 (s, 9H). NH proton not observed. LCMS-B: rt 5.38 min; m/z (positive ion) 498.3 [M+H]$^+$, m/z (negative ion) 496.3 [M−H]$^-$.

e) 2-(4-(Benzyloxy)phenyl)-4-methyl-6-(piperidin-4-yl)-1H-benzo[d]imidazole (49)

tert-Butyl 4-(2-(4-(benzyloxy)phenyl)-4-methyl-1H-benzo[d]imidazol-6-yl)piperidine-1-carboxylate A112 (42 mg, 0.084 mmol), DCM (4 mL) and TFA (1 mL) were stirred for 18 hours at room temperature. The mixture was quenched with saturated potassium carbonate, the volatile solvent removed on a rotary evaporator and the residue extracted with EtOAc (3×20 mL). The pooled EtOAc phases were dried over Na$_2$SO$_4$ and evaporated to give the title compound as a white solid (39 mg, quantitative). LCMS-B: rt 4.42 min; m/z (positive ion) 398.2 [M+H]$^+$; m/z (negative ion) 396.2 [M−H]$^-$ General Procedure Int1: Preparation of 6-amido-3-nitro-pyridin-2-amines

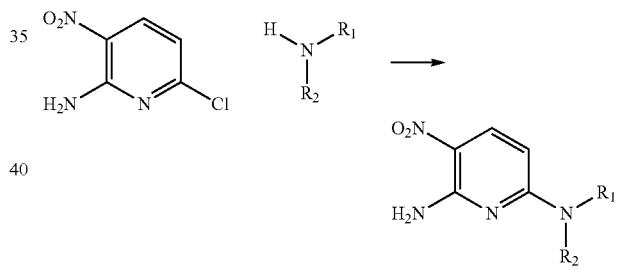

A solution of 6-chloro-3-nitropyridin-2-amine (174 mg, 1.00 mmol), the desired amine (1.20 mmol) and i-Pr$_2$NEt (0.400 mL, 2.31 mmol) in DMF (2 mL) was heated at 85° C. for 17 hours. The solution was cooled to room temperature and water (4 mL) was added. A precipitate formed and the product was isolated by vacuum filtration, washed with water until the filtrates were clear and air dried to give the desired product.

TABLE A

| Example | Amine | Product Name and Structure | LCMS data | Method |
|---|---|---|---|---|
| A113 | HN⟨⟩NHBoc | tert-butyl (1-(6-amino-5-nitropyridin-2-yl)piperidin-4-yl)carbamate | LCMS-B: rt 3.33 min, m/z (positive ion) 360 [M + Na]$^+$, m/z (negative ion) 336 [M − H]$^-$ | Int1 |

TABLE A-continued

| Example | Amine | Product Name and Structure | LCMS data | Method |
|---|---|---|---|---|
| A114 | (structure) | (structure)<br>tert-butyl ((1-(6-amino-5-nitropyridin-2-yl)piperidin-4-yl)methyl)carbamate | LCMS-B: rt 3.37 min, m/z (positive ion) 352 [M + H]⁺ | Int1 |

Example 50-55: Synthesis of 5-amidoimidazopyridines

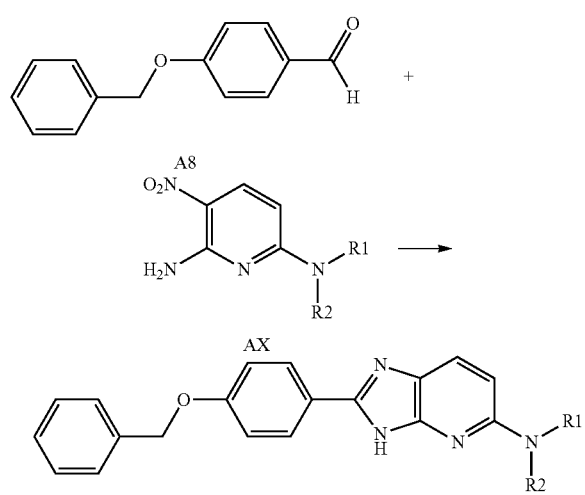

General Procedure C:

A suspension of 4-(benzyloxy)benzaldehyde A8 (102 mg, 0.480 mmol), the desired 6-amido-3-nitropyridin-2-amine (0.400 mmol) and sodium dithionate (209 mg, 1.2 mmol) in EtOH (1.6 mL) and water (1.2 mL) was heated at 110° C. for 15 minutes in a microwave. The mixture was cooled to room temperature and 5 M aqueous ammonium hydroxide solution (1 mL) and EtOAc (3 mL) were added. The layers were separated and the aqueous phase was extracted with EtOAc (3×10 mL). The combined organic layers were washed with brine (5 mL), dried ($Na_2SO_4$), filtered and concentrated in vacuo. The residues were dissolved in the minimum required volume of MeOH and loaded onto an SCX cartridge (10 g) and washed with MeOH (3×10 mL). The product was then eluted with 2 M ammonia in MeOH (3×10 mL), the fractions containing product were combined and concentrated in vacuo to give the desired compound.

TABLE B

| Example | Amound of Int1 | Product Name and Structure | LCMS data | Method |
|---|---|---|---|---|
| A115 | 135 mg, 0.400 mmol A113 | (structure)<br>tert-butyl (1-(2-(4-(benzyloxy)phenyl)-3H-imidazo[4,5-b]pyridin-5-yl)piperidin-4-yl)carbamate | LCMS-B: rt 3.45 min, m/z (positive ion) 500 [M + H]⁺ | C |
| A116 | 140 mg, 0.400 mmol A114 | (structure)<br>tert-butyl ((1-(2-(4-(benzyloxy)phenyl)-3H-imidazo[4,5-b]pyridin-5-yl)piperidin-4-yl)methyl)carbamate | LCMS-B: rt 3.02 min, m/z (positive ion) 514 [M + H]⁺ | C |

General Procedure D:

The desired Boc-protected amines 28, 29, 31, 32, A115, A116 (see table for amounts) were dissolved in DCM (0.5 mL) and treated with TFA (0.5 mL). The resulting solution was stirred at room temperature for 18 hours before the addition of 2 M NaOH until the solution became basic. The aqueous layer was extracted with EtOAc (3×3 mL). The combined organic layers were washed with water (3 mL), brine (3 mL), dried over ($Na_2SO_4$) and concentrated in vacuo. The residue was purified by preparative mass-directed HPLC to give the desired compound.

TABLE C

| Example | Amount of Boc-protected amines | Product Name and Structure | LCMS data | Method |
|---|---|---|---|---|
| 50 | 77.8 mg, 0.151 mmol 28 | 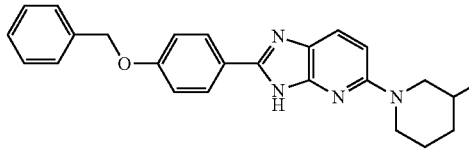<br>(1-(2-(4-(benzyloxy)phenyl)-3H-imidazo[4,5-b]pyridin-5-yl)piperidin-3-yl)methanamine | LCMS-B: rt 2.91 min, m/z (positive ion) 414 [M + H]+ | D |
| 51 | 53.0 mg, 0.103 mmol 29 | 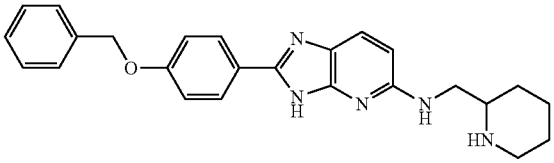<br>2-(4-(benzyloxy)phenyl)-N-(piperidin-2-ylmethyl)-3H-imidazo[4,5-b]pyridin-5-amine | LCMS-B: rt 3.07 min, m/z (positive ion) 414 [M + H]+ | D |
| 52 | 61.9 mg, 0.124 mmol 31 | 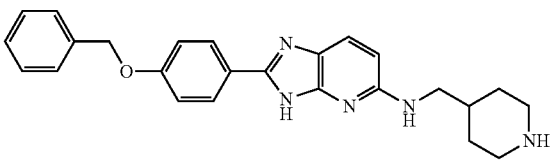<br>2-(4-(benzyloxy)phenyl)-N-(piperidin-4-ylmethyl)-3H-imidazo[4,5-b]pyridin-5-amine | LCMS-B: rt 2.94 min, m/z (positive ion) 414 [M + H]+ | D |
| 53 | 61.9 mg, 0.124 mmol 32 | 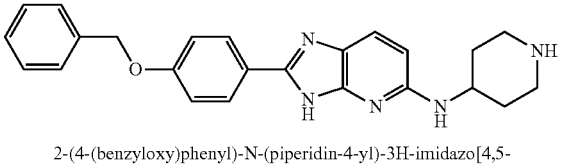<br>2-(4-(benzyloxy)phenyl)-N-(piperidin-4-yl)-3H-imidazo[4,5-b]pyridin-5-amine | LCMS-B: rt 2.92 min, m/z (positive ion) 400 [M + H]+ | D |
| 54 | 21 mg, 0.042 mmol A115 | 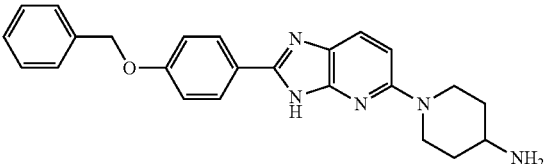<br>1-(2-(4-(benzyloxy)phenyl)-3H-imidazo[4,5-b]pyridin-5-yl)piperidin-4-amine | LCMS-B: rt 2.95 min, m/z (positive ion) 400 [M + H]+ | D |
| 55 | 60.8 mg, 0.118 mmol A116 | 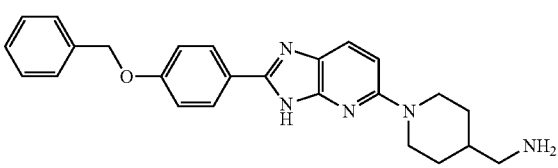<br>(1-(2-(4-(benzyloxy)phenyl)-3H-imidazo[4,5-b]pyridin-5-yl)piperidin-4-yl)methanamine | LCMS-B: rt 2.91 min, m/z (positive ion) 414 [M + H]+ | D |

Intermediate A117: Synthesis of tert-butyl 4-(6-amino-5-nitropyridin-2-yl)piperazine-1-carboxylate

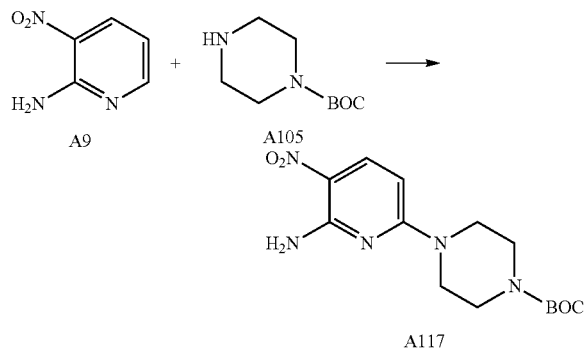

tert-Butyl 4-(6-amino-5-nitropyridin-2-yl)piperazine-1-carboxylate (A117)

A solution of 2-amino-6-chloro-3-nitropyridine A9 (5.00 g, 28.8 mmol), (N)-Boc-piperazine A105 (6.44 g, 34.6 mmol) and i-Pr₂NEt (10.0 mL, 28.8 mmol) in DMF (50 mL) was heated at 85° C. for 16 hours. The orange solution was treated with water (150 mL), the resulting suspension was filtered and the solid was air dried to give the title compound (9.31 g, 100%) as a yellow powder. LCMS-B: rt 3.38 min, m/z (positive ion) 346 [M+Na]⁺.

Intermediate A120: Synthesis of tert-butyl 4-(2-(4-hydroxyphenyl)-3-((2-(trimethylsilyl)ethoxy)methyl)-3H-imidazo[4,5-b]pyridin-5-yl)piperazine-1-carboxylate

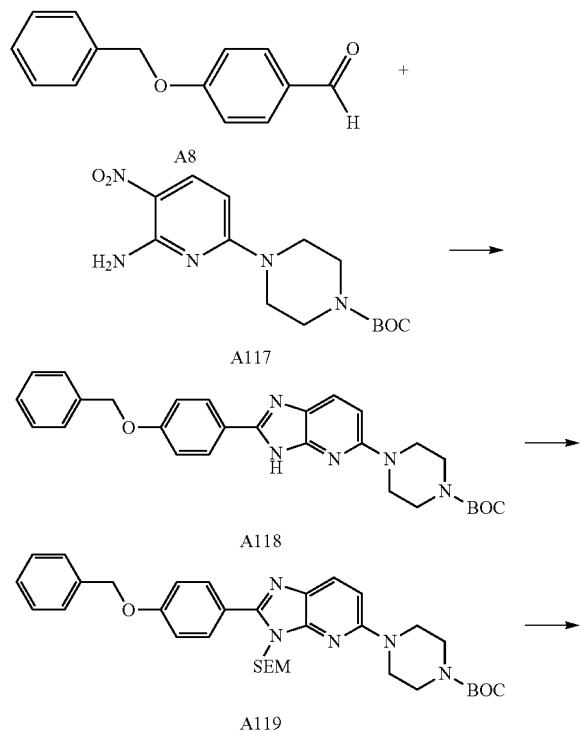

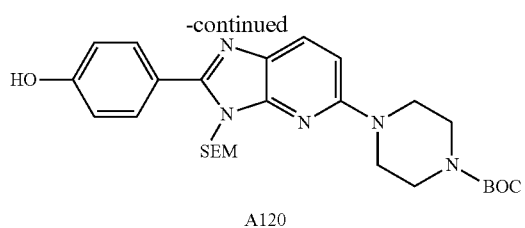

a) tert-Butyl 4-(2-(4-(benzyloxy)phenyl)-3H-imidazo[4,5-b]pyridin-5-yl)piperazine-1-carboxylate (A118)

A 1 M aqueous solution of sodium dithionite (28.0 mL, 28.0 mmol) was added to a stirring suspension of 4-(benzyloxy)benzaldehyde A8 (2.18 g, 10.3 mmol) and tert-butyl 4-(6-amino-5-nitropyridin-2-yl)piperazine-1-carboxylate A117 (3.02 g, 9.34 mmol) in EtOH (40 mL) at room temperature. The suspension was heated at 70° C. for 6 hours. The suspension was cooled to room temperature and treated with 5 M aqueous ammonium hydroxide (20.0 mL, 100 mmol). The resulting suspension was stirred overnight, filtered, and the solid was washed with water (3×20 mL) and dried under vacuum to give the title compound (3.40 g, 75%) as a yellow solid. ¹H NMR (400 MHz, CDCl₃) δ 7.95 (d, J=8.3 Hz, 2H), 7.91-7.84 (m, 1H), 7.49-7.45 (m, 2H), 7.45-7.39 (m, 2H), 7.37 (d, J=7.1 Hz, 1H), 7.08 (d, J=8.9 Hz, 2H), 6.67 (d, J=8.9 Hz, 1H), 5.15 (s, 2H), 3.78-3.29 (m, 8H), 1.51 (s, 9H), NH peak not observed. LCMS-B: rt 3.32 min, m/z (positive ion) 486 [M+H]⁺.

b) tert-Butyl 4-(2-(4-(benzyloxy)phenyl)-3-((2-(trimethylsilyl)ethoxy)methyl)-3H-imidazo[4,5-b]pyridin-5-yl)piperazine-1-carboxylate (A119)

NaH (60% in mineral oil, 448 mg, 11.2 mmol) was added to a stirring solution of tert-butyl 4-(2-(4-(benzyloxy)phenyl)-3H-imidazo[4,5-b]pyridin-5-yl)piperazine-1-carboxylate A118 (3.40 g, 7.00 mmol) in THF (34 mL) and DMF (17 mL) at room temperature under nitrogen. The resulting fine suspension was stirred for 1 hour. SEM-Cl (1.88 g, 11.3 mmol) was added drop-wise and the solution was stirred for 1 hour. A saturated aqueous solution of NaHCO₃ (50 mL) was added and the aqueous layer was extracted with EtOAc (2×75 mL). The combined organic layers were washed with water (2×50 mL), brine (50 mL), dried (MgSO₄), filtered and concentrated in vacuo to give a yellow oil which was purified by column chromatography (120 g SiO₂ cartridge, 10-100% EtOAc in petroleum benzine 40-60° C.) to give the title compound as a pale yellow solid in a 6:1 mixture of regioisomers (4.15 g, 96%). ¹H NMR (400 MHz, CDCl₃) Major Isomer: δ 8.04 (d, J=8.8 Hz, 2H), 7.88 (d, J=8.8 Hz, 1H), 7.49-7.43 (m, 2H), 7.43-7.37 (m, 2H), 7.37-7.30 (m, 1H), 7.10 (d, J=8.8 Hz, 2H), 6.68 (d, J=8.8 Hz, 1H), 5.57 (s, 2H), 5.14 (s, 2H), 3.98-3.75 (m, 2H), 3.68-3.42 (m, 8H), 1.50 (s, 9H), 1.15-0.92 (m, 2H), −0.02 (s, 9H).

c) tert-Butyl 4-(2-(4-hydroxyphenyl)-3-((2-(trimethylsilyl)ethoxy)methyl)-3H-imidazo[4,5-b]pyridin-5-yl)piperazine-1-carboxylate (A120)

A solution of tert-butyl 4-(2-(4-(benzyloxy)phenyl)-3-((2-(trimethylsilyl)ethoxy)methyl)-3H-imidazo[4,5-b]pyridin-5-yl)piperazine-1-carboxylate A119 (3.56 g, 5.78 mmol) in EtOH (42 mL) was treated with Pd/C (47% in water, 860 mg). The flask was evacuated of air and purged with nitrogen three times, then evacuated and purged with hydrogen three times. The suspension was stirred under hydrogen for 5 hours, and then filtered through a pad of Celite, eluting with EtOH (2×20 mL). The filtrate was concentrated in vacuo to give a brown oil which was purified twice by column chromatography (SiO$_2$ cartridge, 0-10% MeOH in DCM then 10-100% EtOAC in petroleum benzine 40-60° C.). The fractions containing product were combined and concentrated in vacuo to give a brown oil. The resultant material was dissolved in the minimum required volume of DCM, and cyclohexane was added slowly until a precipitate formed. The suspension was concentrated in vacuo to give an off-white solid. The solid was purified twice by recrystallisation from acetonitrile (15 mL/g), to give the title compound as a 14:1 mixture of regioisomers and as a colourless solid (1.20 g, 40%); $^1$H NMR (400 MHz, CDCl$_3$) Major Isomer: δ 10.27 (s, 1H), 7.87 (d, J=8.8 Hz, 1H), 7.83 (d, J=8.7 Hz, 2H), 6.87 (d, J=8.8 Hz, 2H), 6.68 (d, J=8.9 Hz, 1H), 5.55 (s, 2H), 4.09-3.76 (m, 2H), 3.58 (s, 9H), 1.49 (s, 9H), 1.19-0.87 (m, 1H), −0.02 (s, 9H). LCMS-A: rt 6.10 min, m/z (positive ion) 526 [M+H]$^+$.

Example 56-60: Ether Synthesis

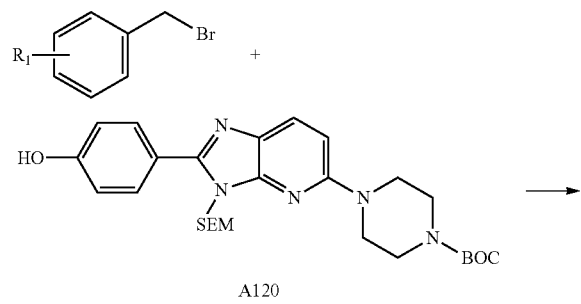

A120

-continued

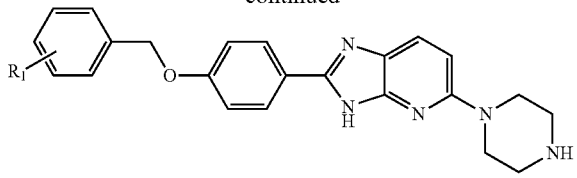

General Procedure E:

A suspension of tert-butyl 4-(2-(4-hydroxyphenyl)-3-((2-(trimethylsilyl)ethoxy)methyl)-3H-imidazo[4,5-b]pyridin-5-yl)piperazine-1-carboxylate A120 (105 mg, 0.200 mmol, 1 equiv), aryl bromide (0.220 mmol, 1.1 equiv), and potassium carbonate (36 mg, 0.26 mmol, 1.3 equiv) in acetone (2 mL) was heated at 50° C. for 18 hours. The solvent was removed by a stream of compressed air while heating the suspension at 50° C. DCM (3 mL) and water (1 mL) were added to the resultant residue and the layers were separated using a phase separation cartridge (1 g). The aqueous layer was extracted with DCM (1 mL) and the combined organic layers were concentrated under a stream of compressed air with heating of the solution at 50° C. The residue was cooled to room temperature and dissolved in DCM (1 mL). TFA (0.5 mL) was added and the solution was stirred for 18 hours at room temperature. The solvent was removed by a stream of compressed air and 2 M NaOH aqueous solution was added until the pH>8. The aqueous layer was extracted with EtOAc (3×20 mL) and the combined organic layers were washed with brine (10 mL) and concentrated by a stream of compressed air. The resultant residue was dissolved in the minimum required volume of MeOH and loaded onto an SCX cartridge (1 g). The cartridge was washed with MeOH (3×3 mL) and the product was eluted with 2 M ammonia in EtOH (3×3 mL). The product fractions were concentrated under a stream of air with heating of the solution at 50° C. The residue was centrifuged with MeOH (1 mL) and the solvent was removed by decantation. This was repeated twice and the resulting solid was dried under vacuum to give the title compound as a colourless solid.

TABLE D

| Example | Product Name and Structure | LCMS data | Method |
|---|---|---|---|
| 56 | ![structure] <br> 5-(piperazin-1-yl)-2-(4-((4-(trifluoromethyl)benzyl)oxy)phenyl)-3H-imidazo[4,5-b]pyridine | LCMS-A: rt 4.73 min, m/z (positive ion) 454 [M + H]$^+$ | E |
| 57 | ![structure] <br> 2-(4-((2-fluorobenzyl)oxy)phenyl)-5-(piperazin-1-yl)-3H-imidazo[4,5-b]pyridine | LCMS-A: rt 4.49 min, m/z (positive ion) 404 [M + H]$^+$ | E |

US 9,856,252 B2

TABLE D-continued

| Example | Product Name and Structure | LCMS data | Method |
|---|---|---|---|
| 58 | 2-(4-((3-fluorobenzyl)oxy)phenyl)-5-(piperazin-1-yl)-3H-imidazo[4,5-b]pyridine | LCMS-A: rt 4.50 min, m/z (positive ion) 404 [M + H]$^+$ | E |
| 59 | 2-(4-((4-fluorobenzyl)oxy)phenyl)-5-(piperazin-1-yl)-3H-imidazo[4,5-b]pyridine | LCMS-A: rt 4.50 min, m/z (positive ion) 404 [M + H]$^+$ | E After pH adjustment the suspension was filtered and then purified by SCX 1g cartridge |
| 60 | 5-(piperazin-1-yl)-2-(4-((2-(trifluoromethyl)benzyl)oxy)phenyl)-3H-imidazo[4,5-b]pyridine | LCMS-A: rt 4.70 min, m/z (positive ion) 454 [M + H]$^+$ | E After pH adjustment the suspension was filtered and then purified by SCX 1g cartridge |

Example 61: Synthesis of 2-(4-(1-phenylethoxy)phenyl)-5-(piperazin-1-yl)-3H-imidazo[4,5-b]pyridine (61)

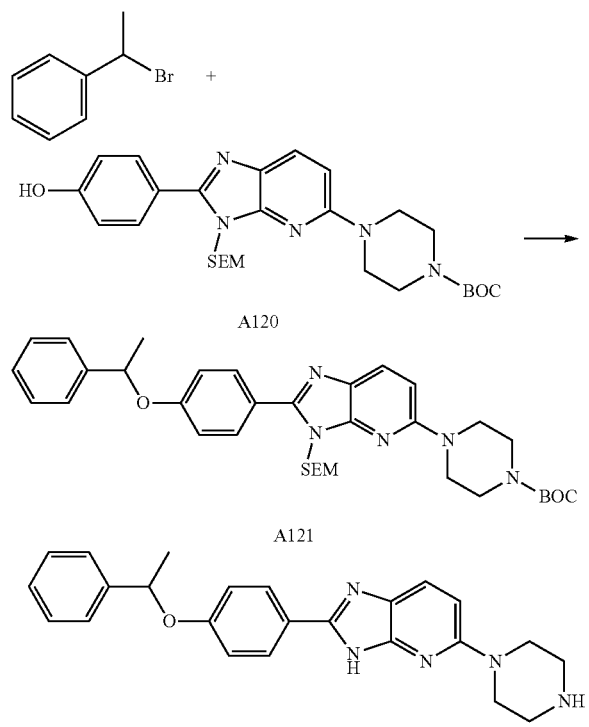

a) tert-Butyl 4-(2-(4-(1-phenylethoxy)phenyl)-3-((2-(trimethylsilyl)ethoxy)methyl)-3H-imidazo[4,5-b]pyridin-5-yl)piperazine-1-carboxylate (A121)

A solution of tert-butyl 4-(2-(4-hydroxyphenyl)-3-((2-(trimethylsilyl)ethoxy)methyl)-3H-imidazo[4,5-b]pyridin-5-yl)piperazine-1-carboxylate A120 (0.200 g, 0.380 mmol), (1-bromoethyl)benzene (84 mg, 0.46 mmol) and potassium carbonate (79 mg, 0.57 mmol) in acetonitrile (2 mL) was stirred vigorously at reflux for 17 hours. The suspension was filtered through a phase separation cartridge and the solids were washed with DCM (2×10 mL). The combined filtrates were concentrated in vacuo. The resulting solid material was purified by column chromatography (12 g SiO$_2$ cartridge, 0-100% EtOAc in petroleum benzine 40-60° C.) to give the title compound as a colourless oil (95 mg, 39%). $^1$H NMR (400 MHz, CDCl$_3$) δ 7.97-7.90 (m, 2H), 7.85 (d, J=8.8 Hz, 1H), 7.42-7.30 (m, 4H), 7.30-7.23 (m, 1H), 7.03-6.90 (m, 2H), 6.66 (d, J=8.8 Hz, 1H), 5.53 (s, 2H), 5.39 (q, J=6.4 Hz, 1H), 3.87-3.80 (m, 2H), 3.57 (s, 8H), 1.67 (d, J=6.4 Hz, 3H), 1.49 (s, 9H), 1.12-0.84 (m, 2H), −0.03 (s, 9H).

b) 2-(4-(1-Phenylethoxy)phenyl)-5-(piperazin-1-yl)-3H-imidazo[4,5-b]pyridine (61)

A solution of tert-butyl 4-(2-(4-hydroxyphenyl)-3-((2-(trimethylsilyl)ethoxy)methyl)-3H-imidazo[4,5-b]pyridin-5-yl)piperazine-1-carboxylate A121 (9.4 mg, 0.015 mmol) and 1 M TBAF in THF (3 mL) was heated at reflux for 4 hours. The solution was cooled to room temperature and concentrated in vacuo. The crude mixture was taken up in a minimal volume of MeOH and loaded onto a SCX cartridge (1 g). The cartridge was washed with MeOH (3×3 mL) and the product was eluted with 2 M ammonia in EtOH (3×3 mL). The product containing fractions were concentrated in vacuo to give a yellow oil. The SCX purification procedure was repeated to give a pale yellow oil which was taken up in 1.25 M HCl in MeOH (1 mL) and heated at 50° C. for 6 hours. The solution was cooled to room temperature and concentrated. The resulting solid was purified by column chromatography (4 g SiO$_2$, 5-20% (10% Et$_3$N in MeOH) in DCM). The fractions containing product were combined and concentrated in vacuo to give the title compound as a colourless solid (0.5 mg, 8%). LCMS-A: rt 4.57 min, m/z (positive ion) 400 [M+H]$^+$, m/z (negative ion) 398 [M−H]$^−$.

Example 62: Synthesis of 2-(4-(benzyloxy)-3-bromophenyl)-6-(piperidin-4-yl)-3H-imidazo[4,5-b]pyridine (62)

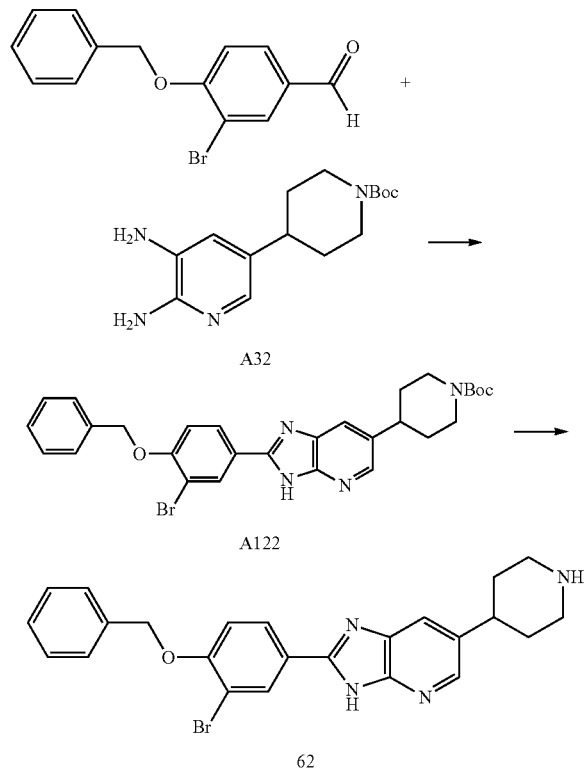

a) tert-Butyl 4-(2-(4-(benzyloxy)-3-bromophenyl)-3H-imidazo[4,5-b]pyridin-6-yl)piperidine-1-carboxylate (A122)

A suspension of 4-(benzyloxy)-3-bromobenzaldehyde (0.100 g, 0.343 mmol) and tert-butyl 4-(5,6-diaminopyridin-3-yl)piperidine-1-carboxylate A32 (102 mg, 0.349 mmol) were refluxed in MeOH (5 mL) over activated 3 Å molecular sieves (0.500 g, activated by heat-gun under vacuum) for 22 hours. The resulting suspension was cooled to room temperature, decanted from the molecular sieves and the solvent was removed in vacuo. THF (5 mL) followed by (diacetoxyiodo)benzene (133 mg, 0.412 mmol) were added under an atmosphere of nitrogen and the mixture was stirred at room temperature for 2 hours. The mixture was concentrated in vacuo and then diluted with EtOAc (20 mL) and a saturated aqueous solution of NaHCO$_3$ (20 mL). The layers were separated and the aqueous layer was extracted with EtOAc (20 mL). The combined organic layers were washed with brine (10 mL), dried (Na$_2$SO$_4$), filtered and concentrated in vacuo to give the crude product which was purified by silica gel chromatography (40 g SiO$_2$ cartridge, 0-100% EtOAc in petroleum benzine 40-60° C.) to give a the title compound (71 mg, 36%) as a pale yellow solid. $^1$H NMR (400 MHz, CDCl$_3$) δ 8.47 (d, J=1.9 Hz, 1H), 8.45 (d, J=2.2 Hz, 1H), 8.21 (dd, J=8.6, 2.2 Hz, 1H), 7.97 (d, J=1.9 Hz, 1H), 7.52 (d, J=7.1 Hz, 2H), 7.43 (t, J=7.4 Hz, 2H), 7.39-7.33 (m, 1H), 7.15 (d, J=8.7 Hz, 1H), 5.28 (s, 2H), 4.32 (s, 2H), 2.96-2.81 (m, 3H), 1.95 (d, J=12.8 Hz, 2H), 1.86-1.71 (m, 2H), 1.50 (s, 9H), NH peak not observed. LCMS-A: rt 6.48 min, m/z (positive ion) 563 [M+H]$^+$, m/z (negative ion) 561 [M−H]$^−$.

b) 2-(4-(Benzyloxy)-3-bromophenyl)-6-(piperidin-4-yl)-3H-imidazo[4,5-b]pyridine (62)

A solution of tert-butyl 4-(2-(4-(benzyloxy)-3-bromophenyl)-3H-imidazo[4,5-b]pyridin-6-yl)piperidine-1-carboxylate A122 (12 mg, 0.021 mmol) in TFA (1 mL) and DCM (1 mL) was stirred for 2 hours at room temperature. The volatiles were removed in vacuo and the residue was partitioned between EtOAc (10 mL) and a saturated aqueous solution of NaHCO$_3$ (5 mL). The aqueous layer was extracted with EtOAc (10 mL). The combined organic layers were washed with brine (5 mL) resulting in a precipitate in the aqueous layer. The aqueous layer was centrifuged for 1 hour and the supernatant was removed. The solid was washed with water (5 mL) and centrifuged for 1 hour. The supernatant was removed and the residue was dried under vacuum for 3 days to give the title compound (5.4 mg, 56%) as an off white solid. $^1$H NMR (400 MHz, CD$_3$OD) δ 8.49 (d, J=2.3 Hz, 1H), 8.47 (d, J=1.9 Hz, 1H), 8.29 (d, J=1.8 Hz, 1H), 8.20 (dd, J=8.7, 2.3 Hz, 1H), 7.54-7.50 (m, 2H), 7.44-7.32 (m, 4H), 5.34 (s, 2H), 3.61-3.54 (m, 2H), 3.28-3.18 (m, 3H), 2.24-2.17 (m, 2H), 2.15-2.04 (m, 2H). LCMS-A: rt 4.76 min, m/z (positive ion) 463 ($^{79}$Br), 465 ($^{81}$Br) [M+H]$^+$, m/z (negative ion) 461 ($^{79}$Br), 463 ($^{81}$Br) [M−H]$^−$.

Example 63: Synthesis of 2-(4-(benzyloxy)-3-(1-methyl-1H-pyrazol-4-yl)phenyl)-6-(piperidin-4-yl)-3H-imidazo[4,5-b]pyridine (63)

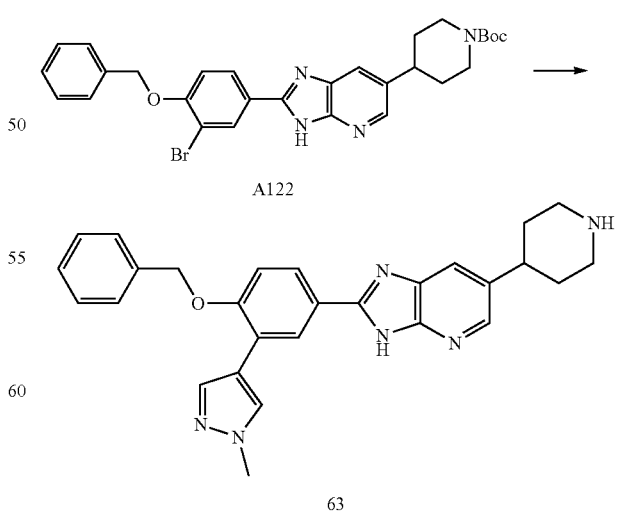

tert-Butyl 4-(2-(4-(benzyloxy)-3-bromophenyl)-3H-imidazo[4,5-b]pyridin-6-yl)piperidine-1-carboxylate A122

(0.020 g, 0.035 mmol), (1-methyl-1H-pyrazol-4-yl)boronic acid (9.0 mg, 0.043 mmol, 1.3 equiv), PdCl$_2$(PPh$_3$)$_4$ (1 mg, 2 μmol, 0.05 equiv) and TBAB (1.0 mg, 4.3 μmol, 0.1 equiv) were stirred in 1,4-dioxane:water 2:1 (1 mL). Next, K$_2$CO$_3$ (12 mg, 0.086 mmol, 2.5 equiv) was added and the reaction mixture was heated under microwave conditions at 90° C. for 45 minutes, 110° C. for 15 minutes and 110° C. for 5 minutes. Water (1 mL) and EtOAc (5 mL) were added and the layers were separated. The aqueous layer was extracted with EtOAc (5 mL) and the organic layers were combined. The organic layer was washed with brine (5 mL), dried (Na$_2$SO$_4$), filtered and concentrated in vacuo to give an orange oil. TFA (0.5 mL) and DCM (0.5 mL) were added and the solution was stirred for 30 minutes at room temperature. The volatiles were removed in vacuo to give a brown oil which was purified by column chromatography (4 g SiO$_2$ cartridge, 10-20% MeOH in DCM then 100% MeOH then 2 M ammonia in MeOH) to give a colourless solid (17.1 mg). The residue was taken up in MeOH (0.5 mL) and loaded onto an SCX cartridge (1 g). The cartridge was washed with MeOH (3×5 mL) and the product was eluted with 2 M ammonia in EtOH (5×5 mL). The fractions containing product were concentrated in vacuo to give the title compound (8.0 mg, 36%, purity 75%) as a yellow solid. LCMS-A: rt 4.62 min, m/z (positive ion) 465 [M+H]$^+$.

Example 64: Synthesis of 2-(4-(benzyloxy)-3-(pyridin-3-yl)phenyl)-6-(piperidin-4-yl)-3H-imidazo[4,5-b]pyridine (64)

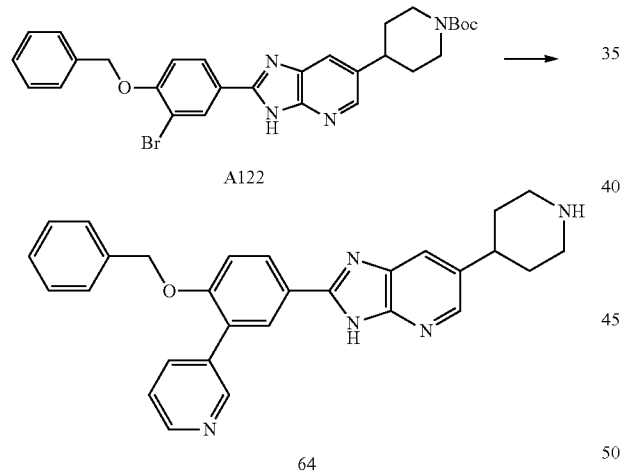

A suspension of tert-butyl 4-(2-(4-(benzyloxy)-3-bromophenyl)-3H-imidazo[4,5-b]pyridin-6-yl)piperidine-1-carboxylate A122 (56 mg, 0.099 mmol), pyridin-3-ylboronic acid (0.12 mmol), PdCl$_2$(PPh$_3$)$_4$ (7.0 mg, 0.010 mmol), TBAB (4.8 mg, 0.015 mmol) and K$_2$CO$_3$ (41 mg, 0.30 mmol) in 1,4-dioxane:water 9:1 (1 mL) was irradiated in the microwave at 130° C. for 45 minutes. Water (3 mL) and EtOAc (10 mL) were added and the layers were separated. The aqueous layer was extracted with EtOAc (10 mL). The organic layers were combined, dried (Na$_2$SO$_4$), filtered and concentrated in vacuo to give an orange oil. The crude material was purified by column chromatography (12 g SiO$_2$ cartridge, 0-10% MeOH in DCM), the fractions containing product were combined and concentrated in vacuo. TFA (0.5 mL) and DCM (0.5 mL) were added to the residue and the solution was stirred for 30 minutes at room temperature. The volatiles were removed in vacuo and the residue was purified by preparative mass-directed HPLC to give the title compound as a colourless solid (12 mg, 26%). LCMS-B: rt 2.86 min, m/z (positive ion) 462[M+H]$^+$, m/z (negative ion) 460 [M−H]$^−$.

Example 65: Synthesis of 2-(4-(benzyloxy)-3-fluorophenyl)-6-(piperidin-4-yl)-3H-imidazo[4,5-b]pyridine (65))

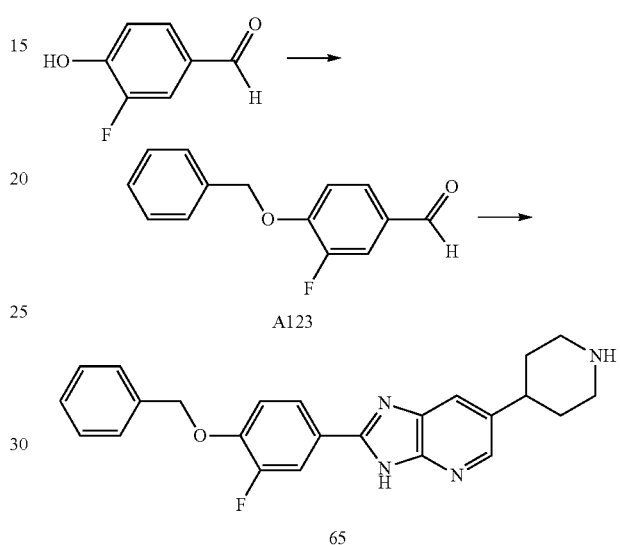

a) 4-(Benzyloxy)-3-fluorobenzaldehyde (A123)

3-Fluoro-4-hydroxybenzaldehyde (1.00 g, 7.14 mmol), K$_2$CO$_3$ (1.48 g, 10.7 mmol), acetonitrile (10 mL) and benzyl bromide (1.02 mL, 8.57 mmol) were stirred vigorously at reflux for 17 hours. The suspension was filtered and the solids were washed with acetonitrile (2×40 mL). The combined filtrates were concentrated in vacuo and the resulting solid material was recrystallised from cyclohexane to give the title compound as a colourless solid (1.26 g, 77%). $^1$H NMR (400 MHz, CDCl$_3$) δ 9.85 (d, J=2.1 Hz, 1H), 7.66-7.58 (m, 2H), 7.47-7.33 (m, 5H), 7.12 (t, J=8.0 Hz, 1H), 5.24 (s, 2H).

b) 2-(4-(Benzyloxy)-3-fluorophenyl)-6-(piperidin-4-yl)-3H-imidazo[4,5-b]pyridine (65)

A suspension of 4-(benzyloxy)-3-fluorobenzaldehyde A123 (86.6 mg, 0.376 mmol) and tert-butyl 4-(5,6-diaminopyridin-2-yl)piperidine-1-carboxylate A31 (0.100 g, 0.342 mmol) in MeOH (1 mL) over activated 3 Å molecular sieves (0.100 g, before activation by heat-gun under vacuum) was irradiated in a microwave at 120° C. for 60 minutes. The resulting mixture was cooled to room temperature, decanted from the molecular sieves and the solvent was removed in vacuo. THF (5 mL) followed by (diacetoxyiodo)benzene (132 mg, 0.410 mmol) were added and the mixture was stirred at room temperature for 18 hours. The solvent was removed in vacuo and the residue was partitioned between EtOAc (15 mL) and a solution of 10% wt/v aqueous NaHCO$_3$ (10 mL). The layers were separated and the aqueous layer was extracted with EtOAc (15 mL). The organic layers were combined, washed with brine (10 mL) and concentrated in vacuo. The crude material was purified using column chromatography (12 g SiO$_2$ cartridge, 0-20% MeOH in DCM), the fractions containing the product were combined and concentrated in vacuo to give the desired intermediate as a pale yellow oil. The material was treated with DCM (3 mL) and TFA (1 mL) and stirred for 10 minutes. The solvent was removed in vacuo and the material was purified by column chromatography (12 g SiO$_2$ cartridge, 0-20% MeOH) to give the title compound as a colourless solid (65 mg, 47%). $^1$H NMR (400 MHz, CD$_3$OD) δ 8.32 (d, J=2.0 Hz, 1H), 7.97-7.87 (m, 3H), 7.53-7.45 (m, 2H), 7.43-7.38 (m, 2H), 7.37-7.32 (m, 2H), 5.28 (s, 2H), 3.59-3.51 (m, 2H), 3.25-3.10 (m, 3H), 2.21-2.14 (m, 2H), 2.08-1.95 (m, 2H). LCMS-A: rt 4.73 min, m/z (positive ion) 403 [M+H]$^+$.

Example 66: Synthesis of methyl 2-(benzyloxy)-5-(6-(piperidin-4-yl)-3H-imidazo[4,5-b]pyridin-2-yl)benzoate dihydrogen chloride salt (66)

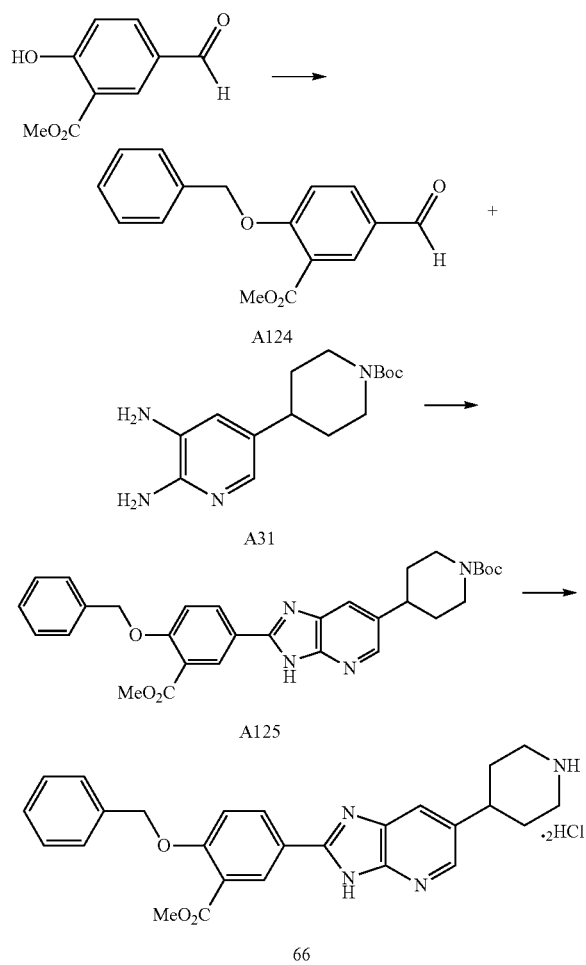

a) Methyl 2-(benzyloxy)-5-formylbenzoate (A124)

Methyl 5-formylsalicylate (5.00 g, 27.8 mmol), potassium carbonate (5.26 g, 41.7 mmol), acetonitrile (50 mL) and benzyl bromide (4.0 mL, 34 mmol) were combined and stirred vigorously at reflux for 17 hours. Further portions of benzyl bromide (4 mL, 34 mL) and potassium carbonate (5.26 g, 41.7 mmol) were added and the mixture was refluxed for 2 days. The suspension was filtered and the solids washed with acetonitrile (2×40 mL). The combined filtrates were concentrated in vacuo and the resulting oil was purified by column chromatography (120 g SiO$_2$ cartridge, 0-80% EtOAc in petroleum benzine 40-60° C.) to give the title compound as a colourless oil (3.85 g, 51%). $^1$H NMR (400 MHz, CDCl$_3$) δ 9.92 (d, J=0.5 Hz, 1H), 8.36 (d, J=2.2 Hz, 1H), 7.98 (dd, J=8.7, 2.2 Hz, 1H), 7.51-7.47 (m, 2H), 7.44-7.37 (m, 2H), 7.37-7.30 (m, 1H), 7.14 (d, J=8.7 Hz, 1H), 5.30 (s, 2H), 3.94 (s, 3H). LCMS-B: rt 3.44 min, m/z (positive ion) 293 [M+Na]$^+$, m/z (negative ion) 269 [M–H]$^-$.

b) tert-Butyl 4-(2-(4-(benzyloxy)-3-(methoxycarbonyl)phenyl)-3H-imidazo[4,5-b]pyridin-6-yl)piperidine-1-carboxylate (A125)

A suspension of methyl 2-(benzyloxy)-5-formylbenzoate A 124 (0.270 g, 1.00 mmol) and tert-butyl 4-(5,6-diaminopyridin-3-yl)piperidine-1-carboxylate A31 (292 mg, 1.00 mmol) in MeOH (3 mL) over activated 3 Å molecular sieves (0.100 g, before activation by heat-gun under vacuum) was irradiated in a microwave at 120° C. for 2 hours. The resulting mixture was cooled to room temperature, decanted from the molecular sieves and the solvent was removed in vacuo. THF (3 mL) followed by (diacetoxyiodo)benzene (387 mg, 1.20 mmol) were added and the mixture was stirred at room temperature for 14 hours. The solvent was removed in vacuo and the residue was partitioned between DCM (25 mL) and a saturated aqueous solution of NaHCO$_3$ (25 mL). The layers were separated and the aqueous layer was extracted with DCM (25 mL). The organic layers were combined, washed with brine (25 mL) and concentrated in vacuo. The crude material was purified using column chromatography (12 g SiO$_2$ cartridge, 50-100% EtOAc in petroleum benzine 40-60° C. then 0-20% MeOH in EtOAc), the fractions containing the product were combined and concentrated in vacuo to give the desired intermediate as an orange oil. The orange solid was taken up in MeOH (1 mL) and centrifuged for 10 minutes. The supernatant was removed and the solid was centrifuged in a further portion of MeOH (1 mL) for 10 minutes. The supernatant was removed and the solid was dried under vacuum to give the title compound as an off-white solid (109 mg, 19%). LCMS-A: rt 3.47 min, m/z (positive ion) 543 [M+H]$^+$.

c) Methyl 2-(benzyloxy)-5-(6-(piperidin-4-yl)-3H-imidazo[4,5-b]pyridin-2-yl)benzoate dihydrogen chloride salt (66)

A solution of tert-butyl 4-(2-(4-(benzyloxy)-3-(methoxycarbonyl)phenyl)-3H-imidazo[4,5-b]pyridin-6-yl)piperidine-1-carboxylate A125 (10.1 mg, 0.0186 mmol) in 1.25 M HCl in MeOH (1.00 mL, 1.25 mmol) was heated at 55° C. for 3 hours. The reaction mixture was cooled to room temperature and concentrated in vacuo to give the title compound a colourless solid (8.6 mg, 90%). $^1$H NMR (400 MHz, d$_6$-DMSO) δ 9.15-8.88 (m, 2H), 8.66 (d, J=2.3 Hz, 1H), 8.48 (dd, J=8.9, 2.4 Hz, 1H), 8.39 (d, J=1.9 Hz, 1H), 8.06 (s, 1H), 7.56-7.48 (m, 3H), 7.43 (t, J=7.4 Hz, 2H), 7.34 (t, J=7.2 Hz, 1H), 5.37 (s, 2H), 3.89 (s, 3H), 5H obscured by water peak, 2.08-1.97 (m, 4H). LCMS-A: rt 4.63 min, m/z (positive ion) 443 [M+H]$^+$; m/z (negative ion) 441 [M–H]$^-$.

Example 67: Synthesis of 2-(benzyloxy)-5-(6-(piperidin-4-yl)-3H-imidazo[4,5-b]pyridin-2-yl)benzoic acid dihydrochloride salt (67)

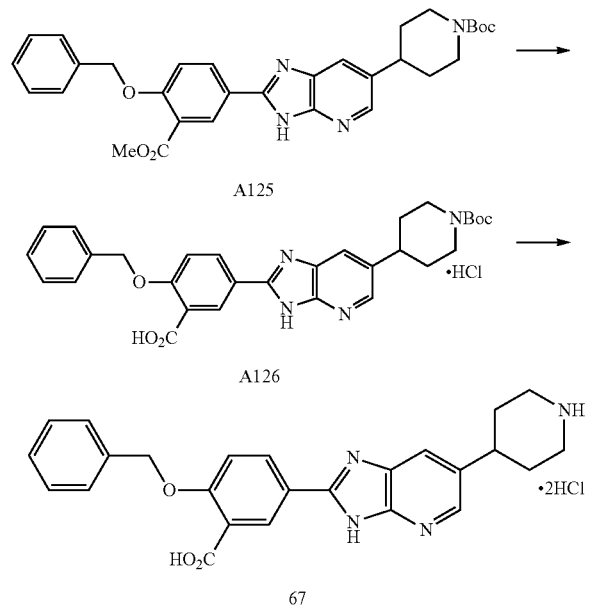

a) 2-(Benzyloxy)-5-(6-(1-(tert-butoxycarbonyl)piperidin-4-yl)-3H-imidazo[4,5-b]pyridin-2-yl)benzoic acid hydrogen chloride salt (A126)

A suspension of tert-butyl 4-(2-(4-(benzyloxy)-3-(methoxycarbonyl)phenyl)-3H-imidazo[4,5-b]pyridin-6-yl)piperidine-1-carboxylate A125 (0.100 g, 0.184 mmol), 1 M aqueous NaOH (1.0 mL, 1.0 mmol) and MeOH (1 mL) was heated at 85° C. for 3 hours. The resulting solution was cooled to room temperature and the volatiles were removed in vacuo. The solution was diluted with water (10 mL), extracted with DCM (2×10 mL) and the organic layer was discarded. The aqueous layer was acidified with 6 M HCl (1 mL) and the resulting suspension was filtered, washed with water (2×5 mL) and air dried to give the title compound as a colourless powder. The filtrate was extracted with EtOAc:MeOH (6:1, 2×35 mL). The organic layers were combined, washed with brine (30 mL), dried (Na$_2$SO$_4$), filtered and concentrated in vacuo. Toluene (3 mL) was added and concentrated in vacuo to give the title compound as a colourless powder (Combined total 101 mg, 95%) LCMS-B: rt 3.29 min, m/z (positive ion) 529 [M+H]$^+$.

b) 2-(Benzyloxy)-5-(6-(piperidin-4-yl)-3H-imidazo[4,5-b]pyridin-2-yl)benzoic acid dihydrochloride salt (67)

A suspension of 2-(benzyloxy)-5-(6-(1-(tert-butoxycarbonyl)piperidin-4-yl)-3H-imidazo[4,5-b]pyridin-2-yl)benzoic acid A126 (7.0 mg, 0.012 mmol) and 4 M HCl in 1,4-dioxane (1 mL, 4 mmol) were stirred at 55° C. for 4 hours. The reaction mixture was concentrated in vacuo to give the title compound as a colourless solid (6.0 mg, 97%). $^1$H NMR (400 MHz, d$_6$-DMSO) δ 8.89-8.78 (m, 1H), 8.70 (d, J=9.5 Hz, 1H), 8.59 (d, J=2.4 Hz, 1H), 7.95 (dd, J=8.8, 2.4 Hz, 1H), 8.36-8.30 (m, 1H), 7.95 (br s, 1H), 7.59-7.50 (m, 2H), 7.50-7.38 (m, 3H), 7.35 (t, J=7.3 Hz, 1H), 5.35 (s, 2H), 3.16-2.87 (m, 4H), 2.19-1.85 (m, 4H), 2×NH peaks not observed. LCMS-B: rt 2.95 min, m/z (positive ion) 429 [M+H]$^+$.

Example 68: Synthesis of 2-(benzyloxy)-5-(6-(piperidin-4-yl)-3H-imidazo[4,5-b]pyridin-2-yl)benzamide dihydrogen chloride salt (68)

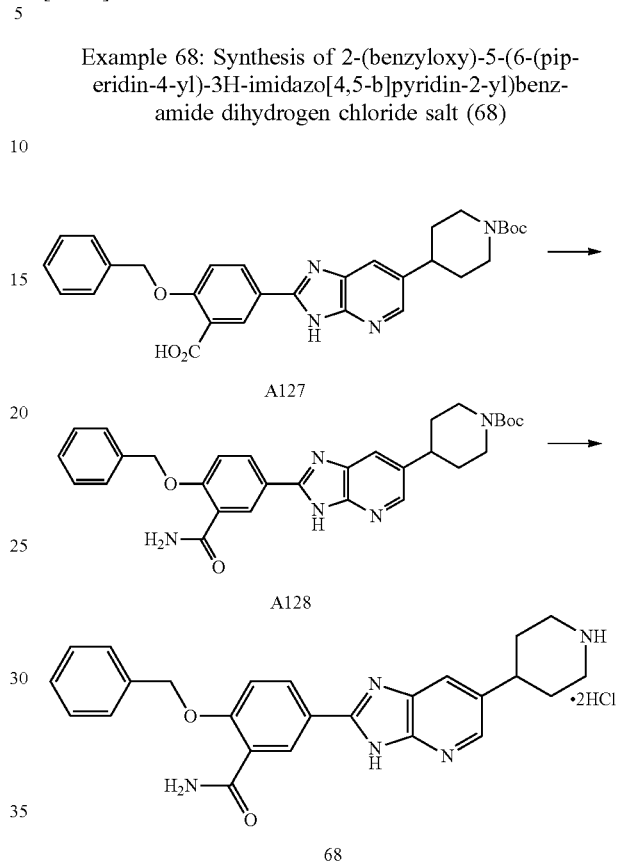

a) tert-Butyl 4-(2-(4-(benzyloxy)-3-carbamoylphenyl)-3H-imidazo[4,5-b]pyridin-6-yl)piperidine-1-carboxylate (A128

SOCl$_2$ (13 μL, 0.18 mmol) was added to a suspension of 2-(benzyloxy)-5-(6-(1-(tert-butoxycarbonyl)piperidin-4-yl)-3H-imidazo[4,5-b]pyridin-2-yl)benzoic acid A127 (63.0 mg, 0.119 mmol) and DMF (2 drops) in DCM (1.6 mL) under N$_2$ at room temperature. Further portions of SOCl$_2$ (52 μL, 0.72 mmol) and DMF (1 mL) were added and the resultant solution was stirred for 30 minutes before a 28-30% ammonium hydroxide solution (1 mL) was added. The reaction mixture was stirred for 1 hour, concentrated in vacuo and the residue partitioned between water (10 mL) and EtOAc (20 mL). A precipitate formed and was isolated by filtration to give a crop of title compound as a colourless solid. The filtrate layers were separated and the aqueous layer was extracted with EtOAc (20 mL). The organic layers were combined, washed with 1 M aqueous NaOH (15 mL), water (15 mL), brine (15 mL) dried (MgSO$_4$), filtered and concentrated in vacuo. The crude product was purified by column chromatography (12 g SiO$_2$ cartridge, 0-10% MeOH in DCM) the fractions containing product were combined and concentrated in vacuo to give a second crop of the title compound as a colourless solid (Combined total 29.0 mg, 46%). LCMS-B: 3.31 min, m/z (positive ion) 528 [M+H]$^+$, m/z (negative ion) 526 [M−H]$^−$.

b) 2-(Benzyloxy)-5-(6-(piperidin-4-yl)-3H-imidazo[4,5-b]pyridin-2-yl)benzamide dihydrogen chloride salt (68)

A suspension of tert-butyl 4-(2-(4-(benzyloxy)-3-carbamoylphenyl)-3H-imidazo[4,5-b]pyridin-6-yl)piperidine-1-carboxylate A128 (7.7 mg, 0.015 mmol) and 1.25 M HCl in MeOH (1 mL, 1.25 M) was heated at 55° C. for 4 hours. The reaction mixture was concentrated in vacuo to give the title compound as a colourless solid (6.7 mg, 83%). LCMS-B: rt 2.87 min, m/z (positive ion) 428 [M+H]⁺.

Example 69: Synthesis of 2-(4-(benzyloxy)-3-(1-methyl-1H-pyrazol-4-yl)phenyl)-5-(4-(ethylsulfonyl)piperazin-1-yl)-3H-imidazo[4,5-b]pyridine (69)

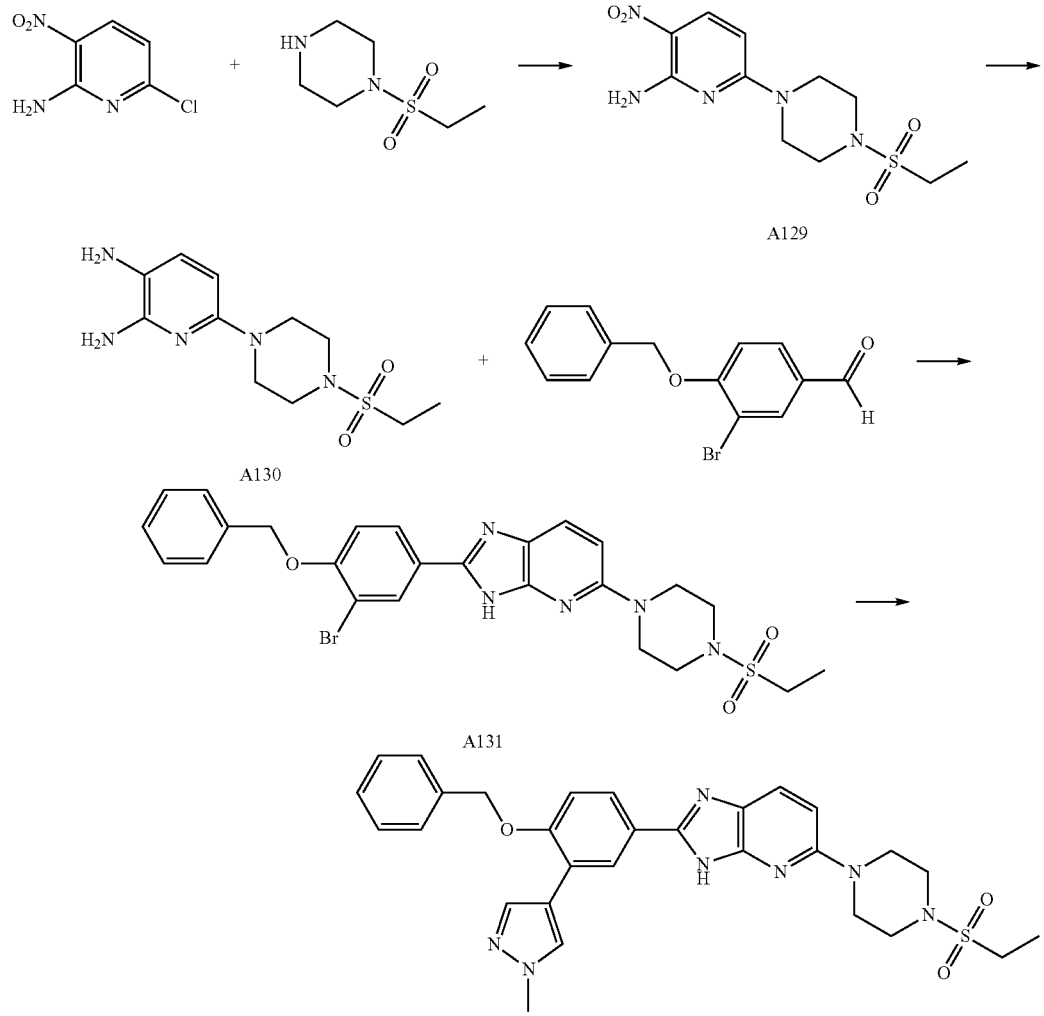

a) 6-(4-(Ethylsulfonyl)piperazin-1-yl)-3-nitropyridin-2-amine (A129)

A solution of 6-chloro-3-nitropyridin-2-amine (2.50 g, 14.4 mmol), 1-(ethylsulfonyl)piperazine (3.08 g, 17.3 mmol) and DIPEA (5.02 mL, 28.8 mmol) in DMF (25 mL) was heated at 85° C. for 1 hour. The yellow solution was treated with water (50 mL) and cooled to room temperature. The suspension was filtered and the solid air dried to give the title compound (4.29 g, 95%) as a bright yellow solid. LCMS-A: rt 5.64 min, m/z (positive ion) 316 [M+H]⁺.

b) 6-(4-(Ethylsulfonyl)piperazin-1-yl)pyridine-2,3-diamine (A130)

A suspension of tert-butyl 4-(6-amino-5-nitropyridin-2-yl)piperazine-1-carboxylate A129 (2.06 g, 6.53 mmol) and 10% Pd/C (47% water wet, 400 mg) in EtOH (50 mL) was stirred at 50° C. under an atmosphere of hydrogen for 17 hours. The suspension was filtered through Celite and the filtrate was concentrated in vacuo to give the title compound (1.84 g, 99%) as a brown/purple crystalline solid. ¹H NMR (400 MHz, d₆-DMSO) δ 6.70 (d, J=8.0 Hz, 1H), 5.85 (d, J=8.1 Hz, 1H), 5.16 (s, 2H), 4.03 (br, s, 2H), 3.27-3.15 (m, 8H), 3.04 (q, J=7.3 Hz, 2H), 1.20 (t, J=7.4 Hz, 3H). LCMS-B: rt 2.60 min, m/z (positive ion) 286 [M+H]⁺.

c) 2-(4-(Benzyloxy)-3-bromophenyl)-5-(4-(ethylsulfonyl)piperazin-1-yl)-3H-imidazo[4,5-b]pyridine (A131)

A suspension of 4-(benzylaoxy)-3-bromobenzaldehyde (1.12 g, 3.86 mmol) and 6-(4-(ethylsulfonyl)piperazin-1-yl)

pyridine-2,3-diamine A130 (1.00 g, 3.50 mmol) in MeOH (30 mL) over activated 3 Å molecular sieves (0.500 g, before activation by heat-gun under vacuum) was irradiated in a microwave at 130° C. for 2×60 minutes, then 140° C. for 15 minutes. The resulting suspension was cooled to room temperature, decanted from the molecular sieves and the solvent was removed in vacuo. THF (50 mL) followed by (diacetoxyiodo)benzene (1.35 g, 4.21 mmol) were added and the mixture was stirred at room temperature for 24 hours. The mixture was concentrated in vacuo and diluted with MeOH (5 mL). The solution was loaded onto an SCX cartridge (10 g) and washed with MeOH (4×20 mL). The product was eluted with 2 M $NH_3$ in EtOH (3×50 mL) and the fractions containing product were concentrated in vacuo. The crude material was purified by column chromatography twice ((12 g $SiO_2$ cartridge, 0-10% MeOH in DCM) then (12 g $SiO_2$ cartridge, 0-10% MeOH in EtOAc), to give the title compound (789 mg, 40%) as a brown solid. $^1$H NMR (400 MHz, $d_6$-DMSO) δ 8.34 (d, J=2.2 Hz, 1H), 8.06 (dd, J=8.6, 2.2 Hz, 1H), 7.89-7.73 (m, 1H), 7.51-7.46 (m, 2H), 7.44-7.39 (m, 2H), 7.34 (t, J=8.0 Hz, 2H), 6.83 (d, J=8.9 Hz, 1H), 5.27 (s, 2H), 3.58 (s, 4H), 3.30 (d, J=5.1 Hz, 4H), 3.07 (q, J=7.4 Hz, 2H), 1.22 (t, J=7.4 Hz, 3H), NH peak not observed. LCMS-A: rt 3.73 min, m/z (positive ion) 566 ($^{79}$Br), 568 ($^{81}$Br) [M+H]$^+$, m/z (negative ion) 564 ($^{79}$Br), 566 ($^{81}$Br) [M−H]$^−$.

d) 2-(4-(Benzyloxy)-3-(1-methyl-1H-pyrazol-4-yl)phenyl)-5-(4-(ethylsulfonyl)piperazin-1-yl)-3H-imidazo[4,5-b]pyridine (69)

To a stirred suspension of 2-(4-(benzyloxy)-3-bromophenyl)-5-(4-(ethylsulfonyl)piperazin-1-yl)-3H-imidazo[4,5-b]pyridine A131 (0.050 g, 0.090 mmol), (1-methyl-1H-pyrazol-4-yl)boronic acid (40.0 mg, 0.192 mmol), $PdCl_2(PPh_3)_4$ (0.010 g, 0.015 mmol) and TBAB (8.4 mg, 0.026 mmol, 0.29 equiv) in 1,4-dioxane:water 9:1 (1 mL) was added $K_2CO_3$ (37 mg, 0.27 mmol) and the reaction mixture was irradiated in the microwave at 110° C. for 15 minutes. Water (1 mL) and EtOAc (5 mL) were added and the layers were separated. The aqueous layer was extracted with EtOAc (5 mL) and the organic layers were combined. The organic layers were washed with brine (5 mL), dried ($Na_2SO_4$), filtered, and concentrated in vacuo to give an orange oil that was purified by two iterations of column chromatography (4 g $SiO_2$ cartridge, 0-10% MeOH in DCM, then 12 g $SiO_2$ cartridge, 0-10% MeOH in DCM) to give a pale yellow solid. The material was suspended in MeOH (3 mL), sonicated for 5 min and centrifuged for 10 minutes. The supernatant was removed and the solid washed with MeOH (1 mL). The suspension was centrifuged again for 10 minutes and the supernatant was removed. The solid was dried under vacuum to give the title compound (13.0 mg, 26%). $^1$H NMR (400 MHz, $d_6$-DMSO) δ 8.38 (d, J=2.3 Hz, 1H), 8.16 (s, 1H), 7.96 (d, J=0.8 Hz, 1H), 7.94 (dd, J=8.8, 2.3 Hz, 1H), 7.82 (d, J=8.5 Hz, 1H), 7.57-7.49 (m, 2H), 7.47-7.40 (m, 2H), 7.39-7.32 (m, 1H), 7.27 (d, J=8.6 Hz, 1H), 6.83 (d, J=8.9 Hz, 1H), 5.32 (s, 2H), 3.87 (s, 3H), 3.66-6.58 (m, 4H), 3.33-3.28 (m, 4H), 3.10 (q, J=7.4 Hz, 2H), 1.23 (t, J=7.4 Hz, 3H). LCMS-A: rt 5.12 min, m/z (positive ion) 558 [M+H]$^+$.

Example 70-73: General Addition of Heterocycles by Suzuki Coupling

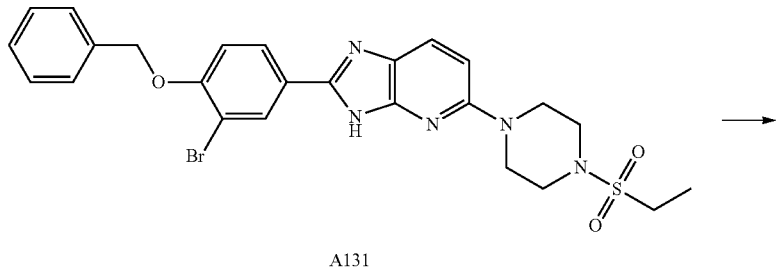

A131

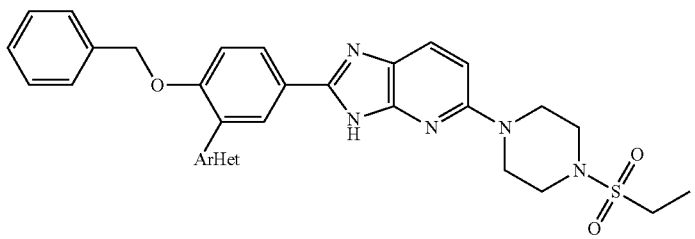

ArHet

General Procedure F:

To a stirred suspension of 2-(4-(benzyloxy)-3-bromophenyl)-5-(4-(ethylsulfonyl)piperazin-1-yl)-3H-imidazo[4,5-b]pyridine A131 (51 mg, 0.090 mmol), the desired boronic acid (0.11 mmol, 1.1 equiv), $PdCl_2(PPh_3)_2$ (7 mg, 0.009 mmol, 0.1 equiv) and TBAB (6 mg, 0.009 mmol, 0.1 equiv) in 1,4-dioxane:water (3:1, 1 mL) was added $K_2CO_3$ (38 mg, 0.27 mmol, 3 equiv). The reaction mixture was irradiated in the microwave at 130° C. for 45 minutes. Water (3 mL) and EtOAc (10 mL) were added and the layers were separated. The aqueous layer was extracted with EtOAc (10 mL). The organic layers were combined and dried ($Na_2SO_4$), filtered and concentrated in vacuo. The crude material was purified by column chromatography (12 g $SiO_2$ cartridge, 0-10% MeOH in DCM) and the fractions containing product were combined and concentrated in vacuo to give the title compound.

TABLE E

| Example | Boronic acid | Product Name and Structure | LCMS data | Method |
|---|---|---|---|---|
| 70 | | 2-(4-(Benzyloxy)-3-(1H-pyrazol-5-yl)phenyl)-5-(4-(ethylsulfonyl)piperazin-1-yl)-3H-imidazo[4,5-b]pyridine | LCMS-B: rt 3.24 min, m/z (positive ion) 544 [M + H]+, m/z (negative ion) 542 [M − H]− | F |
| 71 | | 2-(4-(Benzyloxy)-3-(pyridin-3-yl)phenyl)-5-(4-(ethylsulfonyl)piperazin-1-yl)-3H-imidazo[4,5-b]pyridine | LCMS-B: rt 3.23 min, m/z (positive ion) 555 [M + H]+, m/z (negative ion) 553 [M − H]− | F |
| 72 | | 2-(4-(Benzyloxy)-3-(pyrimidin-5-yl)phenyl)-5-(4-(ethylsulfonyl)piperazin-1-yl)-3H-imidazo[4,5-b]pyridine | LCMS-A: rt 5.17 min, m/z (positive ion) 566 [M + H]+ | F |
| 73 | | 2-(4-(benzyloxy)-3-(1H-pyrazol-4-yl)phenyl)-5-(4-(ethylsulfonyl)piperazin-1-yl)-3H-imidazo[4,5-b]pyridine | LCMS-A: rt 5.01 min, m/z (positive ion) 544 [M + H]+, m/z (negative ion) 542 [M − H]− | F |

Example 74: Synthesis of 2-(4-(benzyloxy)-3-methylphenyl)-5-(4-(ethylsulfonyl)piperazin-1-yl)-3H-imidazo[4,5-b]pyridine (74)

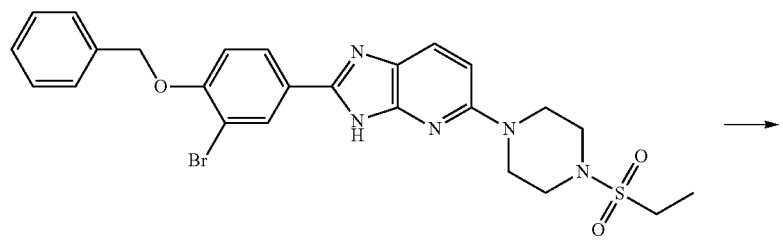

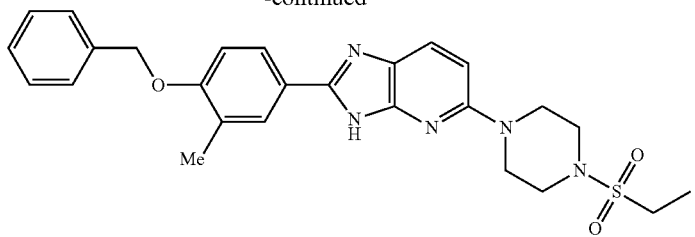

74

A suspension of 2-(4-(benzyloxy)-3-bromophenyl)-5-(4-(ethylsulfonyl)piperazin-1-yl)-3H-imidazo[4,5-b]pyridine A131 (55.7 mg, 0.100 mmol), DABAL-AlMe₃ (26.9 mg, 0.105 mmol), Pd₂dba₃ (8.6 mg, 0.015 mmol) and X-Phos (14 mg, 0.030 mmol) in THF (0.8 mL) was degassed with nitrogen before heating in a microwave for 15 minutes at 120° C. An aqueous solution of HCl (1 M, 1 mL) was added and the mixture was extracted with EtOAc (3×5 mL). The aqueous layer was adjusted to pH 5 with aqueous NaOH (2 M) and then extracted with DCM (3×20 mL). The combined organic layers were washed with brine (10 mL), dried (Na₂SO₄), filtered and concentrated in vacuo. The crude material was purified by column chromatography (12 g SiO₂ cartridge, 80%-100% EtOAc in petroleum benzine 40-60° C.) to give the title compound (22 mg, 45%). ¹H NMR (400 MHz, CDCl₃) δ 9.77 (s, 1H), 7.89 (d, J=8.7 Hz, 1H), 7.83 (s, 1H), 7.71 (d, J=8.3 Hz, 1H), 7.48-7.44 (m, 2H), 7.44-7.37 (m, 2H), 7.37-7.30 (m, 1H), 6.97 (d, J=8.5 Hz, 1H), 6.66 (d, J=8.8 Hz, 1H), 5.15 (s, 2H), 3.66 (t, J=5.0 Hz, 4H), 3.41 (t, J=5.0 Hz, 4H), 2.97 (q, J=7.4 Hz, 2H), 2.34 (s, 3H), 1.39 (t, J=7.4 Hz, 3H). LCMS-B: rt 3.40 min, m/z (positive ion) 492 [M+H]⁺; m/z (negative ion) 490 [M−H]⁻.

Example 75: Synthesis of 2-(4-(benzyloxy)-3-methoxyphenyl)-5-(4-(ethylsulfonyl)piperazin-1-yl)-3H-imidazo[4,5-b]pyridine (75)

A 25% sodium methoxide solution in MeOH was prepared by adding freshly cut sodium (430 mg) portion-wise into anhydrous MeOH (4 mL) under a nitrogen atmosphere at room temperature. The 25% sodium methoxide solution (0.200 mL, 0.952 mmol) was added to a stirring suspension of 2-(4-(benzyloxy)-3-bromophenyl)-5-(4-(ethylsulfonyl)piperazin-1-yl)-3H-imidazo[4,5-b]pyridine A131 (0.050 g, 0.090 mmol), CuCl (8.9 mg, 0.090 mmol), DMF (500 μL) and MeOH (250 μL) in a tube at room temperature under N₂. The tube was sealed and heated at 120° C. for 17 hours. The reaction mixture was cooled to room temperature and partitioned between EtOAc (5 mL) and a saturated aqueous solution of NH₄Cl (5 mL). The layers were separated and the aqueous layer was extracted with EtOAc (2×5 mL). The combined organic layers were washed with water (10 mL), brine (10 mL) and a saturated aqueous solution of NH₄Cl (10 mL), dried (Na₂SO₄), filtered and concentrated in vacuo. The crude material was purified by column chromatography (12 g SiO₂ cartridge, 80-100% EtOAc in petroleum benzine 40-60° C. then 0-10% MeOH in EtOAc) to give the title compound as a pale yellow solid (6.4 mg, 14%). ¹H NMR (400 MHz, CD₃OD) δ 7.96-7.52 (m, 3H), 7.52-7.43 (m, 2H), 7.41-7.35 (m, 2H), 7.35-7.28 (m, 1H), 7.09 (s, 1H), 6.84 (d, J=7.6 Hz, 1H), 5.17 (s, 2H), 3.94 (s, 3H), 3.66 (t, J=4.7 Hz, 4H), 3.38 (t, J=4.5 Hz, 4H), 3.06 (q, J=7.4 Hz, 2H), 1.34 (t, J=7.4 Hz, 3H). LCMS-B: rt 3.26 min, m/z (positive ion) 508 [M+H]⁺, m/z (negative ion) 506 [M−H]⁻.

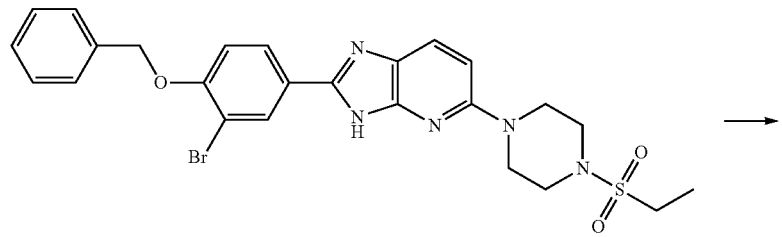

A131

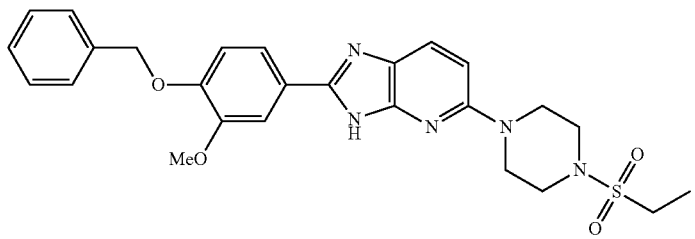

75

Example 76: Synthesis of ethyl 2-(2-(4-(benzyloxy)phenyl)-3H-imidazo[4,5-b]pyridin-7-yl)acetate (76)

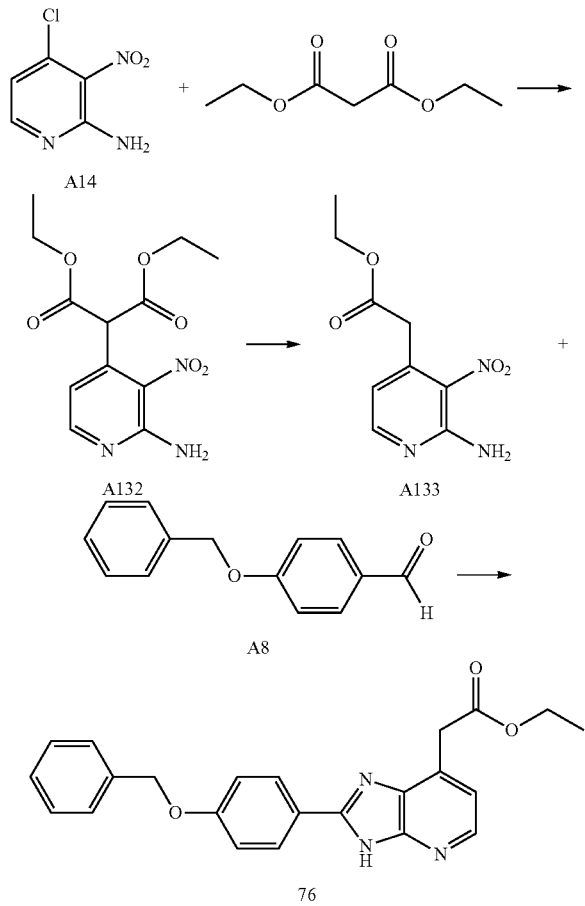

a) Diethyl 2-(2-amino-3-nitropyridin-4-yl)malonate (A132)

NaH (60% dispersion in mineral oil, 0.830 g, 20.7 mmol) was added to a solution of diethyl malonate (3.16 mL, 20.7 mmol) in NMP (50 mL) and the resulting solution was stirred at room temperature for 10 minutes. 4-Chloro-3-nitropyridin-2-amine A14 (1.00 g, 5.76 mmol) was then added and the mixture heated at 50° C. for 2 hours. The mixture was cooled to room temperature and diluted with EtOAc (250 mL) and water (100 mL). The organic layer was separated and washed with water (100 mL) followed by brine (100 mL). This process was repeated three times before the organic layer was dried ($Na_2SO_4$), filtered and the filtrate concentrated under reduced pressure to give a yellow oil which was purified by silica gel column chromatography (40 g $SiO_2$ cartridge, 0-100% EtOAc in petroleum benzine 40-60° C.) to give the title compound as a yellow solid (1.69 g, 99%). $^1$H NMR (400 MHz, $d_6$-DMSO) δ 8.28 (d, J=4.9 Hz, 1H), 7.53 (s, 2H), 6.58 (d, J=5.0 Hz, 1H), 5.20 (s, 1H), 4.18 (qd, J=7.1, 0.9 Hz, 4H), 1.18 (t, J=7.1 Hz, 6H). LCMS-B: rt 3.20 min, m/z (positive ion) 298 [M+H]$^+$.

b) Ethyl 2-(2-amino-3-nitropyridin-4-yl)acetate (A133)

LiCl (0.719 g, 17.0 mmol) was added to a suspension of diethyl 2-(2-amino-3-nitropyridin-4-yl)malonate A132 (1.68 g, 5.65 mmol) in DMSO (25 mL) and water (25 mL). The mixture was heated at 130° C. for 18 hours before being cooled to room temperature and diluted with EtOAc (250 mL) and water (200 mL). The organic layer was separated and washed with water (100 mL), brine (100 mL), dried (sodium sulfate), filtered and the volatiles removed in vacuo to give a yellow semi-solid which was purified by silica gel column chromatography (40 g $SiO_2$ cartridge, 0-100% EtOAc in petroleum benzine 40-60° C.) to give the title compound as a yellow solid (1.10 g, 86%). $^1$H NMR (400 MHz, $d_6$-DMSO) δ 8.20 (d, J=4.7 Hz, 1H), 7.45 (s, 2H), 6.67 (d, J=4.7 Hz, 1H), 4.08 (q, J=7.1 Hz, 2H), 3.92 (s, 2H), 1.17 (t, J=7.1 Hz, 3H). LCMS-B: rt 3.05 min, m/z (positive ion) 226 [M+H]$^+$.

c) Ethyl 2-(2-(4-(benzyloxy)phenyl)-3H-imidazo[4,5-b]pyridin-7-yl)acetate (76)

A freshly prepared aqueous solution of sodium dithionite (1.00 M, 3.33 mL, 3.33 mmol) was added to a suspension of 4-(benzyloxy)benzaldehyde A8 (0.259 g, 1.22 mmol) and ethyl 2-(2-amino-3-nitropyridin-4-yl)acetate A133 (0.250 g, 1.11 mmol) in EtOH (7 mL). The resulting yellow suspension was heated under microwave irradiation at 110° C. for 15 minutes. The mixture was cooled to room temperature, an aqueous solution of $NH_4OH$ (5 M, 2 mL) was added and the reaction mixture was stirred for 5 minutes at room temperature. The resulting mixture was filtered, and the solid was washed with water (10 mL) and air dried to give the title compound as a cream solid (0.054 g, 13%). $^1$H NMR (400 MHz, $d_6$-DMSO) δ 13.11 (s, 1H), 8.22 (s, 1H), 8.17 (d, J=8.8 Hz, 2H), 7.49 (d, J=7.1 Hz, 2H), 7.45-7.39 (m, 2H), 7.38-7.32 (m, 1H), 7.21 (d, J=8.4 Hz, 2H), 7.13 (d, J=3.9 Hz, 1H), 5.21 (s, 2H), 4.13 (q, J=7.1 Hz, 2H), 4.07 (s, 2H), 1.20 (t, J=7.1 Hz, 3H). LCMS-B: rt 3.27 min, m/z (positive ion) 388 [M+H]$^+$.

Example 77: Synthesis of 2-(2-(4-(benzyloxy)phenyl)-3H-imidazo[4,5-b]pyridin-7-yl)acetic acid (77)

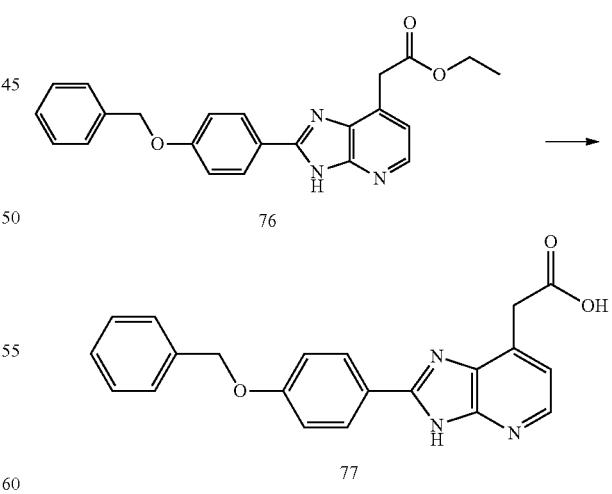

LiOH—$H_2O$ (0.019 g, 0.45 mmol) was added to a mixture of ethyl 2-(2-(4-(benzyloxy)phenyl)-3H-imidazo[4,5-b]pyridin-7-yl)acetate 76 (0.035 g, 0.090 mmol) in MeOH (1 mL), THF (3 mL) and water (1 mL). The resulting mixture was stirred for 5 hours at room temperature before the volatiles were removed in vacuo. The residue was taken up in EtOAc (25 mL) and 2 M aqueous NaOH (25 mL) and the layers separated. The aqueous layer was acidified with 2 M aqueous HCl to pH 1 and then EtOAc (25 mL) was added. A solid precipitate which was insoluble in both the aqueous and organic phases was isolated by filtration, washed with water (15 mL) and allowed to air dry for 18 hours to give the title compound as a white solid (16 mg, 49%). $^1$H NMR (400 MHz, $d_6$-DMSO) δ 8.49 (d, J=4.7 Hz, 1H), 8.33 (d, J=8.5 Hz, 2H), 7.53-7.47 (m, 3H), 7.43 (t, J=7.3 Hz, 2H), 7.40-7.34 (m, 1H), 7.32 (d, J=8.9 Hz, 2H), 5.26 (s, 2H), 4.27 (s, 2H). LCMS-B: rt 3.07 min, m/z (positive ion) 360 [M+H]$^+$.

Example 78: Synthesis of 2-(4-(benzyloxy)phenyl)-7-methyl-3H-imidazo[4,5-b]pyridine (78)

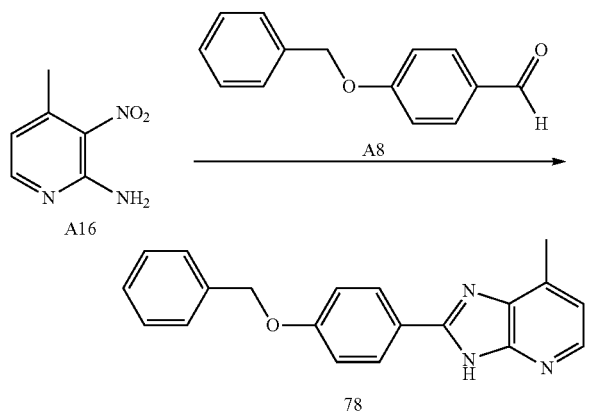

To a suspension of 4-(benzyloxy)benzaldehyde A8 (0.076 g, 0.36 mmol) and 4-methyl-3-nitropyridin-2-amine A17 (0.050 g, 0.33 mmol) in EtOH (2.0 mL) was added an aqueous solution of sodium dithionite (1.00 M, 0.980 mL, 0.980 mmol). The resulting yellow suspension was irradiated in a microwave reactor at 110° C. for 15 min. The mixture was cooled to room temperature and a 28% w/w aqueous solution of NH$_4$OH (1 mL) was added. The mixture was stirred for 5 minutes and then filtered to give a yellow solid. The crude material was purified by silica gel chromatography (12 g SiO$_2$ cartridge, 0-100% EtOAc in petroleum benzine 40-60° C.) to give the title compound (0.014 g, 14%) as a white solid. $^1$H NMR (400 MHz, $d_6$-DMSO) δ 13.16 (br s, 1H), 8.18 (d, J=8.8 Hz, 2H), 8.14 (d, J=4.9 Hz, 1H), 7.52-7.47 (m, 2H), 7.46-7.38 (m, 2H), 7.39-7.31 (m, 1H), 7.20 (d, J=9.0 Hz, 2H), 7.02 (d, J=4.9 Hz, 1H), 5.21 (s, 2H), 2.58 (s, 3H). LCMS-B: rt 3.09 min, m/z (positive ion) 316.2 [M+H]$^+$.

Example 79: Synthesis of 2-(4-(benzyloxy)phenyl)-5-(piperazin-1-ylmethyl)-3H-imidazo[4,5-b]pyridine (79)

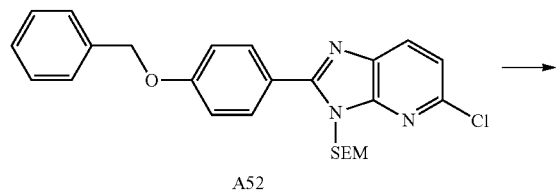

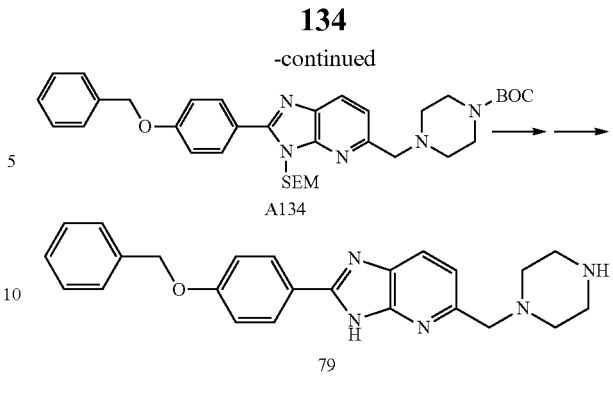

a) tert-Butyl 4-((2-(4-(benzyloxy)phenyl)-3-((2-(trimethylsilyl)ethoxy)methy)-3H-imidazo[4,5-b]pyridin-5-yl)methyl)piperazine-1-carboxylate (A134)

In a microwave tube, 2-(4-(benzyloxy)phenyl)-5-chloro-3-((2-(trimethylsilyl) ethoxy)methyl)-3H-imidazo[4,5-b]pyridine A52 (0.032 g, 0.069 mmol), Pd(OAc)$_2$ (0.001 g, 0.003 mmol), XPhos (0.003 g, 0.007 mmol), Cs$_2$CO$_3$ (0.067 g, 0.21 mmol) and potassium (4-tert-butoxycarbonylpiperazin-1-yl)methyltrifluoroborate (0.022, 0.072 mmol) were suspended in THF:H$_2$O (10:1, 1 mL). The mixture was irradiated in a microwave at 110° C. for 12 hours, cooled and then concentrated to dryness. The crude material was purified by silica gel chromatography (12 g SiO$_2$ cartridge, 0-100% EtOAc in petroleum benzine 40-60° C., then 0-20% MeOH in EtOAc) to give the title compound (0.025 g, 58%) as a pale yellow solid. $^1$H NMR (400 MHz, d-Acetone) δ 8.17-8.10 (m, 2H), 7.98 (d, J=8.1 Hz, 1H), 7.60-7.49 (m, 2H), 7.47 (d, J=8.2 Hz, 1H), 7.45-7.38 (m, 2H), 7.39-7.31 (m, 1H), 7.24-7.18 (m, 2H), 5.72 (s, 2H), 5.25 (s, 2H), 3.97-3.80 (m, 2H), 3.78 (s, 2H), 3.47-3.36 (m, 4H), 2.56-2.41 (m, 4H), 1.43 (s, 9H), 1.07-0.97 (m, 2H), −0.02 (s, 9H). LCMS-A: rt 5.61 min, m/z (positive ion) 630.3 [M+H]$^+$.

b) 2-(4-(Benzyloxy)phenyl)-5-(piperazin-1-ylmethyl)-3H-imidazo[4,5-b]pyridine (79)

tert-Butyl-4-((2-(4-(benzyloxy)phenyl)-3-((2-(trimethylsilyl)ethoxy)methyl)-3H-imidazo[4,5-b]pyridin-5-yl)methyl)piperazine-1-carboxylate A134 (0.020 g, 0.032 mmol) was dissolved in DCM (2 mL) under an atmosphere of nitrogen. TFA (1 mL) was added and the mixture was stirred at room temperature for 17 hours. The reaction mixture was concentrated in vacuo and the resulting solid was dissolved in EtOAc (20 mL) and aqueous NaOH (2 M, 20 mL). The layers were separated and the aqueous phase was extracted with EtOAc (20 mL). The combined organics were washed with brine (20 mL), dried (Na$_2$SO$_4$), filtered and concentrated in vacuo to give the title compound (0.013 g, 98%) as an off-white solid. $^1$H NMR (400 MHz, CDCl$_3$) δ 7.95 (d, J=8.4 Hz, 1H), 7.91-7.85 (m, 2H), 7.42-7.23 (m, 5H), 7.19-7.15 (m, 1H), 7.04 (d, J=8.1 Hz, 2H), 5.08 (s, 2H), 3.66 (s, 2H), 2.97 (br s, 4H), 2.51 (br s, 4H). LCMS-A: rt 4.50 min, m/z (positive ion) 400.2 [M+H]$^+$.

Example 80: Synthesis of ethyl 2-(2-(4-(benzyloxy)phenyl)-3H-imidazo[4,5-b]pyridin-5-yl)acetate (80)

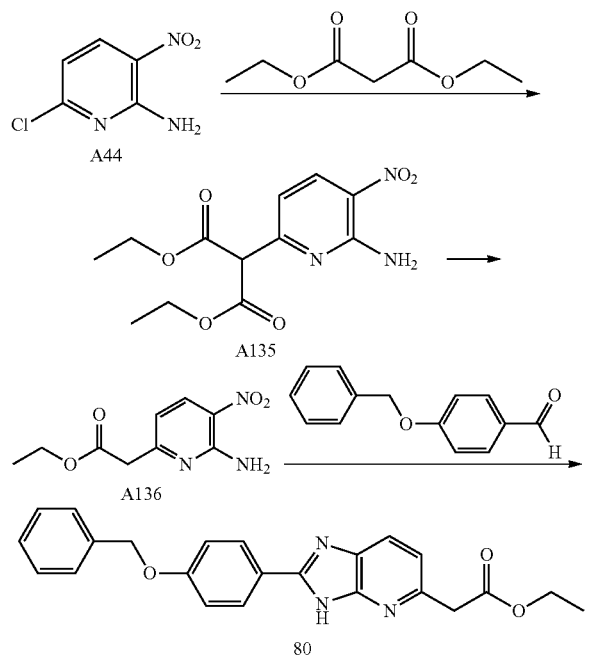

a) Diethyl 2-(6-amino-5-nitropyridin-2-yl)malonate (A135)

NaH (60% dispersion in mineral oil, 0.830 g, 20.7 mmol) was added to a solution of diethyl malonate (3.16 mL, 20.7 mmol) in NMP (50 mL) and the resulting solution stirred at room temperature for 10 minutes. After this time, 6-chloro-3-nitropyridin-2-amine A44 (1.00 g, 5.76 mmol) was added and the mixture heated at 50° C. for 2 hours. The mixture was cooled to room temperature and diluted with EtOAc (250 mL) and water (100 mL). The organic layer was separated and washed sequentially with water (100 mL) followed by brine (100 mL). This process was repeated three times before the organic layer was dried ($Na_2SO_4$), filtered and concentrated in vacuo to give a red oil. The crude material was purified by silica gel chromatography (40 g $SiO_2$ cartridge, 0-100% EtOAc in petroleum benzine 40-60° C.) to give the title compound (1.49 g, 70%) as an orange solid. $^1$H NMR (400 MHz, $d_6$-DMSO) δ 8.41 (d, J=8.5 Hz, 1H), 7.94 (br s, 2H), 6.76 (d, J=8.6 Hz, 1H), 5.03 (s, 1H), 4.17 (qd, J=7.1, 5.8 Hz, 4H), 1.20 (dt, J=14.1, 7.1, 7.1 Hz, 6H). LCMS-A: rt 6.20 min, m/z (positive ion) 298.1 $[M+H]^+$.

b) Ethyl 2-(6-amino-5-nitropyridin-2-yl)acetate (A136)

To a suspension of diethyl 2-(6-amino-5-nitropyridin-2-yl)malonate A135 (1.19 g, 4.03 mmol) in DMSO (25 mL) and water (25 mL) was added LiCl (0.513 g, 12.1 mmol) and the resulting mixture was heated at 130° C. for 18 hours. After cooling to room temperature the mixture was diluted with EtOAc (250 mL) and water (200 mL). The organic layer was separated and washed with water (100 mL), brine (100 mL), dried ($Na_2SO_4$), filtered and concentrated in vacuo to give a yellow semi-solid. This material was purified by silica gel chromatography (12 g $SiO_2$ cartridge, 0-100% EtOAc in petroleum benzine 40-60° C.) to give the title compound (0.350 g, 39%) as a yellow solid. $^1$H NMR (400 MHz, $d_6$-DMSO) δ 8.35 (d, J=8.5 Hz, 1H), 7.92 (brs, 2H), 6.72 (d, J=8.5 Hz, 1H), 4.10 (q, J=7.1, 7.1 Hz, 2H), 3.76 (s, 2H), 1.18 (t, J=7.1 Hz, 3H). LCMS-A: rt 5.79 min, m/z (positive ion) 226.1 $[M+H]^+$.

c) Ethyl 2-(2-(4-(benzyloxy)phenyl)-3H-imidazo[4,5-b]pyridin-5-yl)acetate (80)

To a suspension of 4-(benzyloxy)benzaldehyde A8 (0.209 g, 0.987 mmol) and ethyl 2-(6-amino-5-nitropyridin-2-yl)acetate A136 (0.202 g, 0.897 mmol) in EtOH (6 mL) was added an aqueous solution of sodium dithionite solution (1.00 M, 2.69 mL, 2.69 mmol). The resulting yellow suspension was heated at 70° C. and stirred for 17 hours. After cooling to room temperature, 28% w/w aqueous solution of $NH_4OH$ (4 mL) was added and the mixture was stirred for a further 5 minutes. The mixture was concentrated in vacuo and the crude material was purified by silica gel chromatography (40 g $SiO_2$ cartridge, 20-100% EtOAc in petroleum benzine 40-60° C.) to give the title compound (0.072 g, 21%) as a yellow solid. $^1$H NMR (400 MHz, $CDCl_3$) δ 12.51 (br s, 1H), 7.94 (d, J=8.3 Hz, 2H), 7.82-7.64 (m, 1H), 7.36-7.26 (m, 3H), 7.26-7.17 (m, 2H), 7.03-6.89 (m, 1H), 6.81 (d, J=8.4 Hz, 2H), 4.91 (s, 2H), 3.96 (q, J=7.1 Hz, 2H), 3.74 (s, 2H), 1.04 (t, J=7.1 Hz, 3H). LCMS-B: rt 3.28 min, m/z (positive ion) 388.2 $[M+H]^+$.

Example 81: Synthesis of ethyl 2-(2-(4-(phenoxymethyl)phenyl)-3H-imidazo[4,5-b]pyridin-5-yl)acetate (81)

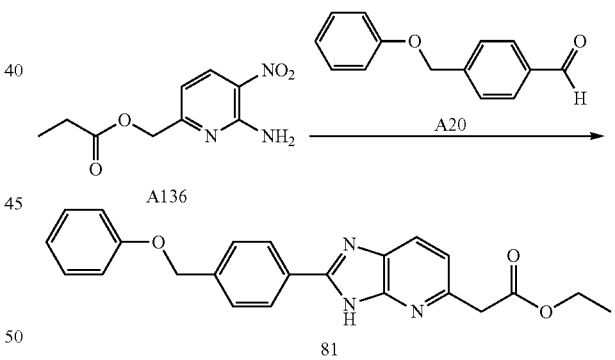

Ethyl 2-(2-(4-(phenoxymethyl)phenyl)-3H-imidazo[4,5-b]pyridin-5-yl)acetate (81)

To a suspension of 4-(phenoxymethyl)benzaldehyde A20 (0.104 g, 0.488 mmol) and (6-amino-5-nitropyridin-2-yl)methyl propionate A136 (0.100 g, 0.444 mmol) in EtOH (4 mL) was added an aqueous solution of sodium dithionite (1.00 M, 1.33 mL, 1.33 mmol). The resulting yellow suspension was irradiated in a microwave at 110° C. for 15 minutes. The mixture was cooled to room temperature, a 28% w/w aqueous solution of $NH_4OH$ (2 mL) was added and the mixture was stirred for 5 minutes. The suspension was filtered to give a yellow solid that was purified by silica gel chromatography (12 g $SiO_2$ cartridge, 0-100% EtOAc in petroleum benzine 40-60° C.) to give the title compound (0.020 g, 12%) as a pale yellow solid. $^1$H NMR (400 MHz, d$_6$-DMSO) δ 8.22 (d, J=8.3 Hz, 2H), 8.05-7.97 (m, 1H), 7.70-7.56 (m, 2H), 7.37-7.26 (m, 2H), 7.22 (d, J=8.2 Hz, 1H), 7.04 (d, J=7.8 Hz, 2H), 6.95 (t, J=7.3 Hz, 1H), 5.20 (s, 2H), 4.10 (q, J=7.1 Hz, 2H), 3.92 (s, 2H), 1.19 (t, J=7.1 Hz, 3H). LCMS-A: rt 6.00 min, m/z (positive ion) 388.2 [M+H]$^+$.

Example 82: Synthesis of 2-(2-(4-(benzyloxy)phenyl)-3H-imidazo[4,5-b]pyridin-5-yl)acetic acid (82)

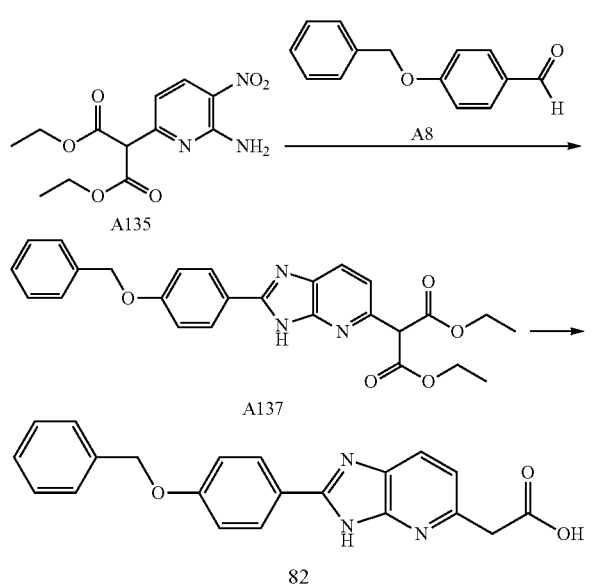

a) Diethyl 2-(2-(4-(benzyloxy)phenyl)-3H-imidazo[4,5-b]pyridin-5-yl)malonate (A137)

To a suspension of 4-(benzyloxy)benzaldehyde A8 (0.196 g, 0.925 mmol) and diethyl 2-(6-amino-5-nitropyridin-2-yl)malonate A135 (0.250 g, 0.841 mmol) in EtOH (6 mL) was added an aqueous solution of sodium dithionite (1.00 M, 2.52 mL, 2.52 mmol). The resulting yellow suspension was irradiated in a microwave at 110° C. for 30 minutes. The mixture was cooled to room temperature, a 28% w/w aqueous solution of NH$_4$OH (4 mL) was added and the reaction mixture was stirred for 5 minutes. The mixture was concentrated in vacuo and the crude material was purified by silica gel chromatography (40 g SiO$_2$ cartridge, 0-100% EtOAc in petroleum benzine 40-60° C., then 0-20% MeOH in EtOAc) to give the title compound (0.050 g, 13%) as a yellow semi-solid. $^1$H NMR (400 MHz, CDCl$_3$) δ 10.57 (br s, 1H), 7.96 (d, J=8.9 Hz, 2H), 7.47-7.28 (m, 7H), 7.08-6.96 (m, 2H), 5.09 (s, 2H), 5.00 (s, 1H), 4.25 (qd, J=7.1, 5.9 Hz, 4H), 1.26 (t, J=7.1 Hz, 6H). LCMS-A: rt 6.29 min, m/z (positive ion) 460.2 [M+H]$^+$.

b) 2-(2-(4-(Benzyloxy)phenyl)-3H-imidazo[4,5-b]pyridin-5-yl)acetic acid (82)

To a solution of diethyl 2-(2-(4-(benzyloxy)phenyl)-3H-imidazo[4,5-b]pyridin-5-yl)malonate A137 (0.040 g, 0.087 mmol) in EtOH (2 mL) was added aqueous NaOH (2 M, 2 mL). This mixture was heated at 100° C. for 1 hour and then cooled to room temperature. The volatiles were removed in vacuo and the remaining mixture was acidified with aqueous HCl (2 M, ~3 mL) and extracted with DCM (3×10 mL). The organics were combined, dried (Na$_2$SO$_4$), filtered and concentrated in vacuo to give the title compound (0.020 g, 64%) as an off-white solid. $^1$H NMR (400 MHz, d$_6$-DMSO) δ 12.40 (s, 1H), 8.16 (d, J=8.8 Hz, 2H), 8.01 (d, J=8.1 Hz, 1H), 7.51-7.45 (m, 2H), 7.45-7.39 (m, 2H), 7.38-7.31 (m, 1H), 7.29-7.18 (m, 3H), 5.23 (s, 2H), 3.86 (s, 2H), OH proton not observed LCMS-B: rt 3.12 min, m/z (positive ion) 360.2 [M+H]$^+$.

Example 83: Synthesis of 2-(4-(benzyloxy)phenyl)-6-(1-(methylsulfonyl)piperidin-4-yl)-3H-imidazo[4,5-b]pyridine (83)

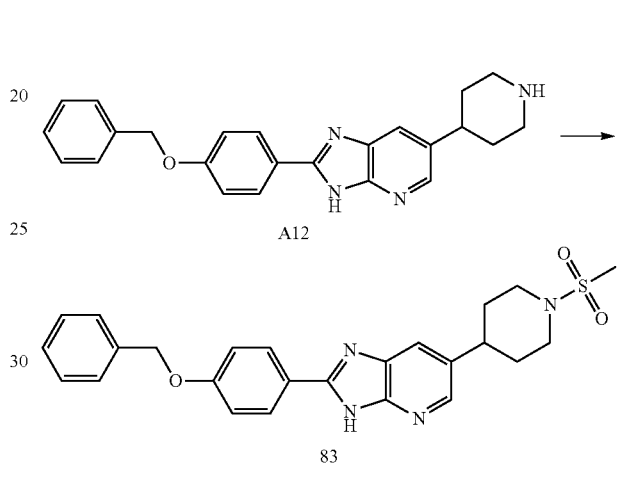

A suspension of 2-(4-(benzyloxy)phenyl)-6-(piperidin-4-yl)-1H-imidazo[4,5-b]pyridine 12 (0.020 g, 0.052 mmol) in DCM (1 mL) was cooled to 0° C. and then treated with DIPEA (0.009 mL, 0.05 mmol). After 5 minutes, methanesulfonyl chloride (0.004 mL, 0.05 mmol) was added and the mixture was stirred at 0° C. for 2 hours. Water (1 mL) was added and the mixture was warmed to room temperature. The mixture was extracted with DCM (3×10 mL) and the combined organic layers were washed with brine, dried (Na$_2$SO$_4$) and concentrated in vacuo to give the title compound (0.006 g, 25%) as a white solid. $^1$H NMR (400 MHz, d$_6$-DMSO) δ 13.19 (s, 1H), 8.23 (s, 1H), 8.19-8.08 (m, 2H), 7.83 (s, 1H), 7.53-7.46 (m, 2H), 7.45-7.39 (m, 2H), 7.39-7.31 (m, 1H), 7.25-7.12 (m, 2H), 5.21 (s, 2H), 3.76-3.67 (m, 2H), 2.92 (s, 3H), 2.90-2.75 (m, 3H), 1.99-1.88 (m, 2H), 1.80 (qd, J=12.5, 4.0 Hz, 2H). LCMS-B: rt 3.22 min, m/z (positive ion) 463.2 [M+H]$^+$.

Example 84: Synthesis of tert-butyl 4-(2-(4-(phenoxymethyl)phenyl)-3H-imidazo[4,5-b]pyridin-5-yl)piperidine-1-carboxylate (84)

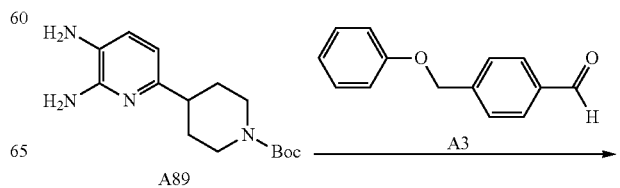

-continued

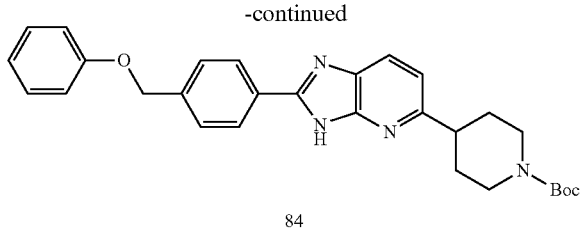

84

4-(Phenoxymethyl)benzaldehyde A20 (0.177 g, 0.834 mmol), tert-butyl 4-(5,6-diaminopyridin-2-yl)piperidine-1-carboxylate A89 (0.244 g, 0.834 mmol) and activated 4 Å sieves (1 g, before activation by heat-gun under vacuum) were combined in a flask, to which MeOH (10 mL) was added. The reaction mixture was heated at reflux for 4 days. The suspension was cooled to room temperature, filtered through a pad of Celite and the solvent was removed in vacuo. THF (10 mL) followed by (diacetoxyiodo)benzene (0.322 g, 1.00 mmol) were added under an atmosphere of nitrogen and the reaction was stirred at room temperature for 2 hours. The mixture was concentrated in vacuo and diluted with EtOAc (100 mL) and a saturated aqueous solution of NaHCO$_3$ (100 mL). The layers were separated and the aqueous layer was extracted with EtOAc (100 mL). The combined organic fractions were washed with brine (100 mL), dried (Na$_2$SO$_4$), filtered and concentrated in vacuo to give the crude product which was purified by silica gel chromatography (40 g SiO$_2$ cartridge, 0-100% EtOAc in petroleum benzine 40-60° C.) to give the title compound (0.191 g, 47%) as a white solid. $^1$H NMR (400 MHz, d$_6$-DMSO) δ 13.49 (br s, 1H), 8.27-8.16 (m, 2H), 7.95 (s, 1H), 7.62 (d, J=8.0 Hz, 2H), 7.39-7.25 (m, 2H), 7.17 (d, J=8.2 Hz, 1H), 7.10-7.01 (m, 2H), 6.95 (tt, J=7.3, 1.1 Hz, 1H), 5.19 (s, 2H), 4.09 (d, J=11.0 Hz, 2H), 3.03-2.76 (m, 3H), 1.87 (d, J=12.7 Hz, 2H), 1.66 (qd, J=12.6, 4.2 Hz, 2H), 1.43 (s, 9H). LCMS-A: rt 6.38 min, m/z (positive ion) 485.2 [M+H]$^+$.

Example 85: Synthesis of 2-(4-(phenoxymethyl)phenyl)-5-(piperidin-4-yl)-3H-imidazo[4,5-b]pyridine (85)

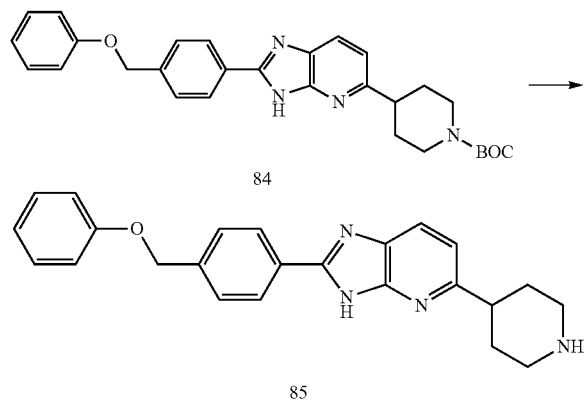

tert-Butyl 4-(2-(4-(phenoxymethyl)phenyl)-3H-imidazo[4,5-b]pyridin-5-yl)piperidine-1-carboxylate 84 (0.191 g, 0.394 mmol) was dissolved in DCM (15 mL) under an atmosphere of nitrogen. TFA (2 mL) was added and the mixture was stirred at room temperature for 20 hours. The reaction mixture was concentrated in vacuo and the resulting solid was dissolved in EtOAc (50 mL) and aqueous NaOH (2 M, 50 mL). The layers were separated and the aqueous phase was extracted with EtOAc (50 mL). The combined organic layers were washed with brine (50 mL), dried (Na$_2$SO$_4$), filtered and concentrated in vacuo to give the title compound (0.164 g, 100%) as an off-white solid. $^1$H NMR (400 MHz, d$_6$-DMSO) δ 8.27-8.16 (m, 2H), 7.91 (d, J=8.2 Hz, 1H), 7.61 (d, J=8.3 Hz, 2H), 7.31 (dd, J=8.7, 7.2 Hz, 2H), 7.12 (d, J=8.2 Hz, 1H), 7.06-7.02 (m, 2H), 6.95 (t, J=7.3 Hz, 1H), 5.19 (s, 2H), 3.08-3.01 (m, 2H), 2.82 (m, 1H), 2.61 (td, J=11.8, 2.3 Hz, 2H), 1.84-1.76 (m, 2H), 1.68 (qd, J=12.4, 3.9 Hz, 2H) NH proton signal not observed. LCMS-B: rt 2.97 min, m/z 385.3 (positive ion) [M+H]$^+$.

Example 86: Synthesis of 5-(1-methylpiperidin-4-yl)-2-(4-(phenoxymethyl)phenyl)-3H-imidazo[4,5-b]pyridine (86)

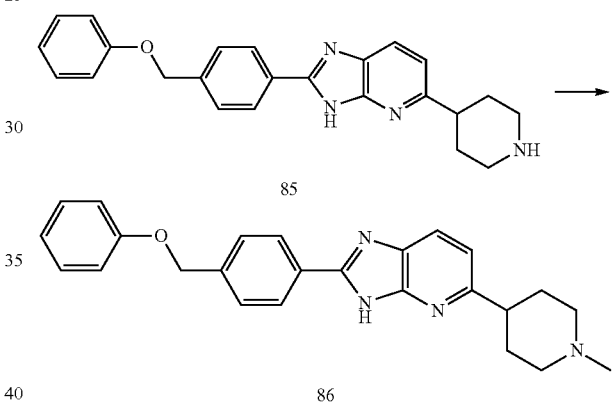

To a solution of 2-(4-(phenoxymethyl)phenyl)-5-(piperidin-4-yl)-3H-imidazo[4,5-b]pyridine 85 (0.030 g, 0.078 mmol) in anhydrous MeOH (6 mL) was added a 37% w/w aqueous solution of formaldehyde (0.017 mL, 0.23 mmol) under an atmosphere of nitrogen followed by sodium triacetoxyborohydride (0.066 g, 0.31 mmol). The mixture was stirred for 18 hours before the volatiles were removed in vacuo. The residue was diluted with EtOAc (20 mL) and a saturated aqueous solution of NaHCO$_3$ (20 mL), the layers were separated and the aqueous phase extracted with EtOAc (20 mL). The combined organic layers were washed with brine (30 mL), dried (Na$_2$SO$_4$), filtered and concentrated in vacuo to give a semi-solid which was taken up in a 1:1 mixture of DCM/Et$_2$O (~3 mL) and concentrated in vacuo to give the title compound (0.027 g, 87%) as an off-white solid. $^1$H NMR (400 MHz, d$_6$-DMSO) Some signals appear as a mixture of rotamers, denoted with an (*): δ 13.52* (s, 0.75H), 13.07* (s, 0.25H), 8.22 (d, J=8.4 Hz, 2H), 7.96* (d, J=8.2 Hz, 0.7H), 7.84* (d, J=8.2 Hz, 0.3H), 7.65* (d, J=8.7 Hz, 0.6H), 7.61* (d, J=8.0 Hz, 1.4H), 7.31 (dd, J=8.7, 7.2 Hz, 2H), 7.17 (d, J=8.1 Hz, 1H), 7.04 (dd, J=8.6, 1.2 Hz, 2H), 6.99-6.92 (m, 1H), 5.19 (s, 2H), 2.92 (d, J=10.5 Hz, 2H), 2.78-2.68 (m, 1H), 2.23 (s, 3H), 2.11-1.94 (m, 2H), 1.90-1.81 (m, 4H). LCMS-A: rt 4.78 min, m/z (positive ion) 399.2 [M+H]⁺.

Example 87: Synthesis of 2-(4-(benzyloxy)phenyl)-5-(1-(methylsulfonyl)piperidin-4-yl)-3H-imidazo[4,5-b]pyridine (87)

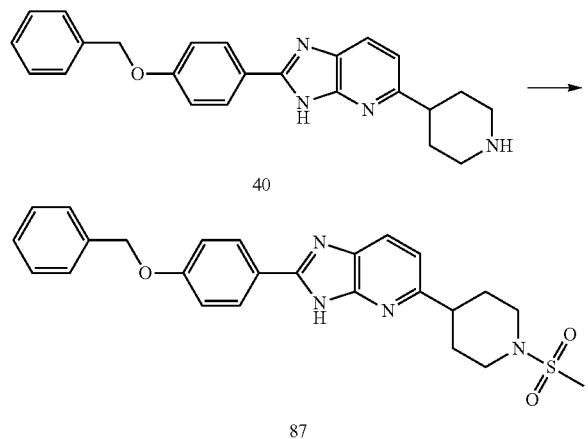

A solution of 2-(4-(benzyloxy)phenyl)-5-(piperidin-4-yl)-3H-imidazo[4,5-b]pyridine 40 (0.050 g, 0.13 mmol) in THF (2 mL) was cooled to 0° C. To this solution, DIPEA (0.023 mL, 0.130 mmol) was added and then, after 5 minutes, methanesulfonyl chloride (0.010 mL, 0.130 mmol) was added. The mixture was stirred at 0° C. for 1 hour before water (2 mL) was added, and a fine precipitate formed. The volatiles were removed in vacuo and the remaining aqueous suspension was centrifuged for 10 minutes. The water was decanted from the solid pellet and a second aliquot of water (2 mL) was added. The mixture was centrifuged for 10 minutes, followed by decantation of the water and vacuum drying of the precipitate to give the title compound (0.050 g, 83%) as a yellow solid. ¹H NMR (400 MHz, d₆-DMSO) δ 13.24 (s, 1H), 8.18-8.12 (m, 2H), 7.82 (d, J=7.9 Hz, 1H), 7.50-7.45 (m, 2H), 7.44-7.38 (m, 2H), 7.37-7.32 (m, 1H), 7.19-7.12 (m, 2H), 7.06 (d, J=7.8 Hz, 1H), 5.19 (s, 2H), 3.69 (dt, J=11.8, 3.0 Hz, 2H), 2.91 (s, 3H), 2.86 (td, J=12.1, 2.6 Hz, 3H), 2.03-1.96 (m, 2H), 1.84 (qd, J=12.4, 4.0 Hz, 2H). LCMS-B: rt 3.28 min, m/z (positive ion) 463.2 [M+H]⁺.

Example 88: Synthesis of ethyl 4-(2-(4-(benzyloxy)phenyl)-3H-imidazo[4,5-b]pyridin-5-yl)piperidine-1-carboxylate (88)

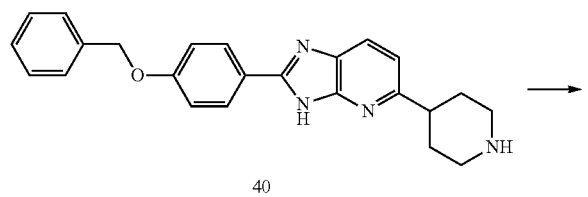

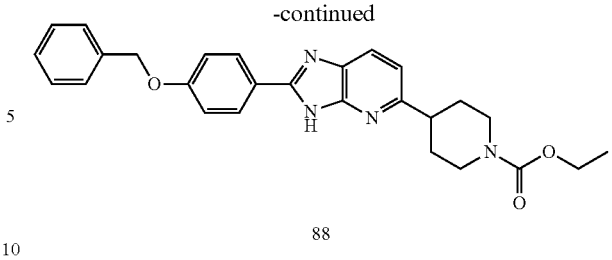

A solution of 2-(4-(benzyloxy)phenyl)-5-(piperidin-4-yl)-3H-imidazo[4,5-b]pyridine 40 (0.050 g, 0.13 mmol) in THF (2 mL) was cooled to 0° C. To this solution, DIPEA (0.023 mL, 0.13 mmol) was added and then, after 5 minutes, ethyl chloroformate (0.012 mL, 0.130 mmol) was added. The mixture was stirred at 0° C. for 1 hour before water (2 mL) was added, and a fine precipitate formed. The volatiles were removed in vacuo and the aqueous suspension centrifuged for 10 minutes. The water was decanted from the solid pellet and a second aliquot of water (2 mL) was added. The mixture was centrifuged for 10 minutes followed by decantation of the water and vacuum drying of the precipitate gave the title compound (0.048 g, 81%) as an off-white solid. ¹H NMR (400 MHz, d₆-DMSO) 13.26 (br s, 1H), 8.17-8.10 (m, 2H), 7.88 (br s, 1H), 7.51-7.46 (m, 2H), 7.44-7.39 (m, 2H), 7.37-7.32 (m, 1H), 7.19 (d, J=8.4 Hz, 2H), 7.13 (d, J=8.2 Hz, 1H), 5.20 (s, 2H), 4.17-4.06 (m, 2H), 4.06 (q, J=7.1, Hz, 2H), 2.96 (td, J=8.0, 4.4 Hz, 3H), 1.88 (d, J=11.9 Hz, 2H), 1.68 (qd, J=12.6, 4.2 Hz, 2H), 1.20 (t, J=7.1 Hz, 3H). LCMS-B: rt 3.40 min, m/z (positive ion) 457.3 [M+H]⁺.

Example 89: Synthesis of 2-(4-(benzyloxy)phenyl)-5-(1-(cyclopropylsulfonyl)piperidin-4-yl)-3H-imidazo[4,5-b]pyridine (89)

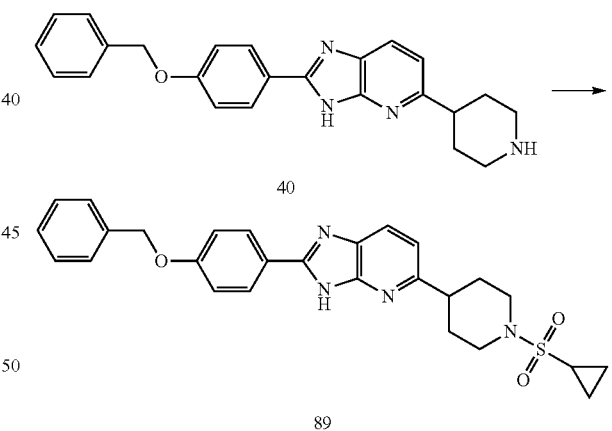

A solution of 2-(4-(benzyloxy)phenyl)-5-(piperidin-4-yl)-3H-imidazo[4,5-b]pyridine 40 (0.050 g, 0.13 mmol) in THF (2 mL) was cooled to 0° C. To this solution, DIPEA (0.023 mL, 0.13 mmol) was added and then, after 5 minutes, cyclopropane sulfonyl chloride (0.013 mL, 0.13 mmol) was added. The mixture was stirred at 0° C. for 5 hours, then at room temperature for 72 hours. Water (2 mL) was added and a fine precipitate formed. The volatiles were removed in vacuo and the aqueous suspension was centrifuged for 10 minutes. The water was decanted from the solid pellet and a second aliquot of water (2 mL) was added. The mixture was centrifuged for 10 minutes, followed by decantation of the water. The aqueous supernatants were combined and extracted with EtOAc (2×10 mL). The organic layers were combined, washed with brine, dried (Na₂SO₄), filtered and concentrated in vacuo to reveal the title compound (0.043 g, 68%) as a yellow solid. ¹H NMR (400 MHz, d₆-DMSO) δ 13.38 (br s, 1H), 8.20-8.11 (m, 2H), 7.90 (d, J=8.0 Hz, 1H), 7.54-7.45 (m, 2H), 7.44-7.38 (m, 2H), 7.38-7.31 (m, 1H), 7.18 (dd, J=10.3, 8.6 Hz, 3H), 5.21 (s, 2H), 3.79-3.69 (m, 2H), 3.04-2.88 (m, 3H), 2.68-2.58 (m, 1H), 2.06-1.96 (m, 2H), 1.83 (qd, J=12.7, 4.2 Hz, 2H), 1.05-0.91 (m, 4H). LCMS-B: rt 3.32 min, m/z (positive ion) 489.3 [M+H]⁺.

Example 90: Synthesis of 2-(4-(benzyloxy)phenyl)-5-(1-(ethylsulfonyl)piperidin-4-yl)-3H-imidazo[4,5-b]pyridine (90)

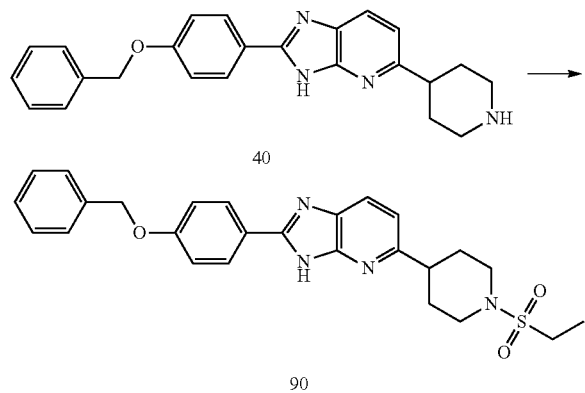

A solution of 2-(4-(benzyloxy)phenyl)-5-(piperidin-4-yl)-3H-imidazo[4,5-b]pyridine 40 (0.050 g, 0.13 mmol) in THF (2 mL) was cooled to 0° C. To this was added DIPEA (0.023 mL, 0.13 mmol), then after 5 minutes, ethanesulfonyl chloride (0.012 mL, 0.13 mmol). The mixture was stirred at 0° C. for 2 hours before water (2 mL) was added, and a fine precipitate formed. The volatiles were removed in vacuo and the aqueous suspension was centrifuged for 10 minutes. Water was decanted from the solid pellet before the centrifuge/decantation process was repeated, first with another portion of water (2 mL) and then with a portion of Et₂O (2 mL). Vacuum drying of the solid precipitate gave the title compound (0.048 g, 77%) as an off-white solid. ¹H NMR (400 MHz, d₆-DMSO) Some signals appear as a mixture of rotamers, denoted with an (*): δ 13.36* (s, 0.7H), 12.90* (s, 0.3H), 8.17-8.12 (m, 2H), 7.87* 7.93* (d, J=8.2 Hz, 0.6H), 7.81* (d, J=8.2 Hz, 0.4H), 7.51-7.46 (m, 2H), 7.44-7.38 (m, 2H), 7.38-7.32 (m, 1H), 7.19 (m, 3H), 5.21 (d, J=3.5 Hz, 2H), 3.78-3.70 (m, 2H), 3.13-3.05 (m, 2H), 3.01-2.89 (m, 3H), 2.02-1.94 (m, 2H), 1.81 (qd, J=12.2, 3.9 Hz, 2H), 1.25 (td, J=7.4, 2.8 Hz, 3H). LCMS-A: rt 5.59 min, m/z (positive ion) 477.2 [M+H]⁺.

Example 91: Synthesis of 2-(4-(benzyloxy)phenyl)-5-(4-(methylsulfonyl)piperazin-1-yl)-3H-imidazo[4,5-b]pyridine (91)

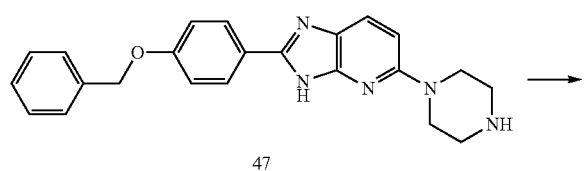

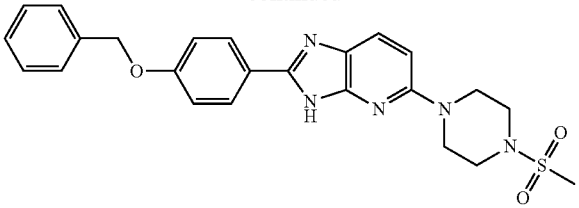

A solution of 2-(4-(benzyloxy)phenyl)-5-(piperazin-1-yl)-3H-imidazo[4,5-b]pyridine 47 (0.020 g, 0.052 mmol) in DMF (1 mL) was cooled to 0° C. To this was added DIPEA (0.009 mL, 0.05 mmol), then after 5 minutes, methanesulfonyl chloride (0.0040 mL, 0.052 mmol). The mixture was stirred at 0° C. for 1 hour before water (6 mL) was added, and a fine precipitate formed. The suspension was centrifuged for 10 minutes before the supernatant was decanted off from the solid pellet. The centrifuge/decantation process was repeated, first with another portion of water (6 mL) and then with a portion of Et₂O (3 mL). Vacuum drying of the solid precipitate gave the title compound (0.018 g, 75%) as a yellow solid. ¹H NMR (400 MHz, d₆-DMSO) δ 13.15 (s, 1H), 8.10-8.05 (m, 2H), 7.82 (d, J=8.8 Hz, 1H), 7.50-7.46 (m, 2H), 7.44-7.38 (m, 2H), 7.37-7.32 (m, 1H), 7.16 (d, J=8.9 Hz, 2H), 6.85 (d, J=8.9 Hz, 1H), 5.19 (s, 2H), 3.65 (t, J=5.0 Hz, 4H), 3.25 (t, J=5.0 Hz, 4H), 2.91 (s, 3H). LCMS-B: rt 3.12 min, m/z (positive ion) 464.3 [M+H]⁺.

Example 92: Synthesis of 2-(4-(benzyloxy)phenyl)-5-(4-(cyclopropylsulfonyl)piperazin-1-yl)-3H-imidazo[4,5-b]pyridine (92)

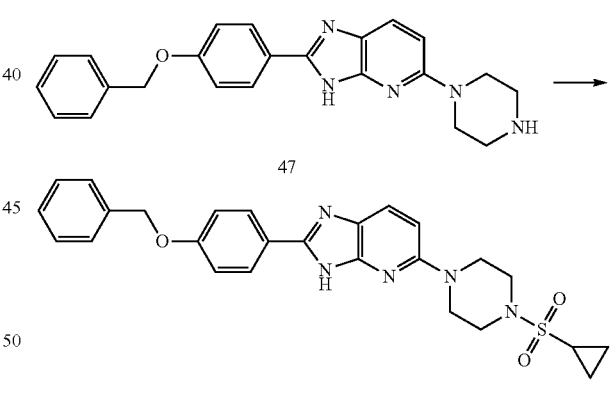

A solution of 2-(4-(benzyloxy)phenyl)-5-(piperazin-1-yl)-3H-imidazo[4,5-b]pyridine 47 (0.020 g, 0.052 mmol) in DMF (1 mL) was cooled to 0° C. To this was added DIPEA (0.009 mL, 0.052 mmol), then after 5 minutes, cyclopropanesulfonyl chloride (0.0053 mL, 0.052 mmol) was added. The reaction mixture was stirred at 0° C. for 1 hour before water (6 mL) was added, and a precipitate formed. The suspension was centrifuged for 10 minutes, and the solution was decanted off from the solid pellet. The centrifuge/decantation process was repeated, first with another portion of water (6 mL) and then with a portion of Et₂O (3 mL). Vacuum drying of the solid precipitate gave the title compound (0.017 g, 67%) as an off-white solid. ¹H NMR (400

MHz, d$_6$-DMSO) δ 13.00 (br s, 1H), 8.09-8.04 (m, 2H), 7.81 (br s, 1H), 7.50-7.46 (m, 2H), 7.44-7.39 (m, 2H), 7.37-7.32 (m, 1H), 7.15 (d, J=8.4 Hz, 2H), 6.83 (d, J=8.8 Hz, 1H), 5.19 (s, 2H), 3.66-3.61 (m, 4H), 2.69-2.60 (m, 1H), 1.03-0.92 (m, 4H). Four proton signals from the piperazine ring are obscured by the water signal. LCMS-B: rt 3.25 min, m/z (positive ion) 490.2 [M+H]$^+$.

Example 93: Synthesis of 2-(2-(4-(benzyloxy)phenyl)-3H-imidazo[4,5-b]pyridin-7-yl)-N-methylacetamide (93)

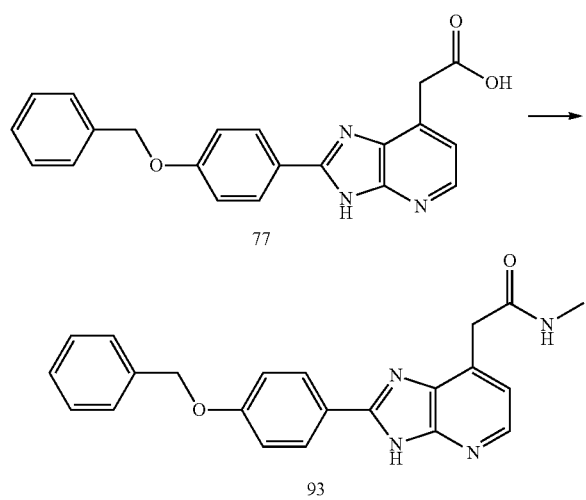

To a suspension of 2-(2-(4-(benzyloxy)phenyl)-3H-imidazo[4,5-b]pyridin-7-yl)acetic acid 77 (0.050 g, 0.14 mmol), EDCI.HCl (0.080 g, 0.42 mmol) and DMAP (0.051 g, 0.42 mmol) in dry DCM (5 mL) under a nitrogen atmosphere was added a 33% w/w solution of methylamine in EtOH (0.021 mL, 0.17 mmol). The solution was stirred for 17 hours before being diluted with DCM (5 mL). The mixture was washed with 1 M HCl (2×10 mL), a saturated aqueous solution of NaHCO$_3$ (10 mL), brine and concentrated in vacuo. The crude material was purified by silica gel chromatography (12 g SiO$_2$ cartridge, 0-100% EtOAc in petroleum benzine 40-60° C., then 0-20% MeOH in EtOAc) to give the title compound (0.010 g, 19%) as a white solid. $^1$H NMR (400 MHz, d$_6$-DMSO) δ 13.35 (br s, 1H), 8.23 (br s, 1H), 8.18 (d, J=7.8 Hz, 2H), 8.08-8.01 (m, 1H), 7.49 (d, J=7.2 Hz, 2H), 7.44-7.39 (m, 2H), 7.38-7.33 (m, 1H), 7.20 (d, J=8.5 Hz, 2H), 7.14-7.09 (m, 1H), 5.21 (s, 2H), 3.85 (s, 2H), 2.62 (d, J=4.6 Hz, 3H). LCMS-B: rt 3.07 min, m/z (positive ion) 373.2 [M+H]$^+$.

Example 94: Synthesis of 2-(2-(4-(benzyloxy)phenyl)-3H-imidazo[4,5-b]pyridin-7-yl)-N,N-dimethylacetamide (94)

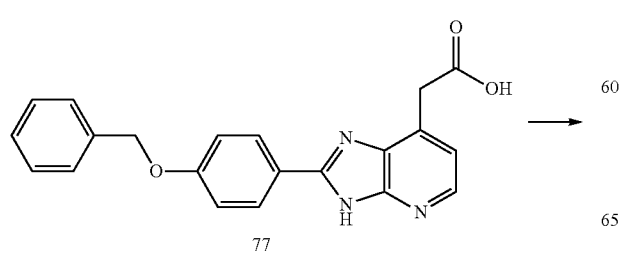

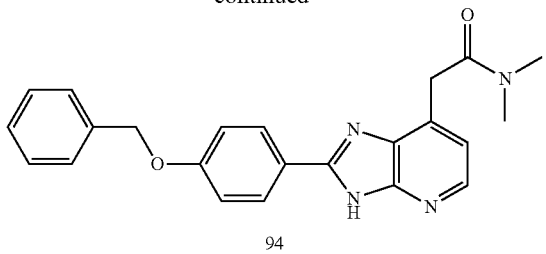

To a solution of 2-(2-(4-(benzyloxy)phenyl)-3H-imidazo[4,5-b]pyridin-7-yl)acetic acid 77 (0.050 g, 0.14 mmol), EDCI.HCl (0.080 g, 0.42 mmol) and DMAP (0.051 g, 0.42 mmol) in dry DCM (5 mL) under a nitrogen atmosphere was added a 33% w/w solution of dimethylamine in EtOH (0.030 mL, 0.17 mmol). The solution was stirred for 17 hours. The mixture was diluted with DCM (5 mL) and washed with 1 M HCl (2×10 mL), a saturated aqueous solution of NaHCO$_3$ (10 mL), brine and concentrated in vacuo. The crude material was purified by silica gel chromatography (12 g SiO$_2$ cartridge, 0-100% EtOAc in petroleum benzine 40-60° C., then 0-20% MeOH in EtOAc) to give the title compound (0.015 g, 28%) as a white solid. $^1$H NMR (400 MHz, d$_6$-DMSO): some signals appear as a mixture of rotamers, denoted with an (*) δ 13.36* (br s, 0.7H), 12.67* (br s, 0.3H), 8.24* (s, 0.4H), 8.17* (d, J=8.8 Hz, 2.6H), 7.49 (d, J=7.2 Hz, 2H), 7.45-7.38 (m, 2H), 7.39-7.32 (m, 1H), 7.25* (s, 0.5H), 7.20* (d, J=8.5 Hz, 1.5H), 7.04* (d, J=4.5 Hz, 0.7H), 6.98* (s, 0.3H), 5.21 (s, 2H), 4.07 (s, 2H), 3.12 (s, 3H), 2.86 (s, 3H). LCMS-B: rt 3.10 min, m/z (positive ion) 387.2 [M+H]$^+$.

Example 95: Synthesis of tert-butyl 4-(2-(4-(benzylthio)phenyl)-3H-imidazo[4,5-b]pyridin-5-yl)piperazine-1-carboxylate (95)

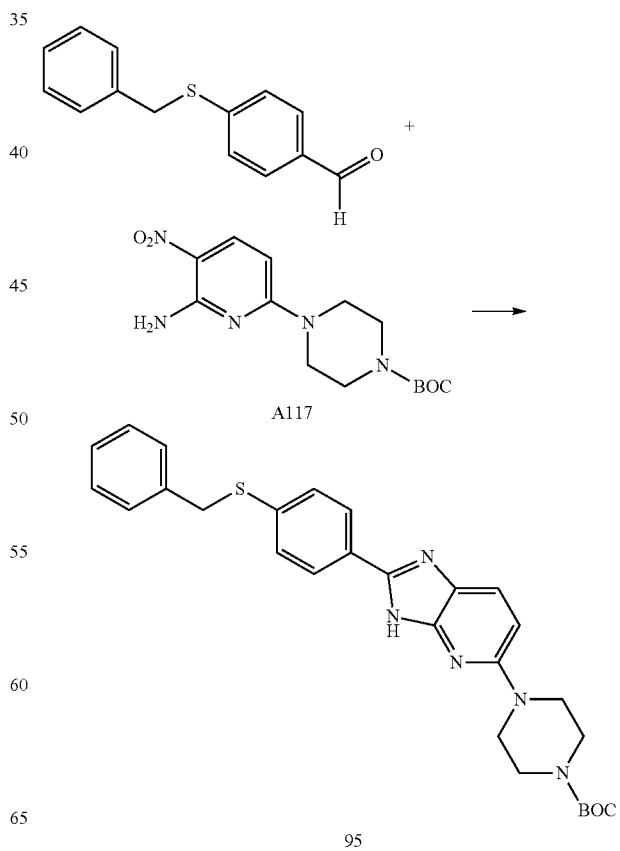

tert-Butyl 4-(2-(4-(benzylthio)phenyl)-3H-imidazo[4,5-b]pyridin-5-yl)piperazine-1-carboxylate (95)

A solution of sodium dithionite (85%, 0.23 g, 1.1 mmol), tert-butyl 4-(6-amino-5-nitropyridin-2-yl)piperazine-1-carboxylate A117 (0.12 g, 0.37 mmol) and benzyl 4-formylphenyl sulfide (0.093 g, 0.41 mmol) in EtOH (1.6 mL) and water (1.0 mL) was bubbled with nitrogen for 5 minutes and then heated under microwave irradiation at 70° C. for 16 hours and then at 110° C. for 1.3 hours. The reaction mixture was cooled to room temperature and treated with a 5 M ammonium hydroxide solution (2.0 mL) and stirred at ambient temperature for 1.5 hours. The suspension was filtered, washed with water (2×10 mL) and the solid dried in vacuo to give the title compound as a yellow solid (0.12 g, 65%). $^1$H NMR (300 MHz, d$_6$-DMSO) b 8.03 (d, J=8.58 Hz, 2H), 7.83 (d, J=8.80 Hz, 1H), 7.38-7.47 (m, 4H), 7.20-7.37 (m, 4H), 6.80 (d, J=9.02 Hz, 1H), 4.33 (s, 2H), 3.43-3.57 (m, 8H), 1.44 (s, 9H).

Example 96: Synthesis of 2-(4-(benzylthio)phenyl)-5-(piperazin-1-yl)-3H-imidazo[4,5-b]pyridine (96)

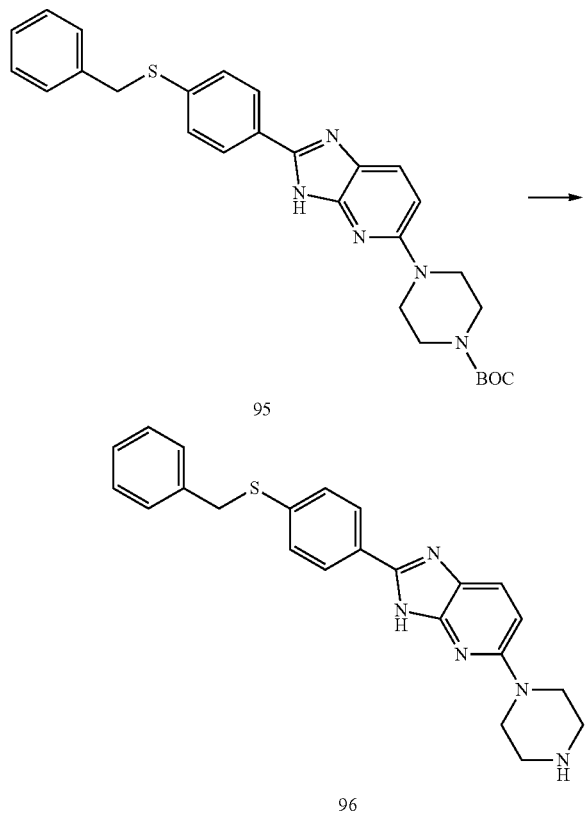

To a solution of tert-butyl 4-(2-(4-(benzylthio)phenyl)-3H-imidazo[4,5-b]pyridin-5-yl)piperazine-1-carboxylate 95 (0.0020 g, 0.040 mmol) in DCM (2 mL) was added TFA (0.5 mL). The mixture was stirred at ambient temperature for 2 hours before the volatiles were removed in vacuo. The residue was loaded onto an SCX cartridge (1 g). which was washed with MeOH (10 mL) and then with 2 M ammonia in MeOH (10 mL). The basic fractions were combined and the solvent was removed in vacuo to give the title compound as yellow oil (0.015 g, 93%). $^1$H NMR (300 MHz, CD$_3$OD) δ 7.91 (d, J=8.36 Hz, 2H), 7.76 (d, J=8.80 Hz, 1H), 7.18-7.45 (m, 7H), 6.80 (d, J=8.80 Hz, 1H), 4.23 (s, 2H), 3.53-3.63 (m, 4H), 2.95-3.02 (m, 4H).

Example 97: Synthesis of 2-(4-(benzyloxy)phenyl)-5-(1-(ethylsulfonyl)-1,2,3,6-tetrahydropyridin-4-yl)-3H-imidazo[4,5-b]pyridine (97)

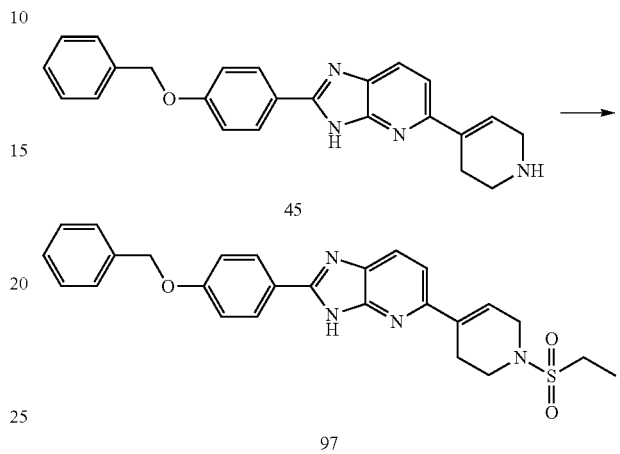

A suspension of 2-(4-(benzyloxy)phenyl)-5-(1,2,3,6-tetrahydropyridin-4-yl)-3H-imidazo[4,5-b]pyridine 45 (0.038 g, 0.10 mmol) in THF (1.5 mL) was cooled to 0° C. To this suspension was added DIPEA (0.017 mL, 0.10 mmol) and then, after 5 minutes, ethanesulfonyl chloride (0.010 mL, 0.10 mmol). The mixture was stirred at 0° C. for 6 hours and then overnight at room temperature. An additional portion of DIPEA (0.0085 mL, 0.050 mmol) was added, followed by ethanesulfonyl chloride (0.005 mL, 0.050 mmol) after 5 minutes. The reaction mixture was stirred at 0° C. for 6 hours and then at room temperature overnight. Water (1.5 mL) was added and the volatiles removed in vacuo. The resulting precipitate was filtered, washed with water (~20 mL) then air dried to give the crude material as an orange solid which was purified by silica gel chromatography (12 g SiO$_2$ cartridge, 0-100% EtOAc in petroleum benzine 40-60° C.) to give the title compound as an off-white solid (0.010 g, 21%). $^1$H NMR (400 MHz, d$_6$-DMSO) δ 13.43 (brs, 1H), 8.19-8.14 (m, 2H), 7.95 (s, 1H), 7.51-7.47 (m, 3H), 7.46-7.39 (m, 2H), 7.38-7.33 (m, 1H), 7.20 (d, J=8.4 Hz, 2H), 6.70 (s, 1H), 5.21 (s, 2H), 4.02-3.98 (m, 2H), 3.49 (t, J=5.6 Hz, 2H), 3.14 (q, J=7.4 Hz, 2H), 2.76 (d, J=1.6 Hz, 2H), 1.24 (t, J=7.2 Hz, 3H). LCMS-A: rt 5.81 min, m/z (positive ion) 475.2 [M+H]$^+$.

Example 98: Synthesis of 1-(4-(2-(4-(benzyloxy)phenyl)-3H-imidazo[4,5-b]pyridin-5-yl)-3,6-dihydropyridin-1 (2H)-yl)ethan-1-one (98)

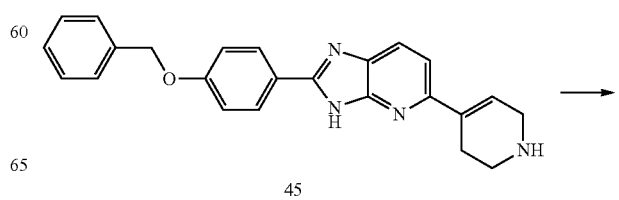

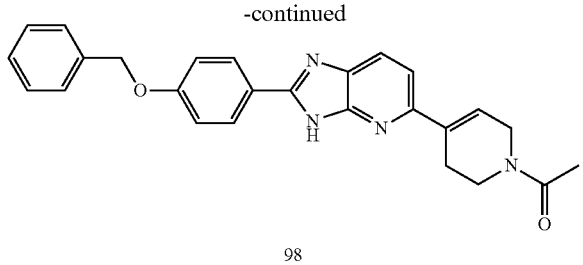

98

A suspension of 2-(4-(benzyloxy)phenyl)-5-(1,2,3,6-tetrahydropyridin-4-yl)-3H-imidazo[4,5-b]pyridine 45 (0.063 g, 0.13 mmol) in THF (3.5 mL) was cooled to 0° C. To this was added DIPEA (0.051 g, 0.39 mmol) and then, after 5 minutes, acetyl chloride (0.015 g, 0.20 mmol) was added. The reaction mixture was stirred at 0° C. for 2.75 hours. Water (3.5 mL) was added and the volatiles were removed in vacuo. The resulting precipitate was filtered, washed with water (~20 mL) and air dried to give the crude material as an orange solid which was purified by silica gel chromatography (12 g SiO$_2$ cartridge, 0-100% EtOAc in petroleum benzine 40-60° C., then 0-15% MeOH in EtOAc) to yield the title compound as a pale yellow solid (0.031 g, 56%). $^1$H NMR (400 MHz, d$_6$-DMSO): some signals appear as a mixture of rotamers, denoted with an (*) δ 13.34 (br s, 1H), 8.19-8.14 (m, 2H), 7.93 (d, J=8.0 Hz, 1H), 7.52-7.45 (m, 3H), 7.45-7.39 (m, 2H), 7.38-7.33 (m, 1H), 7.23-7.17 (m, 2H), 6.67 (s, 1H), 5.21 (s, 2H), 4.20 (dd, J=23.5, 3.2 Hz, 2H), 3.68 (dt, J=11.8, 5.6 Hz, 2H), 2.75 (s, 1H), 2.64 (s, 1H), 2.10 (s, 1.5H*), 2.06 (s, 1.5H*). LCMS-A: rt 5.40 min, m/z (positive ion) 425.2 [M+H]$^+$.

Example 99: Synthesis of 5-(1-methylpiperidin-3-yl)-2-(4-(phenoxymethyl)phenyl)-3H-imidazo[4,5-b]pyridine (99)

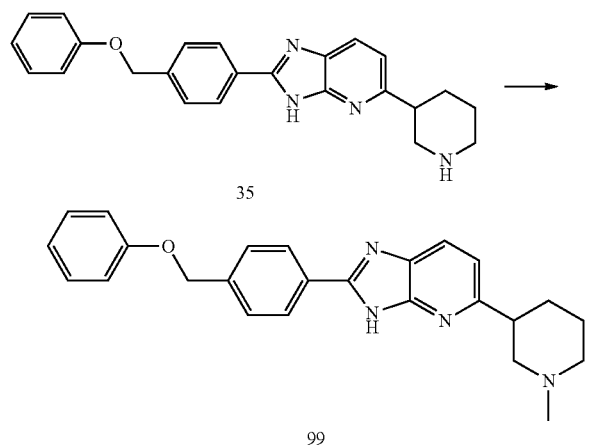

To a solution of 2-(4-(phenoxymethyl)phenyl)-5-(piperidin-3-yl)-3H-imidazo[4,5-b]pyridine 35 (0.030 g, 0.078 mmol) in anhydrous MeOH (6 mL) was added a 37% w/w aqueous solution of formaldehyde (0.019 mL, 0.23 mmol), followed by sodium triacetoxyborohydride (0.066 g, 0.31 mmol). The mixture was stirred at room temperature for 18 hours and the volatiles were removed in vacuo. The residue was diluted with EtOAc (30 mL) and a saturated aqueous solution of NaHCO$_3$ (30 mL). The aqueous layer was extracted with EtOAc (2×30 mL), then the combined organic layers were washed with brine (50 mL), dried (Na$_2$SO$_4$), then concentrated in vacuo to give the title compound as a pale brown oil (0.027 g, 87%). $^1$H NMR (400 MHz, d$_6$-DMSO) δ 13.50 (br s, 1H), 8.24-8.19 (m, 2H), 7.92 (d, J=7.5 Hz, 1H), 7.62 (d, J=8.0 Hz, 2H), 7.35-7.28 (m, 2H), 7.17 (d, J=8.2 Hz, 1H), 7.07-7.02 (m, 2H), 6.96 (tt, J=7.3, 1.0 Hz, 1H), 5.19 (s, 2H), 3.05-2.99 (m, 1H), 2.99-2.93 (m, 1H), 2.81 (d, J=11.0 Hz, 1H), 2.20 (s, 3H), 2.14-2.06 (m, 1H), 1.95-1.89 (m, 1H), 1.86 (dd, J=11.2, 2.8 Hz, 1H), 1.74 (dt, J=11.7, 3.1 Hz, 1H), 1.70-1.50 (m, 2H). LCMS-A: rt 4.76 min, m/z (positive ion) 399.2 [M+H]$^+$.

Example 100: Synthesis of 2-(4-(benzyloxy)phenyl)-6-(piperazin-1-yl)-3H-imidazo[4,5-b]pyridine (100)

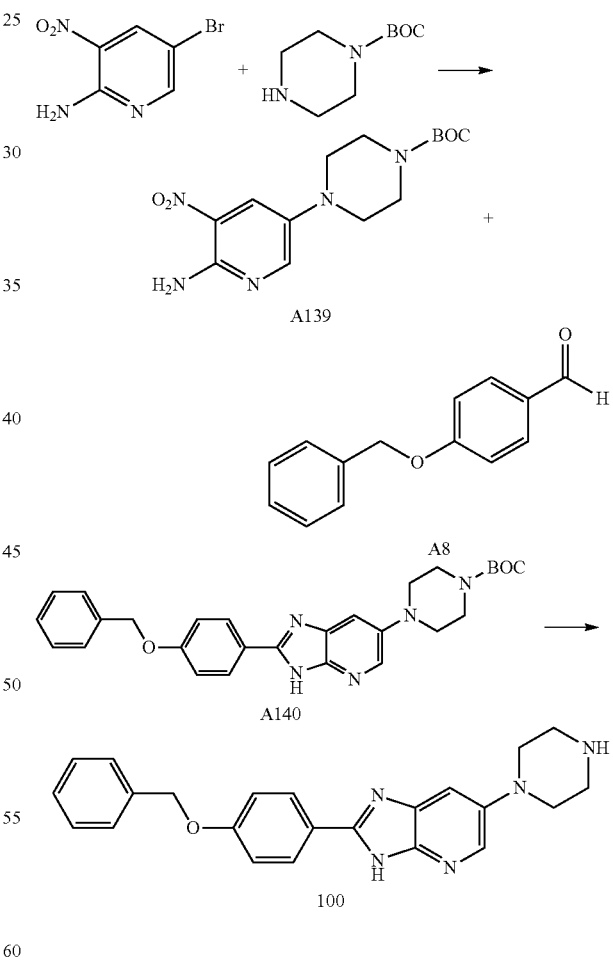

a) tert-Butyl 4-(6-amino-5-nitropyridin-3-yl)piperazine-1-carboxylate (A139)

5-Bromo-3-nitropyridin-2-amine (0.250 g, 1.15 mmol), 1-boc-piperazine (0.320 g, 1.72 mmol) and RuPhos palladacycle precatalyst (19 mg, 2 mol %) were loaded into a tube and flushed with nitrogen. A solution of LiHMDS (1 M in toluene, 3.0 mL, 3.0 mmol) was added and the mixture was stirred at room temperature under nitrogen. After 30 minutes, anhydrous THF (3 mL) was added and stirring was continued at room temperature under nitrogen. After 18 hours, the mixture was added to a saturated aqueous solution of ammonium chloride (10 mL), diluted with EtOAc (30 mL) and water (20 mL), and the resulting mixture was filtered. The aqueous phase was extracted with EtOAc (2×30 mL), the pooled organic phases were washed with brine (50 mL), dried over sodium sulfate and the volatiles removed under reduced pressure. The crude material was purified by column chromatography (24 g SiO$_2$ cartridge, 0-60% EtOAc in petroleum benzine 40-60° C.) to give the title compound as a red solid (40 mg, 11%). $^1$H NMR (400 MHz, CDCl$_3$) δ 8.25 (d, J=2.8 Hz, 1H), 7.92 (d, J=2.8 Hz, 1H), 6.46 (s, 2H), 3.63-3.57 (m, 4H), 3.06-2.99 (m, 4H), 1.48 (s, 9H). LCMS-A: rt 6.19 min, m/z (positive ion) 324.2 [M+H]$^+$.

b) tert-Butyl 4-(2-(4-(benzyloxy)phenyl)-3H-imidazo[4,5-b]pyridin-6-yl)piperazine-1-carboxylate (A140)

A mixture of tert-butyl 4-(6-amino-5-nitropyridin-3-yl)piperazine-1-carboxylate A139 (40 mg, 0.12 mmol), 4-(benzyloxy)benzaldehyde A8 (32 mg, 0.15 mmol), sodium dithionite (54 mg, 0.31 mmol), water (1 mL) and EtOH (1.5 mL) was irradiated in the microwave (110° C./20 minutes). The crude material was irradiated again in the microwave (110° C./20 minutes). The crude mixture was added to water (25 mL) and extracted with EtOAc (3×25 mL). The pooled organic phases were washed with brine (50 mL), dried over sodium sulfate and the volatiles evaporated in vacuo. The crude material was purified by column chromatography (4 g SiO$_2$ cartridge, 0-100% EtOAc in petroleum benzine 40-60° C.), giving to give a pale yellow solid. The crude solid was washed with diethyl ether (2×0.5 mL) and dried under vacuum to give the title compound as a pale yellow solid (8.9 mg, 15%). $^1$H NMR (400 MHz, d$_6$-DMSO) δ 8.17-8.08 (m, 3H), 7.53-7.38 (m, 5H), 7.38-7.31 (m, 1H), 7.18 (d, J=8.8 Hz, 2H), 5.20 (s, 2H), 3.53-3.49 (m, 4H), 3.14-3.07 (m, 4H), 1.43 (s, 9H), NH peak not observed. LCMS-A: rt 5.72 min, m/z (positive ion) 486.3 [M+H]$^+$; m/z (negative ion) 484.2 [M−H]$^−$.

c) 2-(4-(Benzyloxy)phenyl)-6-(piperazin-1-yl)-3H-imidazo[4,5-b]pyridine (100)

A mixture of tert-butyl 4-(2-(4-(benzyloxy)phenyl)-3H-imidazo[4,5-b]pyridin-6-yl)piperazine-1-carboxylate A140 (8.4 mg, 0.017 mmol), DCM (2 mL) and TFA (0.5 mL) were stirred at room temperature. After three hours, the mixture was diluted with 5% w/v aqueous solution of sodium hydroxide (25 mL) and extracted with EtOAc (3×25 mL). The pooled organic phases were washed with brine (50 mL), dried over sodium sulfate and concentrated in vacuo to give the title compound as an off-white solid (7 mg, >99%). $^1$H NMR (400 MHz, CD$_3$OD) δ 8.17 (d, J=2.5 Hz, 1H), 8.07-8.02 (m, 2H), 7.51 (d, J=2.5 Hz, 1H), 7.49-7.45 (m, 2H), 7.42-7.36 (m, 2H), 7.35-7.30 (m, 1H), 7.19-7.14 (m, 2H), 5.19 (s, 2H), 3.23-3.17 (m, 4H), 3.09-3.03 (m, 4H). LCMS-A: rt 4.55 min, m/z (positive ion) 386.2 [M+H]$^+$; m/z (negative ion) 384.2 [M−H]$^−$.

Example 101: Synthesis of 1-(2-(4-(benzyloxy)phenyl)-3H-imidazo[4,5-b]pyridin-5-yl)-4-methylpiperidin-4-ol (101)

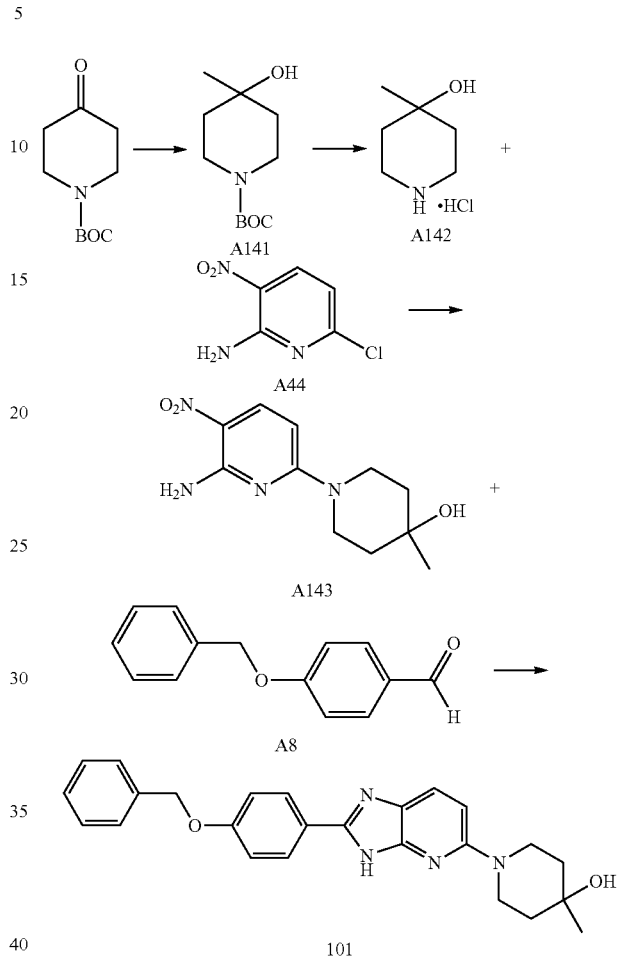

a) tert-Butyl 4-hydroxy-4-methylpiperidine-1-carboxylate (A141)

tert-Butyl 4-oxopiperidine-1-carboxylate (1.0 g, 5.0 mmol) was dissolved in anhydrous Et$_2$O (10 mL) and cooled to −10° C. under nitrogen. A solution of methylmagnesium bromide (3 M in Et$_2$O, 2.5 mL, 7.5 mmol) was added drop-wise and the mixture stirred for 5 minutes. The cooling bath was removed and the slurry was stirred at room temperature for 2 hours. The mixture was quenched with a saturated aqueous solution of ammonium chloride (10 mL) and then diluted with water (20 mL) and diethyl ether (20 mL). The aqueous phase was extracted with diethyl ether (2×30 mL), the pooled organic extracts were washed with brine (50 mL), dried over sodium sulfate and concentrated in vacuo to give the title compound as a colourless oil (1.05 g, 97%). $^1$H NMR (400 MHz, CDCl$_3$) δ 3.76-3.64 (m, 2H), 3.29-3.16 (m, 2H), 1.66 (s, 1H), 1.45 (s, 9H), 1.25 (s, 3H) 4H obscured by solvent.

b) 4-Methylpiperidin-4-ol hydrochloride (A142)

tert-Butyl 4-hydroxy-4-methylpiperidine-1-carboxylate A141 (1.05 g, 4.90 mmol), 1,4-dioxane (30 mL) and 4 M HCl in 1,4-dioxane (10 mL) were stirred together for 3 hours. The mixture was concentrated in vacuo, the solid residue suspended in diethyl ether (20 mL), the solvent decanted from the solid and the solid washed with diethyl ether (20 mL). The solid was dried under vacuum to give the title compound as a white solid (584 mg, 79%). $^1$H NMR (400 MHz, d$_6$-DMSO) δ 8.97 (br s, 1H), 8.85 (br s, 1H), 4.66 (br s, 1H), 3.08-2.93 (m, 4H), 1.74-1.53 (m, 4H), 1.15 (s, 3H). LCMS-A rt: 1.38 min, m/z (positive ion) 116.3 [M+H]$^+$.

c) 1-(6-Amino-5-nitropyridin-2-yl)-4-methylpiperidin-4-ol (A143)

6-Chloro-3-nitropyridin-2-amine A44 (174 mg, 1.00 mmol), 4-methylpiperidin-4-ol hydrochloride A142 (167 mg, 1.10 mmol), potassium carbonate (415 mg, 3.00 mmol) and DMF (5 mL) were heated to 100° C. for 3 hours. The mixture was returned to room temperature, diluted with water (30 mL) and cooled at 4° C. for 3 hours. The precipitate was collected by filtration to give the title compound as a yellow solid (152 mg, 60%). $^1$H NMR (400 MHz, CDCl$_3$) δ 8.16 (d, J=9.5 Hz, 1H), 6.11 (d, J=9.5 Hz, 1H), 4.15 (s, 2H), 3.53-3.35 (m, 2H), 1.70-1.60 (m, 4H), 1.58 (s, 3H), 1.21 (s, 1H), NH$_2$ protons not observed. LCMS-A: rt 5.29 min, m/z (positive ion) 253.2 [M+H]$^+$.

d) 1-(2-(4-(Benzyloxy)phenyl)-3H-imidazo[4,5-b]pyridin-5-yl)-4-methylpiperidin-4-ol (101)

1-(6-Amino-5-nitropyridin-2-yl)-4-methylpiperidin-4-ol A143 (150 mg, 0.60 mmol), 4-(benzyloxy)benzaldehyde A8 (151 mg, 0.714 mmol), sodium dithionite (259 mg, 1.50 mmol), water (2 mL) and EtOH (3 mL) were stirred in a sealed vessel at 70° C. After 18 hours, the mixture was cooled to room temperature, diluted with water (30 mL) and extracted with EtOAc (3×25 mL). The pooled organic phases were washed with brine (30 mL), dried over sodium sulfate and concentrated in vacuo. The crude material was purified by column chromatography (12 g SiO2 cartridge, 0-20% MeOH in DCM) to give the title compound as a yellow solid (25 mg, 10%). $^1$H NMR (400 MHz, d$_6$-DMSO) δ 12.83 (s, 1H), 8.05 (d, J=8.9 Hz, 2H), 7.73 (d, J=8.9 Hz, 1H), 7.53-7.32 (m, 5H), 7.12 (d, J=8.9 Hz, 2H), 6.75 (d, J=9.2 Hz, 1H), 5.18 (s, 2H), 4.33 (s, 1H), 3.87-3.72 (m, 2H), 1.57-1.45 (m, 4H), 1.15 (s, 3H), 2H obscured by solvent. LCMS-A: rt 4.97 min, m/z (positive ion) 415.2 [M+H]$^+$, m/z (negative ion) 413.2 [M−H]$^-$.

Example 102: Synthesis of 2-(phenoxymethyl)-4-(6-(piperidin-4-yl)-3H-imidazo[4,5-b]pyridin-2-yl)thiazole (102)

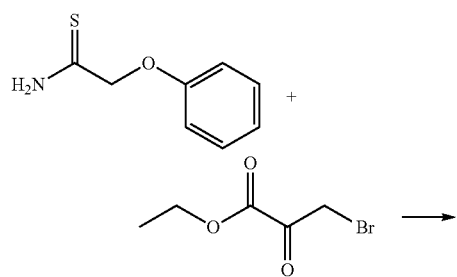

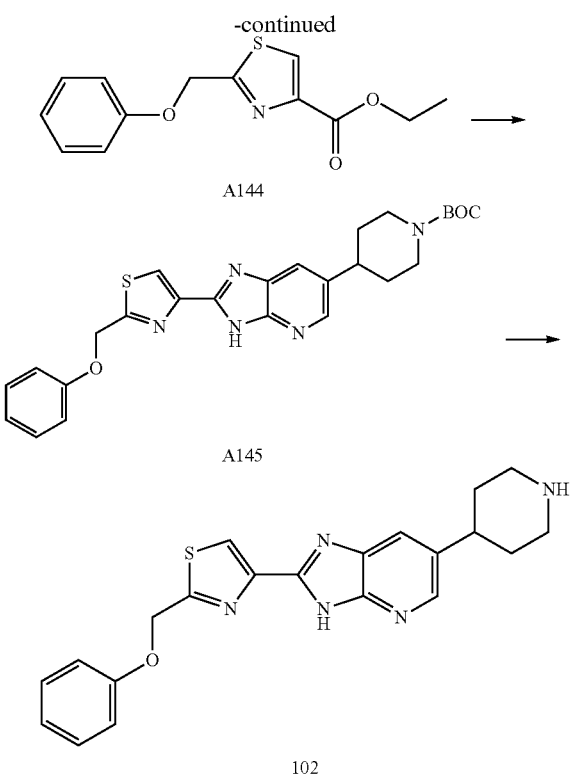

a) Ethyl 2-(phenoxymethyl)thiazole-4-carboxylate (A144)

2-Phenoxyethanethioamide (0.858 g, 5.13 mmol) and ethyl bromopyruvate (0.645 mL, 5.13 mmol) were dissolved in acetone (40 mL) and anhydrous magnesium sulfate (0.617 g, 5.13 mmol) was added. The reaction mixture was then heated at reflux for 18 hours. The mixture was cooled to room temperature and filtered through Celite and the filter cake was washed with EtOAc (5×20 mL). The combined organic washes were concentrated in vacuo to give the crude material as a brown gum which was purified by column chromatography (40 g SiO2 cartridge, 0-100% EtOAc in petroleum benzine 40-60° C.) to give the title compound as a pale yellow solid (631 mg, 47%). $^1$H NMR (400 MHz, CDCl$_3$) δ 8.20 (s, 1H), 7.34-7.28 (m, 2H), 7.04-6.96 (m, 3H), 5.41 (s, 2H), 4.44 (q, J=7.1 Hz, 2H), 1.42 (t, J=7.2 Hz, 3H). LCMS-A: rt 6.50 min, m/z (positive ion) 264.1 [M+H]$^+$.

b) 2-(Phenoxymethyl)thiazole-4-carbaldehyde (A145)

Ethyl 2-(phenoxymethyl)thiazole-4-carboxylate A144 (0.300 g, 1.14 mmol) was dissolved in DCM (10 mL) and cooled to −78° C. DIBAL-H (25 wt/% in toluene, 0.814 mL, 1.71 mmol) was added drop-wise and the mixture stirred under nitrogen at −78° C. for 3 hours. The mixture was quenched with a 10% w/v aqueous solution of citric acid (20 mL), the cooling bath was removed and the mixture stirred at room temperature for 20 minutes. The mixture was diluted with water (10 mL) and DCM (20 mL), filtered, and the filtrate aqueous phase extracted with DCM (2×20 mL). The pooled organic extracts were washed with brine (50 mL), dried over sodium sulfate and concentrated in vacuo. Purification by column chromatography (40 g SiO$_2$ cartridge, 0-10% EtOAc in DCM) resulted in 2-(phenoxymethyl)thiazole-4-carbaldehyde (125 mg, 0.570 mmol) this was combined with tert-butyl 4-(5,6-diaminopyridin-3-yl)piperidine-1-carboxylate A32 (183 mg, 0.627 mmol) and 3 Å molecular sieves (500 mg) and refluxed in MeOH (10 mL) under air. After 65 hours the mixture was cooled to room temperature and diluted with MeOH (20 mL). The mixture was filtered, the solids washed with MeOH (20 mL) and the combined filtrates concentrated in vacuo. The crude material was purified by column chromatography (12 g SiO$_2$ cartridge, 0-20% MeOH in DCM) and the fractions containing product were combined and the solvent removed in vacuo. The resulting residue was washed with diethyl ether. The organic washes and the crude solid were combined, then purified by column chromatography (12 g SiO$_2$ cartridge, 0-100% EtOAc in petroleum benzine 40-60° C.). The resulting material was slurried in diethyl ether (5 mL), the mixture diluted with petroleum benzine 40-60° C. (20 mL), the solvents were decanted and the solid dried under vacuum to give the title compound as an off-white solid (26 mg, 5%). The isolated material was used in the next step without further purification. LCMS-A: rt 3.36 min, m/z (positive ion) 492.2 [M+H]$^+$, m/z (negative ion) 490.2 [M−H]$^−$.

c) 2-(Phenoxymethyl)-4-(6-(piperidin-4-yl)-3H-imidazo[4,5-b]pyridin-2-yl)thiazole (102)

tert-Butyl 4-(2-(2-(phenoxymethyl)thiazol-4-yl)-2,3-dihydro-1H-imidazo[4,5-b]pyridin-6-yl)piperidine-1-carboxylate A145 (25 mg, 0.051 mmol), DCM (4 mL) and TFA (1 mL) were stirred at room temperature for 18 hours. The mixture was quenched with 5% w/v aqueous sodium hydroxide (25 mL) and the volatiles were removed in vacuo. The resulting solid was collected by filtration, washed with water (2×2 mL) and air dried to give the title compound as a white solid (10 mg, 53%). $^1$H NMR (400 MHz, d$_6$-DMSO) δ 8.49 (s, 1H), 8.27 (d, J=1.6 Hz, 1H), 7.73 (s, 1H), 7.39-7.32 (m, 2H), 7.15-7.10 (m, 2H), 7.05-6.99 (m, 1H), 5.55 (s, 2H), 3.05 (d, J=11.7 Hz, 2H), 2.81-2.71 (m, 1H), 2.66-2.57 (m, 2H), 1.75 (d, J=12.4 Hz, 2H), 1.59 (qd, J=12.2, 3.9 Hz, 2H), 2×NH protons not observed. LCMS-A: rt 4.52 min, m/z (positive ion) 392.2 [M+H]$^+$.

Example 103: Synthesis of 7-(2-(4-(benzyloxy)phenyl)-3H-imidazo[4,5-b]pyridin-5-yl)-3-methyl-5,6,7,8-tetrahydro-[1,2,4]triazolo[4,3-a]pyrazine (103)

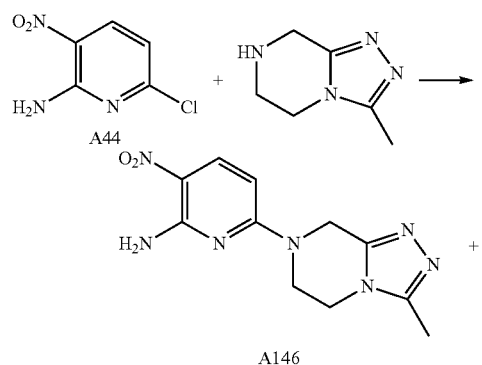

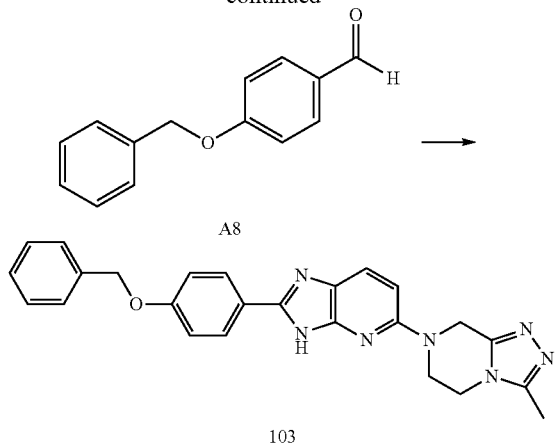

a) 6-(3-Methyl-5,6-dihydro-[1,2,4]triazolo[4,3-a]pyrazin-7(8H)-yl)-3-nitropyridin-2-amine (A146)

6-Chloro-3-nitropyridin-2-amine A44 (0.15 g, 0.86 mmol), 3-methyl-5,6,7,8-tetrahydro-[1,2,4]triazolo[4,3-a]pyrazine (125 mg, 0.907 mmol), DMF (2 mL) and DIPEA (0.301 mL, 1.73 mmol) were irradiated in the microwave at 100° C. for 30 minutes. The cooled mixture was added to water (40 mL), the precipitate collected by filtration, washed with water (2 mL) and air dried to give the title compound as a yellow solid (194 mg, 82%). $^1$H NMR (400 MHz, d$_6$-DMSO) δ 8.15 (d, J=9.5 Hz, 1H), 7.95 (br s, 2H), 6.52 (d, J=9.5 Hz, 1H), 5.05 (s, 2H), 4.15 (t, J=5.5 Hz, 2H), 4.00 (t, J=5.4 Hz, 2H), 2.30 (s, 3H). LCMS-B rt 2.73 min, m/z (positive ion) 276.1 [M+H]$^+$.

b) 7-(2-(4-(Benzyloxy)phenyl)-3H-imidazo[4,5-b]pyridin-5-yl)-3-methyl-5,6,7,8-tetrahydro-[1,2,4]triazolo[4,3-a]pyrazine (103)

6-(3-Methyl-5,6-dihydro-[1,2,4]triazolo[4,3-a]pyrazin-7(8H)-yl)-3-nitropyridin-2-amine A146 (0.100 g, 0.363 mmol), 4-(benzyloxy)benzaldehyde A8 (0.081 g, 0.38 mmol), sodium dithionite (0.190 g, 1.09 mmol), water (1 mL) and EtOH (1.6 mL) were stirred in a sealed vessel at 70° C. After 18 hours, the mixture was added to 5 M aqueous ammonia (10 mL), the precipitate collected by filtration and washed with 5 M aqueous ammonia (3 mL). Purification of the precipitate by column chromatography (Isolera Biotage, 4 g SiO$_2$ cartridge, 0-20% MeOH in DCM) gave the title compound as a yellow solid (48 mg, 30%). $^1$H NMR (400 MHz, d$_6$-DMSO) δ 12.96 (s, 1H), 8.07 (d, J=8.8 Hz, 2H), 7.83 (d, J=8.8 Hz, 1H), 7.48 (d, J=7.0 Hz, 2H), 7.44-7.38 (m, 2H), 7.38-7.31 (m, 1H), 7.15 (d, J=8.9 Hz, 2H), 6.98 (d, J=8.8 Hz, 1H), 5.19 (s, 2H), 4.87 (s, 2H), 4.10-3.97 (m, 4H), 2.30 (s, 3H). LCMS-B: rt 3.17 min, m/z (positive ion) 438.2 [M+H]$^+$.

Example 104: Synthesis of 2-(1-benzyl-1H-pyrazol-4-yl)-6-(piperidin-4-yl)-3H-imidazo[4,5-b]pyridine (104)

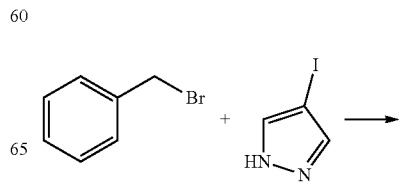

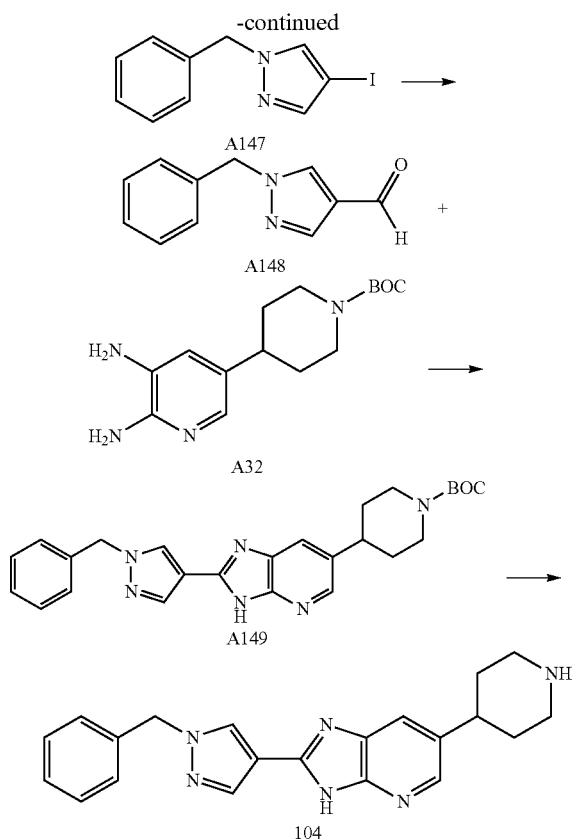

a) 1-Benzyl-4-iodo-1H-pyrazole (A147)

4-Iodo-1H-pyrazole (1.00 g, 5.16 mmol) in DMF (15 mL) was cooled to 0° C. before sodium hydride (60% w/w dispersion in mineral oil, 258 mg, 6.44 mmol) was added. After 15 minutes, benzyl bromide (0.674 mL, 6.44 mmol) was added and the mixture stirred at room temperature. After two hours, the mixture was added to water (200 mL), cooled at 4° C. for one hour then filtered. The collected solid was washed with cyclohexane (2×3 mL) and air dried to give the title compound as a white solid (0.859 g, 59%). $^1$H NMR (400 MHz, $CDCl_3$) δ 7.51 (s, 1H), 7.36 (s, 1H), 7.35-7.28 (m, 3H), 7.21-7.17 (m, 2H), 5.27 (s, 2H). LCMS-B: 3.48 min, m/z (positive ion) 285.1 [M+H]$^+$.

b) 1-Benzyl-1H-pyrazole-4-carbaldehyde (A148)

1-Benzyl-4-iodo-1H-pyrazole A147 (859 mg, 3.02 mmol) in THF (5 mL) was cooled to 0° C. under nitrogen before a 2.0 M solution of isopropylmagnesium chloride in THF (1.66 mL, 3.33 mmol) was added. After 1 hour, DMF (0.5 mL) was added. The mixture was stirred for 30 minutes at 0° C. then a further 30 minutes at room temperature. The mixture was quenched with a saturated aqueous solution of ammonium chloride (10 mL), diluted with water (20 mL) and extracted with $CHCl_3$ (3×25 mL). The pooled organics were washed with brine (50 mL), dried with sodium sulfate and concentrated in vacuo. The crude material was purified by column chromatography (12 g $SiO_2$ cartridge, 0-50% EtOAc in hexanes) to give the title compound as a colourless oil (170 mg, 30%). $^1$H NMR (400 MHz, $CDCl_3$) δ 9.83 (s, 1H), 8.00 (s, 1H), 7.88 (s, 1H), 7.42-7.33 (m, 3H), 7.29-7.25 (m, 2H), 5.33 (s, 2H). LCMS-B: rt 3.10 min, m/z (positive ion) 187.1 [M+H]$^+$.

c) tert-Butyl 4-(2-(1-benzyl-1H-pyrazol-4-yl)-3H-imidazo[4,5-b]pyridin-6-yl)piperidine-1-carboxylate (A149)

1-Benzyl-1H-pyrazole-4-carbaldehyde A148 (85.0 mg, 0.456 mmol), tert-butyl 4-(5,6-diaminopyridin-3-yl)piperidine-1-carboxylate A32 (133 mg, 0.456 mmol) and absolute EtOH (1.5 mL) were heated to 80° C. After 18 hours, the mixture was cooled and the solvent evaporated. THF (1 mL) and $PhI(OAc)_2$ (147 mg, 0.456 mmol) were added and the mixture stirred for three hours at room temperature. The mixture was added to water (30 mL) and extracted with EtOAc (3×30 mL). The pooled organic phases were washed with brine, dried over sodium sulfate and concentrated in vacuo. Purification by column chromatography (4 g $SiO_2$ cartridge, 0-100% EtOAc in hexanes, then 0-20% MeOH in EtOAc) gave the title compound as an orange-brown solid (71 mg, 34%). LCMS-B: rt 3.23 min, m/z (positive ion) 459.3 [M+H]$^+$.

d) 2-(1-Benzyl-1H-pyrazol-4-yl)-6-(piperidin-4-yl)-3H-imidazo[4,5-b]pyridine (104)

tert-Butyl 4-(2-(1-benzyl-1H-pyrazol-4-yl)-3H-imidazo [4,5-b]pyridin-6-yl)piperidine-1-carboxylate A149 (0.070 g, 0.15 mmol), DCM (10 mL) and TFA (1 mL) were combined and stood for 2.5 hours. The mixture was quenched with 10% w/v aqueous sodium hydroxide (20 mL) and the volatiles removed in vacuo. The residue was extracted with EtOAc (3×30 mL), the pooled organics were washed with brine (30 mL), dried over sodium sulfate and concentrated in vacuo to give the title compound as an off-white solid (40 mg, 73%). $^1$H NMR (400 MHz, $d_6$-DMSO) δ 8.48 (s, 1H), 8.14 (s, 1H), 8.13-8.12 (m, 1H), 7.69 (s, 1H), 7.41-7.29 (m, 5H), 5.44 (s, 2H), 3.09-3.01 (m, 2H), 2.77-2.68 (m, 1H), 2.66-2.58 (m, 2H), 1.77-1.70 (m, 2H), 1.60 (qd, J=12.3, 3.9 Hz, 2H), 2H not observed. LCMS-B: rt 2.75 min, m/z (positive ion) 359.3 [M+H]$^+$, m/z (negative ion) 357.2 [M−H]$^-$.

Intermediate A150: Synthesis of tert-butyl 2-(4-(benzyloxy)phenyl)-5-chloro-3H-imidazo[4,5-b]pyridine-3-carboxylate

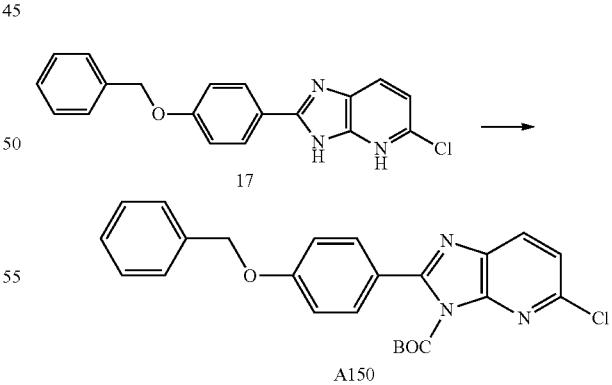

tert-butyl 2-(4-(benzyloxy)phenyl)-5-chloro-3H-imidazo[4,5-b]pyridine-3-carboxylate (A150)

To a solution of 2-(4-(benzyloxy)phenyl)-5-chloro-3H-imidazo[4,5-b]pyridine 17 (25.3 g, 75.2 mmol) in anhydrous THF (200 mL) was added di-tert-butyl dicarbonate (25.9 g, 113 mmol), DMAP (0.919 g, 7.52 mmol) and Et₃N (15.7 mL, 113 mmol) and the mixture was stirred at 65° C. for 2 hours. The mixture was cooled, concentrated in vacuo, and the resulting oily residue was partitioned between EtOAc (1 L) and a 1:1 mixture of water: saturated aqueous solution of NH₄Cl (1 L). The mixture was filtered and the biphasic filtrate mixture was separated. The organic layer was washed with an aqueous 0.5 M HCl solution (1 L), brine (1 L), dried (Na₂SO₄) and concentrated in vacuo to give the title compound (30.8 g, 94%). ¹H NMR (400 MHz, CDCl₃) δ 8.20 (d, J=8.4 Hz, 1H), 7.68-7.62 (m, 2H), 7.47-7.33 (m, 5H), 7.31 (d, J=8.5 Hz, 1H), 7.09-7.04 (m, 2H), 5.15 (s, 2H), 1.47 (s, 9H).

Examples 105-107

Suzuki on tert-butyl 2-(4-(benzyloxy)phenyl)-5-chloro-3H-imidazo[4,5-b]pyridine-3-carboxylate (A150)

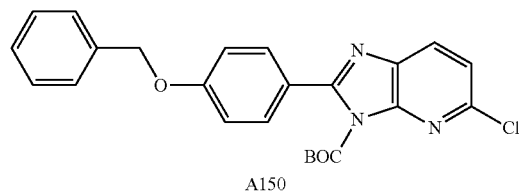

A150

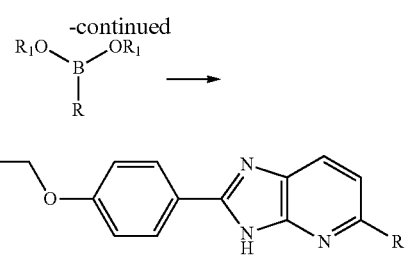

General Procedure G:

A suspension of tert-butyl 2-(4-(benzyloxy)phenyl)-5-chloro-3H-imidazo[4,5-b]pyridine-3-carboxylate A150 (0.100 g, 0.229 mmol), a boronic acid or boronic pinacol ester (0.41 mmol), XPhos (22 mg, 0.046 mmol) and K₃PO₄ (61 mg, 0.29 mmol, 1.25 equiv) in DME (3.0 mL) was sonicated for 10 minutes before Pd₂(dba)₃ (21 mg, 0.023 mmol) was added. The reaction mixture was irradiated in the microwave at 110° C. for 20 minutes, then loaded onto silica gel and separated by column chromatography (24 g SiO₂ cartridge, 0-100% EtOAc in petroleum benzine 40-60° C.). The resulting residue was dissolved in DCM (5 mL), TFA (0.5 mL) was added and the mixture stirred at room temperature for 3 hours. The volatiles were removed under reduced pressure and the residue was loaded onto an SCX cartridge (1 g). The cartridge was washed with MeOH (15 mL) and the product was eluted with 0.5 M NH₃ in 1,4-dioxane (15 mL). The fractions containing product were combined and the volatiles removed in vacuo to yield the desired product.

TABLE E

| Example | Product Name and Structure | LCMS data | Method |
|---|---|---|---|
| 105 | 5-(2-(4-(Benzyloxy)phenyl)-5-cyclopropyl-3H-imidazo[4,5-b]pyridine | LCMS-A: rt 3.46 min, m/z (positive ion) 342.2 [M + H]⁺. | G From cyclopropyl-boronic acid |
| 106 | 2-(4-(Benzyloxy)phenyl)-5-(pyrimidin-5-yl)-3H-imidazo[4,5-b]pyridine | LCMS-A: rt 3.57 min, m/z (positive ion) 380.2 [M + H]⁺. | G From methyl-1H-pyrazole boronic acid pinicol ester |
| 107 | 2-(4-(Benzyloxy)phenyl)-5-(1-methyl-1H-pyrazol-4-yl)-3H-imidazo[4,5-b]pyridine | LCMS-A: rt 3.51 min, m/z (positive ion) 382.2 [M + H]⁺. | G From pyrimidine-5-boronic acid |

PRMT5 Biochemical Assay

Compounds of the invention may be tested for in vitro activity in the following assay: A histone H4 derived peptide is used as substrate (amino acid sequence: Ser-Gly-Arg-Gly-Lys-Gly-Gly-Lys-Gly-Leu-Gly-Lys-Gly-Gly-Ala-Lys-Arg-His-Arg-Lys-Val-N H$_2$). Full-length PRMT5 enzyme (NCBI Reference sequence NP_006100.2) was co-expressed with His$_6$-MEP50 in insect cells and purified via Nickel immobilized metal affinity and gel filtration chromatography ("the enzyme").

The 6 μL assay reactions are run in Greiner brand black 384-well low volume plates. All reactions contained assay buffer (phosphate buffered saline, 0.01% (v/v) Tween-20, 0.01% (w/v) albumin from chicken egg white, 1 mM dithiothreitol, 200 nM peptide substrate, 1 μM S-Adenosyl methionine, and 15 ng/reaction enzyme, with the enzyme being omitted from negative control reactions. Compounds were added in a volume of 100 nL from dilution series prepared in DMSO, positive and negative control reactions receiving the same volume DMSO without compound. The plates were sealed with adhesive seals and incubated for 4 hours at 37° C. Reaction progress was measured using the Transcreener™ EPIGEN methyltransferase assay (Bell-Brook Labs, Madison, Wis.) as recommended by the manufacturer. To each reaction 2 μL detection mix were added, containing coupling enzymes, fluorescence polarisation tracer, and AMP antibody. Plates were incubated for 90 minutes before being read on a PerkinElmer EnVision™ plate reader in fluorescence polarisation mode. IC$_{50}$ values were obtained from the raw readings by calculating percent inhibition (%1) for each reaction relative to controls on the same plate (% I=(I−CN)/(CP−CN) where CN/CP are the averages of the negative/positive reactions, respectively), then fitting the % I data vs. compound concentration [I] to % I=(A+((B−A)/(1+((C/[I])^D)))) where A is the lower asymptote, B is the upper asymptote, C is the IC$_{50}$ value, and D is the slope.

Results

| Example | IC$_{50}$ (uM) |
| --- | --- |
| 1 | 1.494 |
| 2 | 2.218 |
| 3 | 3.971 |
| 4 | 0.182 |
| 5 | 0.633 |
| 6 | 1.318 |
| 7 | 0.890 |
| 8 | 0.767 |
| 9 | 0.431 |
| 10 | 0.375 |
| 11 | 0.482 |
| 12 | 0.122 |
| 13 | 0.339 |
| 14 | 1.008 |
| 15 | 1.719 |
| 16 | 0.107 |
| 17 | 4.093 |
| 18 | 0.914 |
| 19 | 1.688 |
| 20 | 0.847 |
| 21 | 0.774 |
| 22 | 0.487 |
| 23 | 0.497 |
| 24 | 0.570 |
| 25 | 0.619 |
| 26 | 0.132 |
| 27 | 0.148 |
| 28 | 1.679 |
| 29 | 0.970 |
| 30 | 2.664 |
| 31 | 1.237 |
| 32 | 0.827 |
| 33 | 0.609 |
| 34 | 1.048 |
| 35 | 0.204 |
| 36 | 0.700 |
| 37 | 0.592 |
| 38 | 2.391 |
| 39 | 0.726 |
| 40 | 0.223 |
| 41 | 1.483 |
| 42 | 0.710 |
| 43 | 0.335 |
| 44 | 2.667 |
| 45 | 0.083 |
| 46 | 0.703 |
| 47 | 0.197 |
| 48 | 0.450 |
| 49 | 2.625 |
| 50 | 0.317 |
| 51 | 0.547 |
| 52 | 0.935 |
| 53 | 0.581 |
| 54 | 0.583 |
| 55 | 0.426 |
| 56 | 1.864 |
| 57 | 0.981 |
| 58 | 0.333 |
| 59 | 0.535 |
| 60 | 1.661 |
| 61 | 2.869 |
| 62 | 0.331 |
| 63 | 0.215 |
| 64 | 0.336 |
| 65 | 0.276 |
| 66 | 0.608 |
| 67 | 3.722 |
| 68 | 1.285 |
| 69 | 0.447 |
| 70 | 1.110 |
| 71 | 0.542 |
| 72 | 17.102 |
| 73 | 2.006 |
| 74 | 1.365 |
| 75 | 0.306 |
| 76 | 2.101 |
| 77 | 0.901 |
| 78 | 0.633 |
| 79 | 0.680 |
| 80 | 0.687 |
| 81 | 2.654 |
| 82 | 2.390 |
| 83 | 1.111 |
| 84 | 0.866 |
| 85 | 0.151 |
| 86 | 0.151 |
| 87 | 0.355 |
| 88 | 0.477 |
| 89 | 1.345 |
| 90 | 0.148 |
| 91 | 0.820 |
| 92 | 0.279 |
| 93 | 2.136 |
| 94 | 1.020 |
| 95 | 2.820 |
| 96 | 0.585 |
| 97 | 0.217 |
| 98 | 0.166 |
| 99 | 0.148 |
| 100 | 0.327 |
| 101 | 0.224 |
| 102 | 1.109 |

-continued

| Example | IC₅₀ (uM) |
|---------|-----------|
| 103 | 0.560 |
| 104 | 2.646 |
| 105 | 1.499 |
| 106 | 8.999 |
| 107 | 1.672 |

PRMT5 Biomarker Assay

Compounds of the invention may be tested for potency to inhibit the histone H4 Arginine 3 dimethylation mark in the following assay:

The cell line TE11 was seeded at a density of 12,000 cells per well in 96 well tissue culture plates in DME medium and 10% foetal bovine serum, and allowed to adhere overnight under standard culture conditions (37° C., 5% $CO_2$). Compound dilutions prepared in DMSO were added to the medium, with negative control wells reserved for treatment with DMSO only and positive controls receiving a potent PRMT5 inhibitor. The concentration of the inhibitor had been previously determined to give maximum inhibition of the methylation. After incubation for 72 hours, cells were washed twice in ice-cold PBS, lysed in lysis buffer (20 mM Tris pH 7.4, 135 mM NaCl, 1.5 mM $MgCl_2$, 1 mM EGTA, 10% glycerol and 1% Triton-X100), centrifuged at 15,000×g and the supernatants collected for subsequent analysis. The methylation level was determined using the EpiQuik™ Global Di-Methyl Histone H4R3 Quantification ELISA Kit (Epigentek, Farmingdale, N.Y.) as per the manufacturer's recommendations; in parallel the total protein amount in the lysate was quantified using a Lowry protein assay. The methylation level was corrected for the total protein amount of each sample, normalised to the controls, and the data fitted against a four-parameter logistic model to determine the 50% inhibitory concentration ($IC_{50}$).

Results

| Example | IC₅₀ (uM) |
|---------|-----------|
| 4 | 0.127 |
| 9 | 0.645 |
| 16 | 1.826 |
| 40 | 0.731 |
| 45 | 1.212 |

REFERENCES

| | |
|---|---|
| Aggarwal et al., 2010 | Aggarwal et al., Cancer Cell 18, 329-340 (2010) DOI 10.1016/j.ccr.2010.08.012 |
| Berger, 2008 | Berger, Nat. Cell Biol., 10, 1389-1390 (2008) DOI: 10.1038/ncb1 208-1389 |
| Chen et al., 2009 | Chen et al., Proc. Natl. Acad. Sci USA, 106, 13433-13438 (2009) DOI: 10.1073/pnas.0906455106 |
| Cho et al., 2012 | Cho et al., EMBO J., 31(7), 1785-1797 (2012) DOI: 10.1038/emboj.2012.17 |
| Durant et al., 2009 | Durant et al., Cell Cycle, 8, 801-802 (2009) |
| Gu et al., 2012 | Gu et al., Biochem J., 446(2), 235-241 (2012) DOI: 10.1042/BJ20120768 |
| He Y, 2013 | He et al., J Transl Med, 11, 14 (2013) |
| Jansson et al., 2008 | Jansson et al., Nature Cell Biology, 10(12), 1431-1439 (2008) DOI: 10.1038/ncb1802 |
| Kanduri et al., 2010 | Kanduri et al., Blood, 115, 296-305 (2010) DOI: 10.1182/blood-2009-07-232868 |
| Kim et al., 2005 | Kim et al., Clin Cancer Res, 11, 473-482 (2005) |
| Krause et al., 2007 | Krause et al., Pharmacol. Ther., 113, 50-87 (2007) |
| Le Guezennec et al., 2006 | Le Guezennec et al., Mol. Cell Biol., 26, 843-851 (2006) |
| Nicholas et al., 2012 | Nicholas et al., Cancer Res, 72(8), S1 (2012) DOI: 10.1158/1538-7445.AM2012-LB-254 |
| Pal et al., 2003 | Pal et al., Mol. Cell Biol., 23, 7475-7487 (2003) |
| Pal et al., 2007 | Pal et al., EMBO J, 26, 3558-3569 (2007) |
| Pollack et al., 1999 | Pollack et al., J. Biol., Chem., 274, 31531-31542 (1999) |
| Powers et al., 2011 | Powers et al., Cancer Res, 71, 5579-5588 (2011) DOI: 10.1158/0008-5472.CAN-11-0458 |
| Rank et al., 2010 | Rank et al., Blood, 116(9), 1585-1592 (2010) DOI: 10.1182/blood-2009-10-251116 |
| Scoumanne et al., 2009 | Scoumanne et al., Nucleic Acids Res., 37, 4965-4976 (2009) DOI: 10.1093/nar/gkp516 |
| Wang et al., 2008 | Wang et al., Mol. Cell Biol., 28, 626-6277 (2008) |
| Zhongping et al., 2012 | Zhongping et al., PLoS ONE 7(8): e440332012 (2012) DOI: 10.1371/journal.pone.0044033 |

The invention claimed is:
1. A compound of formula I:

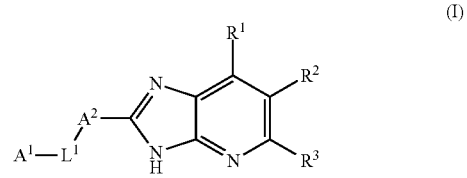

(I)

wherein:
$A^2$ is selected from:

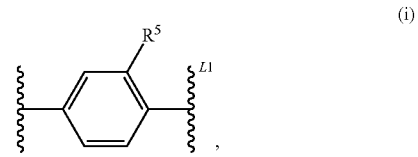

(i)

where $R^5$ is selected from H, Br, F, methyl, OMe, carboxy, $C_{1-4}$ alkyl ester, carboxamide, $C_{5-7}$ N-containing heteroaryl group, which is optionally substituted by a $C_{1-4}$ alkyl group;
(ii) a $C_5$ heteroarylene group, containing 2 or 3 ring heteroatoms, where the bonds to L1 and the core are β to one another;
$L^1$ is selected from:
 (i) $^{A1}$—O—$CH_2$—$^{A2}$;
 (ii) $^{A1}$—$CH_2$—O—$^{A2}$;
 (iii) $^{A1}$—C(=O)—NH—$^{A2}$;
 (iv) $^{A1}$—$CH_2$—S—$^{A2}$;
 (v) $^{A1}$—$CH_2$—$^{A2}$; and
 (vi) $^{A1}$—CH($CH_3$)—O—$^{A2}$;
$A^1$ is phenyl, optionally substituted by F or $CF_3$;
(a) one of $R^2$ and $R^3$ is $L^2$-$A^3$, where $L^2$ is selected from the group consisting of: a single bond, $CH_2$, O, NH, NMe, NH—$CH_2$, and NMe-$CH_2$; and $A^3$ is selected from:
 (i) a $C_{5-10}$ non-aromatic N-containing heterocyclic group, which is optionally substituted by one or two groups selected from OH, $NH_2$, $CH_2N(R^6)_2$, $C_{1-4}$ alkyl, $C_{1-4}$ alkylacyl, $C_{1-4}$ alkyl ester, oxo and $C_{1-4}$ alkyl sulfonyl, where each $R^6$ is independently selected from H, $C_{1-4}$ alkyl, $C_{1-4}$ alkylacyl and $C_{1-4}$ alkyl ester; and
    (ii) a $C_{5-7}$ non-aromatic, non-N-containing heterocyclic group;
(b) $R^1$ is selected from:
    (i) H;
    (ii) Halo;
(c) the other one of $R^2$ and $R^3$ is H.

2. A compound according to claim 1, wherein $L^1$ is selected from:
    (i) $^{A1}$—O—CH$_2$—$^{A2}$;
    (ii) $^{A1}$—CH$_2$—O—$^{A2}$; and
    (iii) $^{A1}$—C(=O)—NH—$^{A2}$.

3. A compound according to claim 1, wherein $L^1$ is selected from:
    (vi) $A^1$-S—CH$_2$-$A^2$;
    (vii) $A^1$-CH$_2$-$A^2$; and
    (viii) $A^1$-CH(CH$_3$)—O-$A^2$.

4. A compound according to claim 1, wherein $A^1$ is unsubstituted phenyl.

5. A compound according to claim 1, wherein $A^2$ is:

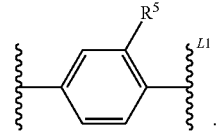

6. A compound according to claim 5, wherein $R^5$ is H.

7. A compound according to claim 1, wherein $L^2$ is selected from the group consisting of: a single bond, O, NH, NH—CH$_2$, and NMe-CH$_2$.

8. A compound according to claim 7, wherein $L^2$ is selected from the group consisting of: a single bond, O and NH.

9. A compound according to claim 8, wherein $L^2$ is a single bond.

10. A compound according to claim 7, wherein $A^3$ is a non-aromatic $C_{5-10}$ N-containing heterocyclic group, which is optionally substituted by one or two groups selected from OH, NH$_2$, CH$_2$NH$_2$, $C_{1-4}$ alkyl, $C_{1-4}$ alkylacyl, $C_{1-4}$ alkyl ester, oxo and $C_{1-4}$ alkyl sulfonyl.

11. A compound according to claim 10, wherein the $C_{5-7}$ N-containing heterocyclic group is selected from piperidinyl, tetrahydropyridinyl, morpholino, thiomorpholino (including oxidized forms thereof) and piperazinyl.

12. A compound according to claim 1, wherein $R^3$ is $L^2$-$A^3$, where $A^3$ is piperidinyl or piperazinyl, and $L^2$ is selected from a single bond, —O—, —NH—, —NMe-, —CH$_2$— and —NH—CH$_2$—.

13. A compound according to claim 1 which is selected from the group consisting of:
2-(4-(phenoxymethyl)phenyl)-6-(piperidin-4-yl)-3H-imidazo[4,5-b]pyridine (9);
1-(4-(2-(4-(phenoxymethyl)phenyl)-3H-imidazo[4,5-b]pyridin-6-yl)piperidin-1-yl)ethanone (10);
6-(1-methylpiperidin-4-yl)-2-(4-(phenoxymethyl)phenyl)-3H-imidazo[4,5-b]pyridine (11);
2-(4-(benzyloxy)phenyl)-6-(piperidin-4-yl)-3H-imidazo[4,5-b]pyridine (12);
1-(4-(2-(4-(Benzyloxy)phenyl)-3H-imidazo[4,5-b]pyridin-6-yl)piperidin-1-yl)ethanone (13);
6-(piperidin-4-yl)-2-(4-((4-(trifluoromethyl)benzyl)oxy)phenyl)-3H-imidazo[4,5-b]pyridine (14);
tert-butyl 3-(2-(4-(phenoxymethyl)phenyl)-3H-imidazo[4,5-b]pyridine-6-yl)piperidine-1-carboxylate (15);
2-(4-(phenoxymethyl)phenyl)-6-(piperidin-3-yl)-3H-imidazo[4,5-b]pyridine (16);
2-(4-(benzyloxy)phenyl)-5-(piperidin-4-yloxy)-3H-imidazo[4,5-b]pyridine (18);
4-(2-(4-(benzyloxy)phenyl)-3H-imidazo[4,5-b]pyridin-5-yl)morpholine (19);
1-(2-(4-(benzyloxy)phenyl)-3H-imidazo[4,5-b]pyridin-5-yl)piperazin-2-one (21);
4-(2-(4-(benzyloxy)phenyl)-3H-imidazo[4,5-b]pyridin-5-yl)thiomorpholine (23);
4-(2-(4-(benzyloxy)phenyl)-3H-imidazo[4,5-b]pyridin-5-yl)thiomorpholine 1-oxide (24);
4-(2-(4-(benzyloxy)phenyl)-3H-imidazo[4,5-b]pyridin-5-yl)thiomorpholine 1,1-dioxide (25);
2-(4-(benzyloxy)phenyl)-5-(4-methylpiperazin-1-yl)-3H-imidazo[4,5-b]pyridine (26);
2-(4-(benzyloxy)phenyl)-5-(4-(ethylsulfonyl)piperazin-1-yl)-3H-imidazo[4,5-b]pyridine (27);
tert-butyl ((1-(2-(4-(benzyloxy)phenyl)-3H-imidazo[4,5-b]pyridin-5-yl)piperidin-3-yl)methyl)carbamate (28);
tert-butyl 2-(((2-(4-(benzyloxy)phenyl)-3H-imidazo[4,5-b]pyridin-5-yl)amino)methyl)piperidine-1-carboxylate (29);
tert-butyl 3-((2-(4-(benzyloxy)phenyl)-3H-imidazo[4,5-b]pyridin-5-yl)(methyl)amino)piperidine-1-carboxylate (30);
tert-butyl 4-(((2-(4-(benzyloxy)phenyl)-3H-imidazo[4,5-b]pyridin-5-yl)amino)methyl)piperidine-1-carboxylate (31);
tert-butyl 4-((2-(4-(benzyloxy)phenyl)-3H-imidazo[4,5-b]pyridin-5-yl)amino)piperidine-1-carboxylate (32);
4-(2-(4-(benzyloxy)phenyl)-3H-imidazo[4,5-b]pyridin-5-yl)piperazin-2-one (33);
tert-butyl 3-(2-(4-(phenoxymethyl)phenyl)-3H-imidazo[4,5-b]pyridin-5-yl)piperidine-1-carboxylate (34);
2-(4-(phenoxymethyl)phenyl)-5-(piperidin-3-yl)-3H-imidazo[4,5-b]pyridine (35);
tert-butyl 4-(2-(4-(benzyloxy)phenyl)-3H-imidazo[4,5-b]pyridin-5-yl)piperidine-1-carboxylate (39);
2-(4-(benzyloxy)phenyl)-5-(piperidin-4-yl)-3H-imidazo[4,5-b]pyridine (40);
7-chloro-2-(4-(phenoxymethyl)phenyl)-5-(piperidin-4-yl)-1H-imidazo[4,5-b]pyridine (42);
2-(4-(benzyloxy)phenyl)-5-(1,2,3,6-tetrahydropyridin-4-yl)-3H-imidazo[4,5-b]pyridine (45);
(R)-2-amino-1-(4-(2-(4-(benzyloxy)phenyl)-3H-imidazo[4,5-b]pyridin-5-yl)piperidin-1-yl)propan-1-one (46);
2-(4-(benzyloxy)phenyl)-5-(piperazin-1-yl)-3H-imidazo[4,5-b]pyridine (47);
(1-(2-(4-(benzyloxy)phenyl)-3H-imidazo[4,5-b]pyridin-5-yl)piperidin-3-yl)methanamine (50);
2-(4-(benzyloxy)phenyl)-N-(piperidin-2-ylmethyl)-3H-imidazo[4,5-b]pyridin-5-amine (51);
2-(4-(benzyloxy)phenyl)-N-(piperidin-4-ylmethyl)-3H-imidazo[4,5-b]pyridin-5-amine (52);
2-(4-(benzyloxy)phenyl)-N-(piperidin-4-yl)-3H-imidazo[4,5-b]pyridin-5-amine (53);
1-(2-(4-(benzyloxy)phenyl)-3H-imidazo[4,5-b]pyridin-5-yl)piperidin-4-amine (54);
(1-(2-(4-(benzyloxy)phenyl)-3H-imidazo[4,5-b]pyridin-5-yl)piperidin-4-yl)methanamine (55);
5-(piperazin-1-yl)-2-(4-((4-(trifluoromethyl)benzyl)oxy)phenyl)-3H-imidazo[4,5-b]pyridine (56);

2-(4-((2-fluorobenzyl)oxy)phenyl)-5-(piperazin-1-yl)-3H-imidazo[4,5-b]pyridine (57);
2-(4-((3-fluorobenzyl)oxy)phenyl)-5-(piperazin-1-yl)-3H-imidazo[4,5-b]pyridine (58);
2-(4-((4-fluorobenzyl)oxy)phenyl)-5-(piperazin-1-yl)-3H-imidazo[4,5-b]pyridine (59);
5-(piperazin-1-yl)-2-(4-((2-(trifluoromethyl)benzyl)oxy)phenyl)-3H-imidazo[4,5-b]pyridine (60);
2-(4-(1-phenylethoxy)phenyl)-5-(piperazin-1-yl)-3H-imidazo[4,5-b]pyridine (61);
2-(4-(benzyloxy)-3-bromophenyl)-6-(piperidin-4-yl)-3H-imidazo[4,5-b]pyridine (62);
2-(4-(benzyloxy)-3-(1-methyl-1H-pyrazol-4-yl)phenyl)-6-(piperidin-4-yl)-3H-imidazo[4,5-b]pyridine (63);
2-(4-(benzyloxy)-3-(pyridin-3-yl)phenyl)-6-(piperidin-4-yl)-3H-imidazo[4,5-b]pyridine (64);
2-(4-(benzyloxy)-3-fluorophenyl)-6-(piperidin-4-yl)-3H-imidazo[4,5-b]pyridine (65));
methyl 2-(benzyloxy)-5-(6-(piperidin-4-yl)-3H-imidazo[4,5-b]pyridin-2-yl)benzoate dihydrogen chloride salt (66);
2-(benzyloxy)-5-(6-(piperidin-4-yl)-3H-imidazo[4,5-b]pyridin-2-yl)benzoic acid dihydrochloride salt (67);
2-(benzyloxy)-5-(6-(piperidin-4-yl)-3H-imidazo[4,5-b]pyridin-2-yl)benzamide dihydrogen chloride salt (68);
2-(4-(benzyloxy)-3-(1-methyl-1H-pyrazol-4-yl)phenyl)-5-(4-(ethylsulfonyl)piperazin-1-yl)-3H-imidazo[4,5-b]pyridine (69);
2-(4-(Benzyloxy)-3-(1H-pyrazol-5-yl)phenyl)-5-(4-(ethylsulfonyl)piperazin-1-yl)-3H-imidazo[4,5-b]pyridine (70);
2-(4-(Benzyloxy)-3-(pyridin-3-yl)phenyl)-5-(4-(ethylsulfonyl)piperazin-1-yl)-3H-imidazo[4,5-b]pyridine (71);
2-(4-(Benzyloxy)-3-(pyrimidin-5-yl)phenyl)-5-(4-(ethylsulfonyl)piperazin-1-yl)-3H-imidazo[4,5-b]pyridine (72);
2-(4-(benzyloxy)-3-(1H-pyrazol-4-yl)phenyl)-5-(4-(ethylsulfonyl)piperazin-1-yl)-3H-imidazo[4,5-b]pyridine (73);
2-(4-(benzyloxy)-3-methylphenyl)-5-(4-(ethylsulfonyl)piperazin-1-yl)-3H-imidazo[4,5-b]pyridine (74);
2-(4-(benzyloxy)-3-methoxyphenyl)-5-(4-(ethylsulfonyl)piperazin-1-yl)-3H-imidazo[4, 5-b]pyridine (75);
2-(4-(benzyloxy)phenyl)-5-(piperazin-1-ylmethyl)-3H-imidazo[4,5-b]pyridine (79);
2-(4-(benzyloxy)phenyl)-6-(1-(methylsulfonyl)piperidin-4-yl)-3H-imidazo[4,5-b]pyridine (83); or
tert-butyl 4-(2-(4-(phenoxymethyl)phenyl)-3H-imidazo[4,5-b]pyridin-5-yl)piperidine-1-carboxylate (84);
2-(4-(phenoxymethyl)phenyl)-5-(piperidin-4-yl)-3H-imidazo[4,5-b]pyridine (85);
5-(1-methylpiperidin-4-yl)-2-(4-(phenoxymethyl)phenyl)-3H-imidazo[4,5-b]pyridine (86);
2-(4-(benzyloxy)phenyl)-5-(1-(methylsulfonyl)piperidin-4-yl)-3H-imidazo[4,5-b]pyridine (87);
ethyl 4-(2-(4-(benzyloxy)phenyl)-3H-imidazo[4,5-b]pyridin-5-yl)piperidine-1-carboxylate (88);
2-(4-(benzyloxy)phenyl)-5-(1-(cyclopropylsulfonyl)piperidin-4-yl)-3H-imidazo[4,5-b]pyridine (89);
2-(4-(benzyloxy)phenyl)-5-(1-(ethylsulfonyl)piperidin-4-yl)-3H-imidazo[4,5-b]pyridine (90);
2-(4-(benzyloxy)phenyl)-5-(4-(methylsulfonyl)piperazin-1-yl)-3H-imidazo[4,5-b]pyridine (91);
2-(4-(benzyloxy)phenyl)-5-(4-(cyclopropylsulfonyl)piperazin-1-yl)-3H-imidazo[4,5-b]pyridine (92);
2-(2-(4-(benzyloxy)phenyl)-3H-imidazo[4,5-b]pyridin-7-yl)-N-methylacetamide (93);
tert-butyl 4-(2-(4-(benzylthio)phenyl)-3H-imidazo[4,5-b]pyridin-5-yl)piperazine-1-carboxylate (95);
2-(4-(benzylthio)phenyl)-5-(piperazin-1-yl)-3H-imidazo[4,5-b]pyridine (96);
2-(4-(benzyloxy)phenyl)-5-(1-(ethylsulfonyl)-1,2,3,6-tetrahydropyridin-4-yl)-3H-imidazo[4,5-b]pyridine (97);
1-(4-(2-(4-(benzyloxy)phenyl)-3H-imidazo[4,5-b]pyridin-5-yl)-3,6-dihydropyridin-1(2H)-yl)ethan-1-one (98);
5-(1-methylpiperidin-3-yl)-2-(4-(phenoxymethyl)phenyl)-3H-imidazo[4,5-b]pyridine (99);
2-(4-(benzyloxy)phenyl)-6-(piperazin-1-yl)-3H-imidazo[4,5-b]pyridine (100);
1-(2-(4-(benzyloxy)phenyl)-3H-imidazo[4,5-b]pyridin-5-yl)-4-methylpiperidin-4-ol (101);
2-(phenoxymethyl)-4-(6-(piperidin-4-yl)-3H-imidazo[4,5-b]pyridin-2-yl)thiazole (102);
7-(2-(4-(benzyloxy)phenyl)-3H-imidazo[4,5-b]pyridin-5-yl)-3-methyl-5,6,7,8-tetrahydro-[1,2,4]triazolo[4,3-a]pyrazine (103); and
2-(1-benzyl-1H-pyrazol-4-yl)-6-(piperidin-4-yl)-3H-imidazo[4,5-b]pyridine (104).

14. A compound according to claim 8, wherein $A^3$ is a non-aromatic $C_{5-10}$ N-containing heterocyclic group, which is optionally substituted by one or two groups selected from OH, $NH_2$, $CH_2NH_2$, $C_{1-4}$ alkyl, $C_{1-4}$ alkylacyl, $C_{1-4}$ alkyl ester, oxo and $C_{1-4}$ alkyl sulfonyl.

15. A compound according to claim 9, wherein $A^3$ is a non-aromatic $C_{5-10}$ N-containing heterocyclic group, which is optionally substituted by one or two groups selected from OH, $NH_2$, $CH_2NH_2$, $C_{1-4}$ alkyl, $C_{1-4}$ alkylacyl, $C_{1-4}$ alkyl ester, oxo and $C_{1-4}$ alkyl sulfonyl.

16. A pharmaceutical composition comprising a compound according to claim 1, and a pharmaceutically acceptable excipient.

* * * * *